United States Patent
Harris et al.

(10) Patent No.: US 11,390,924 B2
(45) Date of Patent: Jul. 19, 2022

(54) ASSAY AND METHOD

(71) Applicant: Mars, Incorporated, McLean, VA (US)

(72) Inventors: Stephen James Harris, Waltham-on-the-Wolds (GB); Matthew Coates, Waltham-on-the-Wolds (GB); Matthew Ronald Gibbs, Waltham-on-the-Wolds (GB)

(73) Assignee: Mars, Incorporated, McLean, VA (US)

( * ) Notice: Subject to any disclaimer, the term of this patent is extended or adjusted under 35 U.S.C. 154(b) by 260 days.

(21) Appl. No.: 14/898,149

(22) PCT Filed: Jun. 13, 2014

(86) PCT No.: PCT/GB2014/000234
§ 371 (c)(1),
(2) Date: Dec. 14, 2015

(87) PCT Pub. No.: WO2014/199115
PCT Pub. Date: Dec. 18, 2014

(65) Prior Publication Data
US 2016/0138089 A1    May 19, 2016

(30) Foreign Application Priority Data

Jun. 14, 2013 (GB) ...................... 1310691

(51) Int. Cl.
| | | |
|---|---|---|
| *A23K 50/40* | (2016.01) | |
| *A61Q 11/00* | (2006.01) | |
| *C12Q 1/689* | (2018.01) | |
| *G16B 20/00* | (2019.01) | |
| *G16B 40/00* | (2019.01) | |
| *G01N 33/569* | (2006.01) | |
| *G16B 20/20* | (2019.01) | |
| *A61K 8/02* | (2006.01) | |

(52) U.S. Cl.
CPC .............. *C12Q 1/689* (2013.01); *A23K 50/40* (2016.05); *A61K 8/0204* (2013.01); *A61Q 11/00* (2013.01); *G01N 33/56955* (2013.01); *G16B 20/00* (2019.02); *G16B 20/20* (2019.02); *G16B 40/00* (2019.02); *A61K 2800/70* (2013.01); *C12Q 2600/112* (2013.01)

(58) Field of Classification Search
None
See application file for complete search history.

(56) References Cited

U.S. PATENT DOCUMENTS

| | | | |
|---|---|---|---|
| 1,466,578 | A | 8/1923 | Isabel |
| 5,407,661 | A * | 4/1995 | Simone .................. A23K 50/40 424/49 |
| 5,513,663 | A | 5/1996 | Van et al. |
| 6,197,305 | B1 | 3/2001 | Friedman et al. |
| 6,414,036 | B1 | 7/2002 | Ninkov |
| 6,495,176 | B1 | 12/2002 | McGenity et al. |
| 6,574,504 | B1 | 6/2003 | Mazaury et al. |
| 6,623,767 | B1 | 9/2003 | Morice |
| 6,652,892 | B2 | 11/2003 | McGenity et al. |
| 7,691,418 | B2 | 4/2010 | Rossel |
| 7,879,377 | B2 | 2/2011 | Dahl et al. |
| 7,910,139 | B2 | 3/2011 | Bombardelli |
| 2003/0228400 | A1 | 12/2003 | Dahl et al. |
| 2007/0134402 | A1 | 6/2007 | Feder |
| 2008/0026083 | A1 | 1/2008 | Reynolds |
| 2010/0061944 | A1 | 3/2010 | Marshall-Jones et al. |
| 2011/0300197 | A1 * | 12/2011 | McGenity .............. A23K 50/45 424/401 |
| 2013/0330681 | A1 * | 12/2013 | Sacks .................. A61C 17/3436 433/1 |

FOREIGN PATENT DOCUMENTS

| | | |
|---|---|---|
| FR | 2461499 A1 | 2/1981 |
| FR | 2622453 A1 | 5/1989 |
| JP | H08109118 A | 4/1996 |
| KR | 20030074055 A | 9/2003 |

OTHER PUBLICATIONS

What's Living in your Mouth? Cascades Center For Dental Health—Accessed Dec. 11, 2018 at https://cascadesdental.com/whats-living-in-your-mouth/ (provided by Applicant's Representative, attached to interview agenda).*
Culham et al., Journal of Veterinary Dentistry, vol. 15, No. 4, pp. 165-168 (1998).*
Elliott et al., Journal of Clinical Microbiology, vol. 43, No. 11; 2005 (of record).*
Dewhirst et al., PlosOne, vol. 7, No. 4, e36067, pp. 1-12; published Apr. 27, 2012 (of record).*
Culham et al., Journal of Veterinary Dentistry, vol. 15, No. 4, pp. 165-168 (1998) (of record).*
Riggio et al., Veterinary Microbiology, vol. 150, pp. 394-400 (2011) (Year: 2011).*
Dewhirst et al., PlosOne, vol. 7, No. 4, e36067, pp. 1-12; published Apr. 27, 2012 (of record). (Year: 2012).*
Culham et al., Journal of Veterinary Dentistry, vol. 15, No. 4, pp. 165-168 (of record). (Year: 1998).*
Sturgeon et al., Veterinary Microbiology, vol. 162, pp. 891-898 (electronically published Nov. 20, 2012) (Year: 2012).*
Riggio et al., Veterinary Microbiology, vol. 150, pp. 394-400 (2011) (of record). (Year: 2011).*
Elliott et al., Journal of Clinical Microbiology, vol. 43, No. 11; 2005 (of record). (Year: 2006).*
Sturgeon et al., Veterinary Microbiology, vol. 162, pp. 891-898 (Nov. 20, 2012) (of record). (Year: 2012).*

(Continued)

*Primary Examiner* — Soren Harward
*Assistant Examiner* — Paul D Pyla
(74) *Attorney, Agent, or Firm* — Morrison & Foerster LLP

(57) ABSTRACT

The present invention relates to an assay for use in a method of determining the oral health status of a canine animal by identifying certain bacteria present or absent in a sample taken from the animal, and applying the information set out herein for each identified bacteria to statistical models in order to determine the oral health status of the animal.

9 Claims, 78 Drawing Sheets

(56) References Cited

OTHER PUBLICATIONS

D'Aiuto, et al., "Periodontitis: from local infection to systemic diseases", Int J Immunopathol Pharmacol. 18(3 Suppl), Jul.-Sep. 1-11, 2005.
Dewhirst, et al., "The Canine Oral Microbiome", Plos One, vol. 7, No. 4, Apr. 19, 2012, e36067.
Elliott, et al., "Cultivable oral microbiota of domestic dogs", Journal of Clinical Microbiology, American Society for Microbiology, US, Nov. 1, 2005, 5470-5476.
Kortegaard, et al., "Periodontal disease in research beagle dogs—an epidemiological study: Paper", Journal of Small Animal Practice, 49, 2008, 610-616.
Kyllar, et al., "Prevalence of dental disorders in pet dogs", 2005, 496-505.
Lawson, et al., "*Peptostreptococcus canis* sp. nov., isolated from subgingival plaque from canine oral cavity", Anaerobe, vol. 18, No. 6, Dec. 1, 2012, 597-601.
Sturgeon, et al., "Metagenomic analysis of the canine oral cavity as revealed by high-throughput pyrosequencing of the 16S rRNA gene", Veterinary Microbiology, vol. 162, No. 2-4, Mar. 1, 2003, 891-898.
"Periodontal (Gum) Disease, Causes, Symptoms, and Treatments", US Department of Health and Human Services, Jan. 2006, pp. 1-16.
Appendino, et al., "Antibacterial galloylated alkylphloroglucinol glucosides from myrtle (Myrtus communis)", Medicinal & Aromatic Plants Abstracts, National Institute of Science Communication and Information, vol. 28, No. 3, Jun. 2006, XP018018747, 5 pgs.
Aydin, et al., "Determination of nutritional and physical properties of myrtle (*Myrtus communis* L.) fruits growing in Turkey", Journal of Food Engineering, vol. 79, No. 2, Nov. 1, 2006, pp. 453-458; XP005844950.
Casey, et al., "Development of a robust microtitre plate-based assay method for assessment of bioactivity", Microbial methods 58 (Sep. 2004) 327-334 (Abstract only, 2 pgs).

Dard-E-Dandaan, "Qaraabaadeen Azam wa Akmal (20th Gentry AD)", Matba Siddiqi, Delhi, Matba Mustafai, Delhi, 1909 AD, p. 690 (accessed Dec. 29, 2012).
Fenno et al., "The opdB Locus Encodes the Trypsin-Like Peptidase Activity of Treponema denticola Infection and Immunity", Infection and Immunity, Oct. 2001, p. 6193-6200, vol. 69, No. 10 (11 pgs).
Hennet, et al., "Evaluation of the Logan & Boyce Plaque Index for the Study of Dental Plaque Accumulation in Dogs", Res. Vet. Sci., Apr. 2006, 80(2):175-180.
Kuhn, et al., "Comparison of Biofilms Formed by Candidaalbicans and Candidaparapsilosis on Bioprosthetic Surfaces", Infection and Immunity. 70 (2): 878-888, Feb. 2002 (20 pgs).
McEldowney, et al., "Variability of the Influence of Physioichemical Factors Affecting Bacterial Adhesion ot Polystyrene Substrata", Appl Environ Microbiol, 52:460-465, Jan. 1986.
Murad, Khazaain-al-Advia, vol. 1 (20th century AD), Nadeem Yunus Printer, Sheikh Mohd Basheer Sons, Lahore 1911 AD, p. 371 (Accessed online Dec. 29, 2012).
Pratten, et al., "Response of a single species biofilms and microcosm dental plaques to pulsing with chlorhexidine", Journal of Antimicrobial Chemotherapy 42 453-459, Oct. 1998.
Romani, et al., "Identification and quantitation of polyphenols in leaves of *Myrtus communis* L", Chromatographia, Wiesbaden DE, vol. 49, No. 1-2, Jan. 1, 1999 pp. 17-20.
Allaker et al., Prevalence of *Porphyromonas* and *Prevotella* species in the dental plaque of dogs, The Veterinary Record, (1997), 140, 147-148.
Davis et al., A Cross-Sectional Survey of Bacterial Species in Plaque from Client Owned Dogs with Healthy Gingiva, Gingivitis or Mild Periodontitis, PLOSOne, vol. 8, issue 12, e83158, Dec. 2013, 12 pages.
Isogai et al., Ecology of Genus *Porphyromonas* in Canine Periodontal Disease, J. Vet. Med., Series B, vol. 46, No. 7, (1999), 476-483.
McDonald et al., "Characterising the Canine Oral Microbiome by Direct Sequencing of Reverse-Transcribed rRNA Molecules," PLOS One, vol. 11, issue 6, Jun. 2016, e0157046, 17 pages.

* cited by examiner

Table 5

| | A | B | C | D | E | F | G | H | I | J | K | L | M |
|---|---|---|---|---|---|---|---|---|---|---|---|---|---|
| | Obs | Health state | Total count | c_Actinobaculum_sp__COT-375 | c_Actinomyces_sp | c_Actinomyces_sp__COT-252 | c_Actinomyces_sp__COT-324 | c_Aggregatibacter_sp__COT-897 | c_Bacteroidales_bacterium__COT-305 | c_Bacteroides_sp__COT-040 | c_Bacteroidetes_bactre__COT-895 | c_Bacteroidetes_ML-sp__COT-587 | c_Bergeyella_zoohelcum__COT-186 |
| 1 | G_7 | Gingivitis | 12132 | 5 | 76 | 148 | 0 | 41 | 0 | 87 | 0 | 0 | 824 |
| 2 | G_8 | Gingivitis | 10631 | 5 | 18 | 134 | 19 | 0 | 0 | 28 | 1 | 3 | 16 |
| 3 | G_9 | Gingivitis | 25790 | 254 | 432 | 330 | 29 | 2 | 29 | 5 | 0 | 3 | 56 |
| 4 | G_12 | Gingivitis | 15863 | 0 | 28 | 65 | 0 | 75 | 0 | 78 | 124 | 0 | 2737 |
| 5 | G_14 | Gingivitis | 9158 | 73 | 215 | 486 | 518 | 5 | 0 | 8 | 1 | 0 | 2 |
| 6 | G_18 | Gingivitis | 28089 | 161 | 43 | 27 | 41 | 183 | 0 | 233 | 15 | 0 | 27 |
| 7 | G_22 | Gingivitis | 84760 | 133 | 128 | 480 | 28 | 47 | 65 | 1207 | 0 | 13 | 273 |
| 8 | G_30 | Gingivitis | 19864 | 9 | 2 | 127 | 4 | 0 | 13 | 90 | 0 | 25 | 17 |
| 9 | G_35 | Gingivitis | 38047 | 332 | 197 | 572 | 13 | 23 | 2 | 69 | 0 | 35 | 788 |
| 10 | G_40 | Gingivitis | 16495 | 4 | 229 | 719 | 3 | 15 | 0 | 338 | 71 | 0 | 148 |
| 11 | G_42 | Gingivitis | 11958 | 0 | 0 | 21 | 0 | 7 | 0 | 0 | 125 | 0 | 4 |
| 12 | G_52 | Gingivitis | 45301 | 137 | 128 | 618 | 2 | 5 | 1 | 244 | 0 | 0 | 147 |
| 13 | G_53 | Gingivitis | 9922 | 1 | 37 | 19 | 0 | 33 | 0 | 195 | 0 | 0 | 155 |
| 14 | G_63 | Gingivitis | 5611 | 1 | 11 | 8 | 1 | 2 | 0 | 2 | 0 | 3 | 5 |
| 15 | G_64 | Gingivitis | 7175 | 17 | 11 | 68 | 4 | 4 | 1 | 31 | 0 | 3 | 4 |
| 16 | G_65 | Gingivitis | 6366 | 33 | 52 | 246 | 3 | 1 | 0 | 2 | 0 | 0 | 3 |

FIG. 12

Table 5 (cont.)

| | A | B | C | D | E | F | G | H | I | J | K | L | M |
|---|---|---|---|---|---|---|---|---|---|---|---|---|---|
| 18 | G_72 | Gingivitis | 61483 | 13 | 96 | 393 | 12 | 0 | 0 | 727 | 193 | 17 | 9 |
| 19 | G_81 | Gingivitis | 8859 | 2 | 3 | 32 | 0 | 1 | 0 | 76 | 0 | 0 | 151 |
| 20 | G_86 | Gingivitis | 94894 | 6 | 223 | 266 | 1 | 316 | 0 | 29 | 0 | 0 | 13363 |
| 21 | G_96 | Gingivitis | 39243 | 198 | 134 | 1218 | 0 | 19 | 71 | 18 | 1 | 132 | 5 |
| 22 | G_98 | Gingivitis | 17911 | 41 | 64 | 47 | 0 | 0 | 0 | 30 | 0 | 0 | 1108 |
| 23 | G_101 | Gingivitis | 13876 | 3 | 7 | 9 | 1 | 1 | 0 | 0 | 1 | 2 | 5 |
| 24 | G_113 | Gingivitis | 19818 | 45 | 190 | 196 | 6 | 18 | 3 | 82 | 0 | 4 | 224 |
| 25 | G_117 | Gingivitis | 30819 | 29 | 39 | 51 | 13 | 247 | 25 | 158 | 0 | 1 | 478 |
| 26 | G_120 | Gingivitis | 22865 | 113 | 32 | 212 | 1 | 7 | 38 | 14 | 7 | 3 | 56 |
| 27 | G_327 | Gingivitis | 17505 | 183 | 3 | 11 | 0 | 4 | 7 | 728 | 0 | 7 | 84 |
| 28 | G_328 | Gingivitis | 12756 | 67 | 58 | 70 | 0 | 11 | 7 | 124 | 0 | 4 | 86 |
| 29 | G_332 | Gingivitis | 21222 | 187 | 78 | 1767 | 4 | 0 | 0 | 2 | 0 | 0 | 2 |
| 30 | G_135 | Gingivitis | 19363 | 75 | 38 | 48 | 0 | 31 | 3 | 108 | 0 | 0 | 99 |
| 31 | G_139 | Gingivitis | 17129 | 0 | 82 | 78 | 0 | 17 | 3 | 114 | 226 | 0 | 56 |
| 32 | G_143 | Gingivitis | 48153 | 77 | 115 | 832 | 0 | 0 | 0 | 1 | 0 | 1 | 5 |
| 33 | G_148 | Gingivitis | 15897 | 0 | 38 | 186 | 0 | 7 | 0 | 216 | 1 | 0 | 35 |
| 34 | G_149 | Gingivitis | 29961 | 4 | 142 | 901 | 0 | 0 | 0 | 3 | 30 | 0 | 7 |
| 35 | G_353 | Gingivitis | 18102 | 7 | 63 | 58 | 0 | 0 | 1 | 53 | 0 | 7 | 247 |
| 36 | G_361 | Gingivitis | 14798 | 138 | 23 | 73 | 0 | 2 | 1 | 7 | 0 | 0 | 14 |
| 37 | G_369 | Gingivitis | 9811 | 4 | 3 | 88 | 3 | 0 | 14 | 23 | 1 | 0 | 13 |
| 38 | G_170 | Gingivitis | 49000 | 4697 | 1413 | 1794 | 132 | 27 | 3 | 27 | 0 | 7 | 5 |
| 39 | G_172 | Gingivitis | 36843 | 0 | 106 | 287 | 8 | 7 | 37 | 21 | 44 | 33 | 1548 |
| 40 | G_173 | Gingivitis | 57678 | 505 | 459 | 13613 | 111 | 0 | 4 | 12 | 0 | 0 | 10 |
| 41 | G_177 | Gingivitis | 36744 | 504 | 54 | 161 | 1 | 14 | 0 | 26 | 1 | 0 | 352 |
| 42 | G_184 | Gingivitis | 11140 | 0 | 6 | 35 | 0 | 0 | 0 | 190 | 0 | 0 | 148 |
| 43 | G_188 | Gingivitis | 9525 | 8 | 87 | 117 | 0 | 0 | 0 | 9 | 1 | 0 | 9 |
| 44 | G_197 | Gingivitis | 3805 | 0 | 23 | 17 | 0 | 0 | 1 | 26 | 1 | 0 | 2 |
| 45 | G_214 | Gingivitis | 12730 | 10 | 21 | 94 | 0 | 39 | 0 | 449 | 0 | 7 | 127 |
| 46 | G_232 | Gingivitis | 13082 | 26 | 8 | 80 | 0 | 167 | 1 | 267 | 0 | 32 | 329 |
| 47 | G_244 | Gingivitis | 13446 | 13 | 24 | 349 | 17 | 0 | 0 | 2 | 2 | 1 | 2 |
| 48 | G_245 | Gingivitis | 2911 | 4 | 18 | 36 | 109 | 277 | 1 | 150 | 0 | 4 | 76 |
| 49 | G_246 | Gingivitis | 37262 | 13 | 5 | 52 | 0 | 0 | 0 | 1 | 0 | 0 | 0 |

FIG. 12 (cont.)

Table 6 (cont.)

| | A | B | C | D | E | F | G | H | I | J | K | L | M |
|---|---|---|---|---|---|---|---|---|---|---|---|---|---|
| 50 | G_249 | Gingivitis | 19242 | 49 | 11 | 78 | 2 | 5 | 0 | 268 | 0 | 3 | 213 |
| 51 | G_354 | Gingivitis | 16211 | 19 | 112 | 460 | 29 | 6 | 0 | 9 | 0 | 2 | 30 |
| 52 | G_19 | Gingivitis | 34430 | 0 | 71 | 269 | 2 | 9 | 13 | 31 | 0 | 5 | 16 |
| 53 | H_39 | Health | 18024 | 12 | 77 | 72 | 0 | 1 | 0 | 0 | 1 | 0 | 7 |
| 54 | H_48 | Health | 9790 | 0 | 407 | 447 | 1 | 6 | 0 | 107 | 0 | 58 | 106 |
| 55 | H_51 | Health | 7751 | 137 | 11 | 65 | 3 | 0 | 0 | 20 | 0 | 0 | 67 |
| 56 | H_57 | Health | 37038 | 639 | 100 | 127 | 0 | 1 | 0 | 37 | 0 | 0 | 88 |
| 57 | H_58 | Health | 12082 | 39 | 30 | 82 | 3 | 1 | 0 | 14 | 0 | 1 | 127 |
| 58 | H_58 | Health | 10333 | 2 | 3 | 31 | 0 | 2 | 2 | 3 | 7 | 0 | 2826 |
| 59 | H_73 | Health | 12578 | 1 | 1 | 7 | 0 | 55 | 0 | 5 | 20 | 0 | 949 |
| 60 | H_74 | Health | 47661 | 79 | 83 | 414 | 5 | 17 | 3 | 322 | 4 | 6 | 1666 |
| 61 | H_78 | Health | 11952 | 5 | 51 | 169 | 3 | 14 | 0 | 208 | 2 | 1 | 3734 |
| 62 | H_83 | Health | 22743 | 1 | 2 | 1885 | 0 | 1 | 0 | 7 | 1 | 1 | 7 |
| 63 | H_89 | Health | 13540 | 0 | 3 | 2 | 0 | 20 | 0 | 36 | 2 | 0 | 1880 |
| 64 | H_90 | Health | 15858 | 178 | 934 | 2720 | 12 | 0 | 0 | 56 | 5 | 0 | 44 |
| 65 | H_94 | Health | 18898 | 57 | 21 | 154 | 47 | 3 | 7 | 19 | 0 | 1 | 11 |
| 66 | H_307 | Health | 13290 | 1 | 40 | 491 | 0 | 0 | 5 | 2 | 0 | 3 | 1268 |
| 67 | H_308 | Health | 13026 | 4 | 49 | 839 | 1 | 0 | 3 | 35 | 5 | 0 | 302 |
| 68 | H_312 | Health | 29644 | 191 | 58 | 18 | 0 | 0 | 0 | 53 | 0 | 0 | 1917 |
| 69 | H_314 | Health | 13104 | 0 | 12 | 181 | 37 | 0 | 18 | 189 | 0 | 23 | 4 |
| 70 | H_338 | Health | 28763 | 0 | 5 | 35 | 0 | 2 | 0 | 1329 | 17 | 0 | 78 |
| 71 | H_137 | Health | 14686 | 1 | 31 | 186 | 0 | 0 | 0 | 13 | 0 | 1 | 2 |
| 72 | H_145 | Health | 14097 | 38 | 15 | 130 | 0 | 22 | 0 | 136 | 0 | 0 | 49 |
| 73 | H_148 | Health | 36790 | 1711 | 1404 | 1279 | 86 | 1 | 0 | 23 | 0 | 0 | 31 |
| 74 | H_354 | Health | 18025 | 20 | 175 | 112 | 0 | 11 | 0 | 56 | 2 | 0 | 269 |
| 75 | H_356 | Health | 13699 | 2 | 22 | 58 | 0 | 5 | 0 | 0 | 0 | 0 | 14 |
| 76 | H_362 | Health | 11571 | 2 | 135 | 113 | 1 | 2 | 71 | 21 | 84 | 8 | 16 |
| 77 | H_363 | Health | 18004 | 1 | 9 | 56 | 2 | 0 | 14 | 399 | 4 | 11 | 438 |
| 78 | H_364 | Health | 38129 | 300 | 756 | 1988 | 10 | 118 | 0 | 171 | 0 | 5 | 35 |
| 79 | H_365 | Health | 24974 | 0 | 133 | 197 | 44 | 667 | 0 | 43 | 12 | 5 | 2423 |
| 80 | H_366 | Health | 28147 | 0 | 396 | 403 | 0 | 144 | 0 | 489 | 0 | 0 | 6712 |
| 81 | H_368 | Health | 10291 | 0 | 16 | 10 | 2 | 0 | 0 | 51 | 0 | 0 | 2487 |

FIG. 12 (cont.)

Table 5 (cont.)

| | A | B | C | D | E | F | G | H | I | J | K | L | M |
|---|---|---|---|---|---|---|---|---|---|---|---|---|---|
| 82 | H_171 | Health | 14889 | 8 | 99 | 200 | 0 | 11 | 0 | 940 | 0 | 13 | 384 |
| 83 | H_174 | Health | 10127 | 0 | 27 | 357 | 0 | 0 | 0 | 0 | 1 | 0 | 2 |
| 84 | H_175 | Health | 9530 | 0 | 79 | 30 | 0 | 0 | 0 | 0 | 52 | 3 | 3 |
| 85 | H_178 | Health | 75108 | 3192 | 823 | 3284 | 6 | 0 | 0 | 935 | 0 | 18 | 208 |
| 86 | H_186 | Health | 12182 | 4 | 24 | 60 | 2 | 90 | 3 | 86 | 0 | 0 | 957 |
| 87 | H_189 | Health | 25677 | 32 | 10 | 38 | 0 | 7 | 0 | 1187 | 1 | 0 | 5 |
| 88 | H_200 | Health | 19277 | 24 | 181 | 82 | 2 | 10 | 0 | 178 | 1 | 0 | 85 |
| 89 | H_203 | Health | 7317 | 8 | 16 | 26 | 0 | 0 | 0 | 15 | 0 | 0 | 2278 |
| 90 | H_211 | Health | 4740 | 8 | 233 | 25 | 0 | 4 | 0 | 12 | 0 | 1 | 120 |
| 91 | H_217 | Health | 18864 | 19 | 51 | 26 | 3 | 3 | 0 | 15 | 4 | 0 | 298 |
| 92 | H_220 | Health | 18131 | 25 | 133 | 261 | 0 | 17 | 0 | 1 | 160 | 0 | 3 |
| 93 | H_221 | Health | 76802 | 0 | 332 | 28 | 0 | 2444 | 0 | 132 | 0 | 0 | 308 |
| 94 | H_222 | Health | 24761 | 57 | 84 | 29 | 5 | 3 | 3 | 382 | 0 | 6 | 83 |
| 95 | H_223 | Health | 7018 | 8 | 35 | 10 | 0 | 209 | 0 | 48 | 0 | 0 | 254 |
| 96 | H_225 | Health | 14460 | 0 | 4 | 4 | 1 | 5 | 0 | 108 | 219 | 0 | 31 |
| 97 | H_234 | Health | 13332 | 106 | 42 | 7 | 0 | 6 | 0 | 1 | 1 | 5 | 60 |
| 98 | H_235 | Health | 14696 | 2 | 38 | 48 | 0 | 23 | 0 | 23 | 1 | 0 | 327 |
| 99 | H_236 | Health | 9200 | 28 | 5 | 8 | 0 | 1 | 0 | 3 | 0 | 0 | 18 |
| 100 | H_237 | Health | 26932 | 0 | 45 | 54 | 0 | 10 | 0 | 27 | 0 | 0 | 1284 |
| 101 | H_238 | Health | 13638 | 0 | 14 | 19 | 0 | 113 | 1 | 109 | 0 | 2 | 202 |
| 102 | H_239 | Health | 17487 | 0 | 19 | 556 | 87 | 5 | 3 | 45 | 0 | 0 | 32 |
| 103 | H_240 | Health | 14649 | 3 | 30 | 41 | 0 | 8 | 0 | 8 | 0 | 0 | 369 |
| 104 | H_241 | Health | 32149 | 3 | 104 | 308 | 0 | 608 | 0 | 113 | 1 | 0 | 3376 |
| 105 | P_1 | PD1 | 15621 | 14 | 12 | 67 | 0 | 118 | 1 | 178 | 0 | 0 | 30 |
| 106 | P_5 | PD1 | 55952 | 15 | 41 | 2428 | 0 | 1 | 556 | 83 | 0 | 26 | 25 |
| 107 | P_20 | PD1 | 14617 | 156 | 167 | 439 | 43 | 1 | 1 | 11 | 0 | 2 | 0 |
| 108 | P_21 | PD1 | 13750 | 3 | 26 | 175 | 5 | 2 | 0 | 24 | 0 | 0 | 32 |
| 109 | P_24 | PD1 | 12785 | 56 | 84 | 436 | 0 | 0 | 0 | 0 | 0 | 7 | 7 |
| 110 | P_25 | PD1 | 22123 | 452 | 224 | 471 | 0 | 4 | 0 | 52 | 42 | 7 | 244 |
| 111 | P_37 | PD1 | 64080 | 286 | 756 | 3058 | 823 | 1 | 6 | 1 | 0 | 1 | 4 |
| 112 | P_46 | PD1 | 56996 | 108 | 153 | 2198 | 240 | 36 | 13 | 386 | 0 | 48 | 112 |
| 113 | P_49 | PD1 | 33580 | 829 | 135 | 2885 | 61 | 0 | 4 | 20 | 0 | 10 | 30 |

FIG. 12 (cont.)

Table 5 (cont.)

| | A | B | C | D | E | F | G | H | I | J | K | L | M |
|---|---|---|---|---|---|---|---|---|---|---|---|---|---|
| 113 | P_53 | P01 | 37971 | 486 | 139 | 833 | 336 | 0 | 8 | 363 | 1 | 52 | 5 |
| 114 | P_54 | P01 | 23303 | 84 | 7 | 375 | 0 | 24 | 4 | 39 | 0 | 20 | 21 |
| 115 | P_70 | P01 | 17344 | 0 | 8 | 67 | 8 | 0 | 0 | 72 | 0 | 1 | 3 |
| 116 | P_79 | P01 | 10858 | 3 | 20 | 487 | 0 | 0 | 2 | 3 | 0 | 0 | 30 |
| 117 | P_80 | P01 | 46951 | 482 | 174 | 63 | 0 | 2 | 1 | 5 | 14 | 10 | 13 |
| 118 | P_84 | P01 | 22349 | 37 | 38 | 134 | 75 | 1 | 1 | 74 | 18 | 2 | 5 |
| 119 | P_85 | P01 | 2613 | 15 | 3 | 26 | 0 | 1 | 135 | 16 | 65 | 5 | 42 |
| 120 | P_87 | P01 | 13155 | 19 | 45 | 288 | 35 | 0 | 0 | 4 | 0 | 1 | 0 |
| 121 | P_100 | P01 | 19179 | 22 | 27 | 164 | 17 | 1 | 13 | 18 | 3 | 4 | 2 |
| 122 | P_102 | P01 | 13541 | 65 | 155 | 319 | 5 | 6 | 0 | 12 | 0 | 1 | 51 |
| 123 | P_105 | P01 | 15163 | 0 | 25 | 59 | 0 | 0 | 7 | 1 | 0 | 1 | 3 |
| 124 | P_106 | P01 | 56812 | 2123 | 65 | 1807 | 0 | 1 | 12 | 3 | 0 | 2 | 2 |
| 125 | P_109 | P01 | 31560 | 152 | 14 | 125 | 0 | 38 | 8 | 175 | 0 | 21 | 185 |
| 126 | P_111 | P01 | 18442 | 5 | 130 | 2328 | 0 | 3 | 3 | 0 | 17 | 3 | 8 |
| 127 | P_123 | P01 | 16867 | 4 | 11 | 319 | 0 | 0 | 0 | 30 | 0 | 49 | 1 |
| 128 | P_131 | P01 | 17351 | 111 | 2 | 19 | 0 | 8 | 3 | 13 | 8 | 30 | 9 |
| 129 | P_134 | P01 | 50988 | 2348 | 834 | 57 | 13 | 68 | 31 | 14 | 0 | 10 | 253 |
| 130 | P_136 | P01 | 36223 | 155 | 399 | 65 | 0 | 1 | 11 | 4 | 9 | 5 | 309 |
| 131 | P_140 | P01 | 18343 | 23 | 134 | 728 | 12 | 1 | 0 | 0 | 0 | 0 | 13 |
| 132 | P_147 | P01 | 63057 | 52 | 61 | 1233 | 0 | 31 | 0 | 163 | 40 | 0 | 1763 |
| 133 | P_155 | P01 | 38311 | 98 | 48 | 466 | 11 | 5 | 7 | 28 | 0 | 1 | 235 |
| 134 | P_181 | P01 | 18947 | 8 | 93 | 399 | 23 | 2 | 11 | 14 | 0 | 7 | 3 |
| 135 | P_187 | P01 | 10346 | 28 | 114 | 630 | 258 | 4 | 3 | 8 | 0 | 5 | 9 |
| 136 | P_190 | P01 | 15581 | 0 | 2 | 3 | 0 | 0 | 0 | 352 | 73 | 0 | 38 |
| 137 | P_191 | P01 | 14526 | 58 | 146 | 344 | 1 | 3 | 73 | 40 | 94 | 33 | 445 |
| 138 | P_193 | P01 | 39342 | 0 | 1 | 545 | 0 | 0 | 0 | 457 | 1780 | 0 | 27 |
| 139 | P_195 | P01 | 38666 | 1 | 37 | 458 | 0 | 16 | 1 | 83 | 233 | 0 | 6 |
| 140 | P_196 | P01 | 48271 | 329 | 547 | 2372 | 1 | 0 | 0 | 6 | 0 | 32 | 247 |
| 141 | P_205 | P01 | 10354 | 96 | 140 | 174 | 174 | 2 | 3 | 0 | 0 | 7 | 38 |
| 142 | P_206 | P01 | 16150 | 4 | 14 | 155 | 0 | 11 | 1 | 57 | 5 | 2 | 21 |
| 143 | P_208 | P01 | 22374 | 0 | 170 | 322 | 3 | 3 | 0 | 20 | 4 | 5 | 29 |
| 144 | P_210 | P01 | 15575 | 34 | 221 | 468 | 21 | 0 | 0 | 2 | 0 | 2 | 1 |

FIG. 12 (cont.)

Table 5 (cont.)

| | A | B | C | D | E | F | G | H | I | J | K | L | M |
|---|---|---|---|---|---|---|---|---|---|---|---|---|---|
| 146 | P_216 | P01 | 12237 | 9 | 25 | 24 | 17 | 0 | 2 | 3 | 1 | 14 | 2 |
| 147 | P_218 | P01 | 10475 | 28 | 130 | 261 | 193 | 0 | 0 | 2 | 0 | 4 | 2 |
| 148 | P_219 | P01 | 12572 | 118 | 238 | 530 | 39 | 0 | 2 | 11 | 0 | 6 | 2 |
| 149 | P_224 | P01 | 37758 | 548 | 342 | 1590 | 195 | 2 | 1 | 55 | 2 | 7 | 2 |
| 150 | P_226 | P01 | 14662 | 94 | 146 | 415 | 170 | 0 | 7 | 5 | 0 | 3 | 2 |
| 151 | P_228 | P01 | 18792 | 498 | 59 | 44 | 12 | 15 | 0 | 56 | 0 | 7 | 46 |
| 152 | P_233 | P01 | 17047 | 12 | 60 | 98 | 2 | 0 | 8 | 22 | 6 | 13 | 11 |
| 153 | P_248 | P01 | 20136 | 198 | 248 | 723 | 14 | 5 | 1 | 40 | 0 | 17 | 44 |
| 154 | P_8C09 | P01 | 18842 | 9 | 43 | 67 | 5 | 7 | 15 | 18 | 36 | 52 | 80 |
| 155 | P_8C19 | P01 | 14480 | 2 | 79 | 43 | 0 | 0 | 1 | 39 | 0 | 40 | 21 |
| 156 | P_8C21 | P01 | 45443 | 3 | 412 | 98 | 0 | 2 | 0 | 137 | 7 | 2 | 1443 |

FIG. 12 (cont.)

Table 5 (cont.)

| | A | B | C | N | O | P | Q | R | S | T | U | V |
|---|---|---|---|---|---|---|---|---|---|---|---|---|
| | Dog | Health score | Total reads | Cf_Bacteroides_sp._COT-039 | Cf_Campylobacter_sp._COT-012 | Cf_Capnocytophaga_canimorsus | Cf_Capnocytophaga_canimorsus_COT-139 | Cf_Capnocytophaga_sp._COT-339 | Cf_Capnocytophaga_sp._COT-362 | Cf_Corynebacterium_sp._COT-375 | Cf_Crenobacter_JG-41_sp._COT-186 | Cf_Crenotrichales_JG_16_31_sp._COT-466 |
| 2 | G_7 | Gingivitis | 32152 | 56 | 51 | 165 | 233 | 668 | 22 | 0 | 3 | 1 |
| 3 | G_8 | Gingivitis | 10631 | 14 | 42 | 0 | 2 | 1 | 0 | 46 | 48 | 13 |
| 4 | G_9 | Gingivitis | 25795 | 14 | 9 | 0 | 4 | 3 | 23 | 0 | 27 | 156 |
| 5 | G_12 | Gingivitis | 13863 | 78 | 88 | 87 | 39 | 187 | 4 | 0 | 5 | 7 |
| 6 | G_14 | Gingivitis | 9135 | 13 | 2 | 0 | 0 | 0 | 1 | 0 | 32 | 63 |
| 7 | G_18 | Gingivitis | 28089 | 250 | 185 | 4 | 19 | 43 | 6 | 0 | 11 | 5 |
| 8 | G_22 | Gingivitis | 84760 | 569 | 1374 | 199 | 27 | 267 | 59 | 0 | 815 | 68 |
| 9 | G_30 | Gingivitis | 19824 | 17 | 29 | 3 | 1 | 6 | 5 | 0 | 86 | 14 |
| 10 | G_35 | Gingivitis | 38047 | 124 | 339 | 67 | 35 | 38 | 21 | 0 | 255 | 23 |
| 11 | G_40 | Gingivitis | 1E+05 | 799 | 241 | 4 | 1 | 24 | 6 | 0 | 2062 | 198 |
| 12 | G_42 | Gingivitis | 11958 | 2 | 4 | 0 | 10 | 0 | 0 | 0 | 0 | 0 |
| 13 | G_52 | Gingivitis | 40561 | 81 | 556 | 13 | 24 | 320 | 11 | 0 | 118 | 10 |
| 14 | G_62 | Gingivitis | 9972 | 16 | 303 | 44 | 394 | 12 | 14 | 0 | 2 | 0 |
| 15 | G_63 | Gingivitis | 5611 | 42 | 27 | 0 | 21 | 37 | 18 | 0 | 39 | 3 |
| 16 | G_64 | Gingivitis | 7175 | 15 | 77 | 0 | 1 | 13 | 1 | 16 | 15 | 5 |
| 17 | G_65 | Gingivitis | 6306 | 2 | 6 | 0 | 0 | 0 | 10 | 0 | 29 | 49 |

FIG. 12 (cont.)

Table 5 (cont.)

| | A | B | C | N | O | P | Q | R | S | T | U | V |
|---|---|---|---|---|---|---|---|---|---|---|---|---|
| 18 | G_72 | Gingivitis | 61483 | 535 | 241 | 3 | 364 | 208 | 3 | 0 | 124 | 16 |
| 19 | G_81 | Gingivitis | 8859 | 28 | 89 | 5 | 4 | 9 | 0 | 1 | 4 | 0 |
| 20 | G_86 | Gingivitis | 54894 | 70 | 78 | 82 | 429 | 34 | 4 | 0 | 0 | 0 |
| 21 | G_96 | Gingivitis | 58245 | 92 | 38 | 0 | 3 | 1 | 190 | 0 | 147 | 1013 |
| 22 | G_98 | Gingivitis | 17911 | 224 | 66 | 20 | 1 | 3 | 12 | 35 | 27 | 0 |
| 23 | G_101 | Gingivitis | 12878 | 44 | 45 | 0 | 0 | 17 | 5 | 7 | 7 | 4 |
| 24 | G_113 | Gingivitis | 18818 | 148 | 170 | 24 | 15 | 143 | 3 | 0 | 118 | 14 |
| 25 | G_117 | Gingivitis | 30819 | 104 | 417 | 9 | 177 | 1 | 11 | 0 | 48 | 24 |
| 26 | G_120 | Gingivitis | 23555 | 30 | 31 | 13 | 1 | 8 | 19 | 31 | 43 | 14 |
| 27 | G_122 | Gingivitis | 17598 | 182 | 77 | 12 | 9 | 75 | 8 | 0 | 10 | 0 |
| 28 | G_128 | Gingivitis | 12750 | 194 | 172 | 7 | 2 | 4 | 10 | 0 | 20 | 0 |
| 29 | G_132 | Gingivitis | 21221 | 13 | 34 | 0 | 0 | 3 | 13 | 0 | 186 | 143 |
| 30 | G_135 | Gingivitis | 10368 | 77 | 11 | 0 | 8 | 0 | 30 | 0 | 2 | 1 |
| 31 | G_139 | Gingivitis | 17129 | 10 | 50 | 2 | 36 | 12 | 0 | 0 | 11 | 50 |
| 32 | G_143 | Gingivitis | 48153 | 58 | 43 | 0 | 0 | 5 | 1 | 0 | 174 | 1 |
| 33 | G_148 | Gingivitis | 16887 | 8 | 52 | 6 | 5 | 1 | 0 | 0 | 72 | 30 |
| 34 | G_149 | Gingivitis | 29864 | 1 | 8 | 0 | 1 | 3 | 0 | 0 | 103 | 182 |
| 35 | G_153 | Gingivitis | 12182 | 82 | 114 | 25 | 13 | 553 | 8 | 2 | 524 | 0 |
| 36 | G_161 | Gingivitis | 14798 | 31 | 71 | 0 | 7 | 84 | 13 | 0 | 1 | 1 |
| 37 | G_169 | Gingivitis | 3811 | 5 | 78 | 25 | 8 | 0 | 0 | 0 | 92 | 15 |
| 38 | G_170 | Gingivitis | 49000 | 35 | 186 | 18 | 3 | 7 | 2 | 0 | 493 | 88 |
| 39 | G_172 | Gingivitis | 36943 | 11 | 123 | 2 | 317 | 114 | 31 | 0 | 282 | 90 |
| 40 | G_173 | Gingivitis | 57876 | 6 | 13 | 1 | 1 | 0 | 35 | 0 | 1747 | 88 |
| 41 | G_177 | Gingivitis | 36744 | 212 | 912 | 25 | 229 | 117 | 87 | 0 | 3 | 1 |
| 42 | G_184 | Gingivitis | 11140 | 30 | 382 | 8 | 50 | 1 | 0 | 0 | 0 | 0 |
| 43 | G_188 | Gingivitis | 9325 | 81 | 50 | 0 | 0 | 0 | 2 | 0 | 0 | 0 |
| 44 | G_197 | Gingivitis | 3805 | 2 | 17 | 0 | 0 | 0 | 0 | 0 | 10 | 7 |
| 45 | G_214 | Gingivitis | 10519 | 28 | 120 | 0 | 59 | 182 | 3 | 0 | 29 | 7 |
| 46 | G_232 | Gingivitis | 13882 | 136 | 229 | 13 | 13 | 174 | 2 | 0 | 49 | 1 |
| 47 | G_244 | Gingivitis | 13446 | 4 | 9 | 0 | 1 | 0 | 58 | 4 | 51 | 315 |
| 48 | G_245 | Gingivitis | 29114 | 32 | 151 | 5 | 1 | 271 | 3 | 4 | 0 | 0 |
| 49 | G_246 | Gingivitis | 37282 | 304 | 864 | 210 | 1308 | 0 | 23 | 14 | 0 | 0 |

FIG. 12 (cont.)

Table 5 (cont.)

| | A | B | C | N | O | P | Q | R | S | T | U | V |
|---|---|---|---|---|---|---|---|---|---|---|---|---|
| 50 | G_249 | Gingivitis | 19242 | 35 | 128 | 13 | 13 | 178 | 30 | 29 | 13 | 2 |
| 51 | G_C854 | Gingivitis | 16211 | 1 | 18 | 1 | 0 | 1 | 82 | 0 | 0 | 138 |
| 52 | G_19 | Gingivitis | 34480 | 1 | 17 | 1 | 2 | 8 | 0 | 0 | 8 | 5 |
| 53 | H_35 | Health | 16024 | 91 | 39 | 8 | 665 | 2 | 1 | 0 | 22 | 3 |
| 54 | H_48 | Health | 9790 | 12 | 60 | 1 | 3 | 138 | 12 | 0 | 7 | 5 |
| 55 | H_51 | Health | 7751 | 34 | 11 | 3 | 4 | 18 | 0 | 0 | 116 | 7 |
| 56 | H_57 | Health | 37038 | 76 | 208 | 4 | 0 | 71 | 9 | 3 | 15 | 0 |
| 57 | H_58 | Health | 12089 | 91 | 93 | 9 | 5 | 41 | 15 | 0 | 7 | 2 |
| 58 | H_68 | Health | 10333 | 4 | 14 | 53 | 729 | 69 | 26 | 0 | 5 | 7 |
| 59 | H_73 | Health | 12578 | 102 | 214 | 14 | 36 | 86 | 8 | 0 | 1 | 0 |
| 60 | H_74 | Health | 47881 | 222 | 192 | 71 | 182 | 2763 | 2 | 0 | 7 | 5 |
| 61 | H_78 | Health | 13932 | 36 | 26 | 7 | 33 | 98 | 11 | 0 | 18 | 2 |
| 62 | H_83 | Health | 22743 | 181 | 43 | 19 | 8 | 6 | 1 | 0 | 68 | 2 |
| 63 | H_85 | Health | 13540 | 19 | 35 | 2 | 80 | 4471 | 17 | 0 | 0 | 1 |
| 64 | H_90 | Health | 16858 | 19 | 28 | 14 | 1 | 9 | 5 | 0 | 9 | 10 |
| 65 | H_94 | Health | 18898 | 65 | 122 | 48 | 0 | 0 | 4 | 17 | 90 | 7 |
| 66 | H_107 | Health | 13290 | 1 | 22 | 49 | 217 | 30 | 58 | 0 | 23 | 3 |
| 67 | H_108 | Health | 13829 | 167 | 36 | 6 | 6 | 232 | 10 | 0 | 39 | 1 |
| 68 | H_132 | Health | 29544 | 200 | 136 | 21 | 160 | 21 | 375 | 0 | 5 | 1 |
| 69 | H_134 | Health | 13103 | 77 | 244 | 0 | 0 | 3 | 0 | 0 | 258 | 12 |
| 70 | H_135 | Health | 28783 | 33 | 128 | 8 | 46 | 90 | 4 | 0 | 0 | 1 |
| 71 | H_137 | Health | 14686 | 38 | 358 | 39 | 307 | 3 | 38 | 0 | 26 | 0 |
| 72 | H_145 | Health | 14097 | 73 | 99 | 39 | 25 | 169 | 7 | 0 | 25 | 2 |
| 73 | H_146 | Health | 36760 | 46 | 15 | 5 | 2 | 1 | 12 | 0 | 738 | 20 |
| 74 | H_154 | Health | 18025 | 223 | 184 | 77 | 50 | 58 | 5 | 0 | 2 | 3 |
| 75 | H_155 | Health | 13899 | 515 | 178 | 17 | 93 | 0 | 23 | 0 | 28 | 1 |
| 76 | H_162 | Health | 13571 | 62 | 338 | 0 | 1 | 44 | 39 | 0 | 14 | 0 |
| 77 | H_163 | Health | 18304 | 103 | 224 | 26 | 80 | 0 | 5 | 0 | 13 | 3 |
| 78 | H_164 | Health | 36129 | 716 | 391 | 7 | 29 | 8 | 101 | 0 | 282 | 30 |
| 79 | H_165 | Health | 22974 | 64 | 340 | 25 | 80 | 3388 | 33 | 0 | 130 | 19 |
| 80 | H_166 | Health | 28147 | 64 | 32 | 30 | 108 | 822 | 5 | 0 | 0 | 0 |
| 81 | H_168 | Health | 10291 | 7 | 56 | 21 | 7 | 1 | 219 | 0 | 1 | 0 |

FIG. 12 (cont.)

Table 5 (cont.)

| | A | B | C | N | O | P | Q | R | S | T | U | V |
|---|---|---|---|---|---|---|---|---|---|---|---|---|
| 82 | H_171 | Health | 14889 | 136 | 51 | 9 | 10 | 30 | 17 | 0 | 4 | 3 |
| 83 | H_174 | Health | 10137 | 2 | 27 | 5 | 46 | 4006 | 2 | 0 | 0 | 0 |
| 84 | H_175 | Health | 9530 | 265 | 99 | 23 | 12 | 0 | 18 | 0 | 16 | 0 |
| 85 | H_178 | Health | 73106 | 71 | 535 | 72 | 46 | 199 | 68 | 0 | 405 | 116 |
| 86 | H_186 | Health | 12182 | 16 | 71 | 25 | 52 | 0 | 0 | 0 | 7 | 0 |
| 87 | H_199 | Health | 25677 | 72 | 359 | 0 | 36 | 0 | 8 | 0 | 15 | 2 |
| 88 | H_200 | Health | 19277 | 201 | 567 | 12 | 5 | 0 | 2 | 0 | 1 | 0 |
| 89 | H_203 | Health | 7317 | 5 | 11 | 55 | 87 | 1826 | 11 | 0 | 1 | 0 |
| 90 | H_214 | Health | 4720 | 23 | 47 | 3 | 7 | 35 | 1 | 0 | 1 | 0 |
| 91 | H_217 | Health | 10864 | 11 | 109 | 15 | 20 | 79 | 11 | 0 | 3 | 1 |
| 92 | H_220 | Health | 18191 | 6 | 173 | 26 | 5 | 0 | 8 | 0 | 2 | 0 |
| 93 | H_221 | Health | 26818 | 23 | 169 | 8 | 10 | 1 | 5 | 0 | 1 | 1 |
| 94 | H_222 | Health | 24701 | 30 | 58 | 18 | 25 | 20 | 26 | 0 | 19 | 2 |
| 95 | H_223 | Health | 7038 | 23 | 64 | 4 | 16 | 43 | 3 | 0 | 0 | 0 |
| 96 | H_225 | Health | 14480 | 16 | 289 | 0 | 1 | 2 | 3 | 0 | 4 | 0 |
| 97 | H_234 | Health | 13232 | 76 | 112 | 7 | 29 | 125 | 3 | 0 | 5 | 0 |
| 98 | H_235 | Health | 14556 | 5 | 36 | 4 | 10 | 160 | 0 | 0 | 1 | 1 |
| 99 | H_236 | Health | 9290 | 62 | 207 | 0 | 3 | 102 | 0 | 0 | 0 | 0 |
| 100 | H_237 | Health | 20932 | 13 | 25 | 9 | 113 | 7615 | 46 | 0 | 0 | 0 |
| 101 | H_238 | Health | 11636 | 44 | 189 | 73 | 10 | 52 | 10 | 0 | 3 | 0 |
| 102 | H_239 | Health | 17487 | 69 | 129 | 0 | 3 | 51 | 11 | 0 | 55 | 3 |
| 103 | H_240 | Health | 14649 | 193 | 47 | 17 | 354 | 52 | 3 | 0 | 1 | 0 |
| 104 | H_241 | Health | 32149 | 49 | 556 | 48 | 304 | 189 | 10 | 0 | 0 | 2 |
| 105 | P_1 | PD1 | 15621 | 26 | 123 | 1 | 1 | 14 | 0 | 0 | 6 | 17 |
| 106 | P_5 | PD1 | 59958 | 10 | 9 | 0 | 0 | 4 | 0 | 0 | 83 | 41 |
| 107 | P_20 | PD1 | 14617 | 102 | 7 | 4 | 0 | 0 | 18 | 0 | 711 | 117 |
| 108 | P_21 | PD1 | 11750 | 12 | 289 | 1 | 7 | 9 | 1 | 0 | 7 | 1 |
| 109 | P_24 | PD1 | 12785 | 12 | 77 | 0 | 0 | 5 | 13 | 0 | 638 | 36 |
| 110 | P_25 | PD1 | 22125 | 113 | 23 | 33 | 130 | 52 | 31 | 0 | 70 | 15 |
| 111 | P_27 | PD1 | 64890 | 55 | 2 | 0 | 0 | 0 | 7 | 0 | 1032 | 127 |
| 112 | P_46 | PD1 | 56896 | 100 | 362 | 43 | 7 | 119 | 63 | 0 | 177 | 113 |
| 113 | P_49 | PD1 | 33560 | 43 | 38 | 13 | 0 | 23 | 1 | 0 | 1430 | 26 |

FIG. 12 (cont.)

Table 5 (cont.)

| | A | B | C | N | O | P | Q | R | S | T | U | V |
|---|---|---|---|---|---|---|---|---|---|---|---|---|
| 114 | P_53 | P01 | 37971 | 15 | 37 | 4 | 1 | 0 | 40 | 0 | 368 | 108 |
| 115 | P_56 | P01 | 23103 | 170 | 96 | 7 | 1 | 0 | 5 | 0 | 163 | 18 |
| 116 | P_78 | P01 | 17344 | 0 | 41 | 7 | 1 | 0 | 0 | 0 | 144 | 0 |
| 117 | P_79 | P01 | 10658 | 30 | 18 | 0 | 11 | 18 | 0 | 0 | 26 | 1 |
| 118 | P_80 | P01 | 46951 | 84 | 90 | 1 | 1 | 0 | 18 | 0 | 361 | 18 |
| 119 | P_84 | P01 | 22949 | 9 | 16 | 0 | 1 | 1 | 0 | 48 | 136 | 42 |
| 120 | P_85 | P01 | 8619 | 13 | 24 | 0 | 6 | 7 | 4 | 2 | 324 | 5 |
| 121 | P_87 | P01 | 13155 | 0 | 1 | 1 | 0 | 4 | 2 | 0 | 44 | 47 |
| 122 | P_100 | P01 | 19179 | 11 | 4 | 0 | 1 | 5 | 1 | 0 | 123 | 138 |
| 123 | P_102 | P01 | 13541 | 7 | 60 | 4 | 7 | 3 | 4 | 2 | 309 | 87 |
| 124 | P_105 | P01 | 25163 | 4 | 16 | 2 | 0 | 0 | 30 | 0 | 329 | 2 |
| 125 | P_106 | P01 | 58812 | 15 | 18 | 0 | 0 | 1 | 25 | 0 | 961 | 729 |
| 126 | P_108 | P01 | 31560 | 77 | 178 | 8 | 17 | 704 | 0 | 0 | 118 | 3 |
| 127 | P_111 | P01 | 16442 | 52 | 5 | 0 | 2 | 0 | 4 | 0 | 351 | 141 |
| 128 | P_113 | P01 | 16867 | 4 | 26 | 0 | 0 | 0 | 1 | 0 | 10 | 24 |
| 129 | P_131 | P01 | 17951 | 58 | 169 | 39 | 54 | 39 | 0 | 13 | 17 | 5 |
| 130 | P_133 | P01 | 50988 | 380 | 434 | 1 | 1 | 3 | 48 | 0 | 108 | 24 |
| 131 | P_138 | P01 | 36223 | 48 | 118 | 13 | 19 | 4 | 17 | 0 | 25 | 16 |
| 132 | P_140 | P01 | 16348 | 5 | 3 | 0 | 0 | 0 | 1 | 0 | 82 | 98 |
| 133 | P_147 | P01 | 51857 | 165 | 451 | 61 | 120 | 1 | 38 | 0 | 56 | 3 |
| 134 | P_155 | P01 | 38511 | 8 | 41 | 105 | 325 | 0 | 6 | 0 | 53 | 1 |
| 135 | P_181 | P01 | 18947 | 29 | 21 | 0 | 3 | 1 | 0 | 0 | 6 | 1 |
| 136 | P_187 | P01 | 19346 | 3 | 10 | 2 | 0 | 1 | 5 | 0 | 18 | 178 |
| 137 | P_190 | P01 | 15581 | 6 | 27 | 0 | 1 | 0 | 20 | 0 | 131 | 44 |
| 138 | P_191 | P01 | 14529 | 29 | 42 | 0 | 7 | 0 | 2 | 0 | 89 | 21 |
| 139 | P_192 | P01 | 39342 | 19 | 376 | 1 | 4 | 28 | 0 | 0 | 96 | 15 |
| 140 | P_195 | P01 | 38666 | 25 | 96 | 1 | 1 | 2 | 1 | 0 | 411 | 39 |
| 141 | P_196 | P01 | 48271 | 68 | 86 | 0 | 0 | 1 | 16 | 0 | 1352 | 1 |
| 142 | P_205 | P01 | 16854 | 3 | 16 | 1 | 0 | 2 | 18 | 0 | 0 | 62 |
| 143 | P_208 | P01 | 19158 | 4 | 225 | 0 | 0 | 3 | 5 | 0 | 30 | 32 |
| 144 | P_209 | P01 | 22174 | 7 | 17 | 7 | 0 | 69 | 4 | 0 | 6 | 38 |
| 145 | P_210 | P01 | 15375 | 4 | 30 | 0 | 0 | 1 | 1 | 2 | 16 | 55 |

FIG. 12 (cont.)

Table 5 (cont.)

| | A | B | C | N | O | P | Q | R | S | T | U | V |
|---|---|---|---|---|---|---|---|---|---|---|---|---|
| 146 | P_216 | PD1 | 12237 | 0 | 18 | 0 | 0 | 0 | 3 | 0 | 39 | 100 |
| 147 | P_218 | PD1 | 10478 | 3 | 7 | 2 | 0 | 1 | 5 | 0 | 86 | 71 |
| 148 | P_219 | PD1 | 12672 | 138 | 148 | 53 | 3 | 0 | 0 | 14 | 1049 | 133 |
| 149 | P_224 | PD1 | 27758 | 79 | 43 | 0 | 0 | 2 | 190 | 0 | 42 | 144 |
| 150 | P_226 | PD1 | 14662 | 6 | 6 | 0 | 0 | 0 | 502 | 1 | 1 | 98 |
| 151 | P_228 | PD1 | 18702 | 23 | 37 | 1 | 1 | 4 | 7 | 0 | 179 | 53 |
| 152 | P_233 | PD1 | 17047 | 7 | 21 | 0 | 0 | 3 | 4 | 0 | 7 | 94 |
| 153 | P_248 | PD1 | 20118 | 84 | 148 | 5 | 3 | 11 | 18 | 3 | 93 | 6 |
| 154 | P_BC09 | PD1 | 18642 | 11 | 92 | 5 | 19 | 22 | 6 | 0 | 46 | 27 |
| 155 | P_BC19 | PD1 | 14480 | 6 | 69 | 6 | 1 | 8 | 21 | 28 | 5 | 195 |
| 156 | P_BC21 | PD1 | 45433 | 31 | 389 | 17 | 191 | 7 | 0 | 1 | 2 | 0 |

FIG. 12 (cont.)

Table 5 (cont.)

| | A | B | C | W | X | Y | Z | AA | AB | AC | AD | AE | AF |
|---|---|---|---|---|---|---|---|---|---|---|---|---|---|
| | Case | Health state | Total Reads | c_Desulfomicrobium_orale_COT-008 | c_Desulfovibrio_sp._COT-070 | c_Desulfovibrionaceae_sp._COT-059 | c_Escherichia_coli | c_Erysipelotrichaceae_IS-JS_sp._COT-362 | c_F0Factor_alocis_COT-021 | c_F0Factor_sp._COT-043 | c_F0Factor_sp._COT-169 | c_F0Factor_villosus_COT-055 | c_Filifactor_sp._COT-358 |
| 1 | | | | | | | | | | | | | |
| 2 | G_7 | Gingivitis | 12132 | 5 | 0 | 5 | 0 | 1 | 0 | 8 | 0 | 25 | 10 |
| 3 | G_8 | Gingivitis | 10631 | 58 | 1 | 1 | 0 | 19 | 4 | 3 | 0 | 395 | 6 |
| 4 | G_9 | Gingivitis | 25790 | 74 | 196 | 4 | 5 | 87 | 9 | 35 | 0 | 99 | 0 |
| 5 | G_12 | Gingivitis | 15863 | 218 | 0 | 0 | 5 | 3 | 0 | 2 | 0 | 35 | 0 |
| 6 | G_14 | Gingivitis | 9138 | 10 | 22 | 3 | 0 | 58 | 0 | 2 | 0 | 71 | 0 |
| 7 | G_18 | Gingivitis | 29089 | 353 | 14 | 8 | 2 | 4 | 88 | 0 | 0 | 122 | 7 |
| 8 | G_22 | Gingivitis | 84760 | 1458 | 129 | 75 | 5 | 299 | 0 | 142 | 0 | 866 | 6 |
| 9 | G_30 | Gingivitis | 13824 | 118 | 118 | 156 | 3 | 4 | 63 | 56 | 1 | 458 | 0 |
| 10 | G_35 | Gingivitis | 38047 | 285 | 117 | 122 | 3 | 33 | 3 | 0 | 0 | 377 | 79 |
| 11 | G_40 | Gingivitis | 1E+05 | 1436 | 276 | 0 | 2 | 3 | 0 | 4 | 0 | 6429 | 7 |
| 12 | G_42 | Gingivitis | 11958 | 3 | 0 | 0 | 1 | 0 | 0 | 0 | 0 | 1 | 0 |
| 13 | G_52 | Gingivitis | 45503 | 118 | 11 | 0 | 0 | 4 | 0 | 3 | 0 | 373 | 40 |
| 14 | G_60 | Gingivitis | 9922 | 12 | 7 | 0 | 30 | 0 | 0 | 0 | 0 | 4 | 1 |
| 15 | G_63 | Gingivitis | 5611 | 10 | 2 | 3 | 4 | 5 | 0 | 0 | 0 | 19 | 12 |
| 16 | G_64 | Gingivitis | 7175 | 22 | 7 | 11 | 1 | 0 | 0 | 6 | 3 | 274 | 0 |
| 17 | G_65 | Gingivitis | 6366 | 80 | 51 | 0 | 1 | 46 | 0 | 0 | 0 | 47 | 0 |

FIG. 12 (cont.)

Table 5 (cont.)

| | A | B | C | W | X | Y | Z | AA | AB | AC | AD | AE | AF |
|---|---|---|---|---|---|---|---|---|---|---|---|---|---|
| 18 | G_72 | Gingivitis | 61343 | 241 | 29 | 0 | 3 | 0 | 0 | 2 | 0 | 1992 | 2 |
| 19 | G_81 | Gingivitis | 9859 | 40 | 0 | 0 | 3 | 0 | 0 | 3 | 0 | 195 | 1 |
| 20 | G_88 | Gingivitis | 54894 | 8 | 0 | 0 | 19 | 0 | 0 | 0 | 0 | 8 | 161 |
| 21 | G_96 | Gingivitis | 59745 | 138 | 1452 | 0 | 7 | 27 | 0 | 0 | 0 | 720 | 1 |
| 22 | G_98 | Gingivitis | 17911 | 247 | 0 | 0 | 1 | 0 | 0 | 0 | 0 | 239 | 2 |
| 23 | G_101 | Gingivitis | 12876 | 7 | 1 | 0 | 21 | 2 | 0 | 0 | 1 | 22 | 0 |
| 24 | G_113 | Gingivitis | 18818 | 30 | 32 | 33 | 4 | 82 | 0 | 46 | 12 | 90 | 0 |
| 25 | G_117 | Gingivitis | 30819 | 33 | 47 | 57 | 3 | 14 | 0 | 0 | 0 | 180 | 4 |
| 26 | G_120 | Gingivitis | 27655 | 23 | 22 | 0 | 6 | 51 | 72 | 166 | 0 | 172 | 0 |
| 27 | G_122 | Gingivitis | 17585 | 103 | 1 | 0 | 3 | 9 | 5 | 140 | 0 | 138 | 5 |
| 28 | G_128 | Gingivitis | 12750 | 108 | 30 | 0 | 7 | 1 | 0 | 0 | 0 | 247 | 2 |
| 29 | G_133 | Gingivitis | 21122 | 5 | 7 | 4 | 7 | 107 | 0 | 4 | 0 | 1121 | 0 |
| 30 | G_135 | Gingivitis | 10363 | 1 | 1 | 0 | 0 | 1 | 0 | 0 | 1 | 159 | 3 |
| 31 | G_139 | Gingivitis | 17129 | 91 | 0 | 0 | 11 | 0 | 0 | 0 | 0 | 1032 | 5 |
| 32 | G_143 | Gingivitis | 48153 | 7 | 1298 | 0 | 1 | 137 | 0 | 0 | 0 | 10471 | 0 |
| 33 | G_148 | Gingivitis | 18887 | 708 | 2 | 0 | 17 | 0 | 0 | 0 | 0 | 628 | 0 |
| 34 | G_149 | Gingivitis | 29861 | 5 | 2 | 0 | 2 | 0 | 4 | 0 | 0 | 4820 | 0 |
| 35 | G_153 | Gingivitis | 18102 | 39 | 35 | 2 | 7 | 24 | 0 | 1 | 0 | 36 | 3 |
| 36 | G_161 | Gingivitis | 14798 | 0 | 0 | 0 | 18 | 0 | 1 | 12 | 0 | 5 | 3 |
| 37 | G_169 | Gingivitis | 9811 | 289 | 43 | 76 | 1 | 19 | 1 | 4 | 0 | 220 | 0 |
| 38 | G_170 | Gingivitis | 49800 | 71 | 60 | 0 | 7 | 193 | 1 | 22 | 0 | 81 | 1 |
| 39 | G_171 | Gingivitis | 36943 | 142 | 328 | 0 | 1 | 13 | 0 | 0 | 0 | 150 | 0 |
| 40 | G_173 | Gingivitis | 17676 | 26 | 40 | 0 | 1 | 0 | 0 | 0 | 0 | 1840 | 0 |
| 41 | G_177 | Gingivitis | 38744 | 18 | 1 | 0 | 0 | 0 | 0 | 1 | 0 | 1067 | 0 |
| 42 | G_184 | Gingivitis | 11140 | 128 | 0 | 0 | 2 | 0 | 0 | 0 | 0 | 165 | 0 |
| 43 | G_188 | Gingivitis | 9325 | 1 | 1 | 0 | 1 | 0 | 0 | 0 | 0 | 0 | 0 |
| 44 | G_197 | Gingivitis | 3865 | 29 | 0 | 0 | 8 | 2 | 0 | 12 | 0 | 135 | 0 |
| 45 | G_234 | Gingivitis | 12530 | 61 | 0 | 114 | 18 | 0 | 25 | 0 | 0 | 284 | 20 |
| 46 | G_237 | Gingivitis | 13882 | 95 | 30 | 0 | 44 | 0 | 0 | 0 | 0 | 98 | 3 |
| 47 | G_244 | Gingivitis | 13436 | 8 | 3 | 0 | 3 | 125 | 78 | 1 | 0 | 513 | 0 |
| 48 | G_245 | Gingivitis | 29114 | 139 | 13 | 446 | 6 | 11 | 0 | 0 | 0 | 1102 | 0 |
| 49 | G_246 | Gingivitis | 37282 | 1 | 0 | 0 | 7 | 0 | 0 | 0 | 0 | 0 | 1 |

FIG. 12 (cont.)

Table 5 (cont.)

| | A | B | C | W | X | Y | Z | AA | AB | AC | AD | AE | AF |
|---|---|---|---|---|---|---|---|---|---|---|---|---|---|
| 50 | G_249 | Gingivitis | 19242 | 44 | 24 | 3 | 10 | 9 | 0 | 49 | 0 | 130 | 4 |
| 51 | G_CS4 | Gingivitis | 16211 | 1 | 2 | 6 | 4 | 164 | 22 | 1 | 77 | 327 | 3 |
| 52 | G_19 | Gingivitis | 34430 | 114 | 1 | 0 | 0 | 0 | 32 | 0 | 0 | 2341 | 0 |
| 53 | H_39 | Health | 16024 | 1 | 1 | 0 | 0 | 3 | 0 | 0 | 0 | 3 | 0 |
| 54 | H_46 | Health | 9790 | 130 | 0 | 0 | 13 | 1 | 0 | 0 | 0 | 24 | 0 |
| 55 | H_51 | Health | 7751 | 30 | 0 | 0 | 1 | 1 | 0 | 0 | 0 | 288 | 2 |
| 56 | H_57 | Health | 37038 | 337 | 0 | 0 | 0 | 0 | 0 | 0 | 0 | 252 | 98 |
| 57 | H_58 | Health | 12089 | 1 | 5 | 0 | 1 | 0 | 0 | 0 | 0 | 38 | 86 |
| 58 | H_68 | Health | 19338 | 22 | 0 | 0 | 4 | 0 | 0 | 0 | 0 | 68 | 2 |
| 59 | H_73 | Health | 12578 | 7 | 0 | 0 | 24 | 3 | 0 | 0 | 0 | 0 | 1 |
| 60 | H_74 | Health | 47864 | 44 | 4 | 22 | 8 | 0 | 1 | 6 | 0 | 264 | 1 |
| 61 | H_78 | Health | 13932 | 32 | 7 | 0 | 6 | 0 | 0 | 0 | 0 | 42 | 1 |
| 62 | H_83 | Health | 22743 | 27 | 0 | 0 | 2 | 1 | 0 | 0 | 0 | 21 | 0 |
| 63 | H_89 | Health | 13540 | 3 | 1 | 0 | 4 | 0 | 0 | 16 | 0 | 6 | 0 |
| 64 | H_90 | Health | 16858 | 5 | 0 | 0 | 8 | 1 | 2 | 0 | 0 | 146 | 2 |
| 65 | H_94 | Health | 18998 | 130 | 8 | 7 | 1 | 0 | 0 | 60 | 16 | 298 | 0 |
| 66 | H_107 | Health | 13290 | 15 | 3 | 0 | 13 | 4 | 0 | 0 | 0 | 217 | 0 |
| 67 | H_108 | Health | 13826 | 8 | 5 | 0 | 7 | 131 | 0 | 0 | 0 | 203 | 10 |
| 68 | H_117 | Health | 29644 | 6 | 0 | 0 | 1 | 1 | 0 | 0 | 0 | 16 | 7 |
| 69 | H_114 | Health | 15304 | 299 | 63 | 4 | 5 | 9 | 1 | 1 | 0 | 185 | 2 |
| 70 | H_118 | Health | 25783 | 65 | 0 | 0 | 4 | 0 | 43 | 1 | 0 | 367 | 0 |
| 71 | H_137 | Health | 14686 | 33 | 2 | 1 | 12 | 1 | 0 | 0 | 0 | 392 | 1 |
| 72 | H_185 | Health | 14097 | 83 | 11 | 0 | 4 | 9 | 0 | 0 | 0 | 103 | 1 |
| 73 | H_146 | Health | 36760 | 129 | 0 | 0 | 3 | 17 | 0 | 0 | 0 | 248 | 2 |
| 74 | H_154 | Health | 18005 | 74 | 0 | 0 | 0 | 0 | 0 | 0 | 0 | 571 | 357 |
| 75 | H_156 | Health | 13899 | 49 | 2 | 0 | 10 | 0 | 0 | 0 | 0 | 13 | 0 |
| 76 | H_162 | Health | 11571 | 21 | 120 | 0 | 16 | 0 | 1 | 1 | 0 | 374 | 140 |
| 77 | H_183 | Health | 18304 | 104 | 87 | 0 | 5 | 15 | 46 | 4 | 0 | 196 | 0 |
| 78 | H_188 | Health | 36129 | 184 | 1 | 4 | 8 | 248 | 0 | 17 | 0 | 55 | 0 |
| 79 | H_165 | Health | 74976 | 775 | 17 | 0 | 4 | 3 | 0 | 0 | 0 | 117 | 0 |
| 80 | H_166 | Health | 28147 | 0 | 0 | 0 | 11 | 0 | 0 | 0 | 0 | 1 | 0 |
| 81 | H_168 | Health | 10291 | 8 | 1 | 0 | 8 | 0 | 0 | 0 | 0 | 19 | 0 |

FIG. 12 (cont.)

Table 5 (cont.)

| | A | B | C | W | X | Y | Z | AA | AB | AC | AD | AE | AF |
|---|---|---|---|---|---|---|---|---|---|---|---|---|---|
| 82 | H_171 | Health | 14889 | 23 | 0 | 5 | 21 | 0 | 0 | 59 | 2 | 87 | 7 |
| 83 | H_174 | Health | 10127 | 5 | 0 | 0 | 5 | 0 | 0 | 0 | 0 | 3 | 0 |
| 84 | H_175 | Health | 9530 | 252 | 0 | 0 | 1 | 0 | 0 | 0 | 0 | 368 | 0 |
| 85 | H_178 | Health | 73106 | 171 | 47 | 3 | 12 | 80 | 1 | 0 | 0 | 1087 | 0 |
| 86 | H_188 | Health | 12182 | 14 | 3 | 0 | 11 | 0 | 0 | 0 | 0 | 36 | 0 |
| 87 | H_189 | Health | 25877 | 464 | 0 | 0 | 0 | 0 | 0 | 0 | 0 | 363 | 56 |
| 88 | H_206 | Health | 19277 | 6 | 2 | 0 | 10 | 8 | 0 | 1 | 0 | 181 | 8 |
| 89 | H_203 | Health | 7317 | 0 | 0 | 0 | 10 | 0 | 0 | 1 | 1 | 13 | 0 |
| 90 | H_213 | Health | 4740 | 6 | 1 | 3 | 78 | 0 | 0 | 0 | 0 | 10 | 0 |
| 91 | H_217 | Health | 10164 | 38 | 1 | 0 | 13 | 0 | 0 | 0 | 5 | 21 | 6 |
| 92 | H_220 | Health | 18131 | 58 | 0 | 0 | 33 | 0 | 0 | 0 | 0 | 350 | 0 |
| 93 | H_221 | Health | 26808 | 34 | 1 | 0 | 13 | 0 | 0 | 0 | 0 | 41 | 135 |
| 94 | H_222 | Health | 24703 | 70 | 128 | 2 | 8 | 0 | 0 | 0 | 1 | 1556 | 30 |
| 95 | H_223 | Health | 7018 | 32 | 0 | 0 | 82 | 0 | 0 | 0 | 0 | 5 | 3 |
| 96 | H_226 | Health | 14460 | 123 | 0 | 0 | 23 | 0 | 90 | 5 | 0 | 182 | 0 |
| 97 | H_234 | Health | 13232 | 57 | 0 | 0 | 35 | 0 | 0 | 1 | 0 | 21 | 37 |
| 98 | H_235 | Health | 14096 | 9 | 1 | 0 | 23 | 1 | 0 | 0 | 0 | 5 | 4 |
| 99 | H_236 | Health | 9209 | 204 | 0 | 0 | 89 | 0 | 0 | 0 | 0 | 10 | 0 |
| 100 | H_237 | Health | 20932 | 0 | 0 | 0 | 6 | 0 | 0 | 0 | 0 | 1 | 3 |
| 101 | H_238 | Health | 11828 | 5 | 0 | 0 | 36 | 0 | 0 | 0 | 0 | 36 | 0 |
| 102 | H_239 | Health | 17487 | 232 | 181 | 3 | 39 | 0 | 1 | 0 | 0 | 228 | 2 |
| 103 | H_240 | Health | 14633 | 3 | 0 | 0 | 48 | 0 | 0 | 0 | 0 | 8 | 0 |
| 104 | H_243 | Health | 32149 | 18 | 2 | 0 | 6 | 0 | 8 | 0 | 0 | 7 | 1 |
| 105 | P_1 | PD1 | 15621 | 28 | 13 | 44 | 0 | 32 | 11 | 0 | 0 | 362 | 0 |
| 106 | P_5 | PD1 | 59858 | 261 | 784 | 1 | 0 | 13 | 15 | 1330 | 0 | 2119 | 0 |
| 107 | P_20 | PD1 | 14617 | 26 | 2 | 0 | 0 | 203 | 4 | 0 | 0 | 274 | 1 |
| 108 | P_23 | PD1 | 11750 | 14 | 3 | 0 | 88 | 0 | 10 | 5 | 0 | 462 | 1 |
| 109 | P_24 | PD1 | 12783 | 17 | 17 | 1 | 32 | 156 | 16 | 3 | 0 | 145 | 0 |
| 110 | P_25 | PD1 | 22123 | 33 | 1 | 0 | 0 | 2 | 0 | 0 | 0 | 279 | 243 |
| 111 | P_27 | PD1 | 64090 | 152 | 156 | 1 | 7 | 798 | 82 | 1354 | 185 | 4957 | 2 |
| 112 | P_36 | PD1 | 55398 | 621 | 53 | 102 | 5 | 0 | 0 | 478 | 0 | 564 | 0 |
| 113 | P_49 | PD1 | 33960 | 89 | 30 | 0 | 8 | 163 | 80 | 3 | 0 | 1303 | 21 |

FIG. 12 (cont.)

Table 5 (cont.)

| | A | B | C | W | X | Y | Z | AA | AB | AC | AD | AE | AF |
|---|---|---|---|---|---|---|---|---|---|---|---|---|---|
| 114 | P_53 | PD1 | 37971 | 296 | 72 | 0 | 2 | 92 | 382 | 791 | 56 | 303 | 3 |
| 115 | P_56 | PD1 | 23103 | 323 | 534 | 61 | 10 | 33 | 30 | 584 | 7 | 606 | 1 |
| 116 | P_76 | PD1 | 17344 | 724 | 39 | 0 | 0 | 34 | 98 | 0 | 0 | 133 | 0 |
| 117 | P_79 | PD1 | 10658 | 40 | 0 | 0 | 4 | 11 | 0 | 36 | 0 | 765 | 9 |
| 118 | P_80 | PD1 | 46951 | 64 | 8 | 1 | 13 | 42 | 614 | 0 | 0 | 377 | 73 |
| 119 | P_84 | PD1 | 22949 | 36 | 49 | 21 | 4 | 48 | 667 | 282 | 7 | 477 | 0 |
| 120 | P_85 | PD1 | 8619 | 63 | 3 | 41 | 0 | 0 | 0 | 0 | 0 | 159 | 0 |
| 121 | P_87 | PD1 | 13155 | 22 | 10 | 0 | 2 | 339 | 5 | 20 | 27 | 123 | 0 |
| 122 | P_100 | PD1 | 18179 | 93 | 23 | 0 | 0 | 272 | 0 | 7 | 0 | 330 | 0 |
| 123 | P_102 | PD1 | 13541 | 20 | 72 | 2 | 2 | 169 | 192 | 3 | 19 | 23 | 0 |
| 124 | P_103 | PD1 | 25163 | 38 | 0 | 0 | 1 | 1 | 0 | 0 | 0 | 1073 | 1 |
| 125 | P_106 | PD1 | 58813 | 136 | 80 | 4 | 9 | 584 | 439 | 69 | 4 | 181 | 0 |
| 126 | P_108 | PD1 | 31569 | 238 | 26 | 39 | 4 | 14 | 0 | 424 | 0 | 354 | 7 |
| 127 | P_113 | PD1 | 16442 | 14 | 6 | 0 | 1 | 0 | 0 | 0 | 0 | 331 | 3 |
| 128 | P_123 | PD1 | 16867 | 44 | 2 | 0 | 1 | 62 | 0 | 0 | 0 | 1963 | 0 |
| 129 | P_131 | PD1 | 17961 | 191 | 37 | 94 | 7 | 3 | 0 | 6 | 0 | 159 | 5 |
| 130 | P_134 | PD1 | 50988 | 195 | 324 | 37 | 6 | 17 | 0 | 322 | 1 | 197 | 208 |
| 131 | P_138 | PD1 | 36233 | 118 | 10 | 0 | 5 | 2 | 176 | 1 | 0 | 174 | 1 |
| 132 | P_140 | PD1 | 16348 | 5 | 23 | 1 | 7 | 292 | 0 | 0 | 15 | 165 | 0 |
| 133 | P_147 | PD1 | 53057 | 200 | 0 | 0 | 2 | 1 | 9 | 0 | 0 | 1353 | 90 |
| 134 | P_155 | PD1 | 38311 | 179 | 1 | 0 | 6 | 5 | 1 | 0 | 0 | 2093 | 0 |
| 135 | P_181 | PD1 | 18347 | 52 | 0 | 0 | 6 | 16 | 79 | 4 | 0 | 129 | 0 |
| 136 | P_187 | PD1 | 19346 | 89 | 20 | 7 | 5 | 9 | 5 | 40 | 84 | 280 | 1 |
| 137 | P_190 | PD1 | 15581 | 109 | 0 | 0 | 6 | 0 | 3 | 0 | 0 | 672 | 19 |
| 138 | P_191 | PD1 | 14529 | 77 | 42 | 41 | 12 | 3 | 0 | 87 | 0 | 46 | 0 |
| 139 | P_192 | PD1 | 39343 | 708 | 0 | 0 | 4 | 0 | 53 | 0 | 0 | 397 | 0 |
| 140 | P_195 | PD1 | 38666 | 878 | 3 | 0 | 5 | 104 | 512 | 1 | 0 | 892 | 1 |
| 141 | P_196 | PD1 | 46271 | 290 | 0 | 0 | 4 | 0 | 0 | 0 | 0 | 708 | 326 |
| 142 | P_205 | PD1 | 10354 | 3 | 16 | 29 | 8 | 60 | 0 | 307 | 29 | 53 | 0 |
| 143 | P_206 | PD1 | 19158 | 90 | 19 | 24 | 32 | 148 | 0 | 26 | 0 | 473 | 0 |
| 144 | P_208 | PD1 | 22174 | 20 | 2 | 8 | 5 | 9 | 81 | 1 | 3 | 28 | 5 |
| 145 | P_210 | PD1 | 15375 | 6 | 0 | 8 | 0 | 59 | 7 | 38 | 3 | 382 | 0 |

FIG. 12 (cont.)

Table 5 (cont.)

| | A | B | C | W | X | Y | Z | AA | AB | AC | AD | AE | AF |
|---|---|---|---|---|---|---|---|---|---|---|---|---|---|
| 146 | P_218 | PO1 | 12337 | 9 | 29 | 8 | 2 | 29 | 51 | 351 | 0 | 72 | 0 |
| 147 | P_218 | PO1 | 16475 | 2 | 29 | 2 | 10 | 5 | 0 | 0 | 395 | 187 | 0 |
| 148 | P_219 | PO1 | 12572 | 28 | 17 | 1 | 5 | 61 | 23 | 29 | 7 | 22 | 1 |
| 149 | P_324 | PO1 | 27758 | 22 | 32 | 8 | 18 | 341 | 27 | 168 | 0 | 1752 | 1 |
| 150 | P_326 | PO1 | 14662 | 2 | 20 | 0 | 19 | 50 | 0 | 481 | 7 | 393 | 0 |
| 151 | P_328 | PO1 | 18702 | 150 | 56 | 37 | 11 | 186 | 147 | 0 | 0 | 377 | 13 |
| 152 | P_232 | PO1 | 17047 | 130 | 25 | 56 | 20 | 8 | 148 | 7 | 19 | 71 | 0 |
| 153 | P_248 | PO1 | 20116 | 46 | 61 | 0 | 6 | 113 | 0 | 1 | 0 | 472 | 2 |
| 154 | P_BC09 | PO1 | 18642 | 130 | 270 | 280 | 6 | 39 | 0 | 121 | 0 | 105 | 3 |
| 155 | P_BC19 | PO1 | 14480 | 53 | 106 | 31 | 18 | 35 | 5 | 5 | 0 | 54 | 2 |
| 156 | P_BC21 | PO1 | 45443 | 6 | 1 | 27 | 2 | 3 | 0 | 1 | 682 | 38 | 1 |

FIG. 12 (cont.)

Table 5 (cont.)

| | A | B | C | AE | AH | AI | AJ | AK | AL | AM | AN | AO |
|---|---|---|---|---|---|---|---|---|---|---|---|---|
| | Dx | Health state | Total Reads | g_Fusobacterium_sp._OT-369 | g_Fusobacterium_sp._OT-370 | g_Fusobacterium_sp._OT-216 | g_Gemella_palaticanis_OT-050 | g_Gemella_sp._OT-907 | g_Helcococcus_sp._OT-069 | g_Helcococcus_sp._OT-080 | g_Lachnospiraceae_XIVa_[G-2]_sp._OT-082 | g_Lachnospiraceae_XIVa_[G-4]_sp._OT-088 |
| 2 | G_7 | Gingivitis | 12132 | 0 | 299 | 53 | 80 | 16 | 3 | 0 | 2 | 1 |
| 3 | G_8 | Gingivitis | 10631 | 65 | 35 | 13 | 0 | 0 | 72 | 0 | 42 | 0 |
| 4 | G_9 | Gingivitis | 26790 | 8 | 66 | 107 | 118 | 0 | 123 | 336 | 2 | 0 |
| 5 | G_12 | Gingivitis | 15863 | 0 | 44 | 11 | 37 | 1 | 0 | 0 | 0 | 0 |
| 6 | G_14 | Gingivitis | 9138 | 4 | 17 | 48 | 0 | 76 | 8 | 3 | 1 | 0 |
| 7 | G_18 | Gingivitis | 28089 | 0 | 229 | 15 | 4 | 6 | 53 | 0 | 0 | 0 |
| 8 | G_22 | Gingivitis | 84780 | 1367 | 710 | 194 | 10 | 12 | 218 | 0 | 73 | 105 |
| 9 | G_30 | Gingivitis | 19873 | 91 | 151 | 12 | 7 | 3 | 19 | 25 | 9 | 16 |
| 10 | G_35 | Gingivitis | 32047 | 281 | 329 | 154 | 64 | 53 | 618 | 1 | 86 | 0 |
| 11 | G_40 | Gingivitis | 18486 | 0 | 214 | 45 | 2 | 50 | 756 | 1 | 3 | 1 |
| 12 | G_42 | Gingivitis | 11358 | 107 | 3 | 6 | 0 | 0 | 0 | 0 | 0 | 0 |
| 13 | G_52 | Gingivitis | 45501 | 1 | 343 | 168 | 36 | 133 | 312 | 3 | 9 | 0 |
| 14 | G_62 | Gingivitis | 9122 | 0 | 11 | 0 | 47 | 4 | 1 | 0 | 0 | 0 |
| 15 | G_63 | Gingivitis | 5611 | 0 | 5 | 4 | 5 | 4 | 0 | 0 | 1 | 0 |
| 16 | G_64 | Gingivitis | 7175 | 1 | 6 | 0 | 7 | 0 | 5 | 0 | 2 | 0 |
| 17 | G_65 | Gingivitis | 5306 | 0 | 1 | 1 | 3 | 1 | 29 | 0 | 3 | 0 |

FIG. 12 (cont.)

Table 5 (cont.)

| | A | B | C | AG | AH | AI | AJ | AK | AL | AM | AN | AO |
|---|---|---|---|---|---|---|---|---|---|---|---|---|
| 18 | G_72 | Gingivitis | 63483 | 435 | 2130 | 41 | 41 | 4 | 1 | 0 | 2 | 0 |
| 19 | G_81 | Gingivitis | 8809 | 3 | 43 | 0 | 0 | 0 | 2 | 0 | 17 | 0 |
| 20 | G_86 | Gingivitis | 54894 | 0 | 7 | 43 | 152 | 12 | 2 | 0 | 1 | 0 |
| 21 | G_96 | Gingivitis | 59245 | 7 | 26 | 16 | 40 | 14 | 980 | 0 | 28 | 0 |
| 22 | G_98 | Gingivitis | 37911 | 36 | 31 | 22 | 50 | 136 | 2 | 0 | 15 | 0 |
| 23 | G_101 | Gingivitis | 12875 | 7 | 4 | 2 | 0 | 300 | 7 | 1 | 30 | 0 |
| 24 | G_113 | Gingivitis | 18818 | 2 | 184 | 34 | 82 | 68 | 30 | 0 | 2 | 0 |
| 25 | G_117 | Gingivitis | 30819 | 1 | 1128 | 31 | 19 | 125 | 60 | 0 | 8 | 2 |
| 26 | G_120 | Gingivitis | 22683 | 55 | 39 | 402 | 23 | 0 | 73 | 3 | 0 | 114 |
| 27 | G_122 | Gingivitis | 17505 | 71 | 406 | 8 | 3 | 10 | 14 | 0 | 6 | 1 |
| 28 | G_128 | Gingivitis | 12750 | 14 | 221 | 12 | 4 | 26 | 2 | 0 | 3 | 0 |
| 29 | G_132 | Gingivitis | 71222 | 1 | 5 | 22 | 18 | 0 | 180 | 0 | 0 | 1427 |
| 30 | G_135 | Gingivitis | 19383 | 0 | 91 | 14 | 4 | 1 | 9 | 0 | 69 | 0 |
| 31 | G_139 | Gingivitis | 17129 | 53 | 84 | 18 | 28 | 11 | 1 | 0 | 0 | 1 |
| 32 | G_143 | Gingivitis | 48193 | 0 | 25 | 11 | 4 | 60 | 648 | 0 | 65 | 2 |
| 33 | G_146 | Gingivitis | 16887 | 420 | 9 | 38 | 184 | 46 | 0 | 0 | 0 | 0 |
| 34 | G_149 | Gingivitis | 29961 | 69 | 6 | 7 | 4 | 0 | 707 | 0 | 0 | 0 |
| 35 | G_153 | Gingivitis | 38102 | 0 | 53 | 17 | 235 | 38 | 10 | 0 | 4 | 0 |
| 36 | G_161 | Gingivitis | 14798 | 22 | 86 | 20 | 198 | 11 | 1 | 0 | 1 | 0 |
| 37 | G_165 | Gingivitis | 9813 | 13 | 22 | 21 | 1 | 0 | 23 | 0 | 1 | 0 |
| 38 | G_170 | Gingivitis | 49020 | 38 | 30 | 107 | 8 | 2 | 64 | 0 | 1 | 2 |
| 39 | G_172 | Gingivitis | 36943 | 69 | 176 | 33 | 243 | 0 | 162 | 0 | 0 | 0 |
| 40 | G_173 | Gingivitis | 57676 | 10 | 15 | 103 | 3 | 24 | 1429 | 0 | 0 | 0 |
| 41 | G_177 | Gingivitis | 36744 | 0 | 1878 | 46 | 0 | 3 | 0 | 0 | 0 | 0 |
| 42 | G_184 | Gingivitis | 11180 | 0 | 34 | 0 | 0 | 0 | 0 | 0 | 0 | 0 |
| 43 | G_188 | Gingivitis | 9325 | 0 | 9 | 0 | 0 | 7 | 0 | 0 | 233 | 0 |
| 44 | G_197 | Gingivitis | 3805 | 1 | 48 | 1 | 0 | 0 | 12 | 0 | 6 | 1 |
| 45 | G_214 | Gingivitis | 12530 | 84 | 5 | 20 | 23 | 1 | 18 | 0 | 16 | 1 |
| 46 | G_232 | Gingivitis | 13682 | 35 | 222 | 2 | 41 | 71 | 68 | 0 | 1 | 0 |
| 47 | G_244 | Gingivitis | 13446 | 1 | 17 | 8 | 38 | 3 | 1236 | 0 | 0 | 0 |
| 48 | G_245 | Gingivitis | 29114 | 0 | 45 | 1 | 52 | 25 | 6 | 0 | 12 | 0 |
| 49 | G_248 | Gingivitis | 37282 | 72 | 1792 | 28 | 0 | 0 | 0 | 0 | 0 | 0 |

FIG. 12 (cont.)

Table 5 (cont.)

| | A | B | C | AG | AH | AI | AJ | AK | AL | AM | AN | AO |
|---|---|---|---|---|---|---|---|---|---|---|---|---|
| 50 | G_249 | Gingivitis | 39242 | 0 | 282 | 7 | 43 | 24 | 66 | 0 | 8 | 61 |
| 51 | G_CK54 | Gingivitis | 16211 | 3 | 5 | 0 | 43 | 0 | 135 | 42 | 0 | 0 |
| 52 | G_19 | Gingivitis | 34430 | 27 | 10 | 15 | 0 | 0 | 10 | 0 | 5 | 924 |
| 53 | H_39 | Health | 16024 | 0 | 8 | 7 | 0 | 679 | 18 | 0 | 3 | 0 |
| 54 | H_48 | Health | 9738 | 2 | 358 | 5 | 20 | 25 | 6 | 0 | 1 | 4 |
| 55 | H_51 | Health | 7751 | 0 | 53 | 7 | 2 | 13 | 123 | 0 | 66 | 0 |
| 56 | H_57 | Health | 37038 | 0 | 82 | 0 | 18 | 56 | 3 | 0 | 237 | 0 |
| 57 | H_58 | Health | 12089 | 0 | 181 | 8 | 5 | 84 | 5 | 0 | 68 | 0 |
| 58 | H_68 | Health | 19833 | 8 | 5 | 4 | 5 | 5 | 1 | 0 | 0 | 0 |
| 59 | H_73 | Health | 12578 | 20 | 27 | 13 | 4 | 119 | 7 | 0 | 5 | 1 |
| 60 | H_74 | Health | 47861 | 2 | 895 | 2 | 868 | 279 | 40 | 0 | 38 | 5 |
| 61 | H_78 | Health | 11932 | 2 | 53 | 20 | 0 | 303 | 12 | 0 | 15 | 1 |
| 62 | H_83 | Health | 22743 | 5 | 47 | 1 | 0 | 1184 | 13 | 0 | 0 | 0 |
| 63 | H_89 | Health | 13540 | 2 | 134 | 11 | 34 | 109 | 1 | 0 | 0 | 0 |
| 64 | H_90 | Health | 16858 | 15 | 149 | 51 | 87 | 872 | 23 | 132 | 36 | 0 |
| 65 | H_94 | Health | 18898 | 4 | 31 | 0 | 0 | 0 | 196 | 0 | 6 | 5 |
| 66 | H_107 | Health | 13280 | 0 | 21 | 0 | 0 | 21 | 12 | 0 | 2 | 0 |
| 67 | H_108 | Health | 13826 | 0 | 380 | 22 | 23 | 5 | 32 | 0 | 33 | 7 |
| 68 | H_112 | Health | 29564 | 1 | 839 | 552 | 5 | 185 | 0 | 0 | 0 | 0 |
| 69 | H_114 | Health | 13103 | 4 | 266 | 1 | 18 | 1 | 28 | 2 | 1 | 3 |
| 70 | H_138 | Health | 28783 | 37 | 302 | 2 | 308 | 6 | 1 | 0 | 1 | 90 |
| 71 | H_137 | Health | 14686 | 1 | 568 | 1 | 0 | 0 | 14 | 1 | 17 | 0 |
| 72 | H_145 | Health | 14097 | 13 | 128 | 10 | 7 | 7 | 43 | 0 | 24 | 0 |
| 73 | H_146 | Health | 36780 | 0 | 27 | 17 | 24 | 1215 | 48 | 0 | 49 | 0 |
| 74 | H_154 | Health | 18025 | 3 | 207 | 1 | 13 | 1 | 7 | 0 | 59 | 0 |
| 75 | H_156 | Health | 13899 | 0 | 11 | 19 | 2 | 417 | 1 | 0 | 4 | 0 |
| 76 | H_162 | Health | 11571 | 1 | 763 | 59 | 43 | 10 | 0 | 0 | 1 | 0 |
| 77 | H_163 | Health | 18304 | 406 | 347 | 20 | 0 | 0 | 6 | 0 | 21 | 2 |
| 78 | H_164 | Health | 36129 | 27 | 473 | 27 | 23 | 9 | 7 | 0 | 29 | 0 |
| 79 | H_165 | Health | 24874 | 365 | 435 | 25 | 43 | 1 | 5 | 0 | 1 | 0 |
| 80 | H_166 | Health | 28147 | 0 | 41 | 13 | 120 | 61 | 1 | 0 | 1 | 0 |
| 81 | H_168 | Health | 30291 | 8 | 131 | 1 | 0 | 1 | 1 | 3 | 0 | 0 |

FIG. 12 (cont.)

Table 5 (cont.)

| | A | B | C | AG | AH | AI | AJ | AK | AL | AM | AN | AO |
|---|---|---|---|---|---|---|---|---|---|---|---|---|
| 82 | H_171 | Health | 14889 | 2 | 198 | 18 | 37 | 20 | 2 | 1 | 0 | 0 |
| 83 | H_174 | Health | 10327 | 2 | 41 | 27 | 51 | 0 | 1 | 0 | 0 | 0 |
| 84 | H_175 | Health | 9530 | 0 | 127 | 41 | 0 | 3 | 2 | 0 | 19 | 0 |
| 85 | H_178 | Health | 73196 | 54 | 1319 | 108 | 372 | 12 | 1168 | 0 | 93 | 0 |
| 86 | H_186 | Health | 12182 | 5 | 64 | 5 | 110 | 8 | 0 | 0 | 11 | 0 |
| 87 | H_199 | Health | 25677 | 358 | 441 | 38 | 4 | 9 | 0 | 0 | 57 | 0 |
| 88 | H_200 | Health | 19277 | 77 | 619 | 19 | 22 | 5 | 17 | 0 | 5 | 0 |
| 89 | H_203 | Health | 7317 | 0 | 39 | 2 | 30 | 0 | 1 | 0 | 1 | 0 |
| 90 | H_211 | Health | 4740 | 6 | 53 | 21 | 37 | 4 | 1 | 0 | 1 | 0 |
| 91 | H_217 | Health | 10064 | 123 | 64 | 13 | 71 | 6 | 8 | 0 | 3 | 0 |
| 92 | H_220 | Health | 18191 | 379 | 252 | 14 | 1 | 0 | 0 | 0 | 2 | 0 |
| 93 | H_221 | Health | 26308 | 0 | 271 | 19 | 153 | 1 | 0 | 0 | 8 | 0 |
| 94 | H_222 | Health | 24701 | 25 | 545 | 3 | 17 | 3 | 31 | 0 | 17 | 0 |
| 95 | H_223 | Health | 7018 | 0 | 82 | 8 | 33 | 17 | 1 | 0 | 3 | 0 |
| 96 | H_225 | Health | 14469 | 4019 | 5 | 143 | 0 | 5 | 0 | 0 | 2 | 0 |
| 97 | H_234 | Health | 15232 | 868 | 229 | 43 | 23 | 197 | 0 | 0 | 0 | 0 |
| 98 | H_235 | Health | 14596 | 1 | 44 | 3 | 7 | 192 | 0 | 0 | 0 | 0 |
| 99 | H_236 | Health | 9200 | 3 | 9 | 11 | 1 | 5 | 0 | 0 | 8 | 0 |
| 100 | H_237 | Health | 20092 | 0 | 16 | 25 | 0 | 303 | 0 | 0 | 0 | 0 |
| 101 | H_238 | Health | 11638 | 0 | 219 | 2 | 17 | 27 | 11 | 0 | 30 | 0 |
| 102 | H_239 | Health | 17487 | 0 | 103 | 1 | 24 | 19 | 18 | 0 | 5 | 0 |
| 103 | H_240 | Health | 14649 | 7 | 118 | 15 | 4 | 259 | 3 | 0 | 0 | 0 |
| 104 | H_241 | Health | 32349 | 1 | 413 | 19 | 2 | 1282 | 1 | 0 | 0 | 0 |
| 105 | P_3 | PD1 | 15821 | 25 | 264 | 4 | 306 | 5 | 25 | 3 | 0 | 2 |
| 106 | P_5 | PD1 | 55868 | 2 | 376 | 1 | 0 | 0 | 3768 | 0 | 82 | 249 |
| 107 | P_20 | PD1 | 14612 | 4 | 6 | 42 | 0 | 13 | 1 | 0 | 9 | 235 |
| 108 | P_21 | PD1 | 11750 | 108 | 297 | 26 | 72 | 0 | 548 | 0 | 18 | 40 |
| 109 | P_24 | PD1 | 12785 | 8 | 74 | 15 | 3 | 5 | 119 | 49 | 1 | 308 |
| 110 | P_25 | PD1 | 22123 | 33 | 708 | 32 | 52 | 25 | 182 | 126 | 0 | 0 |
| 111 | P_27 | PD1 | 64096 | 0 | 25 | 43 | 2 | 0 | 622 | 7 | 73 | 168 |
| 112 | P_48 | PD1 | 56899 | 35 | 543 | 185 | 3 | 6 | 392 | 7 | 125 | 4 |
| 113 | P_49 | PD1 | 33580 | 2 | 382 | 253 | 1 | 23 | 2938 | 5 | 1 | 0 |

FIG. 12 (cont.)

Table 5 (cont.)

| | A | B | C | AG | AH | AI | AJ | AK | AL | AM | AN | AO |
|---|---|---|---|---|---|---|---|---|---|---|---|---|
| 114 | P_53 | P01 | 37971 | 130 | 73 | 14 | 9 | 8 | 693 | 4 | 36 | 4 |
| 115 | P_56 | P01 | 23193 | 11 | 454 | 82 | 5 | 0 | 114 | 0 | 6 | 0 |
| 116 | P_70 | P01 | 17344 | 4 | 5 | 84 | 1 | 2 | 30 | 0 | 0 | 19 |
| 117 | P_79 | P01 | 10858 | 11 | 334 | 3 | 0 | 3 | 89 | 0 | 25 | 102 |
| 118 | P_80 | P01 | 46951 | 152 | 32 | 50 | 8 | 9 | 135 | 0 | 5 | 1 |
| 119 | P_84 | P01 | 22948 | 111 | 75 | 29 | 78 | 0 | 218 | 0 | 8 | 0 |
| 120 | P_85 | P01 | 8819 | 538 | 32 | 18 | 10 | 7 | 14 | 0 | 9 | 4 |
| 121 | P_87 | P01 | 13155 | 6 | 0 | 6 | 0 | 6 | 24 | 0 | 0 | 33 |
| 122 | P_100 | P01 | 19129 | 143 | 134 | 3 | 23 | 1 | 26 | 0 | 1 | 36 |
| 123 | P_102 | P01 | 15541 | 15 | 85 | 10 | 2 | 0 | 23 | 0 | 1 | 19 |
| 124 | P_105 | P01 | 25183 | 0 | 55 | 10 | 0 | 13 | 7 | 0 | 3 | 0 |
| 125 | P_106 | P01 | 56812 | 27 | 119 | 54 | 77 | 0 | 697 | 0 | 0 | 895 |
| 126 | P_109 | P01 | 31560 | 1 | 324 | 2 | 245 | 18 | 13 | 0 | 1 | 35 |
| 127 | P_111 | P01 | 16482 | 22 | 26 | 61 | 0 | 0 | 0 | 0 | 54 | 0 |
| 128 | P_123 | P01 | 16867 | 1 | 131 | 0 | 0 | 0 | 322 | 0 | 3 | 0 |
| 129 | P_131 | P01 | 17951 | 77 | 25 | 17 | 27 | 14 | 53 | 0 | 4 | 3 |
| 130 | P_134 | P01 | 50988 | 7 | 1616 | 146 | 5 | 888 | 17 | 0 | 3 | 0 |
| 131 | P_136 | P01 | 36223 | 977 | 416 | 80 | 1141 | 3 | 28 | 0 | 51 | 1 |
| 132 | P_140 | P01 | 16345 | 7 | 3 | 49 | 28 | 16 | 297 | 0 | 0 | 89 |
| 133 | P_147 | P01 | 51057 | 249 | 1798 | 20 | 20 | 119 | 3 | 0 | 217 | 1 |
| 134 | P_155 | P01 | 38313 | 8 | 121 | 3 | 0 | 1 | 416 | 0 | 1 | 0 |
| 135 | P_161 | P01 | 12947 | 0 | 19 | 80 | 0 | 31 | 5 | 0 | 6 | 2 |
| 136 | P_167 | P01 | 19948 | 29 | 6 | 52 | 17 | 297 | 78 | 325 | 6 | 128 |
| 137 | P_180 | P01 | 15581 | 191 | 1 | 12 | 4 | 0 | 7 | 0 | 2 | 0 |
| 138 | P_181 | P01 | 14528 | 18 | 83 | 17 | 4 | 2 | 43 | 0 | 0 | 0 |
| 139 | P_182 | P01 | 39842 | 97 | 858 | 13 | 5 | 0 | 1 | 0 | 0 | 0 |
| 140 | P_195 | P01 | 38666 | 5594 | 43 | 617 | 3 | 2 | 116 | 0 | 11 | 0 |
| 141 | P_196 | P01 | 48271 | 1 | 1626 | 19 | 0 | 6 | 601 | 0 | 247 | 1 |
| 142 | P_205 | P01 | 10354 | 4 | 3 | 18 | 41 | 0 | 44 | 0 | 3 | 0 |
| 143 | P_206 | P01 | 16158 | 2072 | 75 | 80 | 15 | 1 | 23 | 0 | 30 | 239 |
| 144 | P_208 | P01 | 72174 | 94 | 51 | 20 | 1919 | 8 | 140 | 36 | 109 | 86 |
| 145 | P_210 | P01 | 15675 | 5 | 0 | 13 | 17 | 18 | 316 | 5 | 244 | 4 |

FIG. 12 (cont.)

Table 5 (cont.)

| | A | B | C | AG | AH | AI | AJ | AK | AL | AM | AN | AO |
|---|---|---|---|---|---|---|---|---|---|---|---|---|
| 146 | P_236 | PD1 | 32237 | 67 | 1 | 19 | 3 | 3 | 4 | 14 | 3 | 0 |
| 147 | P_238 | PD1 | 36475 | 2 | 3 | 4 | 37 | 4 | 19 | 25 | 0 | 0 |
| 148 | P_219 | PD1 | 12572 | 13 | 67 | 20 | 3 | 1 | 57 | 0 | 0 | 0 |
| 149 | P_224 | PD1 | 27758 | 25 | 13 | 17 | 3 | 124 | 589 | 43 | 61 | 219 |
| 150 | P_226 | PD1 | 14662 | 0 | 3 | 57 | 112 | 10 | 18 | 8 | 15 | 0 |
| 151 | P_228 | PD1 | 18702 | 37 | 82 | 22 | 3 | 437 | 20 | 31 | 10 | 0 |
| 152 | P_233 | PD1 | 17637 | 188 | 4 | 7 | 3 | 3 | 5 | 1 | 17 | 4 |
| 153 | P_243 | PD1 | 26116 | 61 | 77 | 36 | 111 | 28 | 206 | 0 | 7 | 0 |
| 154 | P_8C09 | PD1 | 10642 | 85 | 71 | 6 | 15 | 0 | 8 | 9 | 1 | 0 |
| 155 | P_8C19 | PD1 | 14380 | 3 | 50 | 18 | 8 | 0 | 11 | 0 | 1 | 0 |
| 156 | P_8C21 | PD1 | 45343 | 2 | 876 | 37 | 25 | 3 | 0 | 0 | 0 | 0 |

FIG. 12 (cont.)

Table 5 (cont.)

FIG. 12 (cont.)

Table 5 (cont.)

| | A | B | C | AP | AQ | AR | AS | AT | AU | AV | AW | AX | AY |
|---|---|---|---|---|---|---|---|---|---|---|---|---|---|
| 18 | G_72 | Gingivitis | 61493 | 261 | 234 | 3 | 14 | 1752 | 53 | 0 | 1708 | 0 | 42 |
| 19 | G_81 | Gingivitis | 3859 | 25 | 0 | 2 | 1 | 129 | 0 | 0 | 120 | 0 | 70 |
| 20 | G_86 | Gingivitis | 54894 | 536 | 5 | 1147 | 1388 | 3296 | 31 | 0 | 1 | 0 | 1875 |
| 21 | G_96 | Gingivitis | 58245 | 0 | 0 | 13 | 40 | 1 | 273 | 0 | 0 | 1 | 4 |
| 22 | G_98 | Gingivitis | 17911 | 51 | 37 | 264 | 544 | 1478 | 13 | 7 | 161 | 0 | 253 |
| 23 | G_101 | Gingivitis | 12876 | 0 | 1 | 327 | 41 | 1939 | 10 | 14 | 712 | 0 | 69 |
| 24 | G_113 | Gingivitis | 18815 | 30 | 98 | 24 | 305 | 406 | 448 | 7 | 115 | 1 | 49 |
| 25 | G_117 | Gingivitis | 80819 | 112 | 310 | 94 | 9 | 2259 | 2532 | 11 | 197 | 0 | 40 |
| 26 | G_120 | Gingivitis | 22655 | 3 | 0 | 8 | 78 | 70 | 103 | 0 | 36 | 0 | 1 |
| 27 | G_122 | Gingivitis | 17505 | 13 | 3 | 5 | 0 | 361 | 954 | 0 | 25 | 1 | 75 |
| 28 | G_128 | Gingivitis | 12750 | 13 | 0 | 5 | 18 | 200 | 845 | 7 | 37 | 0 | 40 |
| 29 | G_132 | Gingivitis | 21222 | 0 | 2 | 0 | 13 | 1 | 8 | 0 | 21 | 0 | 1 |
| 30 | G_135 | Gingivitis | 19363 | 52 | 0 | 194 | 1 | 907 | 0 | 5 | 18 | 0 | 159 |
| 31 | G_139 | Gingivitis | 17129 | 15 | 21 | 0 | 46 | 283 | 0 | 0 | 66 | 12 | 3 |
| 32 | G_143 | Gingivitis | 48153 | 4 | 1 | 2 | 4 | 19 | 5 | 3 | 3 | 1 | 1 |
| 33 | G_148 | Gingivitis | 16887 | 15 | 0 | 375 | 1 | 75 | 11 | 2 | 24 | 39 | 7 |
| 34 | G_149 | Gingivitis | 29963 | 0 | 2 | 0 | 10 | 2 | 1 | 0 | 4 | 0 | 1 |
| 35 | G_158 | Gingivitis | 18102 | 5 | 7 | 17 | 173 | 1298 | 89 | 367 | 29 | 0 | 47 |
| 36 | G_161 | Gingivitis | 14798 | 3 | 5 | 25 | 6 | 107 | 55 | 59 | 1 | 7 | 17 |
| 37 | G_169 | Gingivitis | 9811 | 0 | 0 | 1 | 0 | 5 | 0 | 0 | 309 | 0 | 3 |
| 38 | G_170 | Gingivitis | 48000 | 3 | 1 | 47 | 333 | 13 | 42 | 0 | 9 | 0 | 14 |
| 39 | G_172 | Gingivitis | 36949 | 3 | 7 | 0 | 2653 | 290 | 766 | 26 | 36 | 0 | 248 |
| 40 | G_173 | Gingivitis | 57476 | 0 | 0 | 7 | 7 | 4 | 5 | 0 | 6 | 0 | 4 |
| 41 | G_177 | Gingivitis | 36734 | 185 | 13 | 3 | 193 | 2203 | 31 | 2 | 935 | 0 | 767 |
| 42 | G_184 | Gingivitis | 11140 | 176 | 0 | 0 | 7 | 612 | 0 | 0 | 0 | 0 | 8 |
| 43 | G_186 | Gingivitis | 3325 | 0 | 0 | 33 | 7 | 90 | 0 | 33 | 0 | 0 | 63 |
| 44 | G_197 | Gingivitis | 3805 | 7 | 5 | 0 | 1 | 29 | 2 | 0 | 44 | 1 | 8 |
| 45 | G_214 | Gingivitis | 12530 | 15 | 0 | 3 | 41 | 364 | 1082 | 10 | 7 | 0 | 13 |
| 46 | G_232 | Gingivitis | 13682 | 4 | 29 | 88 | 24 | 878 | 967 | 63 | 67 | 0 | 49 |
| 47 | G_244 | Gingivitis | 13446 | 1 | 3 | 3 | 28 | 12 | 3 | 2 | 1 | 1 | 1 |
| 48 | G_245 | Gingivitis | 29114 | 31 | 19 | 2 | 21 | 202 | 52 | 95 | 30 | 0 | 14 |
| 49 | G_246 | Gingivitis | 37280 | 707 | 0 | 372 | 1 | 4817 | 1 | 0 | 134 | 0 | 90 |

FIG. 12 (cont.)

Table 5 (cont.)

| | A | B | C | AF | AG | AR | AS | AT | AU | AV | AW | AX | AY |
|---|---|---|---|---|---|---|---|---|---|---|---|---|---|
| 50 | G_349 | Gingivitis | 18342 | 58 | 3 | 54 | 43 | 820 | 301 | 32 | 136 | 42 | 107 |
| 51 | G_0354 | Gingivitis | 16711 | 1 | 0 | 2 | 239 | 91 | 4 | 0 | 0 | 0 | 7 |
| 52 | G_19 | Gingivitis | 34430 | 5 | 0 | 0 | 1 | 25 | 0 | 0 | 8 | 12 | 4 |
| 53 | H_39 | Health | 16024 | 3 | 1 | 0 | 5 | 3818 | 4 | 2 | 268 | 5 | 354 |
| 54 | H_48 | Health | 9790 | 35 | 4 | 0 | 13 | 134 | 36 | 12 | 0 | 0 | 4 |
| 55 | H_51 | Health | 7751 | 0 | 0 | 18 | 2 | 37 | 47 | 0 | 5 | 0 | 30 |
| 56 | H_57 | Health | 37038 | 86 | 24 | 44 | 8 | 1934 | 63 | 10 | 8 | 0 | 114 |
| 57 | H_58 | Health | 12088 | 65 | 11 | 330 | 5 | 141 | 20 | 0 | 11 | 14 | 61 |
| 58 | H_68 | Health | 10333 | 7 | 0 | 113 | 189 | 1304 | 22 | 1 | 5 | 0 | 302 |
| 59 | H_73 | Health | 17678 | 132 | 1 | 8 | 23 | 2226 | 6 | 17 | 8 | 0 | 279 |
| 60 | H_74 | Health | 47863 | 19 | 5 | 8 | 128 | 2271 | 30 | 2196 | 0 | 0 | 164 |
| 61 | H_78 | Health | 11352 | 17 | 4 | 5 | 357 | 1028 | 224 | 0 | 7 | 0 | 141 |
| 62 | H_83 | Health | 22743 | 2 | 0 | 155 | 0 | 4982 | 171 | 0 | 28 | 0 | 2020 |
| 63 | H_89 | Health | 13540 | 14 | 49 | 54 | 349 | 738 | 1 | 19 | 38 | 0 | 188 |
| 64 | H_90 | Health | 19858 | 4 | 0 | 0 | 76 | 131 | 44 | 7 | 0 | 0 | 8 |
| 65 | H_94 | Health | 18898 | 30 | 14 | 1 | 10 | 150 | 112 | 0 | 335 | 0 | 15 |
| 66 | H_107 | Health | 13290 | 1 | 0 | 9 | 1 | 27 | 3 | 0 | 12 | 0 | 635 |
| 67 | H_108 | Health | 13826 | 2 | 0 | 16 | 5 | 173 | 192 | 5 | 1 | 1 | 61 |
| 68 | H_112 | Health | 29564 | 188 | 0 | 607 | 15 | 3384 | 3 | 11 | 1 | 0 | 263 |
| 69 | H_114 | Health | 13104 | 18 | 0 | 3 | 3 | 22 | 123 | 0 | 3 | 0 | 2 |
| 70 | H_116 | Health | 28780 | 184 | 5 | 3 | 27 | 145 | 25 | 0 | 4 | 26 | 4 |
| 71 | H_137 | Health | 14686 | 3 | 0 | 8 | 0 | 50 | 3 | 0 | 0 | 0 | 492 |
| 72 | H_145 | Health | 14097 | 17 | 0 | 957 | 3 | 377 | 87 | 3 | 43 | 0 | 215 |
| 73 | H_146 | Health | 36760 | 122 | 0 | 28 | 287 | 25 | 24 | 0 | 5 | 0 | 13 |
| 74 | H_154 | Health | 18026 | 47 | 0 | 7 | 0 | 324 | 3 | 0 | 148 | 1 | 77 |
| 75 | H_156 | Health | 13898 | 1 | 0 | 5 | 1 | 1369 | 16 | 0 | 5 | 0 | 666 |
| 76 | H_162 | Health | 11573 | 18 | 29 | 35 | 2 | 48 | 41 | 0 | 80 | 0 | 8 |
| 77 | H_163 | Health | 18304 | 93 | 0 | 4 | 2 | 1093 | 429 | 0 | 287 | 23 | 156 |
| 78 | H_164 | Health | 36129 | 4 | 7 | 6 | 352 | 167 | 135 | 0 | 86 | 0 | 57 |
| 79 | H_165 | Health | 24974 | 27 | 116 | 0 | 16 | 885 | 174 | 0 | 269 | 0 | 75 |
| 80 | H_166 | Health | 28147 | 221 | 49 | 14 | 419 | 3815 | 0 | 31 | 20 | 0 | 244 |
| 81 | H_168 | Health | 10391 | 76 | 0 | 18 | 5 | 999 | 1 | 0 | 2 | 0 | 372 |

FIG. 12 (cont.)

Table 5 (cont.)

|    | A     | B      | C     | AP  | AQ  | AR  | AS  | AT   | AU   | AV  | AW   | AX  | AY  |
|----|-------|--------|-------|-----|-----|-----|-----|------|------|-----|------|-----|-----|
| 82 | H_171 | Health | 14089 | 27  | 23  | 28  | 5   | 775  | 83   | 1   | 27   | 0   | 6   |
| 83 | H_174 | Health | 10127 | 23  | 0   | 0   | 0   | 1689 | 1    | 0   | 5    | 0   | 184 |
| 84 | H_175 | Health | 9530  | 0   | 0   | 1   | 0   | 339  | 1    | 0   | 11   | 3   | 14  |
| 85 | H_178 | Health | 73106 | 40  | 0   | 1   | 4   | 158  | 1    | 0   | 2    | 0   | 5   |
| 86 | H_186 | Health | 12182 | 159 | 10  | 6   | 69  | 509  | 688  | 22  | 48   | 0   | 143 |
| 87 | H_189 | Health | 23677 | 3   | 139 | 12  | 5   | 34   | 263  | 0   | 8    | 0   | 5   |
| 88 | H_209 | Health | 14277 | 279 | 0   | 19  | 7   | 251  | 632  | 12  | 1    | 15  | 29  |
| 89 | H_203 | Health | 7217  | 4   | 7   | 12  | 24  | 180  | 13   | 5   | 3    | 0   | 259 |
| 90 | H_211 | Health | 8746  | 12  | 4   | 37  | 8   | 109  | 29   | 0   | 5    | 0   | 385 |
| 91 | H_217 | Health | 10064 | 9   | 16  | 14  | 5   | 313  | 91   | 130 | 38   | 1   | 52  |
| 92 | H_220 | Health | 10131 | 83  | 0   | 1   | 0   | 473  | 10   | 3   | 7    | 0   | 64  |
| 93 | H_221 | Health | 26868 | 30  | 0   | 101 | 34  | 296  | 1922 | 186 | 41   | 0   | 104 |
| 94 | H_222 | Health | 24701 | 30  | 0   | 42  | 10  | 1298 | 38   | 1   | 8    | 17  | 31  |
| 95 | H_223 | Health | 7018  | 5   | 18  | 234 | 27  | 163  | 173  | 0   | 24   | 0   | 6   |
| 96 | H_225 | Health | 13460 | 7   | 0   | 0   | 0   | 50   | 1    | 0   | 14   | 0   | 1   |
| 97 | H_234 | Health | 13232 | 30  | 11  | 68  | 1   | 332  | 22   | 11  | 7    | 0   | 33  |
| 98 | H_235 | Health | 14596 | 50  | 0   | 45  | 44  | 6993 | 1    | 34  | 1034 | 0   | 128 |
| 99 | H_236 | Health | 9200  | 12  | 0   | 50  | 13  | 315  | 46   | 1   | 146  | 54  | 103 |
| 100| H_237 | Health | 20992 | 77  | 0   | 46  | 797 | 2755 | 0    | 1   | 0    | 0   | 356 |
| 101| H_238 | Health | 13638 | 9   | 18  | 659 | 36  | 337  | 57   | 43  | 6    | 0   | 119 |
| 102| H_239 | Health | 17387 | 3   | 37  | 33  | 5   | 185  | 838  | 3   | 19   | 0   | 3   |
| 103| H_240 | Health | 14643 | 132 | 3   | 343 | 0   | 3464 | 27   | 13  | 33   | 0   | 259 |
| 104| H_241 | Health | 32143 | 128 | 23  | 388 | 0   | 3588 | 24   | 3   | 0    | 0   | 119 |
| 105| P_1   | PCI    | 15621 | 1   | 40  | 7   | 4   | 84   | 201  | 0   | 77   | 0   | 14  |
| 106| P_5   | PCI    | 55668 | 0   | 0   | 7   | 0   | 7    | 3    | 0   | 8    | 0   | 3   |
| 107| P_20  | PCI    | 14617 | 0   | 0   | 8   | 18  | 7    | 3    | 0   | 3    | 0   | 2   |
| 108| P_21  | PCI    | 11750 | 8   | 0   | 5   | 0   | 41   | 8    | 0   | 1385 | 1   | 3   |
| 109| P_24  | PCI    | 12785 | 0   | 1   | 4   | 184 | 7    | 3    | 0   | 0    | 0   | 1   |
| 110| P_25  | PCI    | 22123 | 33  | 0   | 108 | 184 | 94   | 116  | 0   | 1    | 0   | 446 |
| 111| P_27  | PCI    | 64090 | 3   | 1   | 3   | 2   | 2    | 5    | 1   | 1    | 2   | 20  |
| 112| P_36  | PCI    | 56296 | 26  | 26  | 17  | 7   | 318  | 1125 | 2   | 49   | 137 | 30  |
| 113| P_39  | PCI    | 33560 | 2   | 0   | 4   | 4   | 15   | 52   | 0   | 3    | 0   | 15  |

FIG. 12 (cont.)

Table 5 (cont.)

| | A | B | C | AP | AQ | AR | AS | AT | AU | AV | AW | AX | AY |
|---|---|---|---|---|---|---|---|---|---|---|---|---|---|
| 114 | P_52 | P01 | 37971 | 2 | 2 | 0 | 5 | 6 | 265 | 0 | 1 | 12 | 0 |
| 115 | P_54 | P01 | 29103 | 0 | 1 | 5 | 31 | 9 | 309 | 0 | 0 | 2 | 13 |
| 116 | P_70 | P01 | 17344 | 0 | 0 | 0 | 1 | 1 | 2 | 0 | 3 | 0 | 1 |
| 117 | P_79 | P01 | 19858 | 4 | 0 | 71 | 1 | 30 | 1 | 0 | 1 | 2 | 27 |
| 118 | P_80 | P01 | 46953 | 4 | 5 | 8 | 5 | 24 | 3 | 1 | 28 | 0 | 9 |
| 119 | P_84 | P01 | 22949 | 68 | 12 | 0 | 0 | 5 | 5 | 2 | 5 | 1 | 0 |
| 120 | P_85 | P01 | 9619 | 0 | 1 | 4 | 0 | 52 | 6 | 2 | 58 | 0 | 4 |
| 121 | P_87 | P01 | 13155 | 0 | 2 | 0 | 0 | 7 | 16 | 0 | 7 | 1 | 0 |
| 122 | P_100 | P01 | 19179 | 1 | 0 | 29 | 8 | 17 | 0 | 0 | 1 | 0 | 18 |
| 123 | P_102 | P01 | 10543 | 1 | 1 | 1 | 303 | 41 | 19 | 0 | 13 | 5 | 4 |
| 124 | P_105 | P01 | 25193 | 0 | 0 | 5 | 1 | 7 | 0 | 0 | 8 | 0 | 0 |
| 125 | P_106 | P01 | 56812 | 0 | 0 | 1 | 8 | 7 | 4 | 0 | 6 | 0 | 0 |
| 126 | P_109 | P01 | 31560 | 73 | 25 | 12 | 23 | 68 | 498 | 26 | 11 | 13 | 15 |
| 127 | P_111 | P01 | 16432 | 0 | 0 | 19 | 0 | 12 | 0 | 0 | 0 | 0 | 15 |
| 128 | P_123 | P01 | 16867 | 0 | 0 | 0 | 0 | 7 | 0 | 0 | 0 | 0 | 0 |
| 129 | P_131 | P01 | 17951 | 1 | 1 | 386 | 0 | 12 | 11 | 0 | 398 | 23 | 160 |
| 130 | P_134 | P01 | 50988 | 41 | 0 | 1621 | 0 | 2085 | 0 | 0 | 141 | 50 | 17 |
| 131 | P_136 | P01 | 38229 | 28 | 20 | 22 | 32 | 640 | 1047 | 1 | 132 | 33 | 71 |
| 132 | P_140 | P01 | 16345 | 2 | 0 | 2 | 43 | 7 | 10 | 0 | 0 | 0 | 4 |
| 133 | P_147 | P01 | 51057 | 125 | 18 | 362 | 63 | 3641 | 786 | 0 | 24 | 0 | 127 |
| 134 | P_155 | P01 | 38911 | 2 | 0 | 211 | 0 | 173 | 3 | 0 | 0 | 43 | 52 |
| 135 | P_181 | P01 | 18947 | 8 | 0 | 87 | 0 | 30 | 16 | 0 | 11 | 13 | 21 |
| 136 | P_187 | P01 | 19346 | 1 | 0 | 0 | 193 | 5 | 2 | 0 | 28 | 0 | 2 |
| 137 | P_190 | P01 | 15981 | 0 | 3 | 115 | 0 | 46 | 8 | 0 | 34 | 0 | 21 |
| 138 | P_191 | P01 | 13529 | 2 | 1 | 1 | 68 | 165 | 95 | 0 | 2 | 2 | 419 |
| 139 | P_192 | P01 | 29342 | 0 | 0 | 2 | 5 | 5 | 0 | 0 | 179 | 0 | 11 |
| 140 | P_195 | P01 | 38686 | 2 | 0 | 14 | 0 | 76 | 147 | 1 | 1 | 58 | 12 |
| 141 | P_198 | P01 | 48271 | 0 | 0 | 149 | 0 | 3494 | 3720 | 0 | 0 | 0 | 1447 |
| 142 | P_205 | P01 | 10954 | 3 | 0 | 0 | 78 | 14 | 17 | 1 | 3 | 0 | 2 |
| 143 | P_206 | P01 | 18158 | 15 | 124 | 2 | 1 | 38 | 54 | 1 | 435 | 23 | 0 |
| 144 | P_208 | P01 | 22174 | 1 | 0 | 2 | 132 | 36 | 27 | 1 | 2 | 0 | 8 |
| 145 | P_210 | P01 | 15575 | 3 | 0 | 1 | 13 | 1 | 3 | 1 | 5 | 1 | 1 |

FIG. 12 (cont.)

Table 5 (cont.)

| | A | B | C | AP | AQ | AR | AS | AT | AU | AV | AW | AX | AY |
|---|---|---|---|---|---|---|---|---|---|---|---|---|---|
| 146 | P_218 | P03 | 12297 | 0 | 1 | 0 | 4 | 2 | 0 | 0 | 0 | 3 | 0 |
| 147 | P_218 | P03 | 10475 | 0 | 0 | 0 | 69 | 2 | 8 | 2 | 0 | 0 | 3 |
| 148 | P_218 | P03 | 12572 | 7 | 0 | 1 | 87 | 4 | 1 | 0 | 18 | 58 | 17 |
| 149 | P_228 | P03 | 27758 | 3 | 1 | 0 | 96 | 11 | 11 | 0 | 11 | 3 | 1 |
| 150 | P_228 | P03 | 14862 | 0 | 0 | 0 | 7 | 2 | 2 | 0 | 0 | 8 | 0 |
| 151 | P_328 | P01 | 18702 | 15 | 0 | 364 | 19 | 77 | 32 | 4 | 48 | 1 | 71 |
| 152 | P_338 | P01 | 17847 | 1 | 0 | 1 | 4 | 8 | 23 | 0 | 5 | 14 | 4 |
| 153 | P_348 | P01 | 20116 | 1 | 1 | 280 | 7 | 40 | 48 | 1 | 31 | 4 | 11 |
| 154 | P_BC09 | P01 | 18642 | 2 | 3 | 1 | 2 | 125 | 76 | 27 | 26 | 27 | 7 |
| 155 | P_BC19 | P01 | 14448 | 3 | 0 | 1 | 5 | 58 | 103 | 1 | 18 | 0 | 18 |
| 156 | P_BC21 | P01 | 4548 | 128 | 3 | 2 | 425 | 2524 | 856 | 22 | 124 | 0 | 181 |

FIG. 12 (cont.)

Table 6 (cont.)

| | A | B | C | A2 | BA | BB | BC | BD | BE | BF | BG | BH |
|---|---|---|---|---|---|---|---|---|---|---|---|---|
| | Org | Health_state | Total Reads | cl_Neisseria_weaveri_CGT-266 | cl_Neisseria_zoodegmatis_CGT-269 | cl_Ottowia_sp._CGT-014 | cl_Pasteurella_sp._CGT-180 | cl_Pasteurella_canis_CGT-179 | cl_Pasteurella_dagmatis_CGT-002 | cl_Pasteurellaceae_sp._CGT-272 | cl_Peptostreptococcaceae_sp._XI-XI-sp._CGT-004 | cl_Peptostreptococcaceae_sp._XI-XI-sp._CGT-095 |
| 1 | | | | | | | | | | | | |
| 2 | G_7 | Gingivitis | 12132 | 303 | 38 | 55 | 1 | 81 | 5 | 2 | 28 | 0 |
| 3 | G_8 | Gingivitis | 10631 | 1 | 31 | 1 | 0 | 7 | 7 | 0 | 225 | 1 |
| 4 | G_9 | Gingivitis | 25226 | 54 | 232 | 14 | 84 | 13 | 2 | 4 | 137 | 0 |
| 5 | G_12 | Gingivitis | 15863 | 0 | 485 | 32 | 3 | 20 | 0 | 53 | 387 | 0 |
| 6 | G_14 | Gingivitis | 9138 | 2 | 2 | 1 | 0 | 0 | 0 | 0 | 935 | 11 |
| 7 | G_18 | Gingivitis | 28089 | 0 | 86 | 3 | 0 | 41 | 0 | 3 | 462 | 17 |
| 8 | G_22 | Gingivitis | 84780 | 24 | 987 | 24 | 0 | 98 | 49 | 11 | 1488 | 42 |
| 9 | G_30 | Gingivitis | 19524 | 14 | 45 | 1 | 1 | 3 | 8 | 2 | 75 | 182 |
| 10 | G_35 | Gingivitis | 38147 | 18 | 1635 | 14 | 0 | 54 | 68 | 5 | 467 | 2 |
| 11 | G_40 | Gingivitis | 15435 | 8 | 817 | 1 | 0 | 17 | 28 | 3 | 1512 | 0 |
| 12 | G_42 | Gingivitis | 11358 | 0 | 53 | 1 | 0 | 5 | 0 | 1 | 0 | 0 |
| 13 | G_52 | Gingivitis | 45501 | 589 | 165 | 5 | 2 | 163 | 316 | 3 | 227 | 3 |
| 14 | G_62 | Gingivitis | 9822 | 86 | 316 | 1 | 0 | 17 | 502 | 10 | 38 | 0 |
| 15 | G_63 | Gingivitis | 5841 | 97 | 112 | 3 | 0 | 0 | 0 | 1 | 23 | 2 |
| 16 | G_64 | Gingivitis | 7175 | 9 | 69 | 0 | 0 | 4 | 24 | 0 | 205 | 6 |
| 17 | G_65 | Gingivitis | 5398 | 1 | 1 | 0 | 1 | 0 | 0 | 0 | 118 | 24 |

FIG. 12 (cont.)

Table 5 (cont.)

| | A | B | C | AZ | 9A | 9B | 9C | 9D | 9E | 9F | 9G | 9H |
|---|---|---|---|---|---|---|---|---|---|---|---|---|
| 18 | G_72 | Gingivitis | 61483 | 109 | 1579 | 1 | 0 | 18 | 505 | 1 | 528 | 0 |
| 19 | G_81 | Gingivitis | 8869 | 39 | 187 | 1 | 0 | 20 | 71 | 13 | 16 | 0 |
| 20 | G_86 | Gingivitis | 54894 | 1527 | 44 | 72 | 0 | 192 | 223 | 5 | 17 | 0 |
| 21 | G_96 | Gingivitis | 39245 | 1 | 7 | 0 | 13 | 2 | 0 | 1 | 225 | 0 |
| 22 | G_98 | Gingivitis | 17911 | 0 | 478 | 12 | 3 | 93 | 0 | 16 | 191 | 0 |
| 23 | G_103 | Gingivitis | 12676 | 1 | 503 | 15 | 3 | 8 | 24 | 3625 | 16 | 1 |
| 24 | G_113 | Gingivitis | 19818 | 26 | 180 | 3 | 0 | 46 | 57 | 4 | 88 | 31 |
| 25 | G_117 | Gingivitis | 30819 | 3 | 365 | 7 | 3 | 64 | 13 | 6 | 97 | 0 |
| 26 | G_120 | Gingivitis | 22855 | 1 | 31 | 3 | 31 | 2 | 2 | 6 | 62 | 18 |
| 27 | G_122 | Gingivitis | 17506 | 6 | 114 | 0 | 1 | 6 | 5 | 6 | 227 | 0 |
| 28 | G_128 | Gingivitis | 12750 | 3 | 80 | 5 | 2 | 22 | 0 | 11 | 211 | 0 |
| 29 | G_132 | Gingivitis | 21222 | 0 | 4 | 1 | 30 | 1 | 7 | 1 | 364 | 8 |
| 30 | G_135 | Gingivitis | 10363 | 31 | 67 | 14 | 0 | 23 | 2 | 0 | 247 | 0 |
| 31 | G_139 | Gingivitis | 17129 | 0 | 46 | 3 | 57 | 6 | 13 | 30 | 1733 | 0 |
| 32 | G_143 | Gingivitis | 88153 | 2 | 19 | 3 | 1 | 10 | 2 | 1 | 1369 | 0 |
| 33 | G_148 | Gingivitis | 16887 | 1 | 45 | 6 | 0 | 16 | 19 | 7 | 226 | 0 |
| 34 | G_149 | Gingivitis | 23981 | 1 | 3 | 0 | 0 | 1 | 1 | 0 | 1036 | 0 |
| 35 | G_153 | Gingivitis | 18307 | 59 | 942 | 2 | 3 | 20 | 82 | 90 | 44 | 8 |
| 36 | G_161 | Gingivitis | 14738 | 50 | 27 | 2 | 3 | 7 | 11 | 214 | 3 | 0 |
| 37 | G_168 | Gingivitis | 9811 | 2 | 301 | 0 | 0 | 27 | 0 | 7 | 259 | 16 |
| 38 | G_170 | Gingivitis | 49900 | 125 | 34 | 13 | 1 | 3 | 2 | 1 | 767 | 1 |
| 39 | G_172 | Gingivitis | 36943 | 0 | 51 | 120 | 116 | 39 | 13 | 5 | 502 | 0 |
| 40 | G_173 | Gingivitis | 57676 | 0 | 2 | 0 | 0 | 0 | 0 | 0 | 1827 | 0 |
| 41 | G_177 | Gingivitis | 38744 | 0 | 1154 | 39 | 0 | 99 | 3 | 2 | 112 | 1 |
| 42 | G_184 | Gingivitis | 11340 | 0 | 184 | 0 | 0 | 1 | 4 | 1 | 240 | 0 |
| 43 | G_188 | Gingivitis | 9325 | 19 | 304 | 13 | 0 | 5 | 28 | 0 | 188 | 0 |
| 44 | G_197 | Gingivitis | 3805 | 0 | 20 | 0 | 3 | 10 | 5 | 1 | 28 | 0 |
| 45 | G_214 | Gingivitis | 12530 | 19 | 3 | 5 | 0 | 4 | 3 | 5 | 28 | 0 |
| 46 | G_232 | Gingivitis | 13682 | 54 | 202 | 2 | 0 | 12 | 56 | 30 | 125 | 1 |
| 47 | G_244 | Gingivitis | 13446 | 0 | 4 | 2 | 50 | 0 | 1 | 2 | 68 | 0 |
| 48 | G_245 | Gingivitis | 29114 | 7 | 21 | 9 | 18 | 18 | 3 | 27 | 904 | 0 |
| 49 | G_246 | Gingivitis | 37282 | 0 | 2759 | 13 | 0 | 643 | 4 | 4 | 1 | 0 |

FIG. 12 (cont.)

Table 5 (cont.)

| | A | B | C | AZ | BA | BB | BC | BD | BE | BF | BG | BH |
|---|---|---|---|---|---|---|---|---|---|---|---|---|
| 50 | G_249 | Gingivitis | 19347 | 87 | 195 | 59 | 241 | 45 | 268 | 29 | 105 | 56 |
| 51 | G_0364 | Gingivitis | 16211 | 6 | 3 | 0 | 241 | 2 | 1 | 0 | 359 | 32 |
| 52 | G_18 | Gingivitis | 34430 | 87 | 6 | 0 | 8 | 17 | 10 | 4 | 9 | 0 |
| 53 | H_39 | Health | 19024 | 3 | 1274 | 28 | 0 | 230 | 1212 | 0 | 8 | 0 |
| 54 | H_48 | Health | 9790 | 444 | 12 | 1 | 0 | 63 | 297 | 19 | 137 | 0 |
| 55 | H_51 | Health | 7793 | 2 | 15 | 8 | 0 | 4 | 2 | 0 | 75 | 0 |
| 56 | H_57 | Health | 37088 | 68 | 40 | 3 | 0 | 122 | 125 | 0 | 441 | 0 |
| 57 | H_58 | Health | 12080 | 30 | 59 | 19 | 7 | 14 | 5 | 9 | 48 | 0 |
| 58 | H_68 | Health | 19333 | 35 | 29 | 40 | 2 | 32 | 39 | 0 | 14 | 0 |
| 59 | H_73 | Health | 12578 | 1 | 1829 | 6 | 0 | 744 | 7 | 8 | 17 | 0 |
| 60 | H_74 | Health | 47881 | 519 | 1191 | 6 | 4 | 139 | 225 | 419 | 194 | 0 |
| 61 | H_78 | Health | 13327 | 7 | 40 | 19 | 0 | 12 | 6 | 1 | 83 | 0 |
| 62 | H_83 | Health | 22783 | 259 | 244 | 451 | 0 | 1456 | 36 | 0 | 11 | 0 |
| 63 | H_89 | Health | 13540 | 4 | 844 | 7 | 0 | 15 | 26 | 63 | 17 | 0 |
| 64 | H_90 | Health | 19858 | 21 | 19 | 1 | 0 | 9 | 16 | 2 | 177 | 0 |
| 65 | H_94 | Health | 18898 | 44 | 158 | 0 | 0 | 32 | 32 | 0 | 332 | 16 |
| 66 | H_107 | Health | 13290 | 147 | 321 | 18 | 0 | 50 | 2 | 0 | 3 | 0 |
| 67 | H_108 | Health | 13328 | 63 | 10 | 5 | 5 | 25 | 67 | 23 | 54 | 0 |
| 68 | H_112 | Health | 29544 | 364 | 424 | 20 | 1 | 21 | 4 | 29 | 172 | 0 |
| 69 | H_114 | Health | 13104 | 4 | 15 | 0 | 0 | 248 | 13 | 2 | 136 | 1 |
| 70 | H_118 | Health | 28783 | 4 | 63 | 1 | 126 | 104 | 188 | 14 | 28 | 0 |
| 71 | H_137 | Health | 14686 | 39 | 1157 | 4 | 0 | 339 | 693 | 34 | 12 | 0 |
| 72 | H_145 | Health | 14097 | 17 | 23 | 66 | 0 | 2 | 49 | 5 | 70 | 0 |
| 73 | H_146 | Health | 36760 | 42 | 234 | 15 | 1 | 2 | 0 | 1 | 3115 | 6 |
| 74 | H_154 | Health | 19025 | 1 | 815 | 9 | 0 | 92 | 216 | 50 | 81 | 1 |
| 75 | H_156 | Health | 13898 | 103 | 237 | 2 | 0 | 185 | 857 | 0 | 1 | 1 |
| 76 | H_162 | Health | 13571 | 25 | 67 | 13 | 1 | 27 | 49 | 18 | 293 | 0 |
| 77 | H_163 | Health | 18303 | 8 | 470 | 8 | 1 | 67 | 234 | 0 | 88 | 0 |
| 78 | H_164 | Health | 36129 | 23 | 277 | 4 | 4 | 4 | 2 | 0 | 455 | 5 |
| 79 | H_165 | Health | 24974 | 253 | 248 | 3 | 0 | 129 | 176 | 2 | 274 | 0 |
| 80 | H_166 | Health | 29187 | 1 | 754 | 10 | 1 | 82 | 0 | 34 | 96 | 0 |
| 81 | H_168 | Health | 19291 | 0 | 1188 | 18 | 0 | 36 | 1 | 1 | 5 | 0 |

FIG. 12 (cont.)

Table 5 (cont.)

| | A | B | C | AZ | BA | BB | BC | BD | BE | BF | BG | BH |
|---|---|---|---|---|---|---|---|---|---|---|---|---|
| 82 | H_171 | Health | 14889 | 2 | 178 | 3 | 0 | 7 | 57 | 5 | 62 | 0 |
| 83 | H_174 | Health | 19127 | 1 | 1086 | 46 | 0 | 27 | 61 | 0 | 8 | 1 |
| 84 | H_175 | Health | 9539 | 0 | 73 | 21 | 0 | 0 | 6 | 0 | 98 | 0 |
| 85 | H_178 | Health | 73108 | 38 | 36 | 8 | 13 | 123 | 57 | 1 | 972 | 0 |
| 86 | H_186 | Health | 32182 | 27 | 159 | 0 | 12 | 15 | 35 | 134 | 43 | 0 |
| 87 | H_189 | Health | 25077 | 5 | 19 | 1 | 7 | 8 | 22 | 9 | 368 | 0 |
| 88 | H_200 | Health | 19277 | 155 | 85 | 0 | 0 | 394 | 73 | 25 | 203 | 0 |
| 89 | H_203 | Health | 7317 | 14 | 161 | 13 | 1 | 2 | 1 | 30 | 6 | 0 |
| 90 | H_211 | Health | 4740 | 16 | 726 | 0 | 0 | 40 | 84 | 26 | 6 | 0 |
| 91 | H_217 | Health | 10064 | 2 | 122 | 1 | 7 | 14 | 15 | 62 | 186 | 0 |
| 92 | H_220 | Health | 18391 | 27 | 1261 | 2 | 0 | 73 | 120 | 0 | 119 | 0 |
| 93 | H_221 | Health | 26808 | 7 | 165 | 65 | 5 | 6 | 61 | 40 | 298 | 0 |
| 94 | H_222 | Health | 24701 | 180 | 301 | 1 | 0 | 87 | 73 | 2 | 320 | 0 |
| 95 | H_223 | Health | 7018 | 1 | 542 | 2 | 0 | 26 | 4 | 65 | 31 | 0 |
| 96 | H_225 | Health | 14460 | 0 | 2 | 0 | 0 | 2 | 1 | 1 | 23 | 0 |
| 97 | H_234 | Health | 13232 | 23 | 36 | 1 | 7 | 9 | 39 | 24 | 118 | 0 |
| 98 | H_235 | Health | 14596 | 0 | 864 | 2 | 1 | 10 | 0 | 185 | 18 | 0 |
| 99 | H_236 | Health | 9260 | 4 | 273 | 3 | 0 | 14 | 0 | 0 | 77 | 0 |
| 100 | H_237 | Health | 20932 | 18 | 138 | 100 | 1 | 57 | 9 | 2 | 13 | 0 |
| 101 | H_238 | Health | 11635 | 10 | 33 | 1 | 1 | 39 | 1 | 39 | 53 | 0 |
| 102 | H_239 | Health | 17487 | 0 | 71 | 1 | 0 | 11 | 5 | 4 | 276 | 0 |
| 103 | H_240 | Health | 14649 | 6 | 458 | 15 | 0 | 5 | 8 | 63 | 5 | 0 |
| 104 | H_241 | Health | 12149 | 2 | 204 | 89 | 0 | 143 | 4 | 1 | 215 | 0 |
| 105 | P_1 | PD1 | 15621 | 86 | 42 | 1 | 100 | 13 | 17 | 378 | 74 | 7 |
| 106 | P_5 | PD1 | 55956 | 8 | 7 | 2 | 0 | 8 | 25 | 0 | 149 | 0 |
| 107 | P_20 | PD1 | 14617 | 9 | 11 | 0 | 0 | 5 | 2 | 0 | 470 | 0 |
| 108 | P_21 | PD1 | 11750 | 0 | 649 | 0 | 46 | 4 | 71 | 39 | 37 | 7 |
| 109 | P_24 | PD1 | 12705 | 1 | 2 | 3 | 25 | 13 | 3 | 1 | 81 | 5 |
| 110 | P_25 | PD1 | 22123 | 56 | 94 | 45 | 4 | 31 | 15 | 0 | 597 | 0 |
| 111 | P_27 | PD1 | 64000 | 30 | 92 | 6 | 0 | 1 | 0 | 6 | 3299 | 76 |
| 112 | P_46 | PD1 | 56396 | 27 | 68 | 2 | 0 | 65 | 22 | 3 | 1486 | 73 |
| 113 | P_49 | PD1 | 33580 | 135 | 25 | 0 | 0 | 63 | 7 | 0 | 916 | 24 |

FIG. 12 (cont.)

Table 5 (cont.)

| | A | B | C | AZ | BA | BB | BC | BD | BE | BF | BG | BH |
|---|---|---|---|---|---|---|---|---|---|---|---|---|
| 114 | P_53 | P01 | 17971 | 3 | 13 | 0 | 8 | 3 | 2 | 0 | 729 | 50 |
| 115 | P_56 | P01 | 23103 | 0 | 5 | 2 | 0 | 15 | 10 | 7 | 350 | 2 |
| 116 | P_70 | P01 | 17344 | 1 | 1 | 0 | 0 | 0 | 0 | 0 | 65 | 168 |
| 117 | P_79 | P01 | 10658 | 16 | 15 | 87 | 0 | 14 | 3 | 1 | 32 | 0 |
| 118 | P_80 | P01 | 46951 | 0 | 25 | 58 | 3 | 5 | 19 | 0 | 13768 | 75 |
| 119 | P_84 | P01 | 22949 | 2 | 30 | 0 | 14 | 2 | 0 | 0 | 828 | 0 |
| 120 | P_86 | P01 | 8619 | 0 | 86 | 1 | 1 | 1 | 3 | 1 | 33 | 0 |
| 121 | P_87 | P01 | 13165 | 1 | 2 | 0 | 0 | 0 | 0 | 0 | 797 | 2 |
| 122 | P_100 | P01 | 19179 | 0 | 68 | 9 | 141 | 1 | 1 | 44 | 7183 | 0 |
| 123 | P_102 | P01 | 13541 | 42 | 17 | 12 | 4 | 2 | 1 | 1 | 591 | 0 |
| 124 | P_105 | P01 | 25183 | 0 | 4 | 7 | 0 | 1 | 0 | 1 | 7883 | 0 |
| 125 | P_106 | P01 | 56812 | 1 | 3 | 5 | 189 | 1 | 0 | 0 | 274 | 300 |
| 126 | P_109 | P01 | 31580 | 3 | 21 | 5 | 102 | 89 | 139 | 8 | 283 | 7 |
| 127 | P_111 | P01 | 16442 | 0 | 17 | 0 | 0 | 2 | 0 | 0 | 314 | 0 |
| 128 | P_123 | P01 | 16867 | 0 | 0 | 3 | 0 | 15 | 0 | 0 | 39 | 0 |
| 129 | P_131 | P01 | 17951 | 1 | 420 | 54 | 0 | 13 | 2 | 85 | 38 | 0 |
| 130 | P_134 | P01 | 60086 | 5 | 86 | 233 | 0 | 90 | 4 | 1 | 537 | 0 |
| 131 | P_136 | P01 | 36223 | 23 | 435 | 8 | 130 | 25 | 389 | 68 | 98 | 0 |
| 132 | P_140 | P01 | 18345 | 1 | 1 | 0 | 17 | 1 | 0 | 0 | 359 | 1 |
| 133 | P_147 | P01 | 51087 | 0 | 114 | 17 | 20 | 96 | 82 | 34 | 584 | 1 |
| 134 | P_166 | P01 | 38911 | 6 | 118 | 344 | 2 | 70 | 32 | 1 | 35 | 0 |
| 135 | P_181 | P01 | 18947 | 25 | 42 | 1 | 80 | 9 | 11 | 0 | 138 | 0 |
| 136 | P_187 | P01 | 19346 | 1 | 24 | 0 | 86 | 0 | 0 | 0 | 428 | 0 |
| 137 | P_190 | P01 | 15081 | 0 | 20 | 20 | 1 | 8 | 0 | 0 | 21 | 0 |
| 138 | P_191 | P01 | 14529 | 63 | 14 | 3 | 11 | 4 | 0 | 17 | 20 | 0 |
| 139 | P_192 | P01 | 39342 | 15 | 30 | 2 | 1 | 222 | 3 | 5 | 1298 | 0 |
| 140 | P_195 | P01 | 28666 | 0 | 6 | 3 | 0 | 7 | 7 | 0 | 1684 | 0 |
| 141 | P_198 | P01 | 48271 | 0 | 6 | 54 | 0 | 534 | 0 | 0 | 107 | 0 |
| 142 | P_205 | P01 | 10354 | 0 | 14 | 0 | 34 | 0 | 4 | 2 | 1076 | 27 |
| 143 | P_206 | P01 | 16138 | 4 | 261 | 1 | 2 | 11 | 28 | 5 | 35 | 12 |
| 144 | P_208 | P01 | 22174 | 17 | 38 | 0 | 68 | 0 | 2 | 35 | 9 | 0 |
| 145 | P_210 | P01 | 15575 | 0 | 2 | 1 | 54 | 0 | 1 | 0 | 440 | 0 |

FIG. 12 (cont.)

Table 5 (cont.)

| | A | B | C | AZ | BA | BB | BC | BD | BE | BF | BG | BH |
|---|---|---|---|---|---|---|---|---|---|---|---|---|
| 146 | P_216 | P01 | 12337 | 0 | 1 | 0 | 94 | 0 | 2 | 3 | 677 | 12 |
| 147 | P_218 | P01 | 10475 | 0 | 11 | 0 | 17 | 0 | 0 | 3 | 1569 | 3 |
| 148 | P_219 | P01 | 12572 | 2 | 13 | 5 | 0 | 29 | 2 | 0 | 377 | 11 |
| 149 | P_224 | P01 | 27758 | 1 | 11 | 1 | 18 | 5 | 1 | 0 | 2642 | 4 |
| 150 | P_226 | P03 | 14662 | 1 | 1 | 0 | 1 | 0 | 0 | 0 | 229 | 0 |
| 151 | P_228 | P03 | 18702 | 1 | 31 | 0 | 0 | 2 | 0 | 2 | 3134 | 22 |
| 152 | P_233 | P01 | 17047 | 0 | 7 | 1 | 2 | 1 | 1 | 0 | 94 | 787 |
| 153 | P_248 | P01 | 20116 | 3 | 24 | 3 | 1 | 9 | 2 | 1 | 377 | 0 |
| 154 | P_8C08 | P01 | 18642 | 12 | 35 | 0 | 0 | 33 | 44 | 42 | 107 | 184 |
| 155 | P_8C19 | P01 | 13480 | 3 | 19 | 11 | 0 | 1 | 5 | 1 | 7 | 9 |
| 156 | P_8C23 | P01 | 45443 | 2512 | 283 | 73 | 96 | 140 | 29 | 5 | 286 | 0 |

FIG. 12 (cont.)

Table 5 (cont.)

| | A | B | C | BI | BJ | BK | BL | BM | BN | BO |
|---|---|---|---|---|---|---|---|---|---|---|
| | Eog | health_state | Total Reads | G_Porphyromonadaceae_NL_BS_UL_SP_OOT-071 | G_Porphyromonadaceae_NL_BS_UL_SP_OOT-217 | G_Porphyromonadaceae_NL_BS_UL_SP_OOT-821 | G_Porphyromonadaceae_NL_BS_UL_SP_OOT-124 | G_Porphyromonadaceae_NL_BS_UL_SP_OOT-356 | G_Porphyromonadaceae_NL_BS_UL_SP_OOT-367 | G_Porphyromonadaceae_NL_BS_UL_SP_OOT-028 |
| 2 | G_7 | Gingivitis | 12132 | 36 | 3 | 1 | 3 | 0 | 0 | 4 |
| 3 | G_8 | Gingivitis | 10631 | 42 | 5 | 0 | 4 | 0 | 1 | 23 |
| 4 | G_9 | Gingivitis | 26790 | 389 | 2 | 0 | 0 | 13 | 1 | 331 |
| 5 | G_12 | Gingivitis | 15863 | 64 | 4 | 0 | 0 | 0 | 0 | 20 |
| 6 | G_13 | Gingivitis | 9138 | 261 | 2 | 1 | 1 | 0 | 0 | 162 |
| 7 | G_18 | Gingivitis | 28089 | 209 | 435 | 234 | 145 | 371 | 4 | 165 |
| 8 | G_22 | Gingivitis | 84780 | 402 | 1020 | 562 | 269 | 96 | 3 | 380 |
| 9 | G_30 | Gingivitis | 19833 | 205 | 7 | 1 | 17 | 9 | 5 | 136 |
| 10 | G_35 | Gingivitis | 38067 | 71 | 0 | 0 | 19 | 2 | 0 | 68 |
| 11 | G_40 | Gingivitis | 11406 | 325 | 0 | 0 | 325 | 40 | 2 | 482 |
| 12 | G_42 | Gingivitis | 11988 | 0 | 1 | 0 | 0 | 0 | 0 | 0 |
| 13 | G_52 | Gingivitis | 45501 | 174 | 54 | 2 | 2 | 71 | 4 | 124 |
| 14 | G_62 | Gingivitis | 9172 | 2 | 0 | 0 | 1 | 4 | 0 | 1 |
| 15 | G_63 | Gingivitis | 5611 | 18 | 26 | 0 | 0 | 3 | 0 | 9 |
| 16 | G_64 | Gingivitis | 7178 | 77 | 3 | 0 | 13 | 30 | 3 | 8 |
| 17 | G_65 | Gingivitis | 5338 | 110 | 314 | 0 | 0 | 8 | 2 | 78 |

FIG. 12 (cont.)

Table 5 (cont.)

| | A | B | C | BI | BJ | BK | BL | BM | BN | BO |
|---|---|---|---|---|---|---|---|---|---|---|
| 18 | G_72 | Gingivitis | 61483 | 50 | 1 | 0 | 1 | 1 | 0 | 29 |
| 19 | G_81 | Gingivitis | 8859 | 31 | 1 | 0 | 0 | 1 | 0 | 5 |
| 20 | G_86 | Gingivitis | 54864 | 2 | 5 | 0 | 6 | 34 | 0 | 1 |
| 21 | G_96 | Gingivitis | 59745 | 597 | 0 | 16 | 249 | 2 | 34 | 969 |
| 22 | G_98 | Gingivitis | 17911 | 1 | 2 | 0 | 0 | 2 | 0 | 6 |
| 23 | G_101 | Gingivitis | 12879 | 3 | 0 | 0 | 0 | 0 | 1 | 2 |
| 24 | G_113 | Gingivitis | 18818 | 140 | 11 | 6 | 5 | 102 | 6 | 80 |
| 25 | G_117 | Gingivitis | 30819 | 439 | 144 | 36 | 164 | 223 | 5 | 19 |
| 26 | G_120 | Gingivitis | 22635 | 175 | 2 | 1 | 27 | 4 | 116 | 257 |
| 27 | G_122 | Gingivitis | 17505 | 62 | 14 | 0 | 7 | 11 | 0 | 80 |
| 28 | G_128 | Gingivitis | 12750 | 169 | 0 | 0 | 0 | 0 | 0 | 41 |
| 29 | G_132 | Gingivitis | 21222 | 79 | 238 | 0 | 5 | 7 | 1 | 364 |
| 30 | G_135 | Gingivitis | 39383 | 50 | 0 | 0 | 0 | 1 | 0 | 11 |
| 31 | G_138 | Gingivitis | 17129 | 110 | 2 | 0 | 0 | 2 | 0 | 60 |
| 32 | G_143 | Gingivitis | 48153 | 0 | 969 | 0 | 1 | 0 | 1 | 874 |
| 33 | G_148 | Gingivitis | 16887 | 0 | 0 | 0 | 1 | 0 | 0 | 13 |
| 34 | G_149 | Gingivitis | 29561 | 80 | 0 | 0 | 0 | 1 | 0 | 2 |
| 35 | G_153 | Gingivitis | 38102 | 7 | 5 | 0 | 0 | 24 | 0 | 19 |
| 36 | G_161 | Gingivitis | 14798 | 18 | 0 | 0 | 2 | 0 | 0 | 19 |
| 37 | G_165 | Gingivitis | 9811 | 252 | 2 | 0 | 20 | 0 | 0 | 145 |
| 38 | G_170 | Gingivitis | 39000 | 350 | 295 | 0 | 6 | 10 | 3 | 262 |
| 39 | G_172 | Gingivitis | 36943 | 2 | 1 | 0 | 113 | 0 | 0 | 121 |
| 40 | G_173 | Gingivitis | 57676 | 1569 | 777 | 2 | 34 | 0 | 1 | 385 |
| 41 | G_177 | Gingivitis | 36734 | 2 | 0 | 0 | 0 | 0 | 0 | 132 |
| 42 | G_184 | Gingivitis | 11140 | 1 | 0 | 0 | 0 | 96 | 0 | 0 |
| 43 | G_188 | Gingivitis | 9325 | 0 | 0 | 0 | 0 | 0 | 0 | 0 |
| 44 | G_197 | Gingivitis | 2895 | 5 | 5 | 20 | 0 | 0 | 0 | 2 |
| 45 | G_214 | Gingivitis | 12530 | 215 | 0 | 0 | 163 | 0 | 2 | 58 |
| 46 | G_232 | Gingivitis | 13682 | 468 | 0 | 0 | 214 | 0 | 4 | 52 |
| 47 | G_244 | Gingivitis | 13436 | 709 | 3 | 1322 | 7 | 10 | 3 | 281 |
| 48 | G_245 | Gingivitis | 29114 | 2293 | 0 | 1 | 13 | 27 | 0 | 111 |
| 49 | G_246 | Gingivitis | 37282 | 0 | 0 | 1 | 0 | 0 | 0 | 0 |

FIG. 12 (cont.)

Table 5 (cont.)

| | A | B | C | BI | BJ | BK | BL | BM | BN | BO |
|---|---|---|---|---|---|---|---|---|---|---|
| 50 | G_249 | Gingivitis | 19242 | 28 | 2 | 0 | 12 | 5 | 5 | 44 |
| 51 | G_CR54 | Gingivitis | 18211 | 10 | 2 | 0 | 3 | 6 | 44 | 76 |
| 52 | G_19 | Gingivitis | 34430 | 15 | 0 | 0 | 0 | 6 | 0 | 4 |
| 53 | H_38 | Health | 18024 | 0 | 1 | 0 | 0 | 0 | 0 | 2 |
| 54 | H_48 | Health | 9783 | 6 | 0 | 0 | 15 | 2 | 0 | 42 |
| 55 | H_53 | Health | 7751 | 8 | 0 | 0 | 2 | 0 | 2 | 14 |
| 56 | H_57 | Health | 37038 | 2 | 0 | 0 | 0 | 1 | 0 | 48 |
| 57 | H_58 | Health | 12089 | 1 | 0 | 0 | 4 | 1 | 0 | 6 |
| 58 | H_68 | Health | 10333 | 16 | 0 | 0 | 0 | 0 | 0 | 4 |
| 59 | H_73 | Health | 12578 | 1 | 2 | 0 | 0 | 1 | 0 | 9 |
| 60 | H_74 | Health | 47261 | 40 | 0 | 0 | 87 | 0 | 0 | 51 |
| 61 | H_78 | Health | 11932 | 39 | 6 | 0 | 3 | 19 | 0 | 10 |
| 62 | H_83 | Health | 22743 | 1 | 0 | 0 | 0 | 3 | 0 | 8 |
| 63 | H_89 | Health | 13540 | 0 | 0 | 1 | 1 | 0 | 0 | 1 |
| 64 | H_90 | Health | 16858 | 472 | 0 | 0 | 3 | 0 | 0 | 41 |
| 65 | H_94 | Health | 19898 | 116 | 3 | 23 | 11 | 23 | 3 | 32 |
| 66 | H_107 | Health | 13290 | 6 | 0 | 0 | 0 | 0 | 0 | 5 |
| 67 | H_108 | Health | 13826 | 10 | 0 | 0 | 3 | 0 | 0 | 48 |
| 68 | H_112 | Health | 29644 | 2 | 0 | 0 | 0 | 0 | 0 | 2 |
| 69 | H_114 | Health | 19304 | 281 | 65 | 1 | 38 | 1 | 11 | 107 |
| 70 | H_118 | Health | 26783 | 52 | 0 | 1 | 0 | 3 | 0 | 37 |
| 71 | H_137 | Health | 14686 | 4 | 0 | 0 | 1 | 0 | 0 | 3 |
| 72 | H_145 | Health | 14097 | 35 | 17 | 0 | 80 | 3 | 3 | 33 |
| 73 | H_346 | Health | 36780 | 1372 | 205 | 0 | 58 | 98 | 14 | 352 |
| 74 | H_354 | Health | 18025 | 18 | 0 | 9 | 0 | 0 | 0 | 3 |
| 75 | H_356 | Health | 13099 | 3 | 5 | 0 | 0 | 0 | 0 | 4 |
| 76 | H_162 | Health | 11571 | 29 | 4 | 0 | 1 | 4 | 0 | 66 |
| 77 | H_163 | Health | 18304 | 137 | 0 | 47 | 0 | 37 | 0 | 133 |
| 78 | H_164 | Health | 36129 | 38 | 6 | 0 | 40 | 8 | 3 | 238 |
| 79 | H_165 | Health | 24974 | 16 | 0 | 1 | 30 | 143 | 3 | 35 |
| 80 | H_166 | Health | 28147 | 1 | 0 | 0 | 0 | 1 | 0 | 0 |
| 81 | H_168 | Health | 10291 | 1 | 0 | 0 | 1 | 0 | 0 | 1 |

FIG. 12 (cont.)

Table 5 (cont.)

| | A | B | C | BJ | BK | BL | BM | BN | BO |
|---|---|---|---|---|---|---|---|---|---|
| 82 | H_171 | Health | 14888 | 20 | 1 | 0 | 37 | 19 | 1 | 34 |
| 83 | H_174 | Health | 10137 | 1 | 0 | 0 | 0 | 0 | 0 | 1 |
| 84 | H_175 | Health | 9520 | 57 | 0 | 0 | 0 | 0 | 0 | 4 |
| 85 | H_178 | Health | 73306 | 824 | 295 | 41 | 707 | 17 | 14 | 970 |
| 86 | H_186 | Health | 12382 | 35 | 3 | 0 | 28 | 36 | 4 | 30 |
| 87 | H_188 | Health | 25677 | 223 | 0 | 0 | 12 | 7 | 1 | 10 |
| 88 | H_200 | Health | 13277 | 130 | 0 | 0 | 0 | 0 | 0 | 48 |
| 89 | H_203 | Health | 7317 | 5 | 0 | 0 | 5 | 1 | 0 | 1 |
| 90 | H_211 | Health | 4740 | 0 | 14 | 0 | 0 | 15 | 0 | 2 |
| 91 | H_217 | Health | 10064 | 6 | 0 | 5 | 14 | 0 | 0 | 3 |
| 92 | H_220 | Health | 18191 | 105 | 0 | 0 | 0 | 0 | 0 | 0 |
| 93 | H_221 | Health | 26808 | 82 | 0 | 0 | 97 | 86 | 1 | 145 |
| 94 | H_222 | Health | 24301 | 96 | 6 | 0 | 5 | 0 | 0 | 38 |
| 95 | H_223 | Health | 7018 | 12 | 6 | 0 | 1 | 7 | 1 | 16 |
| 96 | H_225 | Health | 14680 | 10 | 0 | 0 | 15 | 0 | 0 | 1 |
| 97 | H_234 | Health | 13232 | 0 | 0 | 0 | 0 | 0 | 0 | 1 |
| 98 | H_235 | Health | 14596 | 1 | 6 | 1 | 0 | 0 | 0 | 4 |
| 99 | H_236 | Health | 9200 | 1 | 0 | 0 | 0 | 1 | 0 | 1 |
| 100 | H_237 | Health | 20352 | 6 | 0 | 0 | 0 | 1 | 0 | 4 |
| 101 | H_238 | Health | 11638 | 71 | 6 | 48 | 7 | 52 | 0 | 28 |
| 102 | H_239 | Health | 17487 | 923 | 0 | 0 | 24 | 5 | 0 | 146 |
| 103 | H_240 | Health | 14649 | 7 | 3 | 34 | 4 | 0 | 0 | 5 |
| 104 | H_241 | Health | 32149 | 795 | 9 | 473 | 2 | 14 | 0 | 4 |
| 105 | P_1 | PD1 | 15621 | 86 | 1 | 10 | 30 | 183 | 21 | 39 |
| 106 | P_5 | PD1 | 55958 | 87 | 8 | 0 | 2 | 0 | 1 | 532 |
| 107 | P_20 | PD1 | 14817 | 38 | 827 | 7 | 4 | 0 | 0 | 37 |
| 108 | P_21 | PD1 | 11750 | 4 | 2 | 2 | 2 | 2 | 0 | 5 |
| 109 | P_24 | PD1 | 12786 | 66 | 9 | 10 | 9 | 8 | 13 | 235 |
| 110 | P_25 | PD1 | 22323 | 227 | 0 | 0 | 3 | 0 | 0 | 2 |
| 111 | P_27 | PD1 | 64090 | 3280 | 1664 | 21 | 2 | 4 | 7 | 224 |
| 112 | P_46 | PD1 | 56396 | 689 | 30 | 335 | 34 | 83 | 0 | 526 |
| 113 | P_49 | PD1 | 33560 | 70 | 279 | 0 | 0 | 0 | 0 | 158 |

FIG. 12 (cont.)

Table 5 (cont.)

| | A | B | C | BI | BJ | BK | BL | BM | BN | BO |
|---|---|---|---|---|---|---|---|---|---|---|
| 114 | P_53 | PO1 | 37973 | 949 | 672 | 0 | 35 | 52 | 64 | 857 |
| 115 | P_56 | PO1 | 29103 | 1148 | 13 | 0 | 5 | 2 | 1 | 185 |
| 116 | P_70 | PO1 | 17344 | 108 | 1 | 0 | 3 | 0 | 0 | 87 |
| 117 | P_79 | PO1 | 10858 | 122 | 0 | 0 | 0 | 0 | 0 | 90 |
| 118 | P_83 | PO1 | 46961 | 1512 | 1559 | 0 | 0 | 0 | 0 | 535 |
| 119 | P_84 | PO1 | 22943 | 331 | 529 | 28 | 118 | 1 | 10 | 352 |
| 120 | P_86 | PO1 | 8619 | 13 | 36 | 3 | 0 | 0 | 0 | 14 |
| 121 | P_87 | PO1 | 13135 | 331 | 1123 | 0 | 5 | 1 | 116 | 76 |
| 122 | P_100 | PO1 | 19179 | 530 | 1061 | 0 | 13 | 0 | 59 | 520 |
| 123 | P_102 | PO1 | 13541 | 126 | 2 | 0 | 12 | 1 | 2 | 298 |
| 124 | P_103 | PO1 | 20363 | 817 | 1 | 0 | 0 | 0 | 1 | 1391 |
| 125 | P_106 | PO1 | 50812 | 413 | 6 | 1 | 0 | 1 | 4 | 674 |
| 126 | P_109 | PO1 | 31960 | 362 | 37 | 1 | 54 | 25 | 3 | 165 |
| 127 | P_113 | PO1 | 18442 | 33 | 0 | 0 | 0 | 0 | 0 | 376 |
| 128 | P_123 | PO1 | 18887 | 92 | 1 | 0 | 0 | 0 | 0 | 5 |
| 129 | P_131 | PO1 | 17951 | 28 | 0 | 4 | 9 | 0 | 1 | 4 |
| 130 | P_134 | PO1 | 50888 | 234 | 84 | 5 | 12 | 0 | 0 | 39 |
| 131 | P_136 | PO1 | 38223 | 143 | 0 | 0 | 0 | 0 | 1 | 29 |
| 132 | P_140 | PO1 | 16945 | 12 | 22 | 0 | 3 | 0 | 330 | 7 |
| 133 | P_147 | PO1 | 51087 | 70 | 0 | 1 | 1 | 3 | 0 | 14 |
| 134 | P_155 | PO1 | 38311 | 3 | 0 | 1 | 0 | 0 | 8 | 4 |
| 135 | P_163 | PO1 | 18347 | 68 | 2 | 7 | 5 | 0 | 16 | 137 |
| 136 | P_167 | PO1 | 19346 | 244 | 155 | 0 | 4 | 8 | 0 | 115 |
| 137 | P_190 | PO1 | 15581 | 556 | 5 | 3 | 1 | 2 | 0 | 1 |
| 138 | P_191 | PO1 | 14509 | 341 | 30 | 0 | 54 | 3 | 4 | 35 |
| 139 | P_192 | PO1 | 38342 | 0 | 0 | 0 | 0 | 0 | 0 | 469 |
| 140 | P_195 | PO1 | 38866 | 290 | 1 | 0 | 126 | 2 | 3 | 877 |
| 141 | P_196 | PO1 | 48271 | 48 | 20 | 0 | 0 | 0 | 0 | 108 |
| 142 | P_205 | PO1 | 10354 | 65 | 1 | 10 | 8 | 72 | 0 | 189 |
| 143 | P_206 | PO1 | 16158 | 60 | 20 | 0 | 6 | 2 | 7 | 47 |
| 144 | P_208 | PO1 | 22174 | 18 | 0 | 0 | 7 | 0 | 0 | 196 |
| 145 | P_210 | PO1 | 15575 | 14 | 12 | 0 | 2 | 10 | 1 | 124 |

FIG. 12 (cont.)

Table 5 (cont.)

| | A | B | C | SI | SJ | SK | SL | SM | SN | SO |
|---|---|---|---|---|---|---|---|---|---|---|
| 146 | P_216 | P01 | 13237 | 11 | 5 | 0 | 0 | 11 | 0 | 129 |
| 147 | P_218 | P01 | 10475 | 737 | 107 | 0 | 4 | 0 | 18 | 151 |
| 148 | P_219 | P01 | 13572 | 86 | 0 | 41 | 51 | 7 | 0 | 453 |
| 149 | P_224 | P01 | 27758 | 493 | 161 | 13 | 1 | 18 | 0 | 268 |
| 150 | P_226 | P01 | 14662 | 174 | 0 | 0 | 0 | 2 | 0 | 66 |
| 151 | P_228 | P01 | 18702 | 280 | 101 | 0 | 34 | 6 | 7 | 295 |
| 152 | P_233 | P01 | 17047 | 28 | 0 | 0 | 20 | 1 | 80 | 178 |
| 153 | P_248 | P01 | 20118 | 684 | 0 | 0 | 13 | 0 | 4 | 326 |
| 154 | P_BC09 | P01 | 18642 | 100 | 8 | 15 | 22 | 1 | 1 | 151 |
| 155 | P_BC19 | P01 | 14480 | 8 | 0 | 2 | 28 | 0 | 2 | 60 |
| 156 | P_BC23 | P01 | 45449 | 45 | 0 | 0 | 6 | 1 | 0 | 61 |

FIG. 12 (cont.)

Table 5 (cont.)

| Gog | Health state | Total Reads | o__Peptostreptococcaceae_XI_[G-6]_sp_OT-107 | o__Peptostreptococcaceae_XI_[G-4]_sp_OT-106 | o__Peptostreptococcaceae_XI_[G-2]_sp_OT-091 | o__Peptostreptococcaceae_sp_OT-106 | o__Porphyromonadaceae_[G-1]_sp_OT-279 | o__Porphyromonas_catoniae_OT-283 | o__Porphyromonas_gulae_OT-662 |
|---|---|---|---|---|---|---|---|---|---|
| G_7 | Gingivitis | 12332 | 4 | 1 | 4 | 34 | 1 | 0 | 96 |
| G_8 | Gingivitis | 10631 | 8 | 4 | 48 | 256 | 9 | 155 | 19 |
| G_9 | Gingivitis | 25790 | 17 | 193 | 85 | 518 | 1 | 69 | 669 |
| G_12 | Gingivitis | 15883 | 0 | 1 | 29 | 23 | 73 | 1 | 1770 |
| G_14 | Gingivitis | 9138 | 0 | 54 | 0 | 100 | 5 | 8 | 230 |
| G_18 | Gingivitis | 38088 | 0 | 7 | 6 | 195 | 45 | 479 | 1299 |
| G_22 | Gingivitis | 84760 | 27 | 40 | 179 | 393 | 674 | 232 | 4485 |
| G_30 | Gingivitis | 19824 | 93 | 43 | 61 | 926 | 19 | 434 | 1436 |
| G_35 | Gingivitis | 38047 | 9 | 48 | 19 | 43 | 14 | 2 | 924 |
| G_40 | Gingivitis | 15406 | 0 | 0 | 2 | 2120 | 68 | 0 | 23 |
| G_42 | Gingivitis | 11938 | 0 | 3 | 0 | 375 | 0 | 0 | 959 |
| G_52 | Gingivitis | 40561 | 0 | 1 | 0 | 3 | 0 | 0 | 62 |
| G_62 | Gingivitis | 9802 | 0 | 0 | 0 | 0 | 1 | 0 | 12 |
| G_63 | Gingivitis | 5611 | 0 | 1 | 4 | 0 | 2 | 0 | 36 |
| G_64 | Gingivitis | 7175 | 3 | 11 | 0 | 0 | 49 | 0 | 184 |
| G_65 | Gingivitis | 6306 | 4 | 103 | 0 | 38 | 0 | 5 | 139 |

FIG. 12 (cont.)

Table 5 (cont.)

| | A | B | C | 8P | 8Q | 8R | 8S | 8T | 8U | 8V |
|---|---|---|---|---|---|---|---|---|---|---|
| 18 | G_72 | Gingivitis | 63483 | 0 | 3 | 0 | 946 | 177 | 156 | 3269 |
| 19 | G_81 | Gingivitis | 8859 | 0 | 1 | 2 | 47 | 8 | 2 | 141 |
| 20 | G_86 | Gingivitis | 54894 | 0 | 0 | 1 | 2 | 4 | 1 | 11 |
| 21 | G_96 | Gingivitis | 59245 | 528 | 3824 | 0 | 51 | 109 | 3 | 4209 |
| 22 | G_98 | Gingivitis | 17911 | 0 | 4 | 5 | 2 | 32 | 0 | 6 |
| 23 | G_103 | Gingivitis | 12876 | 0 | 8 | 24 | 6 | 1 | 0 | 9 |
| 24 | G_113 | Gingivitis | 16818 | 14 | 16 | 33 | 4 | 41 | 1 | 237 |
| 25 | G_117 | Gingivitis | 30819 | 0 | 42 | 432 | 37 | 140 | 0 | 1628 |
| 26 | G_120 | Gingivitis | 22655 | 28 | 57 | 1348 | 5471 | 2 | 211 | 604 |
| 27 | G_122 | Gingivitis | 17505 | 2 | 7 | 11 | 123 | 57 | 33 | 533 |
| 28 | G_128 | Gingivitis | 12750 | 0 | 0 | 3 | 1 | 237 | 0 | 396 |
| 29 | G_132 | Gingivitis | 21322 | 1 | 75 | 3859 | 123 | 0 | 11 | 5 |
| 30 | G_136 | Gingivitis | 16383 | 0 | 0 | 0 | 21 | 0 | 0 | 13 |
| 31 | G_139 | Gingivitis | 17129 | 0 | 0 | 0 | 2130 | 23 | 0 | 1165 |
| 32 | G_143 | Gingivitis | 46153 | 0 | 360 | 13 | 525 | 0 | 130 | 389 |
| 33 | G_148 | Gingivitis | 16887 | 0 | 0 | 2 | 39 | 871 | 11 | 1361 |
| 34 | G_149 | Gingivitis | 29961 | 0 | 1126 | 3 | 5783 | 0 | 0 | 11 |
| 35 | G_153 | Gingivitis | 18102 | 1 | 0 | 0 | 0 | 4 | 0 | 167 |
| 36 | G_161 | Gingivitis | 14798 | 0 | 0 | 0 | 0 | 2 | 0 | 146 |
| 37 | G_169 | Gingivitis | 3831 | 21 | 102 | 49 | 98 | 26 | 41 | 15 |
| 38 | G_170 | Gingivitis | 49000 | 32 | 329 | 737 | 46 | 1 | 3 | 1048 |
| 39 | G_172 | Gingivitis | 36943 | 3 | 72 | 568 | 261 | 68 | 294 | 3363 |
| 40 | G_173 | Gingivitis | 57876 | 0 | 0 | 0 | 28 | 1 | 0 | 85 |
| 41 | G_177 | Gingivitis | 36744 | 0 | 1 | 2 | 1 | 115 | 1 | 100 |
| 42 | G_184 | Gingivitis | 11140 | 0 | 0 | 0 | 0 | 245 | 0 | 5 |
| 43 | G_188 | Gingivitis | 9325 | 0 | 0 | 2 | 0 | 0 | 0 | 482 |
| 44 | G_197 | Gingivitis | 3808 | 0 | 0 | 22 | 191 | 2 | 77 | 144 |
| 45 | G_214 | Gingivitis | 12530 | 12 | 3 | 1 | 51 | 7 | 156 | 357 |
| 46 | G_232 | Gingivitis | 13682 | 0 | 0 | 10 | 105 | 29 | 12 | 285 |
| 47 | G_244 | Gingivitis | 13446 | 1 | 11 | 0 | 133 | 0 | 0 | 21 |
| 48 | G_245 | Gingivitis | 29114 | 0 | 0 | 10 | 28 | 141 | 0 | 156 |
| 49 | G_248 | Gingivitis | 37382 | 0 | 0 | 1 | 0 | 2 | 0 | 2 |

FIG. 12 (cont.)

Table 5 (cont.)

| | A | B | C | BP | BQ | BR | BS | BT | BU | BV |
|---|---|---|---|---|---|---|---|---|---|---|
| 50 | G_249 | Gingivitis | 19242 | 0 | 4 | 35 | 106 | 112 | 22 | 844 |
| 51 | G_C854 | Gingivitis | 16211 | 0 | 383 | 1493 | 536 | 0 | 4 | 11 |
| 52 | G_19 | Gingivitis | 34490 | 17 | 70 | 578 | 5794 | 1 | 136 | 74 |
| 53 | H_38 | Health | 16024 | 0 | 0 | 4 | 3 | 2 | 1 | 7 |
| 54 | H_46 | Health | 9790 | 1 | 7 | 1 | 8 | 78 | 0 | 27 |
| 55 | H_53 | Health | 7751 | 0 | 0 | 15 | 1 | 52 | 12 | 358 |
| 56 | H_57 | Health | 37038 | 0 | 0 | 0 | 2 | 112 | 0 | 51 |
| 57 | H_58 | Health | 12089 | 0 | 1 | 0 | 11 | 92 | 1 | 117 |
| 58 | H_68 | Health | 10333 | 0 | 0 | 0 | 4 | 1 | 0 | 595 |
| 59 | H_73 | Health | 12578 | 0 | 0 | 5 | 3 | 3 | 2 | 89 |
| 60 | H_74 | Health | 47361 | 0 | 1 | 2 | 51 | 69 | 237 | 4 |
| 61 | H_78 | Health | 11932 | 1 | 3 | 10 | 23 | 1 | 0 | 55 |
| 62 | H_83 | Health | 22743 | 0 | 0 | 1 | 2 | 2 | 2 | 164 |
| 63 | H_89 | Health | 13540 | 0 | 1 | 0 | 2 | 3 | 3 | 17 |
| 64 | H_93 | Health | 16858 | 0 | 16 | 0 | 22 | 1 | 12 | 373 |
| 65 | H_94 | Health | 18838 | 10 | 4 | 16 | 30 | 48 | 13 | 2606 |
| 66 | H_107 | Health | 13230 | 0 | 0 | 30 | 1 | 1 | 1 | 377 |
| 67 | H_108 | Health | 13826 | 0 | 1 | 28 | 1154 | 0 | 5 | 782 |
| 68 | H_112 | Health | 29564 | 0 | 0 | 0 | 1 | 38 | 0 | 168 |
| 69 | H_114 | Health | 13104 | 17 | 6 | 1 | 0 | 1 | 4 | 209 |
| 70 | H_118 | Health | 26783 | 0 | 3 | 7 | 467 | 1 | 96 | 571 |
| 71 | H_137 | Health | 14686 | 1 | 11 | 4 | 38 | 8 | 0 | 213 |
| 72 | H_148 | Health | 14097 | 2 | 10 | 2 | 3 | 9 | 81 | 799 |
| 73 | H_146 | Health | 36760 | 0 | 0 | 3 | 0 | 4 | 1 | 8 |
| 74 | H_154 | Health | 18025 | 0 | 0 | 0 | 22 | 26 | 0 | 3 |
| 75 | H_156 | Health | 13899 | 0 | 2 | 0 | 1 | 27 | 0 | 7 |
| 76 | H_162 | Health | 11571 | 1 | 1 | 1 | 1 | 14 | 0 | 6 |
| 77 | H_163 | Health | 18304 | 11 | 81 | 2 | 164 | 0 | 35 | 1287 |
| 78 | H_164 | Health | 36129 | 0 | 114 | 0 | 20 | 251 | 0 | 85 |
| 79 | H_165 | Health | 24974 | 12 | 1 | 28 | 44 | 0 | 82 | 14 |
| 80 | H_166 | Health | 28147 | 0 | 0 | 0 | 0 | 0 | 0 | 1 |
| 81 | H_168 | Health | 10291 | 0 | 4 | 8 | 6 | 0 | 0 | 1 |

FIG. 12 (cont.)

Table 5 (cont.)

| | A | B | C | BP | BQ | BR | BS | BT | BU | BV |
|---|---|---|---|---|---|---|---|---|---|---|
| 82 | H_171 | Health | 14889 | 0 | 2 | 0 | 0 | 24 | 0 | 140 |
| 83 | H_174 | Health | 10327 | 0 | 1 | 0 | 7 | 3 | 0 | 3 |
| 84 | H_175 | Health | 9530 | 0 | 0 | 0 | 1 | 661 | 1 | 5 |
| 85 | H_178 | Health | 73106 | 3 | 45 | 0 | 342 | 13 | 147 | 1485 |
| 86 | H_186 | Health | 12382 | 0 | 0 | 0 | 0 | 0 | 0 | 18 |
| 87 | H_189 | Health | 25877 | 0 | 0 | 2 | 143 | 1894 | 377 | 1 |
| 88 | H_200 | Health | 13277 | 0 | 4 | 0 | 18 | 0 | 0 | 8 |
| 89 | H_203 | Health | 7317 | 0 | 0 | 2 | 0 | 0 | 0 | 3 |
| 90 | H_211 | Health | 4740 | 0 | 0 | 1 | 0 | 2 | 0 | 6 |
| 91 | H_217 | Health | 10864 | 0 | 3 | 2 | 18 | 56 | 0 | 156 |
| 92 | H_220 | Health | 18191 | 0 | 0 | 0 | 140 | 0 | 0 | 1494 |
| 93 | H_221 | Health | 26808 | 0 | 0 | 0 | 32 | 18 | 1 | 82 |
| 94 | H_222 | Health | 34761 | 0 | 28 | 0 | 5082 | 4 | 132 | 83 |
| 95 | H_223 | Health | 7918 | 0 | 1 | 0 | 0 | 7 | 1 | 13 |
| 96 | H_226 | Health | 14460 | 0 | 0 | 0 | 0 | 0 | 0 | 497 |
| 97 | H_234 | Health | 10232 | 0 | 0 | 4 | 2 | 148 | 0 | 49 |
| 98 | H_235 | Health | 14596 | 0 | 2 | 7 | 7 | 10 | 0 | 26 |
| 99 | H_236 | Health | 9200 | 0 | 0 | 0 | 0 | 658 | 0 | 3 |
| 100 | H_237 | Health | 20933 | 0 | 0 | 0 | 0 | 3 | 0 | 2 |
| 101 | H_238 | Health | 11638 | 0 | 0 | 0 | 4 | 12 | 0 | 187 |
| 102 | H_239 | Health | 17487 | 0 | 0 | 0 | 48 | 128 | 0 | 168 |
| 103 | H_240 | Health | 14649 | 0 | 0 | 0 | 2 | 0 | 1 | 3 |
| 104 | H_241 | Health | 32349 | 0 | 0 | 3 | 13 | 10 | 6 | 39 |
| 105 | P_1 | PD1 | 15621 | 1 | 62 | 497 | 14 | 49 | 2 | 82 |
| 106 | P_5 | PD1 | 55958 | 2 | 170 | 283 | 4982 | 1 | 1168 | 114 |
| 107 | P_20 | PD1 | 14617 | 5 | 55 | 1543 | 917 | 5 | 21 | 34 |
| 108 | P_21 | PD1 | 11750 | 0 | 2 | 0 | 175 | 3 | 30 | 172 |
| 109 | P_24 | PD1 | 12785 | 1 | 72 | 1876 | 25 | 4 | 13 | 31 |
| 110 | P_25 | PD1 | 23123 | 0 | 1 | 5 | 328 | 4 | 33 | 842 |
| 111 | P_27 | PD1 | 64090 | 18 | 453 | 318 | 315 | 0 | 56 | 953 |
| 112 | P_46 | PD1 | 56398 | 21 | 85 | 5 | 189 | 202 | 455 | 3829 |
| 113 | P_48 | PD1 | 33560 | 15 | 19 | 45 | 31 | 37 | 21 | 829 |

FIG. 12 (cont.)

Table 5 (cont.)

| | A | B | C | BP | BQ | BR | BS | BT | BU | BV |
|---|---|---|---|---|---|---|---|---|---|---|
| 114 | P_53 | PD1 | 37871 | 301 | 33 | 775 | 192 | 73 | 241 | 838 |
| 115 | P_56 | PD1 | 23103 | 112 | 3 | 135 | 70 | 1 | 74 | 2911 |
| 116 | P_75 | PD1 | 17344 | 14 | 27 | 196 | 74 | 3 | 253 | 3208 |
| 117 | P_79 | PD1 | 10658 | 7 | 50 | 2 | 489 | 0 | 30 | 876 |
| 118 | P_80 | PD1 | 46951 | 25 | 615 | 1896 | 81 | 180 | 8 | 1 |
| 119 | P_84 | PD1 | 22949 | 19 | 136 | 2054 | 303 | 7 | 221 | 888 |
| 120 | P_85 | PD1 | 8619 | 21 | 26 | 7 | 346 | 10 | 37 | 16 |
| 121 | P_87 | PD1 | 13155 | 4 | 59 | 1606 | 45 | 5 | 27 | 84 |
| 122 | P_100 | PD1 | 19179 | 6 | 114 | 648 | 58 | 70 | 2 | 23 |
| 123 | P_102 | PD1 | 13541 | 4 | 385 | 1841 | 41 | 9 | 19 | 151 |
| 124 | P_105 | PD1 | 25163 | 0 | 1 | 4 | 0 | 24 | 0 | 498 |
| 125 | P_106 | PD1 | 56812 | 212 | 454 | 4836 | 1878 | 14 | 29 | 468 |
| 126 | P_108 | PD1 | 31560 | 85 | 84 | 8 | 99 | 19 | 6 | 2204 |
| 127 | P_111 | PD1 | 16442 | 0 | 30 | 682 | 393 | 1 | 0 | 391 |
| 128 | P_123 | PD1 | 16867 | 8 | 1133 | 0 | 3322 | 1 | 97 | 9 |
| 129 | P_131 | PD1 | 17953 | 22 | 30 | 267 | 399 | 18 | 3 | 2211 |
| 130 | P_134 | PD1 | 50568 | 39 | 24 | 18 | 9 | 1022 | 10 | 544 |
| 131 | P_138 | PD1 | 36223 | 13 | 12 | 65 | 733 | 51 | 108 | 1987 |
| 132 | P_140 | PD1 | 18345 | 1 | 274 | 2083 | 376 | 1 | 10 | 28 |
| 133 | P_147 | PD1 | 61657 | 0 | 6 | 6 | 183 | 459 | 1 | 1133 |
| 134 | P_153 | PD1 | 38311 | 2 | 5 | 5 | 4771 | 1 | 6 | 1062 |
| 135 | P_181 | PD1 | 18947 | 20 | 355 | 157 | 4525 | 0 | 145 | 57 |
| 136 | P_187 | PD1 | 19346 | 3 | 864 | 843 | 491 | 8 | 39 | 1 |
| 137 | P_190 | PD1 | 15381 | 0 | 1 | 0 | 1373 | 0 | 4 | 194 |
| 138 | P_191 | PD1 | 14529 | 0 | 38 | 143 | 0 | 5 | 1 | 875 |
| 139 | P_192 | PD1 | 39342 | 0 | 0 | 1 | 178 | 802 | 0 | 8 |
| 140 | P_195 | PD1 | 38666 | 88 | 156 | 1 | 404 | 1 | 4 | 96 |
| 141 | P_196 | PD1 | 48271 | 0 | 0 | 8 | 5 | 390 | 0 | 3 |
| 142 | P_205 | PD1 | 10354 | 26 | 427 | 195 | 529 | 1 | 11 | 35 |
| 143 | P_206 | PD1 | 16158 | 35 | 9 | 18 | 149 | 157 | 0 | 654 |
| 144 | P_208 | PD1 | 22174 | 15 | 70 | 208 | 3439 | 3 | 134 | 101 |
| 145 | P_210 | PD1 | 15575 | 0 | 154 | 968 | 550 | 3 | 14 | 34 |

FIG. 12 (cont.)

Table 5 (cont.)

| | A | B | C | BP | BQ | BR | BS | BT | BU | BV |
|---|---|---|---|---|---|---|---|---|---|---|
| 146 | P_216 | P01 | 12237 | 0 | 841 | 909 | 584 | 7 | 20 | 47 |
| 147 | P_218 | P01 | 10475 | 7 | 125 | 7 | 55 | 0 | 0 | 1 |
| 148 | P_219 | P01 | 12577 | 76 | 484 | 396 | 74 | 9 | 8 | 51 |
| 149 | P_224 | P01 | 27758 | 2 | 605 | 1373 | 68 | 1 | 1 | 85 |
| 150 | P_226 | P01 | 14682 | 3 | 317 | 23 | 625 | 6 | 1 | 23 |
| 151 | P_228 | P01 | 18702 | 68 | 170 | 1260 | 36 | 4 | 5 | 618 |
| 152 | P_233 | P01 | 17047 | 72 | 529 | 1487 | 815 | 24 | 211 | 220 |
| 153 | P_248 | P01 | 20116 | 13 | 91 | 5 | 51 | 31 | 0 | 12 |
| 154 | P_BC09 | P01 | 18682 | 66 | 71 | 749 | 132 | 26 | 92 | 689 |
| 155 | P_BC19 | P01 | 14480 | 18 | 497 | 324 | 32 | 26 | 17 | 430 |
| 156 | P_BC21 | P01 | 45443 | 0 | 0 | 8 | 12 | 0 | 5 | 165 |

FIG. 12 (cont.)

Table 5 (cont.)

| A | B | C | BW | BX | BY | BZ | CA | CB | CC | CD | CE |
|---|---|---|---|---|---|---|---|---|---|---|---|
| | Dx | Health state | Total Reads | g_Porphyromonas_Bulleidi_A_CGT-072 | g_Porphyromonas_macacae_CGT-196 | g_Porphyromonas_sp._CGT-193 | g_Porphyromonas_sp._CGT-161 | g_Prevotella_sp._CGT-195 | g_Prevotella_sp._CGT-262 | g_Prevotella_sp._CGT-298 | g_Porphyromonas_sp._CGT-236 |
| G_7 | Gingivitis | 12332 | 3 | 3 | 12 | 65 | 0 | 0 | 18 | 2 | 32 |
| G_8 | Gingivitis | 10831 | 3 | 54 | 0 | 71 | 0 | 0 | 0 | 8 | 5 |
| G_9 | Gingivitis | 25790 | 1721 | 17 | 0 | 17 | 0 | 79 | 0 | 14 | 85 |
| G_12 | Gingivitis | 15863 | 0 | 0 | 0 | 133 | 10 | 0 | 0 | 0 | 0 |
| G_14 | Gingivitis | 9138 | 4 | 0 | 0 | 7 | 0 | 0 | 0 | 0 | 2 |
| G_18 | Gingivitis | 28089 | 8 | 401 | 0 | 52 | 0 | 47 | 42 | 16 | 28 |
| G_22 | Gingivitis | 84760 | 56 | 1430 | 143 | 358 | 33 | 113 | 192 | 124 | 131 |
| G_30 | Gingivitis | 19824 | 157 | 481 | 186 | 258 | 0 | 9 | 0 | 7 | 217 |
| G_35 | Gingivitis | 38047 | 348 | 5 | 0 | 475 | 0 | 0 | 3 | 48 | 148 |
| G_40 | Gingivitis | 1E+05 | 29317 | 0 | 1 | 1016 | 0 | 0 | 0 | 774 | 0 |
| G_42 | Gingivitis | 11958 | 704 | 0 | 0 | 0 | 0 | 0 | 0 | 1 | 0 |
| G_52 | Gingivitis | 85501 | 579 | 0 | 4 | 508 | 7 | 0 | 18 | 83 | 58 |
| G_62 | Gingivitis | 9922 | 1 | 0 | 0 | 190 | 19 | 0 | 0 | 2 | 0 |
| G_63 | Gingivitis | 5611 | 27 | 0 | 2 | 0 | 1 | 1 | 4 | 1 | 7 |
| G_64 | Gingivitis | 7175 | 296 | 14 | 4 | 10 | 0 | 0 | 0 | 0 | 29 |
| G_65 | Gingivitis | 8306 | 0 | 0 | 0 | 1 | 0 | 2 | 0 | 0 | 4 |

FIG. 12 (cont.)

Table 5 (cont.)

| | A | B | C | BW | BX | BY | BZ | CA | CB | CC | CD | CE |
|---|---|---|---|---|---|---|---|---|---|---|---|---|
| 18 | G_72 | Gingivitis | 61483 | 9650 | 0 | 0 | 442 | 0 | 0 | 0 | 161 | 0 |
| 19 | G_81 | Gingivitis | 8889 | 2 | 2 | 0 | 60 | 0 | 0 | 8 | 29 | 13 |
| 20 | G_86 | Gingivitis | 54894 | 6 | 1 | 0 | 9 | 0 | 0 | 30 | 2 | 1 |
| 21 | G_96 | Gingivitis | 59245 | 345 | 0 | 0 | 14 | 0 | 0 | 0 | 0 | 39 |
| 22 | G_98 | Gingivitis | 17911 | 7 | 0 | 0 | 128 | 1 | 0 | 0 | 0 | 1 |
| 23 | G_101 | Gingivitis | 12876 | 3 | 0 | 1 | 0 | 0 | 0 | 2 | 0 | 0 |
| 24 | G_113 | Gingivitis | 18818 | 122 | 0 | 0 | 117 | 7 | 0 | 0 | 3 | 42 |
| 25 | G_117 | Gingivitis | 30819 | 18 | 2 | 0 | 43 | 0 | 1 | 47 | 16 | 136 |
| 26 | G_120 | Gingivitis | 22866 | 376 | 74 | 0 | 131 | 0 | 88 | 0 | 4 | 10 |
| 27 | G_122 | Gingivitis | 17505 | 1287 | 0 | 0 | 36 | 3 | 0 | 39 | 136 | 88 |
| 28 | G_128 | Gingivitis | 13750 | 9 | 0 | 0 | 322 | 2 | 0 | 22 | 0 | 0 |
| 29 | G_132 | Gingivitis | 21222 | 7 | 0 | 2 | 8 | 0 | 1 | 0 | 0 | 0 |
| 30 | G_135 | Gingivitis | 10363 | 0 | 0 | 0 | 104 | 2 | 0 | 0 | 0 | 2 |
| 31 | G_139 | Gingivitis | 17129 | 0 | 0 | 1 | 3 | 0 | 0 | 0 | 14 | 0 |
| 32 | G_143 | Gingivitis | 48153 | 3 | 1 | 0 | 3 | 2 | 0 | 3 | 22 | 2 |
| 33 | G_148 | Gingivitis | 16887 | 0 | 1 | 0 | 24 | 3 | 0 | 0 | 2 | 0 |
| 34 | G_149 | Gingivitis | 29961 | 38 | 15 | 0 | 5 | 0 | 0 | 0 | 2 | 0 |
| 35 | G_153 | Gingivitis | 18102 | 2 | 2 | 3 | 87 | 96 | 0 | 19 | 42 | 47 |
| 36 | G_161 | Gingivitis | 14798 | 0 | 2 | 0 | 18 | 253 | 0 | 20 | 18 | 0 |
| 37 | G_169 | Gingivitis | 9821 | 1629 | 115 | 5 | 8 | 0 | 84 | 0 | 0 | 0 |
| 38 | G_170 | Gingivitis | 49030 | 97 | 193 | 23 | 16 | 0 | 0 | 0 | 0 | 0 |
| 39 | G_172 | Gingivitis | 36948 | 11 | 0 | 0 | 195 | 1 | 0 | 35 | 4 | 0 |
| 40 | G_173 | Gingivitis | 57876 | 1 | 0 | 4 | 3 | 0 | 0 | 1 | 2 | 1 |
| 41 | G_177 | Gingivitis | 36744 | 0 | 0 | 0 | 183 | 0 | 0 | 12 | 138 | 0 |
| 42 | G_184 | Gingivitis | 11140 | 0 | 0 | 0 | 192 | 5 | 0 | 0 | 39 | 0 |
| 43 | G_188 | Gingivitis | 9328 | 3 | 1 | 0 | 0 | 0 | 0 | 0 | 0 | 0 |
| 44 | G_197 | Gingivitis | 3806 | 10 | 1 | 0 | 161 | 1 | 15 | 0 | 23 | 9 |
| 45 | G_214 | Gingivitis | 12530 | 0 | 10 | 0 | 21 | 0 | 4 | 0 | 46 | 253 |
| 46 | G_232 | Gingivitis | 33682 | 17 | 13 | 1 | 16 | 4 | 0 | 1 | 58 | 36 |
| 47 | G_244 | Gingivitis | 13446 | 25 | 1 | 0 | 8 | 1 | 3 | 3 | 1 | 1 |
| 48 | G_245 | Gingivitis | 29114 | 198 | 1 | 1 | 56 | 3 | 0 | 49 | 1 | 412 |
| 49 | G_246 | Gingivitis | 37282 | 0 | 0 | 0 | 5 | 0 | 0 | 0 | 0 | 0 |

FIG. 12 (cont.)

Table 5 (cont.)

| | A | B | C | BW | BX | BY | BZ | CA | CB | CC | CD | CE |
|---|---|---|---|---|---|---|---|---|---|---|---|---|
| 50 | G_249 | Gingivitis | 13242 | 2 | 3 | 48 | 302 | 17 | 6 | 23 | 88 | 65 |
| 51 | G_C854 | Gingivitis | 16231 | 2 | 45 | 0 | 1 | 0 | 0 | 2 | 0 | 8 |
| 52 | G_39 | Gingivitis | 34430 | 52 | 1686 | 7 | 12 | 0 | 111 | 0 | 21 | 12 |
| 53 | H_39 | Health | 15024 | 3 | 0 | 0 | 8 | 0 | 0 | 0 | 1 | 0 |
| 54 | H_48 | Health | 9790 | 4 | 0 | 24 | 389 | 25 | 0 | 10 | 199 | 0 |
| 55 | H_51 | Health | 7751 | 10 | 1 | 1 | 19 | 2 | 0 | 2 | 1 | 6 |
| 56 | H_57 | Health | 37033 | 31 | 1 | 0 | 88 | 0 | 0 | 6 | 2 | 0 |
| 57 | H_58 | Health | 12069 | 64 | 0 | 0 | 306 | 10 | 0 | 0 | 59 | 0 |
| 58 | H_68 | Health | 10333 | 3 | 3 | 0 | 2 | 3 | 0 | 0 | 6 | 4 |
| 59 | H_73 | Health | 12578 | 9 | 0 | 0 | 737 | 4 | 0 | 0 | 0 | 7 |
| 60 | H_74 | Health | 47861 | 1385 | 8 | 1 | 468 | 52 | 3 | 0 | 823 | 27 |
| 61 | H_78 | Health | 11932 | 909 | 0 | 0 | 73 | 0 | 0 | 148 | 1 | 30 |
| 62 | H_83 | Health | 22743 | 5 | 0 | 0 | 8 | 0 | 0 | 0 | 0 | 15 |
| 63 | H_89 | Health | 13540 | 8 | 2 | 0 | 134 | 1 | 0 | 5 | 0 | 4 |
| 64 | H_90 | Health | 18858 | 6 | 0 | 0 | 127 | 1 | 0 | 18 | 37 | 62 |
| 65 | H_94 | Health | 18898 | 249 | 33 | 10 | 15 | 0 | 48 | 0 | 0 | 6 |
| 66 | H_107 | Health | 13290 | 0 | 0 | 0 | 7 | 0 | 0 | 1 | 36 | 2 |
| 67 | H_108 | Health | 13826 | 8 | 1 | 0 | 128 | 13 | 0 | 3 | 0 | 140 |
| 68 | H_112 | Health | 29544 | 2 | 0 | 0 | 1437 | 1 | 0 | 0 | 0 | 0 |
| 69 | H_114 | Health | 13194 | 303 | 15 | 3 | 106 | 0 | 0 | 0 | 6 | 1 |
| 70 | H_118 | Health | 28783 | 25 | 22 | 2 | 148 | 38 | 4 | 0 | 334 | 2 |
| 71 | H_137 | Health | 14686 | 2 | 8 | 0 | 335 | 0 | 1 | 0 | 15 | 2 |
| 72 | H_145 | Health | 14097 | 8 | 0 | 0 | 36 | 0 | 0 | 0 | 66 | 0 |
| 73 | H_148 | Health | 38766 | 33 | 0 | 1 | 11 | 0 | 0 | 3 | 0 | 2 |
| 74 | H_154 | Health | 18025 | 0 | 0 | 0 | 1 | 2 | 0 | 0 | 24 | 0 |
| 75 | H_156 | Health | 13889 | 0 | 0 | 0 | 1 | 0 | 0 | 0 | 0 | 0 |
| 76 | H_162 | Health | 11371 | 1849 | 1 | 0 | 89 | 1 | 0 | 1 | 67 | 0 |
| 77 | H_163 | Health | 18304 | 1047 | 152 | 0 | 4 | 0 | 0 | 0 | 84 | 0 |
| 78 | H_164 | Health | 36129 | 6 | 92 | 0 | 90 | 0 | 0 | 0 | 30 | 20 |
| 79 | H_165 | Health | 24874 | 1237 | 6 | 0 | 28 | 1 | 0 | 0 | 8 | 1 |
| 80 | H_184 | Health | 28147 | 0 | 0 | 0 | 278 | 0 | 0 | 27 | 7 | 0 |
| 81 | H_188 | Health | 10291 | 2 | 3 | 0 | 80 | 0 | 0 | 0 | 1 | 0 |

FIG. 12 (cont.)

Table 5 (cont.)

| | A | B | C | BW | BX | BY | BZ | CA | CB | CC | CD | CE |
|---|---|---|---|---|---|---|---|---|---|---|---|---|
| 82 | H_171 | Health | 14889 | 8 | 7 | 18 | 859 | 1 | 0 | 74 | 38 | 167 |
| 83 | H_174 | Health | 10137 | 2 | 0 | 0 | 1 | 0 | 0 | 0 | 0 | 0 |
| 84 | H_175 | Health | 9680 | 5 | 0 | 0 | 68 | 0 | 0 | 0 | 0 | 0 |
| 85 | H_178 | Health | 73108 | 24 | 5 | 0 | 364 | 3 | 0 | 1 | 415 | 31 |
| 86 | H_186 | Health | 12182 | 74 | 0 | 0 | 82 | 10 | 0 | 0 | 172 | 0 |
| 87 | H_189 | Health | 25877 | 1 | 0 | 0 | 368 | 2 | 0 | 5 | 133 | 12 |
| 88 | H_200 | Health | 19277 | 35 | 0 | 0 | 1158 | 4 | 0 | 27 | 129 | 21 |
| 89 | H_203 | Health | 7317 | 2 | 1 | 1 | 11 | 5 | 0 | 5 | 3 | 1 |
| 90 | H_211 | Health | 4748 | 6 | 0 | 0 | 37 | 22 | 1 | 0 | 1 | 0 |
| 91 | H_217 | Health | 10064 | 50 | 0 | 0 | 56 | 83 | 0 | 25 | 185 | 0 |
| 92 | H_220 | Health | 18191 | 0 | 0 | 0 | 19 | 0 | 0 | 0 | 941 | 0 |
| 93 | H_221 | Health | 76808 | 267 | 0 | 0 | 120 | 71 | 0 | 2 | 56 | 1 |
| 94 | H_222 | Health | 24703 | 149 | 0 | 0 | 365 | 0 | 0 | 0 | 83 | 2 |
| 95 | H_223 | Health | 7018 | 0 | 1 | 0 | 15 | 5 | 3 | 0 | 0 | 3 |
| 96 | H_225 | Health | 14460 | 540 | 0 | 0 | 1 | 0 | 0 | 0 | 0 | 2 |
| 97 | H_234 | Health | 13232 | 0 | 0 | 0 | 50 | 7 | 0 | 0 | 85 | 0 |
| 98 | H_235 | Health | 14896 | 1 | 1 | 0 | 3 | 11 | 1 | 0 | 0 | 0 |
| 99 | H_236 | Health | 9208 | 2 | 0 | 0 | 7 | 3 | 0 | 0 | 1 | 0 |
| 100 | H_237 | Health | 20932 | 1 | 0 | 0 | 11 | 0 | 0 | 0 | 1 | 1 |
| 101 | H_238 | Health | 11638 | 0 | 0 | 0 | 28 | 20 | 0 | 5 | 4 | 43 |
| 102 | H_239 | Health | 17487 | 97 | 1 | 0 | 278 | 6 | 0 | 200 | 90 | 0 |
| 103 | H_240 | Health | 14649 | 12 | 0 | 0 | 24 | 0 | 0 | 3 | 53 | 7 |
| 104 | H_241 | Health | 32149 | 0 | 7 | 0 | 681 | 0 | 1 | 0 | 0 | 0 |
| 105 | P_1 | PD1 | 15621 | 18 | 5 | 0 | 113 | 193 | 0 | 0 | 1 | 13 |
| 106 | P_5 | PD1 | 55958 | 1921 | 893 | 1 | 763 | 0 | 20 | 0 | 36 | 3 |
| 107 | P_20 | PD1 | 14617 | 6 | 199 | 1 | 3 | 0 | 14 | 0 | 3 | 0 |
| 108 | P_21 | PD1 | 11750 | 34 | 110 | 5 | 243 | 1 | 0 | 0 | 41 | 2 |
| 109 | P_24 | PD1 | 12785 | 16 | 7 | 0 | 8 | 1 | 1 | 0 | 0 | 4 |
| 110 | P_25 | PD1 | 22123 | 804 | 118 | 0 | 342 | 4 | 0 | 0 | 74 | 0 |
| 111 | P_27 | PD1 | 64080 | 297 | 0 | 0 | 7 | 3 | 1 | 1 | 1 | 11 |
| 112 | P_46 | PD1 | 56396 | 248 | 10 | 246 | 1248 | 5 | 1 | 7 | 41 | 272 |
| 113 | P_49 | PD1 | 33560 | 153 | 97 | 5 | 135 | 0 | 12 | 1 | 76 | 17 |

FIG. 12 (cont.)

Table 5 (cont.)

| | A | B | C | BW | BX | BY | BZ | CA | CB | CC | CD | CE |
|---|---|---|---|---|---|---|---|---|---|---|---|---|
| 114 | P_53 | P01 | 37971 | 984 | 131 | 200 | 34 | 2 | 52 | 0 | 2 | 96 |
| 115 | P_56 | P01 | 23103 | 111 | 0 | 198 | 144 | 2 | 0 | 0 | 13 | 137 |
| 116 | P_70 | P01 | 17344 | 38 | 5 | 0 | 2 | 0 | 14 | 0 | 7 | 17 |
| 117 | P_79 | P01 | 10858 | 15 | 19 | 0 | 46 | 0 | 0 | 0 | 33 | 50 |
| 118 | P_80 | P01 | 48151 | 1 | 0 | 0 | 13 | 7 | 0 | 5 | 9 | 0 |
| 119 | P_84 | P01 | 27949 | 24 | 81 | 5 | 75 | 0 | 80 | 1 | 0 | 27 |
| 120 | P_85 | P01 | 8619 | 897 | 506 | 0 | 5 | 0 | 0 | 2 | 99 | 38 |
| 121 | P_87 | P01 | 13353 | 33 | 71 | 4 | 3 | 0 | 134 | 0 | 0 | 3 |
| 122 | P_100 | P01 | 19379 | 1740 | 25 | 2 | 10 | 0 | 4 | 0 | 13 | 0 |
| 123 | P_102 | P01 | 13541 | 152 | 21 | 3 | 11 | 0 | 0 | 0 | 13 | 34 |
| 124 | P_105 | P01 | 25163 | 0 | 0 | 0 | 0 | 0 | 0 | 0 | 0 | 0 |
| 125 | P_108 | P01 | 56612 | 187 | 105 | 3 | 10 | 0 | 84 | 1 | 2 | 27 |
| 126 | P_109 | P01 | 31569 | 3627 | 2 | 422 | 895 | 2 | 0 | 11 | 64 | 466 |
| 127 | P_111 | P01 | 16442 | 1 | 0 | 0 | 3 | 0 | 0 | 0 | 0 | 0 |
| 128 | P_123 | P01 | 16867 | 330 | 1 | 0 | 0 | 0 | 0 | 0 | 26 | 0 |
| 129 | P_131 | P01 | 17951 | 5 | 5 | 0 | 3 | 3 | 0 | 0 | 2 | 2 |
| 130 | P_134 | P01 | 50988 | 198 | 28 | 49 | 895 | 0 | 0 | 7 | 4 | 59 |
| 131 | P_136 | P01 | 36223 | 11 | 360 | 1 | 54 | 383 | 26 | 1 | 45 | 0 |
| 132 | P_140 | P01 | 18345 | 0 | 22 | 0 | 1 | 0 | 1 | 0 | 0 | 3 |
| 133 | P_147 | P01 | 51057 | 356 | 102 | 0 | 58 | 13 | 0 | 117 | 360 | 3 |
| 134 | P_156 | P01 | 38311 | 0 | 58 | 1 | 97 | 0 | 0 | 0 | 156 | 5 |
| 135 | P_181 | P01 | 18547 | 38 | 86 | 0 | 1 | 0 | 0 | 0 | 0 | 1 |
| 136 | P_187 | P01 | 13346 | 65 | 295 | 1 | 14 | 0 | 2 | 0 | 0 | 6 |
| 137 | P_190 | P01 | 15581 | 107 | 2 | 0 | 40 | 1 | 0 | 0 | 159 | 0 |
| 138 | P_191 | P01 | 14629 | 18 | 48 | 0 | 30 | 0 | 0 | 0 | 94 | 9 |
| 139 | P_192 | P01 | 39342 | 1 | 17 | 0 | 6 | 5 | 4 | 0 | 208 | 0 |
| 140 | P_195 | P01 | 38666 | 1 | 1080 | 0 | 5 | 0 | 0 | 0 | 13 | 61 |
| 141 | P_196 | P01 | 48271 | 0 | 0 | 0 | 181 | 0 | 0 | 0 | 323 | 0 |
| 142 | P_205 | P01 | 10354 | 9 | 46 | 0 | 4 | 0 | 16 | 3 | 4 | 2 |
| 143 | P_206 | P01 | 18158 | 0 | 130 | 11 | 25 | 0 | 0 | 4 | 12 | 34 |
| 144 | P_208 | P01 | 22174 | 1 | 196 | 34 | 60 | 0 | 31 | 0 | 3 | 28 |
| 145 | P_210 | P01 | 15575 | 9 | 8 | 1 | 22 | 0 | 0 | 0 | 2 | 9 |

FIG. 12 (cont.)

Table 5 (cont.)

| | A | B | C | BW | BX | BY | BZ | CA | CB | CC | CD | CE |
|---|---|---|---|---|---|---|---|---|---|---|---|---|
| 146 | P_216 | PD1 | 12237 | 81 | 2 | 11 | 0 | 0 | 1 | 2 | 2 | 3 |
| 147 | P_218 | PD1 | 10475 | 25 | 0 | 0 | 15 | 0 | 0 | 0 | 0 | 1 |
| 148 | P_219 | PD1 | 12577 | 12 | 25 | 5 | 4 | 0 | 0 | 0 | 0 | 4 |
| 149 | P_224 | PD1 | 27758 | 3 | 3 | 4 | 73 | 0 | 2 | 4 | 0 | 4 |
| 150 | P_226 | PD1 | 14662 | 67 | 0 | 4 | 10 | 0 | 0 | 0 | 0 | 70 |
| 151 | P_228 | PD1 | 18702 | 103 | 41 | 0 | 76 | 0 | 0 | 0 | 14 | 0 |
| 152 | P_233 | PD1 | 17047 | 48 | 113 | 6 | 1 | 0 | 23 | 1 | 7 | 1 |
| 153 | P_248 | PD1 | 20216 | 350 | 0 | 0 | 80 | 7 | 0 | 9 | 4 | 6 |
| 154 | P_8C09 | PD1 | 18832 | 12 | 330 | 547 | 45 | 0 | 0 | 37 | 52 | 353 |
| 155 | P_8C19 | PD1 | 14480 | 126 | 3 | 0 | 58 | 4 | 0 | 0 | 29 | 271 |
| 156 | P_8C21 | PD1 | 46443 | 7 | 0 | 1 | 3 | 3 | 0 | 3 | 807 | 1 |

FIG. 12 (cont.)

Table 5 (cont.)

| | A | B | C | CF | CG | CH | CI | CJ | CK | CL | CM | CN |
|---|---|---|---|---|---|---|---|---|---|---|---|---|
| | Dog | Health state | Total reads | c_Propionibacterium_sp._CGT-336 | c_Propionibacterium_sp._CGT-321 | c_Propionibacterium_sp._CGT-368 | c_Selenomonas_sputigena_sp._CGT-342 | c_Spirochaeta_sp._CGT-346 | c_Spirochaeta_sp._CGT-379 | c_Streptococcus_Anginosus_CGT-317 | c_Streptococcus_minor_CGT-326 | c_Streptococcus_sp-11_sh_CGT-380 |
| 2 | G_7 | Gingivitis | 12132 | 61 | 292 | 44 | 0 | 0 | 36 | 0 | 39 | 4 |
| 3 | G_8 | Gingivitis | 10681 | 9 | 8 | 13 | 0 | 11 | 0 | 0 | 12 | 4 |
| 4 | G_9 | Gingivitis | 25790 | 81 | 1563 | 57 | 0 | 1 | 0 | 0 | 41 | 59 |
| 5 | G_12 | Gingivitis | 15863 | 22 | 30 | 45 | 0 | 0 | 13 | 0 | 5 | 1 |
| 6 | G_14 | Gingivitis | 9138 | 27 | 1 | 0 | 0 | 0 | 2 | 0 | 148 | 28 |
| 7 | G_15 | Gingivitis | 28089 | 28 | 33 | 36 | 12 | 0 | 3 | 0 | 5 | 67 |
| 8 | G_22 | Gingivitis | 84780 | 87 | 115 | 353 | 0 | 84 | 14 | 0 | 23 | 70 |
| 9 | G_30 | Gingivitis | 19824 | 3 | 3 | 1 | 0 | 0 | 0 | 0 | 9 | 69 |
| 10 | G_36 | Gingivitis | 38047 | 44 | 56 | 7 | 0 | 28 | 47 | 0 | 14 | 11 |
| 11 | G_40 | Gingivitis | 1E+05 | 61 | 8 | 12 | 0 | 67 | 57 | 0 | 6 | 216 |
| 12 | G_42 | Gingivitis | 11958 | 6 | 4 | 28 | 0 | 0 | 0 | 668 | 18 | 0 |
| 13 | G_52 | Gingivitis | 45501 | 35 | 148 | 0 | 0 | 0 | 10 | 0 | 51 | 10 |
| 14 | G_62 | Gingivitis | 8922 | 5 | 8 | 8 | 0 | 0 | 7 | 0 | 1 | 0 |
| 15 | G_63 | Gingivitis | 5611 | 0 | 0 | 154 | 0 | 7 | 1 | 0 | 1 | 4 |
| 16 | G_64 | Gingivitis | 7175 | 8 | 5 | 0 | 0 | 11 | 0 | 0 | 0 | 0 |
| 17 | G_85 | Gingivitis | 8306 | 1 | 8 | 0 | 0 | 0 | 1 | 0 | 0 | 0 |

FIG. 12 (cont.)

Table 5 (cont.)

| | A | B | C | CF | CG | CH | CI | CJ | CK | CL | CM | CN |
|---|---|---|---|---|---|---|---|---|---|---|---|---|
| 18 | G_72 | Gingivitis | 61481 | 36 | 4 | 1032 | 0 | 0 | 40 | 0 | 185 | 40 |
| 19 | G_81 | Gingivitis | 8869 | 14 | 13 | 2 | 0 | 0 | 0 | 0 | 4 | 4 |
| 20 | G_86 | Gingivitis | 54094 | 39 | 105 | 94 | 0 | 0 | 339 | 1 | 426 | 0 |
| 21 | G_96 | Gingivitis | 59245 | 98 | 121 | 37 | 0 | 10 | 0 | 0 | 72 | 1618 |
| 22 | G_98 | Gingivitis | 17911 | 85 | 5 | 17 | 0 | 0 | 3 | 0 | 183 | 3 |
| 23 | G_101 | Gingivitis | 12876 | 138 | 28 | 14 | 0 | 0 | 0 | 0 | 2 | 6 |
| 24 | G_113 | Gingivitis | 18818 | 89 | 51 | 37 | 0 | 12 | 25 | 0 | 64 | 19 |
| 25 | G_117 | Gingivitis | 30812 | 54 | 15 | 71 | 0 | 30 | 35 | 0 | 11 | 56 |
| 26 | G_120 | Gingivitis | 22653 | 7 | 46 | 88 | 0 | 1 | 0 | 0 | 48 | 5 |
| 27 | G_122 | Gingivitis | 17505 | 3 | 39 | 7 | 0 | 7 | 3 | 0 | 12 | 3 |
| 28 | G_128 | Gingivitis | 12750 | 11 | 134 | 2 | 0 | 1 | 2 | 0 | 7 | 4 |
| 29 | G_132 | Gingivitis | 21222 | 2 | 18 | 2 | 0 | 0 | 0 | 0 | 13 | 2 |
| 30 | G_135 | Gingivitis | 18963 | 51 | 26 | 3 | 0 | 0 | 25 | 0 | 27 | 1 |
| 31 | G_139 | Gingivitis | 17129 | 39 | 367 | 42 | 0 | 0 | 1 | 0 | 72 | 0 |
| 32 | G_143 | Gingivitis | 48153 | 7 | 2 | 1 | 0 | 0 | 2 | 0 | 0 | 45 |
| 33 | G_148 | Gingivitis | 15897 | 21 | 32 | 1 | 0 | 0 | 0 | 0 | 0 | 4 |
| 34 | G_149 | Gingivitis | 29961 | 7 | 10 | 77 | 0 | 0 | 0 | 0 | 22 | 0 |
| 35 | G_153 | Gingivitis | 18102 | 3 | 31 | 0 | 0 | 3 | 11 | 0 | 12 | 2 |
| 36 | G_161 | Gingivitis | 14798 | 5 | 14 | 9 | 0 | 0 | 0 | 0 | 0 | 0 |
| 37 | G_169 | Gingivitis | 9811 | 4 | 0 | 0 | 0 | 11 | 4 | 0 | 1 | 73 |
| 38 | G_170 | Gingivitis | 45030 | 58 | 29 | 5 | 0 | 4 | 4 | 0 | 72 | 140 |
| 39 | G_172 | Gingivitis | 36963 | 34 | 14 | 1 | 0 | 0 | 9 | 23 | 108 | 66 |
| 40 | G_173 | Gingivitis | 57876 | 2 | 1 | 1 | 0 | 1 | 1 | 0 | 231 | 18 |
| 41 | G_177 | Gingivitis | 36744 | 307 | 96 | 40 | 0 | 8 | 30 | 0 | 53 | 0 |
| 42 | G_184 | Gingivitis | 11140 | 0 | 0 | 13 | 0 | 0 | 5 | 0 | 1 | 0 |
| 43 | G_188 | Gingivitis | 9325 | 65 | 0 | 94 | 0 | 0 | 26 | 0 | 108 | 1 |
| 44 | G_197 | Gingivitis | 3805 | 0 | 2 | 0 | 0 | 0 | 0 | 0 | 1 | 0 |
| 45 | G_214 | Gingivitis | 17630 | 4 | 7 | 1 | 0 | 29 | 2 | 0 | 7 | 78 |
| 46 | G_232 | Gingivitis | 13682 | 7 | 2 | 5 | 0 | 35 | 15 | 0 | 18 | 13 |
| 47 | G_244 | Gingivitis | 13446 | 20 | 13 | 2 | 0 | 0 | 0 | 0 | 20 | 1 |
| 48 | G_245 | Gingivitis | 29134 | 2 | 10 | 3 | 0 | 27 | 1 | 0 | 19 | 89 |
| 49 | G_248 | Gingivitis | 37282 | 180 | 11 | 36 | 0 | 0 | 1 | 0 | 0 | 0 |

FIG. 12 (cont.)

Table 5 (cont.)

| | A | B | C | CF | CG | CH | CI | CJ | CK | CL | CM | CN |
|---|---|---|---|---|---|---|---|---|---|---|---|---|
| 50 | G_249 | Gingivitis | 19242 | 18 | 49 | 7 | 0 | 36 | 18 | 0 | 12 | 27 |
| 51 | G_C854 | Gingivitis | 18211 | 2 | 22 | 0 | 0 | 2 | 2 | 0 | 13 | 0 |
| 52 | G_19 | Gingivitis | 34430 | 3 | 4 | 6 | 0 | 0 | 15 | 0 | 300 | 16 |
| 53 | H_39 | Health | 16024 | 9 | 67 | 74 | 0 | 0 | 0 | 0 | 1 | 0 |
| 54 | H_48 | Health | 9790 | 0 | 27 | 0 | 0 | 23 | 2 | 0 | 3 | 0 |
| 55 | H_51 | Health | 7751 | 12 | 57 | 0 | 0 | 0 | 0 | 0 | 0 | 0 |
| 56 | H_57 | Health | 37033 | 7 | 154 | 2 | 0 | 0 | 0 | 0 | 15 | 0 |
| 57 | H_58 | Health | 32089 | 80 | 1502 | 45 | 0 | 7 | 1 | 0 | 38 | 3 |
| 58 | H_68 | Health | 10833 | 3 | 34 | 0 | 0 | 0 | 1 | 0 | 16 | 2 |
| 59 | H_73 | Health | 12578 | 113 | 457 | 18 | 0 | 0 | 9 | 0 | 187 | 0 |
| 60 | H_74 | Health | 47861 | 2 | 79 | 1 | 0 | 7 | 61 | 0 | 7 | 7 |
| 61 | H_78 | Health | 11902 | 2 | 0 | 0 | 0 | 0 | 78 | 0 | 5 | 2 |
| 62 | H_83 | Health | 32743 | 13 | 0 | 2 | 0 | 0 | 0 | 0 | 2 | 0 |
| 63 | H_85 | Health | 13540 | 5 | 38 | 0 | 0 | 0 | 19 | 0 | 41 | 0 |
| 64 | H_90 | Health | 16858 | 42 | 5 | 0 | 0 | 3 | 0 | 0 | 678 | 0 |
| 65 | H_94 | Health | 18098 | 11 | 11 | 10 | 0 | 0 | 0 | 0 | 109 | 16 |
| 66 | H_107 | Health | 13290 | 80 | 240 | 3 | 0 | 0 | 0 | 0 | 1 | 7 |
| 67 | H_108 | Health | 13826 | 3 | 13 | 2 | 0 | 0 | 21 | 0 | 13 | 0 |
| 68 | H_112 | Health | 25644 | 129 | 75 | 12 | 0 | 0 | 138 | 0 | 195 | 0 |
| 69 | H_114 | Health | 13104 | 0 | 0 | 2 | 0 | 0 | 0 | 0 | 7 | 33 |
| 70 | H_118 | Health | 28793 | 3 | 1 | 2 | 0 | 4 | 2 | 0 | 5 | 1 |
| 71 | H_137 | Health | 14898 | 19 | 49 | 7 | 0 | 0 | 0 | 2 | 9 | 2 |
| 72 | H_145 | Health | 14097 | 46 | 35 | 82 | 0 | 0 | 3 | 0 | 15 | 4 |
| 73 | H_346 | Health | 26760 | 78 | 176 | 10 | 0 | 0 | 4 | 0 | 12 | 0 |
| 74 | H_354 | Health | 18025 | 16 | 7 | 12 | 0 | 0 | 19 | 0 | 94 | 1 |
| 75 | H_356 | Health | 13099 | 3 | 8 | 0 | 0 | 0 | 0 | 0 | 0 | 0 |
| 76 | H_362 | Health | 11571 | 49 | 36 | 4 | 0 | 0 | 2 | 0 | 3 | 44 |
| 77 | H_363 | Health | 18334 | 108 | 63 | 0 | 0 | 0 | 0 | 0 | 0 | 14 |
| 78 | H_364 | Health | 36129 | 35 | 1564 | 0 | 0 | 18 | 7 | 0 | 0 | 25 |
| 79 | H_365 | Health | 24874 | 5 | 29 | 0 | 0 | 5 | 17 | 0 | 20 | 17 |
| 80 | H_366 | Health | 28147 | 64 | 4 | 0 | 0 | 0 | 70 | 0 | 22 | 0 |
| 81 | H_368 | Health | 10291 | 3 | 2 | 2 | 0 | 1 | 21 | 0 | 127 | 0 |

FIG. 12 (cont.)

Table 5 (cont.)

| | A | B | C | CF | CG | CH | CI | CJ | CK | CL | CM | CN |
|---|---|---|---|---|---|---|---|---|---|---|---|---|
| 82 | H_171 | Health | 14889 | 51 | 43 | 0 | 0 | 5 | 6 | 0 | 8 | 1 |
| 83 | H_174 | Health | 10127 | 40 | 5 | 13 | 0 | 0 | 14 | 0 | 1 | 0 |
| 84 | H_175 | Health | 9530 | 89 | 5 | 13 | 0 | 0 | 0 | 0 | 0 | 1 |
| 85 | H_178 | Health | 78108 | 31 | 213 | 1 | 0 | 0 | 32 | 0 | 18 | 16 |
| 86 | H_186 | Health | 12182 | 6 | 15 | 0 | 0 | 3 | 3 | 0 | 9 | 0 |
| 87 | H_189 | Health | 25677 | 9 | 81 | 3 | 0 | 0 | 5 | 0 | 30 | 1 |
| 88 | H_200 | Health | 39277 | 2 | 3 | 29 | 0 | 0 | 4 | 2 | 204 | 0 |
| 89 | H_203 | Health | 7317 | 8 | 5 | 0 | 0 | 0 | 21 | 0 | 0 | 0 |
| 90 | H_211 | Health | 4740 | 13 | 76 | 9 | 0 | 0 | 6 | 1 | 2 | 0 |
| 91 | H_217 | Health | 19064 | 5 | 19 | 19 | 0 | 5 | 0 | 0 | 34 | 1 |
| 92 | H_220 | Health | 18191 | 0 | 7 | 5 | 0 | 0 | 0 | 0 | 24 | 0 |
| 93 | H_221 | Health | 26808 | 22 | 1188 | 0 | 0 | 0 | 18 | 0 | 46 | 1 |
| 94 | H_222 | Health | 24701 | 17 | 3 | 5 | 0 | 0 | 7 | 0 | 19 | 26 |
| 95 | H_223 | Health | 7018 | 38 | 3 | 18 | 0 | 0 | 20 | 0 | 11 | 0 |
| 96 | H_225 | Health | 14460 | 0 | 0 | 0 | 0 | 0 | 2 | 0 | 1 | 4 |
| 97 | H_234 | Health | 33232 | 19 | 36 | 183 | 0 | 0 | 2 | 0 | 23 | 0 |
| 98 | H_235 | Health | 14596 | 28 | 49 | 1 | 0 | 0 | 4 | 0 | 9 | 1 |
| 99 | H_236 | Health | 9200 | 29 | 759 | 1 | 0 | 0 | 5 | 0 | 5 | 0 |
| 100 | H_237 | Health | 26932 | 6 | 5 | 21 | 0 | 0 | 127 | 0 | 0 | 0 |
| 101 | H_238 | Health | 11698 | 29 | 4 | 1 | 0 | 0 | 35 | 0 | 6 | 0 |
| 102 | H_239 | Health | 17487 | 4 | 1 | 0 | 0 | 35 | 3 | 0 | 6 | 93 |
| 103 | H_240 | Health | 14649 | 37 | 59 | 1 | 0 | 0 | 35 | 0 | 11 | 1 |
| 104 | H_241 | Health | 32149 | 26 | 9 | 130 | 0 | 0 | 228 | 0 | 190 | 2 |
| 105 | P_1 | PD1 | 15621 | 5 | 54 | 6 | 0 | 19 | 8 | 0 | 2 | 3 |
| 106 | P_3 | PD1 | 55958 | 2 | 1 | 0 | 0 | 0 | 0 | 0 | 7 | 230 |
| 107 | P_20 | PD1 | 14617 | 29 | 44 | 12 | 0 | 0 | 1 | 0 | 53 | 1 |
| 108 | P_21 | PD1 | 11750 | 10 | 17 | 1 | 1 | 2 | 2 | 0 | 63 | 0 |
| 109 | P_24 | PD1 | 12786 | 2 | 36 | 0 | 0 | 1 | 0 | 0 | 78 | 9 |
| 110 | P_25 | PD1 | 22103 | 30 | 388 | 12 | 0 | 0 | 12 | 0 | 29 | 0 |
| 111 | P_27 | PD1 | 64090 | 15 | 503 | 4 | 0 | 0 | 0 | 0 | 172 | 21 |
| 112 | P_46 | PD1 | 55396 | 4 | 17 | 1 | 0 | 22 | 1 | 0 | 23 | 38 |
| 113 | P_49 | PD1 | 13560 | 8 | 45 | 0 | 0 | 0 | 0 | 0 | 0 | 16 |

FIG. 12 (cont.)

Table 5 (cont.)

| | A | B | C | CF | CG | CH | CI | CJ | CK | CL | CM | CN |
|---|---|---|---|---|---|---|---|---|---|---|---|---|
| 114 | P_53 | P01 | 37571 | 2 | 21 | 0 | 0 | 3 | 0 | 0 | 2 | 112 |
| 115 | P_56 | P01 | 23103 | 5 | 19 | 1 | 0 | 51 | 0 | 0 | 4 | 300 |
| 116 | P_70 | P01 | 17344 | 1 | 0 | 1 | 0 | 5 | 0 | 0 | 3 | 5 |
| 117 | P_79 | P01 | 10668 | 15 | 4 | 11 | 0 | 0 | 0 | 0 | 35 | 27 |
| 118 | P_80 | P01 | 48951 | 38 | 503 | 0 | 0 | 0 | 7 | 0 | 33 | 7 |
| 119 | P_84 | P01 | 22949 | 2 | 34 | 0 | 1 | 1 | 2 | 0 | 89 | 199 |
| 120 | P_85 | P01 | 8619 | 3 | 2 | 1 | 36 | 3 | 8 | 0 | 8 | 15 |
| 121 | P_87 | P01 | 13155 | 0 | 5 | 0 | 0 | 1 | 0 | 0 | 29 | 39 |
| 122 | P_100 | P01 | 18279 | 4 | 3 | 1 | 0 | 0 | 0 | 0 | 48 | 128 |
| 123 | P_102 | P01 | 13541 | 14 | 43 | 2 | 0 | 3 | 2 | 0 | 18 | 163 |
| 124 | P_105 | P01 | 25163 | 3 | 0 | 17 | 0 | 0 | 0 | 3 | 5 | 0 |
| 125 | P_106 | P01 | 56812 | 7 | 45 | 0 | 0 | 1 | 0 | 0 | 240 | 370 |
| 126 | P_109 | P01 | 31560 | 8 | 49 | 0 | 0 | 70 | 4 | 0 | 52 | 107 |
| 127 | P_111 | P01 | 16442 | 25 | 278 | 43 | 0 | 0 | 0 | 0 | 223 | 11 |
| 128 | P_123 | P01 | 16867 | 0 | 2 | 0 | 0 | 2 | 0 | 20 | 28 | 3 |
| 129 | P_131 | P01 | 17852 | 79 | 186 | 163 | 0 | 16 | 0 | 0 | 5 | 68 |
| 130 | P_134 | P01 | 50868 | 389 | 130 | 28 | 0 | 33 | 2 | 0 | 8 | 102 |
| 131 | P_138 | P01 | 36223 | 25 | 19 | 5 | 0 | 0 | 16 | 0 | 174 | 23 |
| 132 | P_140 | P01 | 16346 | 48 | 18 | 9 | 0 | 2 | 0 | 0 | 335 | 2 |
| 133 | P_147 | P01 | 51057 | 34 | 134 | 79 | 0 | 25 | 22 | 0 | 1712 | 4 |
| 134 | P_155 | P01 | 38311 | 127 | 1 | 100 | 0 | 0 | 1 | 0 | 4 | 39 |
| 135 | P_181 | P01 | 10947 | 122 | 5 | 0 | 0 | 0 | 1 | 0 | 0 | 1 |
| 136 | P_187 | P01 | 19346 | 42 | 134 | 0 | 0 | 1 | 4 | 0 | 138 | 15 |
| 137 | P_190 | P01 | 15551 | 94 | 270 | 2 | 29 | 0 | 5 | 0 | 0 | 1 |
| 138 | P_191 | P01 | 14529 | 1 | 7 | 0 | 0 | 88 | 6 | 0 | 2 | 61 |
| 139 | P_192 | P01 | 39342 | 1 | 3 | 0 | 0 | 0 | 0 | 0 | 0 | 0 |
| 140 | P_195 | P01 | 38666 | 2 | 8 | 1 | 0 | 0 | 0 | 0 | 204 | 2 |
| 141 | P_196 | P01 | 48271 | 4 | 43 | 0 | 1 | 0 | 0 | 7 | 6 | 0 |
| 142 | P_205 | P01 | 10354 | 16 | 22 | 7 | 0 | 0 | 1 | 0 | 54 | 6 |
| 143 | P_206 | P01 | 16558 | 3 | 6 | 0 | 3 | 36 | 1 | 0 | 130 | 5 |
| 144 | P_208 | P01 | 72174 | 1 | 58 | 0 | 89 | 8 | 0 | 512 | 129 | 7 |
| 145 | P_210 | P01 | 15575 | 0 | 168 | 0 | 0 | 0 | 0 | 0 | 40 | 0 |

FIG. 12 (cont.)

Table 5 (cont.)

| | A | B | C | CF | CG | CH | CI | CJ | CK | CL | CM | CN |
|---|---|---|---|---|---|---|---|---|---|---|---|---|
| 146 | P_216 | PD1 | 12237 | 2 | 50 | 0 | 38 | 1 | 0 | 1 | 377 | 112 |
| 147 | P_218 | PD1 | 10475 | 0 | 84 | 0 | 1 | 0 | 0 | 0 | 81 | 5 |
| 148 | P_219 | PD1 | 13572 | 12 | 15 | 0 | 0 | 1 | 0 | 0 | 74 | 254 |
| 149 | P_224 | PD1 | 27758 | 7 | 2 | 0 | 0 | 0 | 0 | 0 | 86 | 0 |
| 150 | P_226 | PD1 | 14662 | 1 | 147 | 34 | 0 | 0 | 0 | 0 | 52 | 40 |
| 151 | P_228 | PD1 | 15703 | 35 | 22 | 45 | 0 | 5 | 3 | 0 | 828 | 32 |
| 152 | P_233 | PD1 | 17047 | 4 | 8 | 0 | 33 | 17 | 0 | 0 | 11 | 60 |
| 153 | P_348 | PD1 | 30138 | 55 | 58 | 41 | 0 | 44 | 0 | 0 | 1 | 43 |
| 154 | P_BC08 | PD1 | 18842 | 0 | 1 | 0 | 0 | 161 | 4 | 0 | 39 | 353 |
| 155 | P_BC19 | PD1 | 14480 | 7 | 9 | 1 | 23 | 8 | 0 | 47 | 72 | 45 |
| 156 | P_BC21 | PD1 | 46433 | 58 | 11 | 115 | 0 | 0 | 36 | 0 | 342 | 0 |

FIG. 12 (cont.)

Table 5 (cont.)

| | A | B | C | CO | CP | CQ | CR | CS | CT | CU |
|---|---|---|---|---|---|---|---|---|---|---|
| | Dog | Health state | Total Reads | ct_Spirochaetales_(G-1)_sp._COT-244 | ct_Treponema_denticola_COT-197 | ct_Treponema_sp._COT-208 | ct_Treponema_sp._COT-260 | ct_Treponema_sp._COT-351 | ct_Treponema_sp._COT-365 | ct_Novosphin_sp._COT-174 |
| 1 | | | | | | | | | | |
| 2 | G_7 | Gingivitis | 12132 | 0 | 33 | 0 | 6 | 0 | 28 | 44 |
| 3 | G_8 | Gingivitis | 10681 | 0 | 45 | 0 | 2 | 3 | 9 | 3 |
| 4 | G_9 | Gingivitis | 25790 | 0 | 46 | 3 | 0 | 2 | 25 | 14 |
| 5 | G_12 | Gingivitis | 15863 | 0 | 25 | 0 | 4 | 0 | 12 | 80 |
| 6 | G_14 | Gingivitis | 9138 | 0 | 6 | 0 | 0 | 0 | 2 | 0 |
| 7 | G_18 | Gingivitis | 38089 | 0 | 76 | 0 | 3 | 0 | 56 | 6 |
| 8 | G_22 | Gingivitis | 84760 | 0 | 837 | 0 | 42 | 15 | 112 | 43 |
| 9 | G_30 | Gingivitis | 13824 | 96 | 230 | 159 | 5 | 71 | 7 | 8 |
| 10 | G_35 | Gingivitis | 38047 | 1 | 122 | 0 | 87 | 0 | 27 | 36 |
| 11 | G_40 | Gingivitis | 1E+05 | 0 | 792 | 0 | 3 | 1 | 38 | 208 |
| 12 | G_42 | Gingivitis | 11958 | 0 | 53 | 0 | 13 | 34 | 5 | 0 |
| 13 | G_52 | Gingivitis | 45501 | 0 | 83 | 0 | 1 | 1 | 2 | 26 |
| 14 | G_62 | Gingivitis | 9922 | 0 | 7 | 0 | 0 | 0 | 1 | 5 |
| 15 | G_63 | Gingivitis | 5611 | 0 | 2 | 0 | 10 | 0 | 0 | 2 |
| 16 | G_64 | Gingivitis | 7175 | 0 | 57 | 0 | 30 | 4 | 4 | 13 |
| 17 | G_65 | Gingivitis | 6508 | 0 | 19 | 0 | 1 | 0 | 0 | 0 |

FIG. 12 (cont.)

Table 5 (cont.)

| | A | B | C | CO | CP | CQ | CR | CS | CT | CU |
|---|---|---|---|---|---|---|---|---|---|---|
| 18 | G_72 | Gingivitis | 61483 | 0 | 447 | 0 | 0 | 1 | 6 | 10 |
| 19 | G_81 | Gingivitis | 8858 | 0 | 34 | 0 | 0 | 0 | 0 | 1 |
| 20 | G_86 | Gingivitis | 54894 | 0 | 3 | 0 | 0 | 0 | 5 | 458 |
| 21 | G_96 | Gingivitis | 59245 | 0 | 343 | 0 | 0 | 7 | 4 | 6 |
| 22 | G_98 | Gingivitis | 17911 | 0 | 2 | 0 | 0 | 0 | 1 | 58 |
| 23 | G_101 | Gingivitis | 12878 | 1 | 16 | 0 | 38 | 1 | 16 | 45 |
| 24 | G_113 | Gingivitis | 18818 | 2 | 43 | 0 | 4 | 3 | 12 | 26 |
| 25 | G_117 | Gingivitis | 30819 | 0 | 142 | 0 | 12 | 22 | 160 | 16 |
| 26 | G_120 | Gingivitis | 22655 | 2 | 35 | 8 | 0 | 3 | 2 | 0 |
| 27 | G_122 | Gingivitis | 17505 | 0 | 100 | 0 | 1 | 12 | 43 | 2 |
| 28 | G_128 | Gingivitis | 12750 | 0 | 89 | 0 | 16 | 0 | 15 | 16 |
| 29 | G_132 | Gingivitis | 21222 | 0 | 12 | 0 | 1 | 1 | 1 | 0 |
| 30 | G_135 | Gingivitis | 10363 | 0 | 2 | 0 | 0 | 0 | 0 | 95 |
| 31 | G_139 | Gingivitis | 17129 | 0 | 94 | 0 | 0 | 0 | 34 | 1 |
| 32 | G_143 | Gingivitis | 48153 | 0 | 44 | 0 | 0 | 5 | 1 | 0 |
| 33 | G_148 | Gingivitis | 16887 | 0 | 541 | 0 | 0 | 0 | 0 | 4 |
| 34 | G_149 | Gingivitis | 29981 | 0 | 0 | 0 | 0 | 0 | 1 | 2 |
| 35 | G_153 | Gingivitis | 18102 | 0 | 20 | 0 | 3 | 0 | 23 | 29 |
| 36 | G_161 | Gingivitis | 14798 | 0 | 13 | 0 | 14 | 0 | 5 | 0 |
| 37 | G_169 | Gingivitis | 9811 | 1 | 144 | 0 | 8 | 18 | 6 | 5 |
| 38 | G_170 | Gingivitis | 40000 | 0 | 58 | 0 | 0 | 0 | 5 | 27 |
| 39 | G_172 | Gingivitis | 36943 | 0 | 227 | 0 | 57 | 21 | 410 | 150 |
| 40 | G_173 | Gingivitis | 57676 | 0 | 10 | 0 | 0 | 0 | 0 | 0 |
| 41 | G_177 | Gingivitis | 36744 | 0 | 43 | 0 | 0 | 0 | 17 | 293 |
| 42 | G_184 | Gingivitis | 11140 | 0 | 3 | 0 | 0 | 0 | 9 | 0 |
| 43 | G_188 | Gingivitis | 9325 | 0 | 4 | 0 | 1 | 0 | 0 | 14 |
| 44 | G_197 | Gingivitis | 3805 | 0 | 15 | 0 | 1 | 0 | 4 | 0 |
| 45 | G_214 | Gingivitis | 12530 | 0 | 138 | 0 | 0 | 0 | 44 | 4 |
| 46 | G_232 | Gingivitis | 13682 | 0 | 114 | 0 | 33 | 7 | 49 | 5 |
| 47 | G_244 | Gingivitis | 13446 | 0 | 7 | 0 | 7 | 0 | 3 | 0 |
| 48 | G_245 | Gingivitis | 29114 | 0 | 395 | 0 | 167 | 62 | 282 | 11 |
| 49 | G_246 | Gingivitis | 37282 | 0 | 0 | 0 | 0 | 0 | 0 | 376 |

FIG. 12 (cont.)

Table 5 (cont.)

| | A | B | C | CO | CP | CQ | CR | CS | CT | CU |
|---|---|---|---|---|---|---|---|---|---|---|
| 50 | G_249 | Gingivitis | 19242 | 0 | 105 | 0 | 313 | 13 | 44 | 121 |
| 51 | G_0854 | Gingivitis | 16211 | 1 | 0 | 0 | 1 | 2 | 3 | 2 |
| 52 | G_19 | Gingivitis | 34430 | 16 | 52 | 0 | 0 | 0 | 0 | 0 |
| 53 | H_39 | Health | 16034 | 0 | 1 | 0 | 0 | 0 | 0 | 39 |
| 54 | H_48 | Health | 9790 | 0 | 114 | 0 | 13 | 0 | 0 | 0 |
| 55 | H_51 | Health | 7751 | 0 | 3 | 0 | 0 | 0 | 2 | 53 |
| 56 | H_57 | Health | 37038 | 0 | 2 | 0 | 0 | 0 | 0 | 16 |
| 57 | H_58 | Health | 12089 | 0 | 3 | 0 | 0 | 0 | 0 | 9 |
| 58 | H_68 | Health | 10333 | 0 | 25 | 0 | 0 | 0 | 0 | 98 |
| 59 | H_73 | Health | 12978 | 0 | 18 | 0 | 0 | 0 | 2 | 15 |
| 60 | H_74 | Health | 47881 | 0 | 19 | 0 | 3 | 11 | 43 | 14 |
| 61 | H_78 | Health | 11932 | 0 | 9 | 0 | 0 | 0 | 1 | 13 |
| 62 | H_83 | Health | 22743 | 0 | 2 | 0 | 0 | 0 | 2 | 207 |
| 63 | H_88 | Health | 13540 | 0 | 3 | 0 | 2 | 0 | 15 | 28 |
| 64 | H_90 | Health | 16858 | 0 | 50 | 0 | 0 | 0 | 2 | 1 |
| 65 | H_94 | Health | 18898 | 0 | 18 | 0 | 2 | 0 | 0 | 4 |
| 66 | H_107 | Health | 15290 | 0 | 0 | 0 | 0 | 1 | 1 | 193 |
| 67 | H_108 | Health | 13836 | 0 | 9 | 0 | 0 | 0 | 0 | 19 |
| 68 | H_112 | Health | 29544 | 0 | 2 | 0 | 1 | 0 | 0 | 82 |
| 69 | H_114 | Health | 13104 | 0 | 100 | 0 | 0 | 0 | 18 | 1 |
| 70 | H_118 | Health | 28783 | 0 | 87 | 0 | 1 | 2 | 1 | 10 |
| 71 | H_137 | Health | 14686 | 2 | 12 | 2 | 0 | 0 | 1 | 16 |
| 72 | H_145 | Health | 14097 | 0 | 88 | 0 | 40 | 0 | 12 | 43 |
| 73 | H_146 | Health | 35780 | 0 | 11 | 0 | 1 | 0 | 0 | 9 |
| 74 | H_154 | Health | 18025 | 0 | 3 | 0 | 0 | 0 | 0 | 2 |
| 75 | H_156 | Health | 13899 | 0 | 17 | 0 | 1 | 1 | 0 | 8 |
| 76 | H_162 | Health | 11571 | 0 | 0 | 0 | 0 | 0 | 34 | 10 |
| 77 | H_163 | Health | 18304 | 0 | 61 | 0 | 0 | 0 | 0 | 20 |
| 78 | H_164 | Health | 36129 | 0 | 182 | 0 | 0 | 0 | 5 | 4 |
| 79 | H_165 | Health | 24974 | 0 | 86 | 0 | 0 | 1 | 30 | 12 |
| 80 | H_166 | Health | 28147 | 0 | 0 | 0 | 0 | 0 | 0 | 34 |
| 81 | H_168 | Health | 10291 | 0 | 4 | 0 | 0 | 0 | 1 | 104 |

FIG. 12 (cont.)

Table 5 (cont.)

|  | A | B | C | CO | CP | CQ | CR | CS | CT | CU |
|---|---|---|---|---|---|---|---|---|---|---|
| 82 | H_171 | Health | 14889 | 0 | 19 | 0 | 0 | 4 | 16 | 4 |
| 83 | H_174 | Health | 10127 | 0 | 0 | 0 | 0 | 0 | 0 | 28 |
| 84 | H_175 | Health | 9530 | 0 | 1 | 0 | 0 | 0 | 0 | 12 |
| 85 | H_178 | Health | 73106 | 0 | 505 | 0 | 0 | 0 | 0 | 16 |
| 86 | H_186 | Health | 12182 | 0 | 17 | 0 | 0 | 1 | 30 | 0 |
| 87 | H_189 | Health | 25677 | 0 | 93 | 0 | 70 | 5 | 135 | 6 |
| 88 | H_200 | Health | 19277 | 0 | 101 | 0 | 0 | 0 | 0 | 5 |
| 89 | H_203 | Health | 7317 | 0 | 4 | 0 | 15 | 0 | 3 | 52 |
| 90 | H_211 | Health | 4740 | 0 | 5 | 0 | 0 | 0 | 8 | 1 |
| 91 | H_217 | Health | 10064 | 0 | 77 | 0 | 0 | 43 | 88 | 4 |
| 92 | H_220 | Health | 18191 | 0 | 92 | 0 | 0 | 0 | 0 | 12 |
| 93 | H_221 | Health | 26808 | 0 | 16 | 0 | 0 | 0 | 7 | 73 |
| 94 | H_222 | Health | 24701 | 0 | 21 | 0 | 0 | 0 | 0 | 16 |
| 95 | H_223 | Health | 7018 | 0 | 30 | 0 | 0 | 0 | 42 | 2 |
| 96 | H_225 | Health | 14460 | 0 | 150 | 0 | 0 | 0 | 0 | 1 |
| 97 | H_234 | Health | 13232 | 0 | 1 | 0 | 0 | 0 | 4 | 1 |
| 98 | H_235 | Health | 14596 | 0 | 0 | 0 | 0 | 0 | 0 | 13 |
| 99 | H_236 | Health | 9200 | 0 | 1 | 0 | 0 | 0 | 1 | 16 |
| 100 | H_237 | Health | 20832 | 0 | 4 | 0 | 0 | 0 | 3 | 266 |
| 101 | H_238 | Health | 11638 | 0 | 65 | 0 | 0 | 0 | 218 | 11 |
| 102 | H_239 | Health | 17487 | 0 | 183 | 0 | 57 | 0 | 57 | 6 |
| 103 | H_240 | Health | 14649 | 0 | 6 | 0 | 4 | 0 | 1 | 71 |
| 104 | H_241 | Health | 32149 | 0 | 112 | 0 | 0 | 0 | 0 | 124 |
| 105 | P_1 | PD1 | 15621 | 4 | 106 | 0 | 7 | 7 | 35 | 4 |
| 106 | P_5 | PD1 | 55958 | 0 | 55 | 0 | 0 | 0 | 0 | 3 |
| 107 | P_20 | PD1 | 14817 | 4 | 3 | 0 | 0 | 0 | 0 | 2 |
| 108 | P_21 | PD1 | 11750 | 0 | 4 | 0 | 0 | 2 | 5 | 8 |
| 109 | P_24 | PD1 | 12785 | 2 | 15 | 3 | 0 | 0 | 2 | 1 |
| 110 | P_25 | PD1 | 22123 | 0 | 38 | 0 | 0 | 0 | 6 | 1017 |
| 111 | P_27 | PD1 | 64090 | 0 | 9 | 0 | 0 | 0 | 0 | 16 |
| 112 | P_46 | PD1 | 56396 | 0 | 298 | 1 | 46 | 129 | 139 | 37 |
| 113 | P_49 | PD1 | 33560 | 5 | 10 | 1 | 0 | 1 | 0 | 2 |

FIG. 12 (cont.)

Table 5 (cont.)

|  | A | B | C | CO | CP | CQ | CR | CS | CT | CU |
|---|---|---|---|---|---|---|---|---|---|---|
| 114 | P_53 | PD1 | 37971 | 191 | 108 | 3 | 0 | 16 | 1 | 4 |
| 115 | P_56 | PD1 | 23103 | 0 | 227 | 0 | 9 | 33 | 132 | 4 |
| 116 | P_70 | PD1 | 17344 | 0 | 1077 | 278 | 0 | 8 | 2 | 2 |
| 117 | P_79 | PD1 | 10858 | 1 | 3 | 0 | 0 | 0 | 0 | 14 |
| 118 | P_80 | PD1 | 46951 | 0 | 92 | 0 | 5 | 0 | 4 | 20 |
| 119 | P_84 | PD1 | 22949 | 0 | 39 | 0 | 2 | 3 | 4 | 0 |
| 120 | P_85 | PD1 | 8619 | 0 | 21 | 0 | 6 | 5 | 24 | 2 |
| 121 | P_87 | PD1 | 13155 | 17 | 4 | 0 | 0 | 0 | 0 | 1 |
| 122 | P_100 | PD1 | 19179 | 0 | 8 | 0 | 0 | 0 | 2 | 32 |
| 123 | P_102 | PD1 | 13541 | 42 | 63 | 1 | 0 | 16 | 3 | 5 |
| 124 | P_105 | PD1 | 25163 | 0 | 123 | 0 | 5 | 0 | 0 | 0 |
| 125 | P_106 | PD1 | 56812 | 38 | 15 | 0 | 1 | 0 | 6 | 10 |
| 126 | P_109 | PD1 | 31560 | 0 | 476 | 0 | 7 | 11 | 180 | 7 |
| 127 | P_111 | PD1 | 16442 | 0 | 9 | 0 | 0 | 0 | 0 | 28 |
| 128 | P_123 | PD1 | 16867 | 0 | 67 | 0 | 0 | 0 | 0 | 0 |
| 129 | P_131 | PD1 | 17951 | 5 | 128 | 0 | 38 | 0 | 41 | 20 |
| 130 | P_134 | PD1 | 50988 | 0 | 174 | 0 | 23 | 8 | 7 | 788 |
| 131 | P_136 | PD1 | 36223 | 1 | 191 | 0 | 6 | 0 | 108 | 16 |
| 132 | P_140 | PD1 | 16345 | 0 | 4 | 0 | 0 | 0 | 1 | 0 |
| 133 | P_147 | PD1 | 51057 | 0 | 70 | 3 | 0 | 0 | 37 | 24 |
| 134 | P_155 | PD1 | 38311 | 0 | 34 | 0 | 0 | 0 | 1 | 57 |
| 135 | P_181 | PD1 | 18947 | 0 | 35 | 0 | 0 | 0 | 0 | 4 |
| 136 | P_187 | PD1 | 19346 | 0 | 32 | 0 | 10 | 1 | 5 | 4 |
| 137 | P_190 | PD1 | 15581 | 0 | 321 | 0 | 0 | 0 | 139 | 5 |
| 138 | P_191 | PD1 | 14529 | 0 | 72 | 0 | 13 | 0 | 85 | 248 |
| 139 | P_192 | PD1 | 39342 | 0 | 262 | 38 | 0 | 8 | 1 | 0 |
| 140 | P_195 | PD1 | 38666 | 0 | 593 | 0 | 5 | 2 | 3 | 1 |
| 141 | P_196 | PD1 | 48271 | 1 | 4 | 0 | 0 | 0 | 1 | 100 |
| 142 | P_205 | PD1 | 10354 | 0 | 21 | 0 | 10 | 0 | 8 | 0 |
| 143 | P_206 | PD1 | 16158 | 0 | 198 | 0 | 8 | 30 | 83 | 0 |
| 144 | P_208 | PD1 | 22174 | 8 | 198 | 281 | 0 | 17 | 18 | 2 |
| 145 | P_210 | PD1 | 15575 | 13 | 18 | 21 | 0 | 1 | 3 | 0 |

FIG. 12 (cont.)

Table 5 (cont.)

| | A | B | C | CO | CP | CQ | CR | CS | CT | CU |
|---|---|---|---|---|---|---|---|---|---|---|
| 146 | P_216 | PD1 | 12237 | 47 | 24 | 1 | 0 | 10 | 1 | 0 |
| 147 | P_218 | PD1 | 10475 | 0 | 7 | 0 | 0 | 0 | 0 | 3 |
| 148 | P_219 | PD1 | 12572 | 0 | 21 | 0 | 2 | 0 | 2 | 31 |
| 149 | P_224 | PD1 | 27758 | 0 | 21 | 0 | 3 | 2 | 1 | 3 |
| 150 | P_226 | PD1 | 14662 | 0 | 3 | 0 | 0 | 0 | 2 | 1 |
| 151 | P_228 | PD1 | 18703 | 0 | 59 | 0 | 2 | 30 | 3 | 0 |
| 152 | P_233 | PD1 | 17947 | 62 | 173 | 84 | 0 | 5 | 3 | 1 |
| 153 | P_248 | PD1 | 20118 | 0 | 123 | 0 | 8 | 28 | 29 | 9 |
| 154 | P_BC08 | PD1 | 18642 | 42 | 555 | 1 | 302 | 261 | 86 | 1 |
| 155 | P_BC19 | PD1 | 14480 | 190 | 296 | 72 | 1 | 4 | 50 | 4 |
| 156 | P_BC21 | PD1 | 45443 | 0 | 27 | 0 | 0 | 8 | 30 | 37 |

FIG. 12 (cont.)

ASSAY AND METHOD

CROSS REFERENCE TO RELATED APPLICATIONS

This application is a U.S. national stage patent application of International Patent Application No. PCT/GB2014/000234, filed Jun. 13, 2014, which claims the priority of GB Application No. 1310691.9, filed Jun. 14, 2013, the entire contents of each of which are incorporated herein by reference.

FIELD OF THE DISCLOSURE

The present invention relates to an assay for use in a method of determining the oral health status of a canine animal by identifying certain bacteria present or absent in a sample taken from the animal, and applying the information set out herein for each identified bacteria to statistical models in order to determine the oral health status of the animal.

BACKGROUND OF THE DISCLOSURE

Periodontal disease is a significant problem in dogs, affecting 56-60% of the adult population. It is an inflammatory disease of the supporting tissues of the teeth with tissue damage eventually leading to tooth loss if left untreated. The aetiological agent of periodontitis is dental plaque, a complex biofilm of bacteria suspended in a matrix of bacterial exudates and secreted products. The activity of some bacteria induces a host immune response and results in inflammation of the gingival tissue referred to as gingivitis (G). If the disease progresses, tissue damage becomes more severe leading to an increasing loss of the periodontal ligament surrounding the tooth and is referred to as early stage periodontitis (PD1). Further progression to advanced periodontitis (PD3-PD4) is characterized by significant destruction of the periodontal ligament and supporting tissues including bone. If left untreated the condition is painful for a prolonged period before eventual tooth loss occurs. There is also some evidence in the human field that periodontitis is a risk factor for numerous other conditions, most notably cardiovascular disease.

Assessment of canine oral health is usually made by performing a clinical examination of the dog's mouth while the animal is under anaesthesia, which is a time consuming and resource intensive process which is not without risk to the animal. Physical characteristics of the teeth and gums are used to determine the levels of gingivitis and periodontitis. If other indicators could be reliably used to determine oral health status there may be benefits both in terms of the need to anaesthetise dogs and the ways in which dogs can be used for oral health research.

Traditional methods used to diagnose periodontitis rely on clinical indicators such as signs of inflammation, probing depths, extent and pattern of loss of clinical attachment and bone and other symptoms including the amount of observable plaque and calculus. Such an examination is costly and requires highly trained professionals to examine patients closely. In the case of dogs thorough examination usually requires the attention of a veterinary dentist. Also routine dental maintenance, scaling and inspection of any diseased areas usually require a general anaesthetic to be applied, further complicating the procedure and increasing the resources required.

It is accepted that bacteria present in human dental plaque are the aetiological agent of periodontal disease; though the specific organisms involved in the initiation of disease and the basis of the subsequent events thereafter are unclear. A working hypothesis is that specific antigens or enzymes produced by bacteria in the plaque biofilm initiate activation of the host inflammatory response, the latter being the main pathological agent of periodontal disease.

The initial stages of disease are observed clinically as red and inflamed gums, defined as gingivitis. Without treatment by removal of the plaque biofilm, gingivitis may progress to early periodontitis. The earliest stage of periodontitis (PD1) is characterised by initial tissue breakdown and loss of up to 25% attachment of the periodontal ligament surrounding the tooth root. In humans, this switch from gingivitis to periodontitis appears to be restricted to 10-15% of the population. The onset of periodontitis is defined by irreversible tissue destruction and if left untreated will progress to extreme periodontitis (PD3-PD4). This is characterised by extensive (50-75%) destruction of the periodontal ligament, gum recession and breakdown of supporting tissues eventually leading to the loss of the tooth. The periodontal disease process can be inhibited in the early stages (PD1) by dental scaling and polishing of the periodontal pocket to remove the source of inflammation (dental plaque) with subsequent regular plaque removal by tooth brushing. As such, increasing the understanding of the early stages of disease, (gingivitis through to PD1) in pet dogs where non-surgical interventions may be effective would be desirable.

The diversity of bacterial species found in the canine oral microbiome has been reported using culture independent molecular methods from 51 dogs. Based on full length 16S rDNA Sanger sequencing, 353 taxa were identified; of these 80% were novel and only 16.4% were shared with the human oral microbiome. This indicates a clear difference between the bacterial populations in human versus canine mouths.

Dewhirst et al., (PLoS One, Vol 7, 2012) describes a study to identify the major species of bacteria present in the canine oral microbiome. This paper describes the major bacteria present in the canine oral microbiome. However, without information linking the different species and genera of bacteria found to specific health conditions (whether healthy, gingivitis or periodontitis) then knowledge about which bacteria are present is not informative with regards to predicting the health state of the animal concerned.

Sturgeon et al., (Vet. Microbiol., Vol. 162, 2013) describe a study that used pyrosequencing of 16S rRNA gene to study oral samples from six healthy dogs. This paper lists the genera found in the six healthy dogs. Since the authors did not test dogs that were not healthy (with gingivitis or periodontitis, for example) it is not possible to tell if any of the genera that they identified are especially characteristic of health. In the absence of these data, simply knowing that these genera are present in some healthy samples is not informative with regard to predicting the health state of the animal concerned.

Thus, there is a clear need to identify particular bacterial species in canine plaque that are significantly associated with health, gingivitis and mild periodontitis.

Therefore, the present invention provides an assay for use in a method for determining the oral health status of a canine animal, the method comprising an assay, wherein the assay comprises means for identifying at least two bacteria selected from the list consisting of Peptostreptococcaceae__XIII__[G-1]__sp.__COT-030
Peptostreptococcaceae__XIII__[G-2]__sp.__COT-077
Capnocytophaga__canimorsus
Moraxella__sp.__COT-017
Escherichia__coli
Fusobacterium__sp.__COT-189
Selenomonas__sputigena__COT-342
Proprionibacterium__sp.__COT-365
Treponema__sp.__COT-200
Corynebacterium__sp.__cluster 88112
Erysipelotrichaceae__[G-3]__sp.__COT-302
Filifactor__sp.__COT-163
Lachnospiraceae__XIVa__[G-3]__sp.
Filifactor__sp.__COT-064
Neisseria__sp.__COT-049
Neisseria__weaveri__COT-269
Peptostreptococcaceae__XI__[G-6]__sp.__COT-067
Capnocytophaga__canimorus__COT-235
Porphyromonas__macacae__COT-192
Treponema__sp.__COT-351
Lachnospiraceae__XIVa__[G-6]__sp.__COT-161
Cardiobacterium__sp.__COT-176
Pasteurellaceae__sp.__COT-271
Peptostreptococcaceae__XI__[G-7]__sp.__COT-155
Schwartzia__sp.__COT-063
Wolinella__succinogenes
Actinobaceria__sp.__COT-376
Clostridiales__[F-2.G-1]__sp.__COT-100__PO005
Clostridiales__III__[G-3]__sp.__COT-388
Desulfovibrionales__sp.__COT-009
Peptostreptococcaceae__XI__[G-3]__sp.__COT-034
Porphyromonas__gulae__I__COT-052
Treponema__sp.__COT-198
*Parvimonas*
*Peptostreptococcus*
*Moraxella*
*Filifactor*
*Schwartzia*
*Treponema*
bacterium__cp04.17
*Capnocytophaga*
*Atopobium*
*Phascolarctobacterium*
*Globicatella*
*Prevotella*
*Curtobacterium*
*Granulicatella*
*Solobacterium* provided that at least one of the bacteria is selected from the list consisting of Peptostreptococcaceae__XIII__[G-1]__sp.__COT-030
Peptostreptococcaceae__XIII__[G-2]__sp.__COT-077
Capnocytophaga__canimorsus
Escherichia__coli
Fusobacterium__sp.__COT-189
Selenomonas__sputigena__COT-342
Proprionibacterium__sp.__COT-365
Treponema__sp.__COT-200
Corynebacterium__sp.__cluster 88112
Erysipelotrichaceae__[G-3]__sp.__COT-302
Filifactor__sp.__COT-163
Lachnospiraceae__XIVa__[G-3]__sp.
Filifactor__sp.__COT-064
Neisseria__sp.__COT-049
Peptostreptococcaceae__XI__[G-6]__sp.__COT-067
Capnocytophaga__canimorus__COT-235
Porphyromonas__macacae__COT-192
Treponema__sp.__COT-351
Lachnospiraceae__XIVa__[G-6]__sp.__COT-161
Cardiobacterium__sp.__COT-176
Peptostreptococcaceae__XI__[G-7]__sp.__COT-155
Schwartzia__sp.__COT-063
Wolinella__succinogenes
Actinobaceria__sp.__COT-376
Clostridiales__[F-2.G-1]__sp.__COT-100__PO005
Clostridiales__III__[G-3]__sp.__COT-388
Desulfovibrionales__sp.__COT-009
Peptostreptococcaceae__XI[G-3]__sp.__COT-034
Treponema__sp.__COT-198
*Parvimonas*
*Filifactor*
*Schwartzia*
bacterium__cp04.17
*Capnocytophaga*
*Atopobium*
*Phascolarctobacterium*
*Globicatella*
*Curtobacterium*
*Granulicatella*
*Solobacterium*

In a sample taken from the animal and applying the information set out in FIG. 12 (table 5 for each identified bacteria to statistical models in order to make a prediction of oral health status.

The assay may also further comprise means for identifying at least one bacteria selected from the list consisting of;

Filifactor__alocis__COT-001
Lachnospiraceae__XIVa__[G-6]__sp.__COT-106
Parvimonas__sp.__COT-035
Peptostreptococcaceae__XI__[G-1]__sp.__COT-006
Peptostreptococcaceae__XI__[G-3]__sp.__COT-104
Peptostreptococcaceae__XI__[G-4]__sp.__COT-021
Porphyromonas__crevioricanis__COT-253
Proprionibacterium__sp.__COT-296
Spirochaeta__sp.__COT-379
Treponema__sp.__COT-359
Actinomyces__sp.__COT-252
Bacteroides__denticanoris__COT-183 (Prevotella__sp?)
Catonella__sp.__COT-257
Chryseobacterium__sp.__COT-320
Pasteurella__canis__COT-273
Prophyromonas__sp.__COT-239
Spirochaeta__sp.__COT-314
Treponema__denticola__COT-197
Actinomyces__catuli
Anerovorax__sp.__COT-066
Bacteroidia__[G-5]__sp.__COT-187
Capnocytophaga__sp.__COT-339
Capnocytophaga__sp.__COT-362
Erysipelotrichaceae__[G-1]__sp.__COT-311
Filifactor__villosus__COT-031
Globicatella__sp.__COT-107
Lachnospiraceae__XIVa__[G-2]__sp.__COT-062
Leucobacter__sp.__COT-288
Parvimonas__sp.__COT-102
Pasteurella__dogmatis__COT-092
Xanthomonadaceae__bacterium
*Leucobacter*
*Odoribacter*
Propionibacteriaceae__bacterium
*Selenomonas*
*Actinomyces*
CDC__Group__NO-1
Clostridiales__III__[G-3]__sp.__COT-388__1P046
*Propionivibrio*
*Xenophilus*
*Corynebacterium*
*Escherichia*
*Lautropia*
*Leptotrichia* in a sample taken from the animal.

Alternatively or additionally, the assay may also comprise means for identifying at least one bacteria selected from the list consisting of;

Peptostreptococcaceae_XI_[G-1]_sp._COT-004
Peptostreptococcaceae_XI_[G-1]_sp._COT-258
Peptostreptococcaceae_XI_[G-6]_sp._COT-068
Porphyromonas_sp._COT-290
Prevotella_sp._COT-195
Prevotella_sp._COT-282
Proprionibacterium_sp._COT-300
Stenotrophomonas_sp._COT-224
Streptococcus_minor_COT-116
Xenophilus_sp._COT-174
Actinomyces_sp.
Actinomyces_sp.Cluster 7595
Anaerovorax_sp._COT-125
Capnocytophaga_sp._COT-254
Catonella_sp._COT-025
Erysipelotrichaceae_[G-4]_sp._COT-381
Frigovirgula_sp._COT-007
Fusobacterium_sp._COT-169
Moraxella_sp._COT-018
Parvimonas_sp._COT-101
Peptostreptococcaceae_XI_[G-2]_sp._COT-047
Peptostreptococcaceae_XI_[G-4]_sp._COT-019
Porphyromonas_gulae_II_COT-052
Porphyromonas_sp._COT-181
Porphyromonas_sp._COT-361
Prevotella_sp._COT-298
Synergistales_[G-1]_sp._COT-178
Treponema_sp._COT-233
*Staphylococcus*
*Tannerella*
*Arcobacter*
*Catonella*
*Chryseobacterium*
*Fusobacterium*

The bacteria identified may be of a particular species or are of a genus. Where a genus is identified, any number of members of that genus can be indicative of a particular oral health status when used in the assay of the invention; the sum of all members of the genus may be used in the predictive models. Where a species is identified, different species from the same genus cannot be assumed to have the same predictive value.

The inventors surveyed the oral microbiota of a sufficiently large canine cohort, at great enough depth to identify significant changes in bacterial taxa (phyla, genera and species) between dogs with healthy gingiva and those with gingivitis or mild periodontitis (PD1), and found important links between certain bacteria and different health states.

In this way, the inventors have developed a more relevant conscious testing methodology whereby the oral health status of the animal is assessed by molecular markers for disease state, such as bacterial species. Such a test allows much higher numbers of animals to be assessed and eliminate the need for general anaesthetics.

The development of such a method also has applications for home-owned pets. A conscious test for oral health state enables more frequent monitoring of a pets oral health and provides encouragement for the use of preventative measures such as oral care treats and tooth brushing.

The oral health status of the canine animal may be classified as healthy, gingivitis or periodontitis. The models used to reliably predict the oral health status can predict health/not health (referred to herein as H/not H), where "not health" means gingivitis or periodontitis, or disease/not disease (also referred to herein as P/not P), where "not disease" means health or gingivitis. In this way, models can be combined in order to predict whether an animal has gingivitis, is healthy or has periodontitis.

The sample from the animal to be tested in the animal may be dental plaque, gingival crevicular fluid saliva, or a mixture of any of these. As an advantage over present methods for determining the oral health status of an animal, such samples can be obtained non-invasively and without the need for anaesthetic or expert veterinary care. The sample may be used in the assay of the invention immediately, or it may be processed and stored for future analysis.

The means to identify the two or more bacteria present in the sample may be Quantitative PCR, sequencing or antibody binding. Fluorescent in situ hybridisation may be used. Methods of extracting DNA or protein from bacteria are well known to one skilled in the art.

The bacteria disclosed herein each have 16S DNA sequences that are used to identify them, as is known in the art. Such sequences are publically available and, as such, enable the design of primers by the skilled person. The COT (canine oral taxon) numbers associated with each species or genus described herein enables its identification through sequencing. The species may, for example, be identified through www.ncbi.nlm.nih.gov/nuccore, carrying out a text search for "canine oral taxon" which produces the list of known species, and their associated COT number. Sequences associated with each species are given, enabling, for example, primer design for species identification within a sample from the animal.

Methods of extracting bacteria from a sample are well known to one skilled in the art, as are techniques for extracting DNA from bacterial cells.

Sequencing techniques are well known in the art, including primer design, PCR techniques, sequencing techniques, and antibody assays, such as ELISAs. Antibodies to bacteria-specific proteins can be generated by the skilled person and used to detect certain bacteria in a sample by routine methods.

The assay may comprise means for identifying from 2 to 20 bacteria, or suitably, from 3 to 10, or 4 to 12 bacteria. Alternatively, the assay may comprise means to identify from 2 to 100 bacteria, 5 to 50 bacteria, or 10 to 30 bacteria selected from the lists of species and genera as set out above.

The step to identify the bacteria in order to determine the oral health status of the animal may comprise determining the presence or absence of two or more of a bacteria selected from the list consisting of;

Peptostreptococcaceae_XIII_[G-1]_sp._COT-030
Peptostreptococcaceae_XIII_[G-2]_sp._COT-077
Capnocytophaga_canimorsus
Moraxella_sp._COT-017
Escherichia_coli
Fusobacterium_sp._COT-189
Selenomonas_sputigena_COT-342
Proprionibacterium_sp._COT-365
Treponema_sp._COT-200
Corynebacterium_sp._cluster 88112
Erysipelotrichaceae_[G-3]_sp._COT-302
Filifactor_sp._COT-163
Lachnospiraceae_XIVa_[G-3]_sp.
Filifactor_sp._COT-064
Neisseria_sp._COT-049
Neisseria_weaveri_COT-269
Peptostreptococcaceae_XI_[G-6]_sp._COT-067
Capnocytophaga_canimorus_COT-235
Porphyromonas_macacae_COT-192
Treponema_sp._COT-351
Lachnospiraceae_XIVa_[G-6]_sp._COT-161
Cardiobacterium_sp._COT-176
Pasteurellaceae_sp._COT-271
Peptostreptococcaceae_XI_[G-7]_sp._COT-155
Schwartzia_sp._COT-063
Wolinella_succinogenes
Actinobaceria_sp._COT-376
Clostridiales_[F-2.G-1]_sp._COT-100_PO005

-continued

Clostridiales__III__[G-3]__sp.__COT-388
Desulfovibrionales__sp.__COT-009
Peptostreptococcaceae__XI__[G-3]__sp.__COT-034
Porphyromonas__gulae__I__COT-052
Treponema__sp.__COT-198
*Parvimonas*
*Peptostreptococcus*
*Moraxella*
*Filifactor*
*Schwartzia*
*Treponema*
bacterium__cp04.17
*Capnocytophaga*
*Atopobium*
*Phascolarctobacterium*
*Globicatella*
*Prevotella*
*Curtobacterium*
*Granulicatella*
*Solobacterium* provided that at least one of the bacteria is selected from the list consisting of;

Peptostreptococcaceae__XIII__[G-1]__sp.__COT-030
Peptostreptococcaceae__XIII__[G-2]__sp.__COT-077
Capnocytophaga__canimorsus
Escherichia__coli
Fusobacterium__sp.__COT-189
Selenomonas__sputigena__COT-342
Proprionibacterium__sp.__COT-365
Treponema__sp.__COT-200
Corynebacterium__sp.__cluster 88112
Erysipelotrichaceae__[G-3]__sp.__COT-302
Filifactor__sp.__COT-163
Lachnospiraceae__XIVa__[G-3]__sp.
Filifactor__sp.__COT-064
Neisseria__sp.__COT-049
Peptostreptococcaceae__XI__[G-6]__sp.__COT-067
Capnocytophaga__canimorus__COT-235
Porphyromonas__macacae__COT-192
Treponema__sp.__COT-351
Lachnospiraceae__XIVa__[G-6]__sp.__COT-161
Cardiobacterium__sp.__COT-176
Peptostreptococcaceae__XI__[G-7]__sp.__COT-155
Schwartzia__sp.__COT-063
Wolinella__succinogenes
Actinobaceria__sp.__COT-376
Clostridiales__[F-2.G-1]__sp.__COT-100__PO005
Clostridiales__III__[G-3]__sp.__COT-388
Desulfovibrionales__sp.__COT-009
Peptostreptococcaceae__XI__[G-3]__sp.__COT-034
Treponema__sp.__COT-198
*Parvimonas*
*Filifactor*
*Schwartzia*
bacterium__cp04.17
*Capnocytophaga*
*Atopobium*
*Phascolarctobacterium*
*Globicatella*
*Curtobacterium*
*Granulicatella*
*Solobacterium* in a sample from the animal. The presence or absence may be referred to as a 'binary' test. The presence or absence may be determined of one or more further bacteria selected from the list consisting of;

Filifactor__alocis__COT-001
Lachnospiraceae__XIVa__[G-6]__sp.__COT-106
Parvimonas__sp.__COT-035
Peptostreptococcaceae__XI__[G-1]__sp.__COT-006

-continued

Peptostreptococcaceae__XI__[G-3]__sp.__COT-104
Peptostreptococcaceae__XI__[G-4]__sp.__COT-021
Porphyromonas__crevioricanis__COT-253
Proprionibacterium__sp.__COT-296
Spirochaeta__sp.__COT-379
Treponema__sp.__COT-359
Actinomyces__sp.__COT-252
Bacteroides__denticanoris__COT-183 (Prevotella__sp?)
Catonella__sp.__COT-257
Chryseobacterium__sp.__COT-320
Pasteurella__canis__COT-273
Prophyromonas__sp.__COT-239
Spirochaeta__sp.__COT-314
Treponema__denticola__COT-197
Actinomyces__catuli
Anerovorax__sp.__COT-066
Bacteroidia__[G-5]__sp.__COT-187
Capnocytophaga__sp.__COT-339
Capnocytophaga__sp.__COT-362
Erysipelotrichaceae__[G-1]__sp.__COT-311
Filifactor__villosus__COT-031
Globicatella__sp.__COT-107
Lachnospiraceae__XIVa__[G-2]__sp.__COT-062
Leucobacter__sp.__COT-288
Parvimonas__sp.__COT-102
Pasteurella__dogmatis__COT-092
Xanthomonadaceae__bacterium
*Leucobacter*
*Odoribacter*
Propionibacteriaceae__bacterium
*Selenomonas*
*Actinomyces*
CDC__Group__NO-1
Clostridiales__III__[G-3]__sp.__COT-388__1P046
*Propionivibrio*
*Xenophilus*
*Corynebacterium*
*Escherichia*
*Lautropia*
*Leptotrichia* in a sample from the animal.

Alternatively or additionally the presence or absence may be determined of one or more further bacteria selected from the list consisting of;

Peptostreptococcaceae__XI__[G-1]__sp.__COT-004
Peptostreptococcaceae__XI__[G-1]__sp.__COT-258
Peptostreptococcaceae__XI__[G-6]__sp.__COT-068
Porphyromonas__sp.__COT-290
Prevotella__sp.__COT-195
Prevotella__sp.__COT-282
Proprionibacterium__sp.__COT-300
Stenotrophomonas__sp.__COT-224
Streptococcus__minor__COT-116
Xenophilus__sp.__COT-174
Actinomyces__sp.
Actinomyces__sp. Cluster 7595
Anaerovorax__sp.__COT-125
Capnocytophaga__sp.__COT-254
Catonella__sp.__COT-025
Erysipelotrichaceae__[G-4]__sp.__COT-381
Frigovirgula__sp.__COT-007
Fusobacterium__sp.__COT-169
Moraxella__sp.__COT-018
Parvimonas__sp.__COT-101
Peptostreptococcaceae__XI__[G-2]__sp.__COT-047
Peptostreptococcaceae__XI__[G-4]__sp.__COT-019
Porphyromonas__gulae__II__COT-052
Porphyromonas__sp.__COT-181
Porphyromonas__sp.__COT-361
Prevotella__sp.__COT-298
Synergistales__[G-1]__sp.__COT-178
Treponema__sp.__COT-233
*Staphylococcus*
*Tannerella*

*Arcobacter*
*Catonella*
*Chryseobacterium*
*Fusobacterium* in a sample from the animal, in order to predict the oral health status of an animal.

The presence of bacteria associated with disease can give an indication that the animal has gingivitis or periodontitis. The absence of a bacteria associated with disease is a good indication that the dog has good oral health. The presence of the health associated bacteria can help to determine how healthy is the mouth of the animal, although is less strong of an indicator than the presence of a disease associated bacterial species or genera. A binary test (determining presence or absence) can involve identifying just one incidence of a bacterial species or there may be a threshold, in that a particular bacterial species or genus is not considered present until the count for that particular species/genera reaches at least 3, or at least 5 or at least 7, or at least 9.

A bacterial count may be determined by the number of times its sequence information is identified in a sample, by qPCR or by colony count. By counts, it is meant an absolute number, rather than a proportional number.

Alternatively or additionally the step to determine the oral health status may comprise determining the proportion of total plaque bacteria of two or more of a bacteria species or genera selected from the list consisting of Peptostreptococcaceae__XIII__[G-1]__sp.__COT-030
Peptostreptococcaceae__XIII__[G-2]__sp.__COT-077
Capnocytophaga__canimorsus
Moraxella__sp.__COT-017
Escherichia__coli
Fusobacterium__sp.__COT-189
Selenomonas__sputigena__COT-342
Proprionibacterium__sp.__COT-365
Treponema__sp.__COT-200
Corynebacterium__sp.__cluster 88112
Erysipelotrichaceae__[G-3]__sp.__COT-302
Filifactor__sp.__COT-163
Lachnospiraceae__XIVa__[G-3]__sp.
Filifactor__sp.__COT-064
Neisseria__sp.__COT-049
Neisseria__weaveri__COT-269
Peptostreptococcaceae__XI__[G-6]__sp.__COT-067
Capnocytophaga__canimorus__COT-235
Porphyromonas__macacae__COT-192
Treponema__sp.__COT-351
Lachnospiraceae__XIVa__[G-6]__sp.__COT-161
Cardiobacterium__sp.__COT-176
Pasteurellaceae__sp.__COT-271
Peptostreptococcaceae__XI__[G-7]__sp.__COT-155
Schwartzia__sp.__COT-063
Wolinella__succinogenes
Actinobaceria__sp.__COT-376
Clostridiales__[F-2.G-1]__sp.__COT-100__PO005
Clostridiales__III__[G-3]__sp.__COT-388
Desulfovibrionales__sp.__COT-009
Peptostreptococcaceae__XI__[G-3]__sp.__COT-034
Porphyromonas__gulae__I__COT-052
Treponema__sp.__COT-198
*Parvimonas*
*Peptostreptococcus*
*Moraxella*
*Filifactor*
*Schwartzia*
*Treponema*
bacterium__cp04.17
*Capnocytophaga*
*Atopobium*
*Phascolarctobacterium*
*Globicatella*
*Prevotella*
*Curtobacterium*
*Granulicatella*
*Solobacterium* provided that at least one of the bacteria is selected from the list consisting of Peptostreptococcaceae__XIII__[G-1]__sp.__COT-030
Peptostreptococcaceae__XIII__[G-2]__sp.__COT-077
Capnocytophaga__canimorsus
Escherichia__coli
Fusobacterium__sp.__COT-189
Selenomonas__sputigena__COT-342
Proprionibacterium__sp.__COT-365
Treponema__sp.__COT-200
Corynebacterium__sp.__cluster 88112
Erysipelotrichaceae__[G-3]__sp.__COT-302
Filifactor__sp.__COT-163
Lachnospiraceae__XIVa__[G-3]__sp.
Filifactor__sp.__COT-064
Neisseria__sp.__COT-049
Peptostreptococcaceae__XI__[G-6]__sp.__COT-067
Capnocytophaga__canimorus__COT-235
Porphyromonas__macacae__COT-192
Treponema__sp.__COT-351
Lachnospiraceae__XIVa__[G-6]__sp.__COT-161
Cardiobacterium__sp.__COT-176
Peptostreptococcaceae__XI__[G-7]__sp.__COT-155
Schwartzia__sp.__COT-063
Wolinella__succinogenes
Actinobaceria__sp.__COT-376
Clostridiales__[F-2.G-1]__sp.__COT-100__PO005
Clostridiales__III__[G-3]__sp.__COT-388
Desulfovibrionales__sp.__COT-009
Peptostreptococcaceae__XI__[G-3]__sp.__COT-034
Treponema__sp.__COT-198
*Parvimonas*
*Filifactor*
*Schwartzia*
bacterium__cp04.17
*Capnocytophaga*
*Atopobium*
*Phascolarctobacterium*
*Globicatella*
*Curtobacterium*
*Granulicatella*
*Solobacterium* in a sample from the animal.

The proportion of total plaque bacteria may be determined, at a further one or more bacteria selected from the list consisting of Filifactor__alocis__COT-001
Lachnospiraceae__XIVa__[G-6]__sp.__COT-106
Parvimonas__sp.__COT-035
Peptostreptococcaceae__XI__[G-1]__sp.__COT-006
Peptostreptococcaceae__XI__[G-3]__sp.__COT-104
Peptostreptococcaceae__XI__[G-4]__sp.__COT-021
Porphyromonas__crevioricanis__COT-253
Proprionibacterium__sp.__COT-296
Spirochaeta__sp.__COT-379
Treponema__sp.__COT-359
Actinomyces__sp.__COT-252
Bacteroides__denticanoris__COT-183
(*Prevotella*__sp?)
Catonella__sp.__COT-257
Chryseobacterium__sp.__COT-320
Pasteurella__canis__COT-273
Prophyromonas__sp.__COT-239
Spirochaeta__sp.__COT-314

-continued

Treponema_denticola_COT-197
Actinomyces_catuli
Anerovorax_sp._COT-066
Bacteroidia_[G-5]_sp._COT-187
Capnocytophaga_sp._COT-339
Capnocytophaga_sp._COT-362
Erysipelotrichaceae_[G-1]_sp._COT-311
Filifactor_villosus_COT-031
Globicatella_sp._COT-107
Lachnospiraceae_XIVa_[G-2]_sp._COT-062
Leucobacter_sp._COT-288
Parvimonas_sp._COT-102
Pasteurella_dogmatis_COT-092
Xanthomonadaceae_bacterium
*Leucobacter*
*Odoribacter*
*Propionibacteriaceae_bacterium*
*Selenomonas*
*Actinomyces*
CDC_Group_NO-1
Clostridiales_III_[G-3]_sp._COT-388_1P046
*Propionivibrio*
*Xenophilus*
*Corynebacterium*
*Escherichia*
*Lautropia*
*Leptotrichia* in a sample from the animal

Alternatively or additional, the proportion of total plaque bacteria may be determined of a further one or more bacteria selected from the list consisting of Peptostreptococcaceae_XI_[G-1]_sp._COT-004
Peptostreptococcaceae_XI_[G-1]_sp._COT-258
Peptostreptococcaceae_XI_[G-6]_sp._COT-068
Porphyromonas_sp._COT-290
Prevotella_sp._COT-195
Prevotella_sp._COT-282
Proprionibacterium_sp._COT-300
Stenotrophomonas_sp._COT-224
Streptococcus_minor_COT-116
Xenophilus_sp._COT-174
Actinomyces_sp.
Actinomyces_sp. Cluster 7595
Anaerovorax_sp._COT-125
Capnocytophaga_sp._COT-254
Catonella_sp._COT-025
Erysipelotrichaceae_[G-4]_sp._COT-381
Frigovirgula_sp._COT-007
Fusobacterium_sp._COT-169
Moraxella_sp._COT-018
Parvimonas_sp._COT-101
Peptostreptococcaceae_XI_[G-2]_sp._COT-047
Peptostreptococcaceae_XI_[G-4]_sp._COT-019
Porphyromonas_gulae_II_COT-052
Porphyromonas_sp._COT-181
Porphyromonas_sp._COT-361
Prevotella_sp._COT-298
Synergistales_[G-1]_sp._COT-178
Treponema_sp._COT-233
*Staphylococcus*
*Tannerella*
*Arcobacter*
*Catonella*
*Chryseobacterium*
*Fusobacterium* in a sample from the animal

By proportion it is meant the percentage of total bacteria within the sample that is formed by a particular bacterial species or genus.

Alternatively or additionally the step to identify the bacteria in order to determine the oral health status may comprise determining the number of counts of two or more of a bacteria species or genera selected from the list consisting of Peptostreptococcaceae_XIII_[G-1]_sp._COT-030
Peptostreptococcaceae_XIII_[G-2]_sp._COT-077
Capnocytophaga_canimorsus
Moraxella_sp._COT-017
Escherichia_coli
Fusobacterium_sp._COT-189
Selenomonas_sputigena_COT-342
Proprionibacterium_sp._COT-365
Treponema_sp._COT-200
Corynebacterium_sp._cluster 88112
Erysipelotrichaceae_[G-3]_sp._COT-302
Filifactor_sp._COT-163
Lachnospiraceae_XIVa_[G-3]_sp.
Filifactor_sp._COT-064
Neisseria_sp._COT-049
Neisseria_weaveri_COT-269
Peptostreptococcaceae_XI_[G-6]_sp._COT-067
Capnocytophaga_canimorus_COT-235
Porphyromonas_macacae_COT-192
Treponema_sp._COT-351
Lachnospiraceae_XIVa_[G-6]_sp._COT-161
Cardiobacterium_sp._COT-176
Pasteurellaceae_sp._COT-271
Peptostreptococcaceae_XI_[G-7]_sp._COT-155
Schwartzia_sp._COT-063
Wolinella_succinogenes
Actinobaceria_sp._COT-376
Clostridiales_[F-2.G-1]_sp._COT-100_PO005
Clostridiales_III_[G-3]_sp._COT-388
Desulfovibrionales_sp._COT-009
Peptostreptococcaceae_XI_[G-3]_sp._COT-034
Porphyromonas_gulae_I_COT-052
Treponema_sp._COT-198
*Parvimonas*
*Peptostreptococcus*
*Moraxella*
*Filifactor*
*Schwartzia*
*Treponema*
bacterium_cp04.17
*Capnocytophaga*
*Atopobium*
*Phascolarctobacterium*
*Globicatella*
*Prevotella*
*Curtobacterium*
*Granulicatella*
*Solobacterium* provided that at least one of the bacteria is selected from the list consisting of Peptostreptococcaceae_XIII_[G-1]_sp._COT-030
Peptostreptococcaceae_XIII_[G-2]_sp._COT-077
Capnocytophaga_canimorsus
Escherichia_coli
Fusobacterium_sp._COT-189
Selenomonas_sputigena_COT-342
Proprionibacterium_sp._COT-365
Treponema_sp._COT-200
Corynebacterium_sp._cluster 88112
Erysipelotrichaceae_[G-3]_sp._COT-302
Filifactor_sp._COT-163
Lachnospiraceae_XIVa_[G-3]_sp.
Filifactor_sp._COT-064
Neisseria_sp._COT-049
Peptostreptococcaceae_XI_[G-6]_sp._COT-067
Capnocytophaga_canimorus_COT-235
Porphyromonas_macacae_COT-192
Treponema_sp._COT-351
Lachnospiraceae_XIVa_[G-6]_sp._COT-161
Cardiobacterium_sp._COT-176
Peptostreptococcaceae_XI_[G-7]_sp._COT-155

-continued

Schwartzia_sp._COT-063
Wolinella_succinogenes
Actinobaceria_sp._COT-376
Clostridiales_[F-2.G-1]_sp._COT-100_PO005
Clostridiales_III_[G-3]_sp._COT-388
Desulfovibrionales_sp._COT-009
Peptostreptococcaceae_XI_[G-3]_sp._COT-034
Treponema_sp._COT-198
*Parvimonas*
*Filifactor*
*Schwartzia*
bacterium_cp04.17
*Capnocytophaga*
*Atopobium*
*Phascolarctobacterium*
*Globicatella*
*Curtobacterium*
*Granulicatella*
*Solobacterium* in a sample from the animal.

The number of counts may be determined of a further one or more bacteria selected from the list consisting of Filifactor_alocis_COT-001
Lachnospiraceae_XIVa_[G-6]_sp._COT-106
Parvimonas_sp._COT-035
Peptostreptococcaceae_XI_[G-1]_sp._COT-006
Peptostreptococcaceae_XI_[G-3]_sp._COT-104
Peptostreptococcaceae_XI_[G-4]_sp._COT-021
Porphyromonas_crevioricanis_COT-253
Proprionibacterium_sp._COT-296
Spirochaeta_sp._COT-379
Treponema_sp._COT-359
Actinomyces_sp._COT-252
Bacteroides_denticanoris_COT-183
(Prevotella_sp?)
Catonella_sp._COT-257
Chryseobacterium_sp._COT-320
Pasteurella_canis_COT-273
Prophyromonas_sp._COT-239
Spirochaeta_sp._COT-314
Treponema_denticola_COT-197
Actinomyces_catuli
Anerovorax_sp._COT-066
Bacteroidia_[G-5]_sp._COT-187
Capnocytophaga_sp._COT-339
Capnocytophaga_sp._COT-362
Erysipelotrichaceae_[G-1]_sp._COT-311
Filifactor_villosus_COT-031
Globicatella_sp._COT-107
Lachnospiraceae_XIVa_[G-2]_sp._COT-062
Leucobacter_sp._COT-288
Parvimonas_sp._COT-102
Pasteurella_dogmatis_COT-092
Xanthomonadaceae_bacterium
*Leucobacter*
*Odoribacter*
*Propionibacteriaceae_bacterium*
*Selenomonas*
*Actinomyces*
CDC_Group_NO-1
Clostridiales_III_[G-3]_sp._COT-388_1P046
*Propionivibrio*
*Xenophilus*
*Corynebacterium*
*Escherichia*
*Lautropia*
*Leptotrichia* in a sample from the animal.

Alternatively or additional, the number of counts may be determined of a further one or more bacteria selected from the list consisting of Peptostreptococcaceae_XI_[G-1]_sp._COT-004
Peptostreptococcaceae_XI_[G-1]_sp._COT-258
Peptostreptococcaceae_XI_[G-6]_sp._COT-068
Porphyromonas_sp._COT-290
Prevotella_sp._COT-195
Prevotella_sp._COT-282
Proprionibacterium_sp._COT-300
Stenotrophomonas_sp._COT-224
Streptococcus_minor_COT-116
Xenophilus_sp._COT-174
Actinomyces_sp.
Actinomyces_sp. Cluster 7595
Anaerovorax_sp._COT-125
Capnocytophaga_sp._COT-254
Catonella_sp._COT-025
Erysipelotrichaceae_[G-4]_sp._COT-381
Frigovirgula_sp._COT-007
Fusobacterium_sp._COT-169
Moraxella_sp._COT-018
Parvimonas_sp._COT-101
Peptostreptococcaceae_XI_[G-2]_sp._COT-047
Peptostreptococcaceae_XI_[G-4]_sp._COT-019
Porphyromonas_gulae_II_COT-052
Porphyromonas_sp._COT-181
Porphyromonas_sp._COT-361
Prevotella_sp._COT-298
Synergistales_[G-1]_sp._COT-178
Treponema_sp._COT-233
*Staphylococcus*
*Tannerella*
*Arcobacter*
*Catonella*
*Chryseobacterium*
*Fusobacterium* in a sample from the animal.

Information such as the (i) presence or absence; (ii) the proportion of total bacteria; or (iii) number of counts of two or more bacterial species or genus can be used individually or in combination in order to predict the oral health status of an animal, as shown by the examples, below.

The present invention also relates to a method of determining the oral health status of a canine animal, the method comprising the use of the assay of the invention to identify at least two bacteria as herein described in a sample taken from the animal and applying the information set out in FIG. 12 (table 5) for each identified bacteria to statistical models in order to make a prediction of oral health status.

Statistical models that are able to be used in order to generate such predictions are well known in the art, using the data included herein, in tables 1 to 5. The data show the number of times a certain species or genus was found in the oral cavity of animals, and whether each animal in which it was found has been classed as being in good oral health, having gingivitis or periodontitis.

This information, combined with information regarding a particular animal obtained from the assay of the invention, and the use of statistical models known to the skilled person (examples of which are described herein) can lead to a prediction that is up to 83% accurate.

Currently, without using methods (that involve invasive procedures and anaesthetics), a canine animal is predicted to have a 50/50 chance of suffering from periodontitis, or not (i.e. being P/not P). Thus, the present invention shows a clear improvement and benefit over current invasive, time consuming and expensive methods.

Once the information on presence/absence and/or proportion and/or counts of two or more bacteria has been obtained, one or more known statistical models can be used to predict the oral health status of the canine animal.

Models are shown in Examples 2 to 12. Further models are known to one skilled in the art. The information obtained can be analysed to produce predictive values to enable the oral health status of an animal (health, gingivitis or periodontitis/disease) to be determined.

By determining the oral health status it is meant that the current status is determined, such as whether the mouth of the animal is in good oral health, has gingivitis or periodontitis at the time of taking the sample. The oral health status prediction may also encompass a prediction on whether a healthy mouth is likely to develop gingivitis or periodontitis, or whether gingivitis is likely to develop into periodontitis, based on the bacterial species or genera that are present/absent and the levels or counts of such bacteria. Thus, the assay of the present invention allows reliable prediction of the future oral health of the animal as well as providing information on the current oral health of the canine animal.

In practice, the method of the invention involves the (non-invasive) collection of a sample from the oral cavity of a canine animal, the use of the assay of the invention to identify the presence or absence of the herein described bacteria in the sample. The information can then be compared to that presented in FIG. 12 (table 51 and suitable statistical models, such as those exemplified herein, can be used to generate a reliable prediction and determination of the oral health status of the animal.

The present invention also provides a method of improving or maintaining the oral health of an animal, the method comprising determining the oral health status of a canine animal using the assay according to the invention and providing to the animal a foodstuff or supplement which is formulated to improve or maintain oral health, depending on the oral health status that has been determined by way of the assay.

Such food products are known in the art, such as those containing active ingredients to improve oral health or those designed to remove plaque by abrasion, analogous to regular tooth-brushing. The amount or frequency of the foodstuff or supplement can be determined depending on the result of the assay. The predicted future health of the animal can also be taken into account when determining how often such oral care foodstuffs should be provided.

The present invention also provides an assay for determining the oral health status of a canine animal, the assay comprising means for identifying at least two bacteria selected from the list consisting of *Anaerovorax*.sp.COT-124, *Actinobaceria*.sp.COT-376, *Actinomyces*.sp., *Actinomyces*.sp.COT-252, *Aquaspirillum*.sp.COT-091, *Bergeyella.zoohelcum*.COT-186, *Brachymonas*.sp.COT-015, *Campylobacters*p.COT-011, *Capnocytophaga.canimorsus*, *Capnocytophaga*.sp.COT-339, *Capnocytophaga*.sp.COT-362, *Cardiobacterium*.sp.COT-176, *Desulfovibrionales*.sp. COT-009, *Escherichia.coli*, *Fusobacterium*.sp.COT-169, *Fusobacterium*.sp.COT-189, g.*Atopobium*, g.*bacterium*.cp04.17, g.*Capnocytophaga*, g.*Corynebacterium*, g.*Ottowia*, g.*Parvimonas*, g.*Prevotella*, g.*Schwartzia*, *Globicatella*.sp.COT-107, LachnospiraceaeXIVa[G-2].sp.COT-062, LachnospiraceaeXIVa[G-4].sp.COT-099, *Lautropia*.sp. COT-060, *Leucobacter*.sp.COT-288, *Parvimonas*.sp.COT-101, PeptostreptococcaceaeXI[G-1].sp.COT-006, PeptostreptococcaceaeXI[G-1].sp.COT-071, PeptostreptococcaceaeXI[G-3].sp.COT-034, PeptostreptococcaceaeXI[G-3].sp.COT-307, PeptostreptococcaceaeXIII[G-2].sp.COT-077, Porphyromonadaceae[G-1].sp.COT-184, *Porphyromonas*.sp.COT-290, *Prevotella*.sp.COT-282, *Prevotella*.sp.COT-298, *Prophyromonas*.sp.COT-239, *Proprionibacterium*.sp.COT-296, *Proprionibacterium*.sp.COT-321, *Proprionibacterium*.sp.COT-365, *Spirochaeta*.sp.COT-314, *Spirochaeta*.sp.COT-379,

*Streptococcus*.sp.cluster2789, *Capnocytophaga.canimorus*.COT-235, *Chloroflexi*[G-1].sp.COT-306, *Desulfovibrio*.sp.COT-070, *Erysipelotrichaceae*[G-3].sp.COT-302, *Filifactor*.sp.COT-064, *Filifactor*.sp.COT-163, *Fusobacterium*.sp.COT-236, g.*bacterium*.cp04.17, g.*Parvimonas*, g.*Phascolarcto.bacterium*, g.*Solobacterium*, g.*Veillonellaceae.bacterium*, *Gemella.palaticanis*.COT-089, *Helcococcus*.sp.COT-069, *Helcococcus*.sp.COT-140, LachnospiraceaeXIVa[G-6].sp.COT-161, *Parvimonas*.sp.COT-101, PeptostreptococcaceaeXI[G-1].sp.COT-004, PeptostreptococcaceaeXI[G-1].sp.COT-258, PeptostreptococcaceaeXI[G-3].sp.COT-104, PeptostreptococcaceaeXI[G-4].sp.COT-019, PeptostreptococcaceaeXI[G-4].sp.COT-019, PeptostreptococcaceaeXI[G-6].sp.COT-067, PeptostreptococcaceaeXIII[G-1].sp.COT-030, PeptostreptococcaceaeXIII[G-2].sp.COT-077, *Porphyromonas.crevioricanis*.COT-253, *Porphyromonas.macacae*.COT-192, *Porphyromonas*.sp.COT-181, *Porphyromonas*.sp.COT-361, *Prevotella*.sp.COT-195, *Proprionibacterium*.sp.COT-296, *Selenomonas.sputigena*.COT-342, *Streptococcus.minor*.COT-116, *Xenophilus*.sp.COT-174, *Bacteroidia*[G-4].sp.COT-387, *Bacteroides.denticanoris*.COT-183(Prevotellasp?), *Desulfomicrobium.orale*.COT-008, *Filifactor.villosus*.COT-031, g.*Moraxella*, g.*Peptostreptococcus*, *Porphyromonas.gulael*.COT-052, *Porphyromonas.gulaell*.COT-052, *Treponema.denticola*.COT-197, *Frigovirgula*.sp.COT-058, *Moraxella*.sp.COT-017, g.*Filifactor*, g.*Treponema*, *Bacteroides.heparinolyticus*.COT-310, *Bacteroides*.sp.COT-040, *Bacteroides.tectus*.COT-039, *Clostridiales*[F-2.G-1].sp.COT-100P0005, *Clostridiales*III[G-3].sp.COT-388, *Neisseria*.sp.COT-049, *Neisseria*.sp. COT-090, *Neisseria.weaveri*.COT-269, *Neisseria.zoodegmatis*.COT-349, *Pasteurella.canis*.COT-273, *Pasteurellaceae*.sp.COT-271, *Pasteurelladogmatis*.COT-092, *Synergistales*[G-1].sp.COT-180, *Synergistales*[G-1].sp.COT-244, *Filifactor*.sp.COT-064, *Peptostreptococcus*.sp.COT-033, *Treponema*.sp.COT-200, *Treponema*.sp.COT-351, *Treponema*.sp.COT-359, *Treponema*.sp.COT-198, *Streptococcus anginosus* COT-117, *Peptostreptococcus*_XI_sp COT-067, *Frigovirgula*_sp_COT-007, g. *Odoribacter*, in a sample taken from the animal and determining the oral health status of the animal.

Should the assay or method of the invention determine the likelihood that the oral health status is "P" (periodontosis/disease), the animal may be referred for a more thorough dental check to determine the next course of action.

If the assay determines that the oral health status is "not H" (i.e. not healthy), a further assay may be carried out to determine whether the status is Phot P. Alternatively or additionally, diet changes (as described above), dental chews (such as Dentastix®), tooth brushing or a dental check may be recommended for the animal. A further test in 1 month, 3 months, 6 months or 12 months may also be recommended.

If the assay determines the likelihood of 'health', a further assay may be recommended in 1 month, 3 months, 6 months or 12 months and for the oral health regime (e.g. diet, dental chews, tooth brushing) to be maintained.

The present invention also provides a method of determining the efficacy of an oral care product in a canine animal, the method comprising determining the oral health status of a canine animal using the assay of the invention; providing to the animal an oral care product for a certain period of time; and determining the oral health status of the animal using the assay of the invention after the period of time has elapsed.

Such a method enables the progress of the improvement of oral health to be monitored, without any invasive or risky procedures to the animal. More than one time point may be used, for example weekly, monthly, every two, three, four, five or six months, or annually. The amount of improvement of the oral health status may give an indication of the efficacy of the oral care product used in the method. Such oral care products or procedures may include foodstuffs, supplements, dental chews, tooth brushing, amongst others.

Such a method allows product efficacy to be tested in a scenario that more closely mimics the real life environment and would have the following impact on the ability to test oral care products. Larger scale trials could be performed, as the choice of animals would not be limited to those in research facilities. The access to animals outside of research facilities also allows longer term trials to be performed allowing the long term benefits of oral care products to be assessed. Products could be tested for their ability to remove plaque and reduce gingivitis rather than for only the ability to prevent the formation of plaque or development of gingivitis. The method also allows the measuring of prevention and the measuring of treatment. Comparison trials between products are able to be performed easily and with no detriment or stress to the animal.

EXAMPLES

The invention will now be described with reference to the following non-limiting figures and examples in which;

FIG. 12 shows sample data from 155 dogs.

EXAMPLE 1

Figure 1:
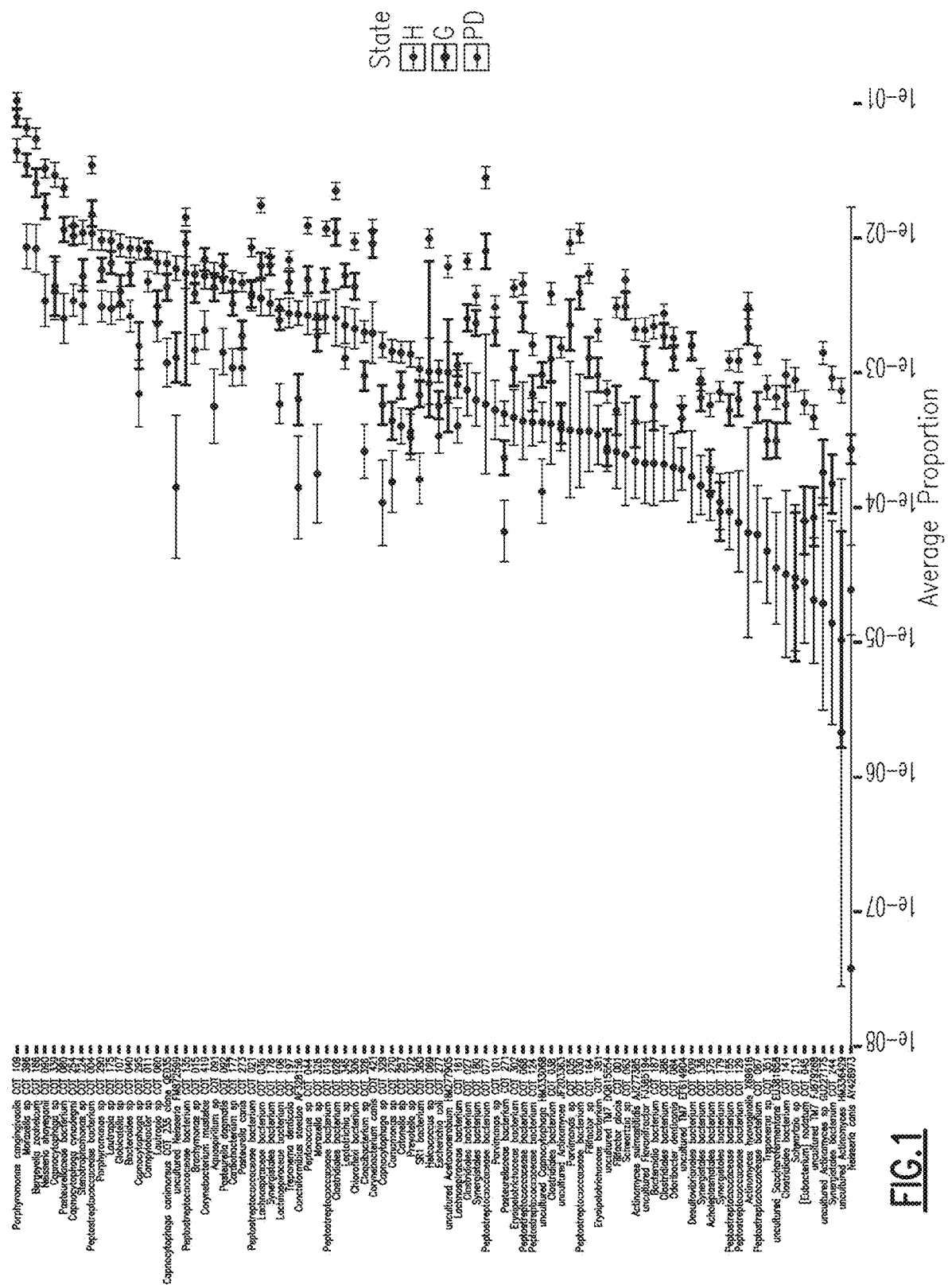
FIG. 1 shows the average proportions with 95% confidence interval for OTUs with a significant health status effect; health, gingivitis and mild periodontitis.

Subgingival plaque samples were collected from 223 dogs with healthy gingiva, gingivitis and mild periodontitis with 72 to 77 samples per health status. DNA was extracted from the plaque samples and subjected to PCR amplification of the V1-V3 region of the 16S rDNA. Pyrosequencing of the PCR amplicons identified a total of 274 operational taxonomic units (OTUs) after bioinformatic and statistical analysis. *Porphyromonas* was the most abundant genus in all disease stages, particularly in health along with *Moraxella* and *Bergeyella*. *Peptostreptococcus, Actinomyces*, and Peptostreptococcaceae were the most abundant genera in mild periodontitis. Logistic regression analysis identified species from each of these genera that were significantly associated with health, gingivitis or mild periodontitis. Principal component analysis showed distinct community profiles in health and disease. The species identified show some similarities with health and periodontal disease in humans but also major differences. In contrast to human, healthy canine plaque was found to be dominated by Gram negative bacterial species whereas Gram positive anaerobic species predominate in disease.

Sampling Strategy and Study Cohort

The study was approved by the WALTHAM® Centre for Pet Nutrition ethical review committee, and run under licensed authority in accordance with the UK Animals (Scientific Procedures) Act 1986. Owner consent was obtained and an owner survey was completed for all dogs included in the study.

Dental assessments, scoring and subgingival plaque sampling were performed by a single veterinary dentist (L. Milella) to avoid variation in scoring. The study cohort comprised client owned pet dogs presented at a veterinary referral dental clinic. Only dogs under anaesthetic for routine dental treatment or treatment for non-periodontal complications e.g. broken teeth or other non-infectious conditions were screened for inclusion in the study. No dogs were anaesthetised solely for the collection of plaque samples. The periodontal health status of each dog was obtained following the Wiggs & Lobprise scoring system (Wiggs & Lobprise, 1997) and plaque samples taken from dogs regarded as having healthy teeth and gums, gingivitis or mild periodontitis (PD1, <25% attachment loss). Dogs were excluded from the study if they had: 1) Significant veterinary oral care within the preceding 3 months; 2) Regular dental care at home i.e. dogs whose teeth are regularly brushed; 3) Systemic or oral antibiotic treatment any of the previous 3 months and 4) Evidence of any extra-oral bacterial infections in the past month. Breeds thought to exhibit an alternative early onset/aggressive form of periodontitis, were also excluded. These breeds were Greyhounds, Yorkshire Terriers, Maltese and Toy Poodles.

Sub-gingival plaque samples were collected using a sterile periodontal probe and placed in 350 µl TE buffer (50 mM Tris pH 7.6, 1 mM EDTA pH 8.0 & 0.5% Tween 20) prior to storage at −20° C.

Healthy dogs were sampled subgingivally at eighteen sites, targeting the teeth most often affected by PD (upper 103-108 bilaterally and lower 404, 408 and 409 bilaterally), to support plaque volumes in the absence of periodontal pockets. Periodontally diseased dogs were sampled for subgingival plaque at up to twelve diseased sites (103, 104, 108, 404, 408, 409 bilaterally) during their normal periodontal treatment. Information on dog age, breed, size, sex and neuter status was collated.

DNA Extraction & Amplification of 16S rDNA

DNA was extracted from the plaque samples using an Epicentre Masterpure Gram Positive DNA Purification Kit, according to the manufacturer's instructions with an additional overnight lysis. Plaque samples were centrifuged at 5000×g for 10 minutes and the cell pellet resuspended in 150 µl of TE buffer. Following vortexing, 1 µl Ready-Lyse Lysozyme (Epicentre, UK) was added and the lysis mix incubated overnight at 37° C. for 18 hrs overnight. After DNA extraction the DNA pellet was suspended in TE buffer (10 mM Tris-CI and 0.5 mM pH 9.0 EDTA) and quantified and the purity ascertained using a NanoDrop ND1000 spectrophotometer (NanoDrop Technologies Inc).

The V1-V3 region of the 16S rDNA was amplified from subgingival plaque DNA extractions using Extensor Hi-Fidelity PCR Enzyme Mix (AB-0792, Thermo, UK) in a 96-well format. A mix of two universal forward primers was used; FLX_27FYM (CGTATCGCCTCCCTCGCGC-CATCAG AGAGTTTGATYMTGGCTCAG) at 9.5 pmol/µl and FLX_27F_Bif (CGTATCGCCTCCCTCGCGC-CATCAG AGGGTTCGATTCTGGCTCAG) at 0.5 pmol/µl (where italics represent FLX Titanium Primer A and bold represents 16S sDNA primer sequence). The latter was included to ensure representation of the genus Bifidobacter, a lower concentration was chosen due to the low representation of this genus in previous studies of canine plaque. The DNA was to be sequenced from the reverse primer thus 20 different 7mer MID tags were included in the reverse primer (CTATGCGCCTTGCCAGCCCGCTCAGXXXXXXXTY ACCGCGGCTGCTGG) where italics represent FLX Titanium Primer B, X represents MID sequence and bold represents 16S sDNA reverse primer sequence.

Library Preparation

Library preparation and sequencing was performed by Beckman Coulter Genomics, UK. The 16S rDNA amplicons were purified with Agencourt AMPure XP beads (Beckman Coulter Inc, UK), quantified using the Quant-iT™ PicoGreen® dsDNA Assay Kit (Invitrogen, UK) then pooled into groups of 20 samples prior to Emulsion PCR. Libraries were then sequenced on a Roche Genome Sequencer FLX Titanium System™ using the FLX Titanium B primer only with a target of ~15,000 unidirectional reads per sample.

Sequence Processing and Analysis

The standard flowgram files (SFF) for each of the 223 samples were initially filtered by selecting reads with at least 360 flows and truncating long reads to 720 flows. Reads were filtered and denoised using the AmpliconNoise software (version V1.21; Quince et al., 2009, 2011). For the initial filtering step, reads were truncated when flow signals dropped below 0.7, indicative of poor quality. A maximum of 20,000 reads per sample were used with exception of a few samples due to the computational demands of the denoising algorithm. Subsequently reads were denoised in three stages; 1) Pyronoise to remove noise from flowgrams resulting from 454 sequencing errors (PyronoiseM parameters −s 60, −c 0.01), 2) Seqnoise to remove errors resulting from PCR amplification (SeqNoiseM parameters −s 25, −c 0.08), 3) Perseus to detect and remove chimeras resulting from PCR recombination. The denoised sequences were then clustered using QIIME, a pipeline for performing microbial community analysis that integrates many third party tools which have become standard in the field. The QIIME script pick_otus.py, which utilises the Uclust software program, was used to cluster sequences with >98% identity. Uclust was run with modified parameters, with gap opening penalty set to 2.0 and gap extension penalty set to 1.0 and —A flag to ensure optimum alignment.

Representative sequences of all observed OTUs that passed the filtering criteria for sequence abundance (see statistical analysis section) across health states were searched against the Canine Oral Microbiome Database (COMD) using BLASTN of NCBI-BLAST 2.2.27+. The COMD sequence database contained 460 published 16S DNA sequences obtained from canine oral taxa (Genbank accession numbers JN713151-JN713566 & KF030193-KF030235). Additionally, representative sequences were searched against the 376,437 sequences in the Silva SSU database release 108. For each representative sequence the best BLAST hit in the COMD database was chosen as the reference sequence. If the alignment did not meet the cut-off criteria of 98% sequence identity and 98% sequence coverage the best hit from the Silva database was chosen. The assignments were checked for redundancies (two or more OTUs assigned to the same reference sequence). Redundancies were resolved by keeping the taxonomy for the OTU with the better match and assigning the next best match to the other OTU.

A multiple sequence alignment (MSA) was constructed by aligning each reference sequence to the Greengenes core set (revision May 3, 2011) with PyNAST using the script align_seqs.py of the Qiime pipeline. The MSA was filtered using the filter_alignment.py script of the Qiime pipeline. The MSA was converted to Phylip interleaved format using ClustalW 2.1. A maximum likelihood tree of 1000 bootstrap replicates was inferred with PhyML 3 revision 20120412. A GTR model of nucleotide substitution was chosen and the proportion of invariant sites was estimated from the data. Evolutionary rates were approximated by a discrete gamma model of eight categories. The tree was visualised and combined with abundance and significance data in iTOL.

A second tree with a reduced amount of taxa was inferred at the genus level. For this purpose all species of the same genus were collated into a single taxon. The 16S sequence of the most abundant species of that genus was used for tree inference using the methods described above. If no genus information was present, taxa forming a Glade in the full tree were grouped together and the new taxon was named e.g. "*Actinomyces* Glade A". Abundance information was added up for all members of each summarised taxon and plotted on the tree using iTOL. The tree was complemented with information on the number of original taxa summarised and the number of significant taxa. See table 3 in which taxa were grouped together.

Statistical Analysis

Health and disease associations: The most abundant OTUs (>0.05%) were analysed using logistic regression analyses (Generalised linear model with a binomial distribution and logit link) for proportions, using the count for the OTU out of the total number of sequences and health status was included as a fixed effect. OTUs were classified in a single group of "rare" taxa if either they were present in each health status group at an average proportion below 0.05% or were present in less than two samples. The 0.05% cut-off was selected based on statistical analysis of data from mock communities containing 17 known species sequenced on five separate 454 runs. The mock communities were analysed for presence and absence of species using a false positive rate of 0.3% (i.e. finding species that were not included in the mock community) and false negative rate of 1.7% (i.e. the failure to identify the species that were known to be present) and aimed for a coefficient of variation of <20% (data not shown). As the data were of very low proportions ~0.1%, a permutation test (1000 repeats) was used to test the robustness of the logistic regression analysis assumptions. The effect of health status for the true data was then compared to the effects from the permutations to give a more robust p-value for the overall effect of health status. The permutation p-values were adjusted according to the false discovery method of Benjamini and Hochberg (1995).

Principal component analysis (PCA) was performed on the log 10 (proportions+0.00003 to allow for zeros) to determine if variability of the most abundant OTUs (>0.05% of total reads) was associated with health status, gender, size and age.

Gram-stain status: The OTUs excluding rares were classified as gram positive or gram negative based on literature searches using the genus name. The number of sequences gram positive or gram negative were then analysed by logistic regression for proportions (adjusting for the total number of sequences and allowing for estimation of over dispersion) with health status as a fixed effect.

Oxygen Requirement: The non-rare OTUs were classified as aerobic, anaerobic or facultative anaerobe based on literature searches using the genus name. The number of sequences of aerobic, anaerobic and facultative anaerobe were then analysed (separately) by logistic regression for proportions (adjusting for the total number of sequences and allowing for estimation of over dispersion) with health status as a fixed effect. All health statuses were significantly different Shannon diversity Index: a linear model was used to analyse the data, with health status as a fixed effect and weighting the variability by health status as there were significant differences in the variability of indexes between health statuses.

Species richness: a linear model was used to analyse all OTUs including the rare sequences with health status as a fixed effect, the total number of sequences as a covariate (to adjust for the differing number of sequences between samples), and weighting the variability by health status (as there were significant differences in the variability of indexes between health statuses.

All analyses were performed in SIMCA-P version 10 (Umetrics).

Results
Study Cohort

Subgingival plaque bacterial communities were sampled from a total of 223 dogs; 72 with healthy gingiva, 77 with gingivitis and 74 with mild periodontitis. Dog size and age are putative risk factors for periodontitis and therefore sample associated metadata was also obtained (see Table 1). The majority of samples were collected from small, medium and large dogs with giant dogs represented at a much lower frequency. As expected the mean age of dogs increased with disease stage and significant differences (p<0.001) were observed in the mean ages of dogs in health compared to gingivitis and gingivitis compared to mild periodontitis using a two-tailed T-test with unequal variance. Lesser significance was observed in health versus gingivitis (p<0.05).

TABLE 1

|  | Health | Gingivitis | Mild periodontitis |
|---|---|---|---|
| Age | 4.5 ± 2.3 years | 5.0 ± 2.8 years | 7.3 ± 3.1 years |
| Gender | 31 female, 41 male | 38 female, 39 male | 32 female, 42 male |
| Neuter status | 38 neutered, 15 entire, 19 unknown | 46 neutered, 11 entire, 20 unknown | 59 neutered, 9 entire, 6 unknown |
| Size | 8 small, 30 medium, 29 large, 3 giant, 2 unknown | 12 small, 31 medium, 30 large, 3 giant, 1 unknown | 23 small, 16 medium, 31 large, 3 giant, I unknown |
| Breed | 57 pure breed, 15 cross breeds | 69 pure breed, 8 cross breeds | 61 pure breed, 13 cross breeds |

Sequence Quality

The 223 canine subgingival plaque samples were analysed by 454-pyrosequencing of the 3' end of the V1-V3 region and a total of 6,071,129 sequence reads were obtained that passed the sequencing providers initial sequence quality filter. After Pyronoise, Seqnoise and chimera removal using Perseus the number of sequence reads was reduced to 3,110,837. The final number of sequence reads per sample ranged from 2,801 to 30,050 with a median number of reads of 11,682, 12,674 and 15,111 from healthy, gingivitis and mild periodontitis samples respectively.

Bacterial Composition of Canine Plaque

The resulting 3,110,837 sequences were assigned to 6,431 operational taxonomic units (OTUs) using U-Clust within QIIME and a cut-off of ≥98% sequence identity. OTUs were classed and grouped as rare if either they were present in each health status group at an average proportion below 0.05% or were present in less than two samples (see methods for rationale). This reduced the number of OTUs analysed to 274 plus the rare group.

Taxonomic assignment of each of the 274 OTUs resulted in 222 (81%) and 30 (11%) mapping to sequences within COMD (Dewhirst et al., 2012) and Silva respectively with ≥98% identity. The remaining 22 OTUs (8%) shared between 91.4% and 97.7% identity to sequences within the Silva database. The majority of the sequences belonged to seven phyla; Firmicutes (28.5%), Bacteroidetes (26.5%), Proteobacteria (17.36%), Actinobacteria (15.3%), Fusobacteria (3.7%), Spirochaetes (1.9%) and TM7 (1.1%). There were also a further five phyla identified; Synergistetes (0.9%), Chloroflexi (0.7%), SRI (0.4%), Tenericutes (0.09%) Elusimicrobia (0.04%) and a small proportion of the sequences were of unknown phylogeny (0.08%). The rare group accounted for the remaining 3.4% of the sequence reads.

The abundance of each of the 99 genera in plaque samples from healthy dogs and those with gingivitis and mild periodontitis are depicted by the green, orange and red outer bars respectively and the grey bar indicates the number of species (OTUs ≥98% sequence identity) in that genus. Of the 274 species identified, the 26 most abundant accounted for approximately 50% of the sequence reads (see Table 2). *Porphyromonas cangingivalis* COT-109 (OTU #2517) was the most abundant taxa representing 7.4% of the total number of sequence reads. *Moraxella* sp. COT-396 (4266) and *Actinomyces canis* COT-409 (OTU #6029) were the next most abundant representing 3.47% and 3.23% of the sequence reads respectively. Five other species each represented between 2% and 2.8% of the population; *Bergeyella zoohelcum* COT-186 (OTU #2232), *Peptostreptococcus* sp. COT_033 (OTU #6027), Peptostreptococcaceae sp. COT_004 (OTU #5570), *Porphyromonas gulae* COT-052 (OTU #2678), *Porphyromonas gingivicanis* COT-022 (OTU #5364). A further 18 OTUs represented between 0.85% and 2% of the population and the remaining 248 OTUs ranged in relative abundance from 0.01% to 0.81%

TABLE 2

| OTU | Species | Percentage Identity | Total number of sequence reads | Proportion of total sequence reads (%) |
|---|---|---|---|---|
| 2517 | Porphyromonas cangingivalis COT-109 | 99.4 | 230327 | 7.40% |
| 4266 | Moraxella sp. COT-396 | 98.9 | 107867 | 3.47% |
| 6029 | Actinomyces canis COT-409 | 99.1 | 100436 | 3.23% |
| 2232 | Bergeyella zoohelcum COT-186 | 99.1 | 87570 | 2.81% |
| 6027 | Peptostreptococcus sp. COT-033 | 99.7 | 74661 | 2.40% |
| 5570 | Peptostreptococcaceae sp. COT-004 | 100.0 | 65764 | 2.11% |
| 2678 | Porphyromonas gulae COT-052 | 100.0 | 64382 | 2.07% |
| 5364 | Porphyromonas gingivicanis COT-022 | 99.7 | 63838 | 2.05% |
| 2908 | Filifactor villosus COT-031 | 100.0 | 60684 | 1.95% |
| 2905 | Actinomyces sp. COT-083 | 100.0 | 60238 | 1.94% |
| 3307 | Actinomyces sp. COT-252 | 100.0 | 56776 | 1.83% |
| 2233 | Neisseria shayeganii COT-090 | 100.0 | 52354 | 1.68% |
| 5572 | Fusobacterium sp. COT-189 | 99.1 | 50612 | 1.63% |
| 3434 | Porphyromonas canoris COT-108 | 100.0 | 47457 | 1.53% |
| 3638 | Porphyromonas gulae COT-052 | 99.7 | 46699 | 1.50% |
| 2576 | Corynebacterium freiburgense COT-403 | 99.7 | 41549 | 1.34% |
| 2463 | Peptostreptococcaceae sp. COT-077 | 100.0 | 39940 | 1.28% |
| 1916 | Clostridiales sp. COT-028 | 100.0 | 39516 | 1.27% |
| 4116 | Fusobacterium sp. COT-169 | 99.4 | 39001 | 1.25% |
| 1678 | Pasteurellaceae sp. COT-080 | 100.0 | 37073 | 1.19% |
| 4929 | Capnocytophaga sp. COT-339 | 100.0 | 36692 | 1.18% |
| 5804 | Erysipelotrichaceae sp. COT-311 | 100.0 | 31319 | 1.01% |
| 368 | Peptostreptococcaceae sp. COT-135 | 100.0 | 31151 | 1.00% |
| 6025 | Lachnospiraceae sp. COT-036 | 100.0 | 29757 | 0.96% |
| 1773 | Moraxella sp. COT-018 | 100.0 | 27348 | 0.88% |
| 5514 | Capnocytophaga cynodegmi COT-254 | 100.0 | 26402 | 0.85% |

Associations with Health and Disease

Logistic regression analysis identified that 90 of the 274 OTUs had a statistically significant effect of health status after randomisation and multiplicity correction. Of these, 54 showed a significant difference between health and gingivitis, 73 showed a significant difference between gingivitis and mild periodontitis and 87 showed a significant difference between health and mild periodontitis (FIG. 1 and table 3).

TABLE 3

| OTU | Species | % Identity | Average Proportion | | | Fold Change | | | Overall Health status p-value (adjusted for multi-plicity) | Pair-wise p-value between Health states | | |
|---|---|---|---|---|---|---|---|---|---|---|---|---|
| | | | H | G | PD1 | H/G | H/PD1 | G/PD1 | | H v G | H v PD1 | G v PD1 |
| 279 | uncultured Actinomyces sp. GU227175 | 96.88 | 0.0000 | 0.0002 | 0.0010 | 0.1000 | 0 | 0.1 | 0.0064 | 0.1255 | 0.0026 | <0.001 |
| 3157 | Bacteroides sp. COT-040 | 100.00 | 0.0086 | 0.0050 | 0.0030 | 1.6000 | 3.2 | 2.1 | 0.0064 | 0.0231 | <0.001 | 0.0057 |
| 6013 | Odoribacter denticanis COT-084 | 99.71 | 0.0002 | 0.0010 | 0.0020 | 0.2000 | 0.1 | 0.7 | 0.0064 | <0.001 | <0.001 | 0.1065 |
| 2232 | Bergeyella zoohelcum COT-186 | 99.14 | 0.0548 | 0.0260 | 0.0080 | 2.1000 | 6.5 | 3.1 | 0.0064 | 0.001 | <0.001 | 0.002 |
| 5389 | Capnocytophaga canimorsus COT-235 | 100.00 | 0.0065 | 0.0040 | 0.0010 | 1.5000 | 5.5 | 3.7 | 0.0064 | 0.0762 | <0.001 | <0.001 |
| 5514 | Capnocytophaga cynodegmi COT-254 | 100.00 | 0.0124 | 0.0100 | 0.0030 | 1.2000 | 3.6 | 3 | 0.0064 | 0.3334 | <0.001 | <0.001 |
| 3849 | Capnocytophaga sp. COT-295 | 100.00 | 0.0084 | 0.0020 | 0.0007 | 5.3000 | 11.9 | 2.3 | 0.0064 | <0.001 | <0.001 | 0.1246 |
| 4929 | Capnocytophaga sp. COT-339 | 100.00 | 0.0296 | 0.0040 | 0.0040 | 6.7000 | 7.2 | 1.1 | 0.0064 | <0.001 | <0.001 | 0.8919 |
| 5624 | Cloacibacterium sp. COT-320 | 99.14 | 0.0020 | 0.0010 | 0.0003 | 2.1000 | 7.7 | 3.6 | 0.0064 | 0.0021 | <0.001 | 0.0016 |
| 5324 | Chloroflexi bacterium COT-306 | 100.00 | 0.0021 | 0.0040 | 0.0090 | 0.5000 | 0.2 | 0.5 | 0.0064 | 0.0206 | <0.001 | <0.001 |
| 3793 | Helcococcus sp. COT-069 | 99.43 | 0.0010 | 0.0050 | 0.0100 | 0.2000 | 0.1 | 0.5 | 0.0064 | <0.001 | <0.001 | 0.0049 |
| 6025 | Lachnospiraceae bacterium COT-036 | 100.00 | 0.0036 | 0.0060 | 0.0170 | 0.6000 | 0.2 | 0.4 | 0.0064 | 0.051 | <0.001 | <0.001 |
| 5844 | Lachnospiraceae bacterium COT-106 | 99.71 | 0.0030 | 0.0020 | 0.0006 | 1.2000 | 5.1 | 4.2 | 0.0064 | 0.2696 | <0.001 | <0.001 |
| 4905 | Peptococcus sp. COT-044 | 99.71 | 0.0027 | 0.0050 | 0.0120 | 0.5000 | 0.2 | 0.4 | 0.0064 | 0.0479 | <0.001 | <0.001 |
| 5883 | Filifactor alocis COT-001 | 99.71 | 0.0003 | 0.0005 | 0.0030 | 0.5000 | 0.1 | 0.2 | 0.0064 | 0.2332 | <0.001 | <0.001 |
| 3747 | Filifactor sp. COT-164 | 100.00 | 0.0004 | 0.0010 | 0.0050 | 0.3000 | 0.1 | 0.2 | 0.0064 | 0.034 | <0.001 | <0.001 |
| 5570 | Peptostreptococcaceae bacterium COT-004 | 100.00 | 0.0109 | 0.0150 | 0.0350 | 0.7000 | 0.3 | 0.4 | 0.0064 | 0.2292 | <0.001 | <0.001 |

TABLE 3-continued

| OTU | Species | % Identity | Average Proportion | | | Fold Change | | | Overall Health status p-value (adjusted for multiplicity) | Pair-wise p-value between Health states | | |
|---|---|---|---|---|---|---|---|---|---|---|---|---|
| | | | H | G | PD1 | H/G | H/PD1 | G/PD1 | | H v G | H v PD1 | G v PD1 |
| 908 | Peptostreptococcaceae bacterium COT-019 | 100.00 | 0.0026 | 0.0050 | 0.0120 | 0.5000 | 0.2 | 0.4 | 0.0064 | 0.0221 | <0.001 | <0.001 |
| 1476 | Peptostreptococcaceae bacterium COT-021 | 100.00 | 0.0037 | 0.0040 | 0.0090 | 1.0000 | 0.4 | 0.5 | 0.0064 | 0.8728 | <0.001 | <0.001 |
| 281 | Peptostreptococcaceae bacterium COT-067 | 99.71 | 0.0001 | 0.0006 | 0.0010 | 0.1000 | 0 | 0.4 | 0.0064 | 0.0014 | <0.001 | <0.001 |
| 2819 | Peptostreptococcaceae bacterium COT-155 | 99.71 | 0.0001 | 0.0005 | 0.0010 | 0.2000 | 0.1 | 0.4 | 0.0064 | 0.0017 | <0.001 | <0.001 |
| 4774 | Peptostreptococcaceae bacterium COT-030 | 100.00 | 0.0004 | 0.0040 | 0.0110 | 0.1000 | 0 | 0.4 | 0.0064 | 0.0024 | <0.001 | <0.001 |
| 2463 | Peptostreptococcaceae bacterium COT-077 | 100.00 | 0.0006 | 0.0080 | 0.0270 | 0.1000 | 0 | 0.3 | 0.0064 | 0.0059 | <0.001 | <0.001 |
| 2539 | Clostridiales bacterium COT-027 | 99.71 | 0.0007 | 0.0030 | 0.0070 | 0.3000 | 0.1 | 0.4 | 0.0064 | 0.0017 | <0.001 | <0.001 |
| 1916 | Clostridiales bacterium COT-028 | 100.00 | 0.0026 | 0.0110 | 0.0220 | 0.2000 | 0.1 | 0.5 | 0.0064 | <0.001 | <0.001 | <0.001 |
| 4926 | Clostridiales bacterium COT-388 | 100.00 | 0.0002 | 0.0020 | 0.0030 | 0.1000 | 0.1 | 0.7 | 0.0064 | <0.001 | <0.001 | 0.0448 |
| 5566 | Schwartzia sp. COT-063 | 99.71 | 0.0002 | 0.0030 | 0.0050 | 0.1000 | 0.1 | 0.6 | 0.0064 | <0.001 | <0.001 | 0.0485 |
| 2677 | Erysipelotrichaceae bacterium COT-302 | 99.71 | 0.0005 | 0.0010 | 0.0040 | 0.4000 | 0.1 | 0.3 | 0.0064 | 0.0573 | <0.001 | <0.001 |
| 5007 | Lautropia sp. COT-175 | 99.71 | 0.0096 | 0.0070 | 0.0030 | 1.4000 | 3.2 | 2.2 | 0.0064 | 0.0678 | <0.001 | 0.0033 |
| 4615 | Brachymonas sp. COT-015 | 99.43 | 0.0054 | 0.0040 | 0.0010 | 1.4000 | 3.6 | 2.6 | 0.0064 | 0.0538 | <0.001 | <0.001 |
| 5022 | Comamonas sp. COT-270 | 100.00 | 0.0015 | 0.0004 | 0.0002 | 3.3000 | 9.3 | 2.8 | 0.0064 | <0.001 | <0.001 | 0.0305 |
| 2233 | Neisseria shayeganii COT-090 | 100.00 | 0.0328 | 0.0170 | 0.0030 | 1.9000 | 9.5 | 5 | 0.0064 | 0.0014 | <0.001 | <0.001 |
| 2139 | uncultured Neisseria FM872599 | 99.71 | 0.0060 | 0.0010 | 0.0001 | 4.6000 | 41.8 | 9.1 | 0.0064 | <0.001 | <0.001 | 0.0271 |
| 4901 | Cardiobacterium sp. COT-177 | 100.00 | 0.0048 | 0.0030 | 0.0010 | 1.5000 | 4.4 | 3 | 0.0064 | 0.0506 | <0.001 | <0.001 |
| 4266 | Moraxella sp. COT-396 | 98.86 | 0.0661 | 0.0350 | 0.0090 | 1.9000 | 7.6 | 4 | 0.0064 | <0.001 | <0.001 | <0.001 |
| 1678 | Pasteurellaceae bacterium COT-080 | 100.00 | 0.0237 | 0.0120 | 0.0030 | 2.0000 | 9.3 | 4.6 | 0.0064 | <0.001 | <0.001 | <0.001 |
| 4930 | Pasteurella canis COT-273 | 100.00 | 0.0047 | 0.0020 | 0.0010 | 2.5000 | 4.3 | 1.7 | 0.0064 | <0.001 | <0.001 | 0.0609 |
| 3811 | Pasteurellaceae bacterium COT-271 | 98.28 | 0.0005 | 0.0002 | 0.0001 | 2.1000 | 7.5 | 3.5 | 0.0064 | 0.0068 | <0.001 | 0.007 |
| 3222 | Treponema denticola COT-197 | 99.71 | 0.0028 | 0.0050 | 0.0070 | 0.6000 | 0.4 | 0.7 | 0.0064 | 0.0287 | <0.001 | 0.0327 |
| 5414 | Synergistales bacterium COT-179 | 99.71 | 0.0001 | 0.0001 | 0.0007 | 1.2000 | 0.2 | 0.1 | 0.0064 | 0.7476 | <0.001 | <0.001 |
| 349 | Synergistales bacterium COT-180 | 98.86 | 0.0006 | 0.0020 | 0.0040 | 0.3000 | 0.2 | 0.6 | 0.0064 | <0.001 | <0.001 | 0.0282 |
| 3928 | Synergistales bacterium COT-244 | 99.71 | 0.0000 | 0.0001 | 0.0009 | 0.1000 | 0 | 0.2 | 0.0064 | 0.0905 | 0.0022 | <0.001 |
| 3912 | SR1 bacterium COT-380 | 100.00 | 0.0011 | 0.0007 | 0.0002 | 1.5000 | 6.5 | 4.2 | 0.0064 | 0.0559 | <0.001 | <0.001 |
| 3006 | Actinomyces suimastitidis AJ277385 | 96.87 | 0.0002 | 0.0004 | 0.0020 | 0.5000 | 0.1 | 0.2 | 0.0104 | 0.2597 | <0.001 | <0.001 |
| 2517 | Porphyromonas cangingivalis COT-109 | 99.43 | 0.1047 | 0.0790 | 0.0450 | 1.3000 | 2.3 | 1.8 | 0.0104 | 0.0753 | <0.001 | 0.004 |
| 2906 | Porphyromonas sp. COT-290 | 100.00 | 0.0097 | 0.0060 | 0.0030 | 1.7000 | 3.1 | 1.9 | 0.0104 | 0.0139 | <0.001 | 0.016 |
| 107 | uncultured Acetoanaerobium HM277905 | 99.71 | 0.0010 | 0.0020 | 0.0060 | 0.6000 | 0.2 | 0.3 | 0.0104 | 0.2774 | <0.001 | <0.001 |
| 477 | Peptostreptococcaceae bacterium COT-068 | 99.71 | 0.0004 | 0.0030 | 0.0050 | 0.2000 | 0.1 | 0.6 | 0.0104 | 0.0013 | <0.001 | 0.0209 |
| 5567 | uncultured Saccharofermentans EU381658 | 93.71 | 0.0000 | 0.0003 | 0.0007 | 0.1000 | 0.1 | 0.5 | 0.0104 | 0.0052 | <0.001 | 0.0088 |
| 3071 | uncultured Flavonifractor FJ365194 | 98.86 | 0.0002 | 0.0010 | 0.0020 | 0.2000 | 0.1 | 0.6 | 0.0104 | 0.0031 | <0.001 | 0.0339 |
| 2999 | uncultured TM7 F1879268 | 97.41 | 0.0000 | 0.0001 | 0.0005 | 0.2000 | 0 | 0.2 | 0.0104 | 0.1184 | <0.001 | <0.001 |
| 3805 | Conchiformibius steedae AF328156 | 99.43 | 0.0028 | 0.0006 | 0.0001 | 4.4000 | 19.7 | 4.5 | 0.0104 | <0.001 | <0.001 | 0.0459 |
| 5219 | Synergistales bacterium COT-138 | 99.71 | 0.0001 | 0.0007 | 0.0009 | 0.2000 | 0.2 | 0.7 | 0.0104 | 0.8218 | <0.001 | 0.1685 |
| 5486 | uncultured Actinomyces JF203363 | 96.02 | 0.0004 | 0.0004 | 0.0020 | 0.9000 | 0.3 | 0.3 | 0.014 | 0.8218 | <0.001 | <0.001 |
| 4401 | Capnocytophaga sp. COT-329 | 99.71 | 0.0016 | 0.0006 | 0.0001 | 2.8000 | 14.7 | 5.3 | 0.014 | <0.001 | <0.001 | 0.0075 |

TABLE 3-continued

| OTU | Species | % Identity | Average Proportion | | | Fold Change | | | Overall Health status p-value (adjusted for multi-plicity) | Pair-wise p-value between Health states | | |
|---|---|---|---|---|---|---|---|---|---|---|---|---|
| | | | H | G | PD1 | H/G | H/PD1 | G/PD1 | | H v G | H v PD1 | G v PD1 |
| 5917 | *Catonella* sp. COT-257 | 100.00 | 0.0014 | 0.0008 | 0.0004 | 1.8000 | 3.5 | 2 | 0.014 | 0.0129 | <0.001 | 0.019 |
| 5573 | Peptostreptococcaceae bacterium COT-129 | 100.00 | 0.0001 | 0.0006 | 0.0010 | 0.1000 | 0.1 | 0.5 | 0.014 | 0.0031 | <0.001 | 0.0133 |
| 5813 | *Synergistales bacterium* COT-178 | 100.00 | 0.0033 | 0.0060 | 0.0070 | 0.5000 | 0.5 | 0.9 | 0.014 | 0.0026 | <0.001 | 0.3083 |
| 5383 | *[Eubacterium] nodatum* COT-045 | 99.71 | 0.0000 | 0.0001 | 0.0006 | 0.3000 | 0 | 0.1 | 0.014 | 0.2527 | <0.001 | <0.001 |
| 3155 | uncultured *Actinomyces* HM336429 | 96.59 | 0.0000 | 0.0000 | 0.0007 | 0.2000 | 0 | 0 | 0.018 | 0.6623 | 0.0816 | 0.0033 |
| 368 | Peptostreptococcaceae bacterium COT-135 | 100.00 | 0.0056 | 0.0090 | 0.0140 | 0.6000 | 0.4 | 0.6 | 0.018 | 0.0483 | <0.001 | 0.021 |
| 6321 | *Prevotella* sp. COT-372 | 100.00 | 0.0014 | 0.0004 | 0.0003 | 3.7000 | 4.1 | 1.1 | 0.0211 | <0.001 | <0.001 | 0.8096 |
| 4924 | *Schwartzia* sp. COT-213 | 98.86 | 0.0000 | 0.0000 | 0.0009 | 1.2000 | 0 | 0 | 0.0211 | 0.9082 | <0.001 | <0.001 |
| 1418 | Erysipelotrichaceae bacterium COT-381 | 99.71 | 0.0003 | 0.0010 | 0.0020 | 0.4000 | 0.2 | 0.5 | 0.0211 | 0.023 | <0.001 | 0.0045 |
| 4647 | *Treponema* sp. COT-351 | 99.72 | 0.0001 | 0.0003 | 0.0008 | 0.1000 | 0.1 | 0.4 | 0.0211 | 0.0102 | <0.001 | 0.0026 |
| 2167 | *Bacteroidia bacterium* COT-187 | 99.71 | 0.0002 | 0.0006 | 0.0020 | 0.4000 | 0.1 | 0.3 | 0.0232 | 0.1237 | <0.001 | <0.001 |
| 5649 | *Parvimonas* sp. COT-101 | 99.43 | 0.0005 | 0.0020 | 0.0030 | 0.3000 | 0.2 | 0.7 | 0.0232 | 0.002 | <0.001 | 0.0682 |
| 1776 | Peptostreptococcaceae bacterium COT-124 | 100.00 | 0.0004 | 0.0007 | 0.0020 | 0.6000 | 0.3 | 0.4 | 0.0232 | 0.2099 | <0.001 | 0.0025 |
| 1163 | *Lautropia* sp. COT-060 | 100.00 | 0.0066 | 0.0030 | 0.0020 | 2.1000 | 2.9 | 1.4 | 0.0232 | 0.0039 | <0.001 | 0.3209 |
| 1406 | *Pasteurella dagmatis* COT-092 | 100.00 | 0.0050 | 0.0060 | 0.0010 | 0.8000 | 3.5 | 4.4 | 0.0232 | 0.3167 | <0.001 | <0.001 |
| 4114 | *Corynebacterium mustelae* COT-419 | 100.00 | 0.0053 | 0.0070 | 0.0020 | 0.8000 | 2.6 | 3.3 | 0.0232 | 0.2333 | 0.0026 | <0.001 |
| 149 | *Corynebacterium canis* COT-421 | 99.72 | 0.0020 | 0.0090 | 0.0110 | 0.2000 | 0.2 | 0.8 | 0.0267 | <0.001 | <0.001 | 0.3379 |
| 1479 | *Campylobacter* sp. COT-011 | 100.00 | 0.0082 | 0.0080 | 0.0050 | 1.0000 | 1.7 | 1.7 | 0.0297 | 0.9003 | 0.0017 | 0.002 |
| 6026 | *Escherichia coli* COT-277 | 99.71 | 0.0010 | 0.0006 | 0.0003 | 1.8000 | 3 | 1.7 | 0.0297 | 0.0115 | <0.001 | 0.0687 |
| 4534 | *Clostridiales bacterium* COT-038 | 100.00 | 0.0004 | 0.0010 | 0.0040 | 0.3000 | 0.1 | 0.3 | 0.0325 | 0.0738 | <0.001 | <0.001 |
| 6024 | *Acholeplasmatales bacterium* COT-375 | 100.00 | 0.0001 | 0.0002 | 0.0006 | 0.7000 | 0.2 | 0.3 | 0.0325 | 0.3626 | <0.001 | <0.001 |
| 1372 | *Globicatella* sp. COT-107 | 100.00 | 0.0088 | 0.0040 | 0.0030 | 2.2000 | 2.7 | 1.2 | 0.0369 | 0.0024 | <0.001 | 0.4696 |
| 6043 | *Parvimonas* sp. COT-035 | 99.43 | 0.0004 | 0.0020 | 0.0090 | 0.2000 | 0 | 0.2 | 0.0369 | 0.0632 | <0.001 | <0.001 |
| 5021 | *Moraxella* sp. COT-328 | 100.00 | 0.0027 | 0.0020 | 0.0002 | 1.4000 | 14.9 | 10.6 | 0.0369 | 0.2247 | <0.001 | <0.001 |
| 811 | Lachnospiraceae bacterium COT-161 | 99.43 | 0.0008 | 0.0010 | 0.0004 | 0.7000 | 2 | 2.8 | 0.0369 | 0.1519 | 0.0161 | <0.001 |
| 214 | *Neisseria canis* AY426973 | 100.00 | 0.0000 | 0.0003 | 0.0000 | 0.0000 | 0 | 11 | 0.0369 | 0.377 | 0.5199 | <0.001 |
| 4265 | *Desulfovibrionales bacterium* COT-009 | 100.00 | 0.0002 | 0.0020 | 0.0020 | 0.1000 | 0.1 | 1 | 0.0369 | <0.001 | <0.001 | 0.8891 |
| 5681 | uncultured *Capnocytophaga* HM333068 | 100.00 | 0.0004 | 0.0010 | 0.0001 | 0.4000 | 3.2 | 7.3 | 0.0392 | 0.0089 | 0.0185 | <0.001 |
| 2577 | *Leptotrichia* sp. COT-345 | 100.00 | 0.0023 | 0.0050 | 0.0020 | 0.4000 | 1.5 | 3.5 | 0.0392 | 0.0031 | 0.2767 | <0.001 |
| 3358 | *Aquaspirillum* sp. COT-091 | 99.14 | 0.0053 | 0.0040 | 0.0006 | 1.2000 | 9.3 | 7.7 | 0.0411 | 0.4646 | <0.001 | <0.001 |
| 564 | *Stenotrophomonas* sp. COT-224 | 98.86 | 0.0110 | 0.0050 | 0.0030 | 2.1000 | 3.5 | 1.7 | 0.0411 | 0.0045 | <0.001 | 0.1232 |
| 138 | uncultured TM7 EF614904 | 98.00 | 0.0002 | 0.0005 | 0.0006 | 0.4000 | 0.3 | 0.8 | 0.0411 | 0.0085 | <0.001 | 0.4009 |
| 1158 | *Actinomyces hyovaginalis* X69616 | 97.63 | 0.0001 | 0.0020 | 0.0030 | 0.0000 | 0 | 0.7 | 0.0488 | 0.0133 | 0.006 | 0.1989 |
| 4778 | *Clostridiales bacterium* COT-141 | 99.71 | 0.0000 | 0.0006 | 0.0010 | 0.1000 | 0 | 0.6 | 0.0488 | 0.011 | 0.0025 | 0.0893 |
| 3319 | uncultured TM7 DQ815554 | 97.41 | 0.0003 | 0.0003 | 0.0007 | 0.9000 | 0.4 | 0.4 | 0.0488 | 0.8595 | <0.001 | <0.001 |

Of the most abundant health associated species, *Moraxella* sp. COT 396 (QIIME OTU #4266, 6.61%), *Bergeyella zoohelcum* COT-186 (OTU #2232, 5.48%), *Neisseria shayeganii* COT-090 (OTU #2233, 3.28%) and Pasteurellaceae sp. COT-080 (OTU #1678, 2.37%) were significantly more abundant in health and gingivitis than in mild periodontitis and were also significantly more abundant in health than gingivitis (See table 3). *Capnocytophaga* sp. COT-339 (OTU #4929, 2.96%), *Stenotrophomonas* sp. COT-224 (OTU #564, 1.1%) were also significantly more abundant in health than in gingivitis and mild periodontitis but the relative abundance in gingivitis and mild periodontitis were not significantly different. Again, *Porphyromonas cangingivalis* COT-109 (OTU #2517, 10.47%) and *Capnocytophaga cynodegmi* COT-254 (OTU #5514, 1.24%) were significantly more abundant in health and gingivitis than in mild periodontitis but the relative abundance in health and gingivitis did not significantly differ.

The most abundant disease associated species included Peptostreptococcaceae sp. COT-004 (OTU #5570, 3.5%) and Lachnospiraceae sp. COT-036 (OTU #6025, 1.7%) which were significantly more abundant in mild periodontitis than health and gingivitis and did not significantly differ in their relative abundance in health and gingivitis.

*Clostridiales* sp. COT-028 (OTU #1916, 2.2%), Peptostreptococcaceae sp. COT-135 (OTU #368, 1.4%), Peptostreptococcaceae sp. COT-077 (OTU #2463, 2.7%), *Peptococcus* sp. COT-044 (OTU #4905, 1.2%), Peptostreptococcaceae sp. COT-019 (OTU #908, 1.2%) and Peptostreptococcaceae sp. COT-030 (OTU #4774, 1.1%) were also significantly more abundant in mild periodontitis than in health and gingivitis but were also more abundant in gingivitis than health. *Corynebacterium canis* COT-421 (OTU #149, 1.1%) was significantly more abundant in mild periodontitis and gingivitis than health but gingivitis and mild periodontitis samples were not significantly different.

Figure 2:
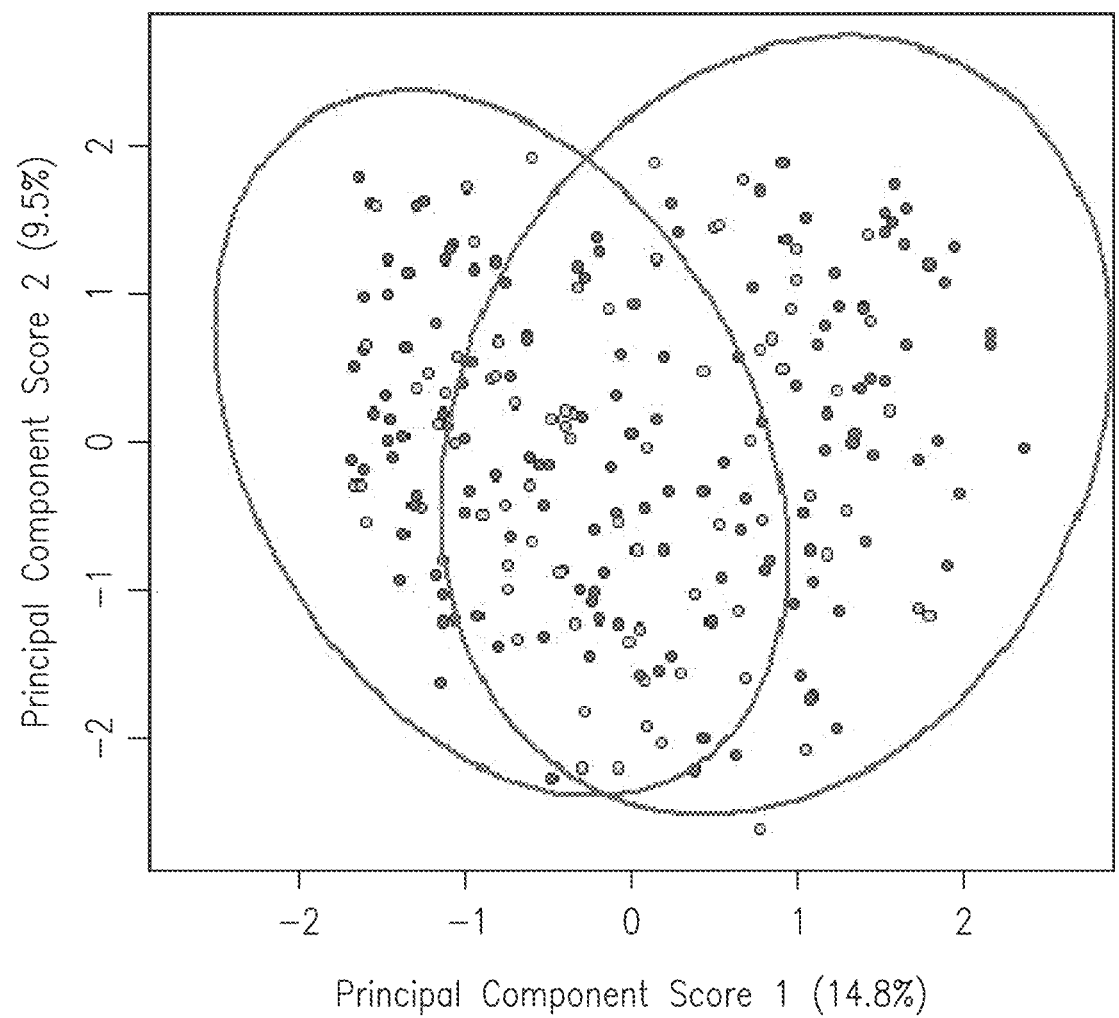
FIG. 2 shows principal component analysis performed on the log 10 proportions of OTUs identified in each individual by health status; health, gingivitis and PD1.

Principal component analysis was used to investigate correlations of OTUs with health status, age, size and gender. The first component explained 14.7% and the second component 9.5% of the variability in the OTU $\log_{10}$ proportions (see FIG. 2). Discrete clustering of healthy and mild periodontitis samples was seen, whilst gingivitis samples overlaid both health and mild periodontitis clusters. Gender, size and age did not appear to show any distinct clusters.

Gram-Stain Status and Oxygen Requirements

Figure 3A:
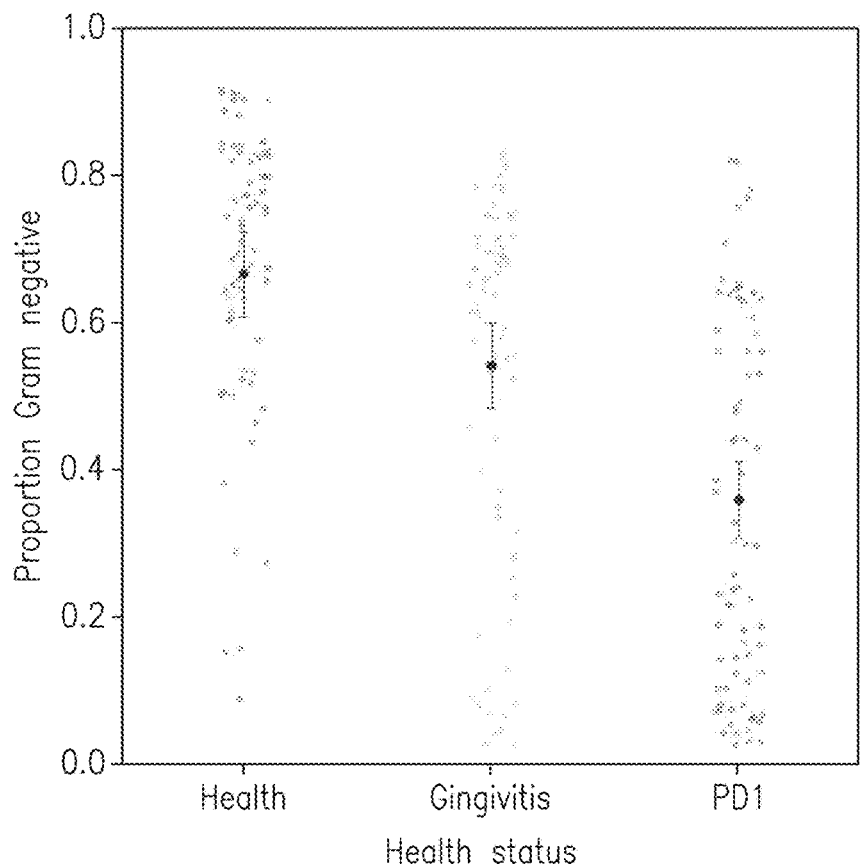
FIG. 3a shows proportions of Gram negative OTUs for each sample by health status; health, gingivitis and mild periodontitis: black bars indicate mean proportion of OTUs that are Gram negative with 95% confidence intervals.
Figure 3B:
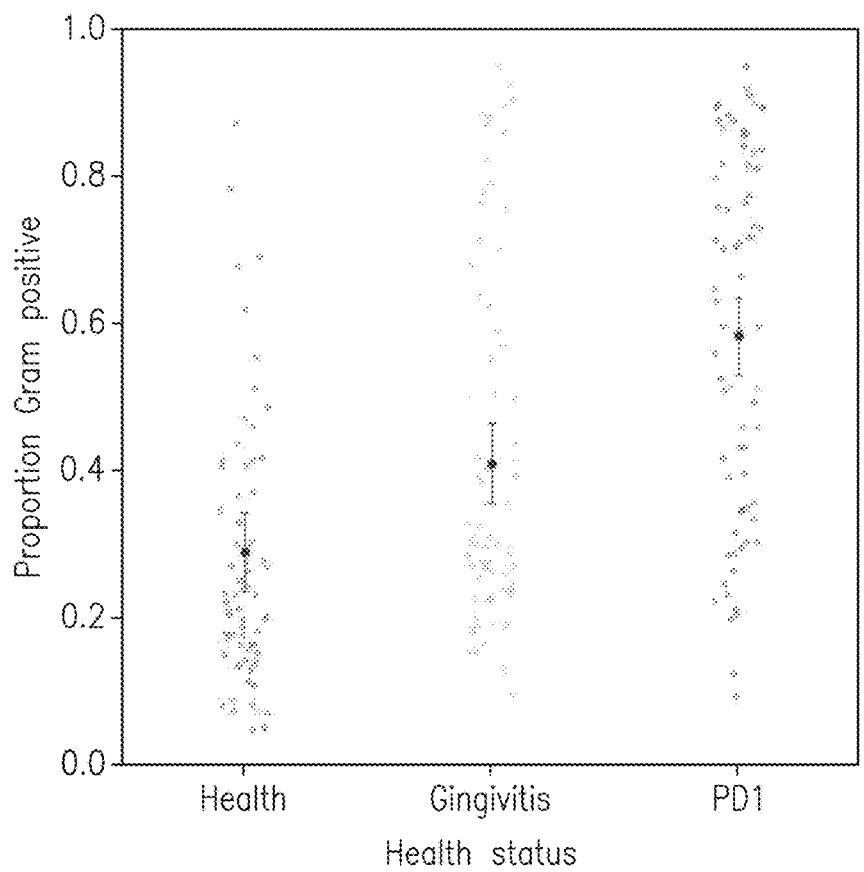
FIG. 3b shows proportions of Gram positive OTUs for each sample by health status; health, gingivitis and mild periodontitis; black bars indicate mean proportion of OTUs that are Gram positive with 95% confidence intervals.

The probable Gram-stain status was determined by literature searches followed by logistic regression analysis of proportions of Gram positive or Gram negative non-rare OTUs; this showed that health, gingivitis and mild periodontitis groups were significantly different. Samples from dogs with mild periodontitis had a significantly higher proportion of Gram positive OTUs than those from dogs with gingivitis (P<0.001) and healthy gingiva (P<0.001). Gingivitis samples had a significantly higher proportion of Gram positive OTUs than samples from the healthy group (P=0.003; see FIG. 3). These data show that plaque samples from dogs with mild periodontitis have a higher proportion of Gram positive species whereas those isolated from healthy gingiva are dominated by Gram negatives.

Figure 4A:
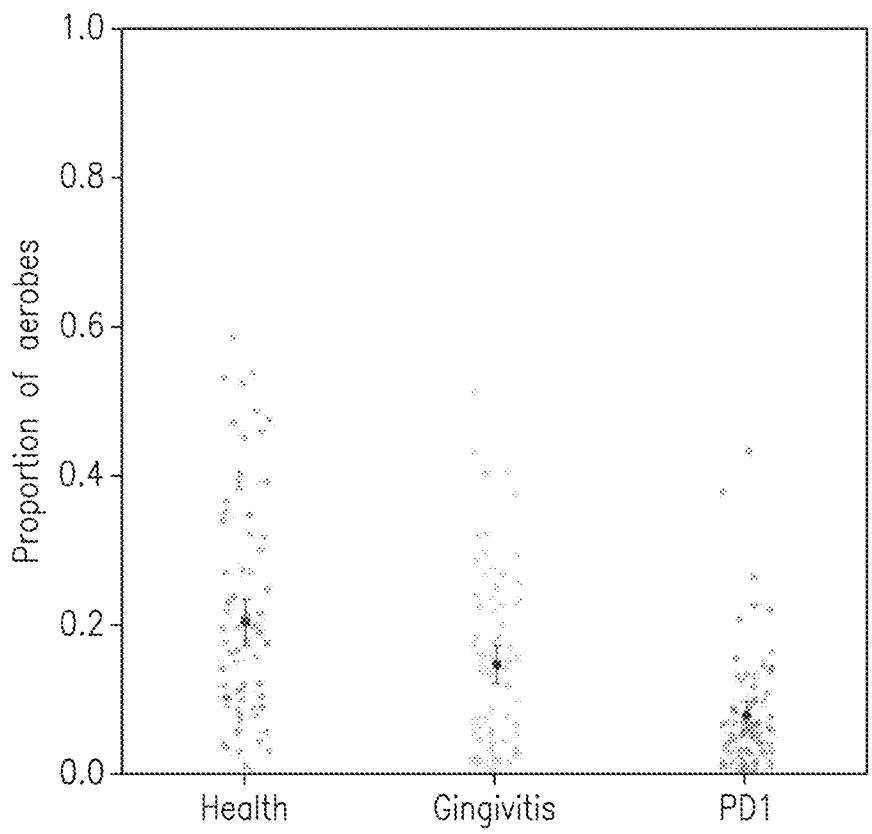
FIG. 4a shows proportions of aerobes for each sample by health status; health, gingivitis and mild periodontitis; black bars indicate mean proportion of species that are aerobic with 95% confidence intervals.
Figure 4B:
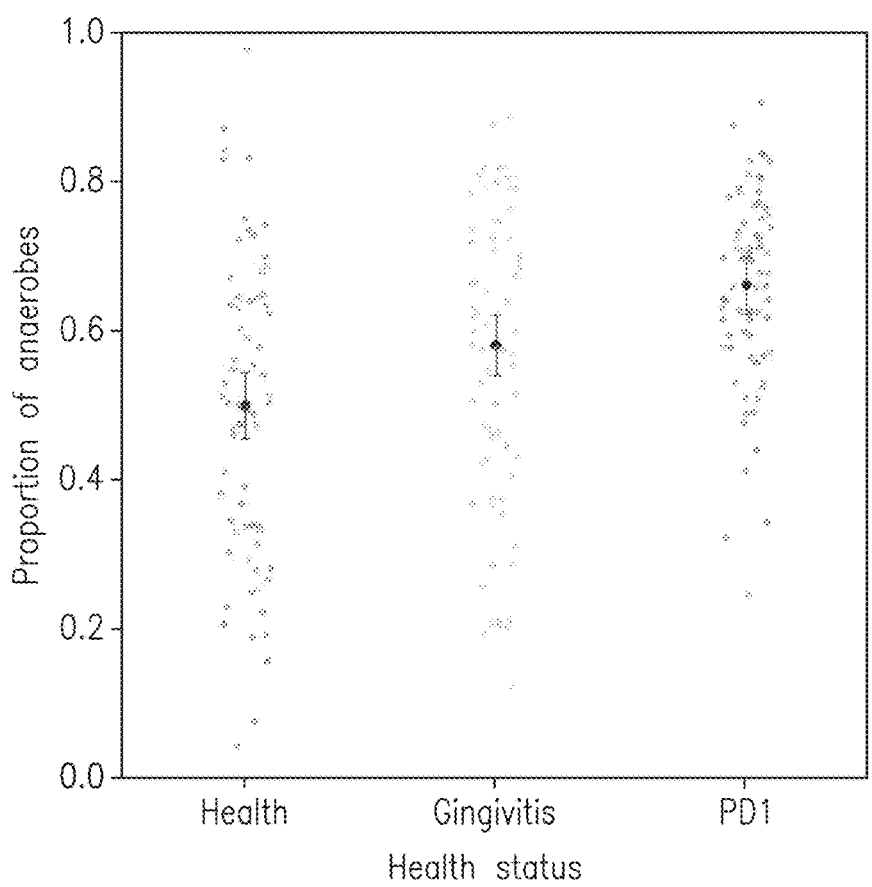
FIG. 4b shows proportions of anaerobes for each sample by health status; health, gingivitis and mild periodontitis; black bars indicate mean proportion of species that are anaerobic with 95% confidence intervals.
Figure 4C:
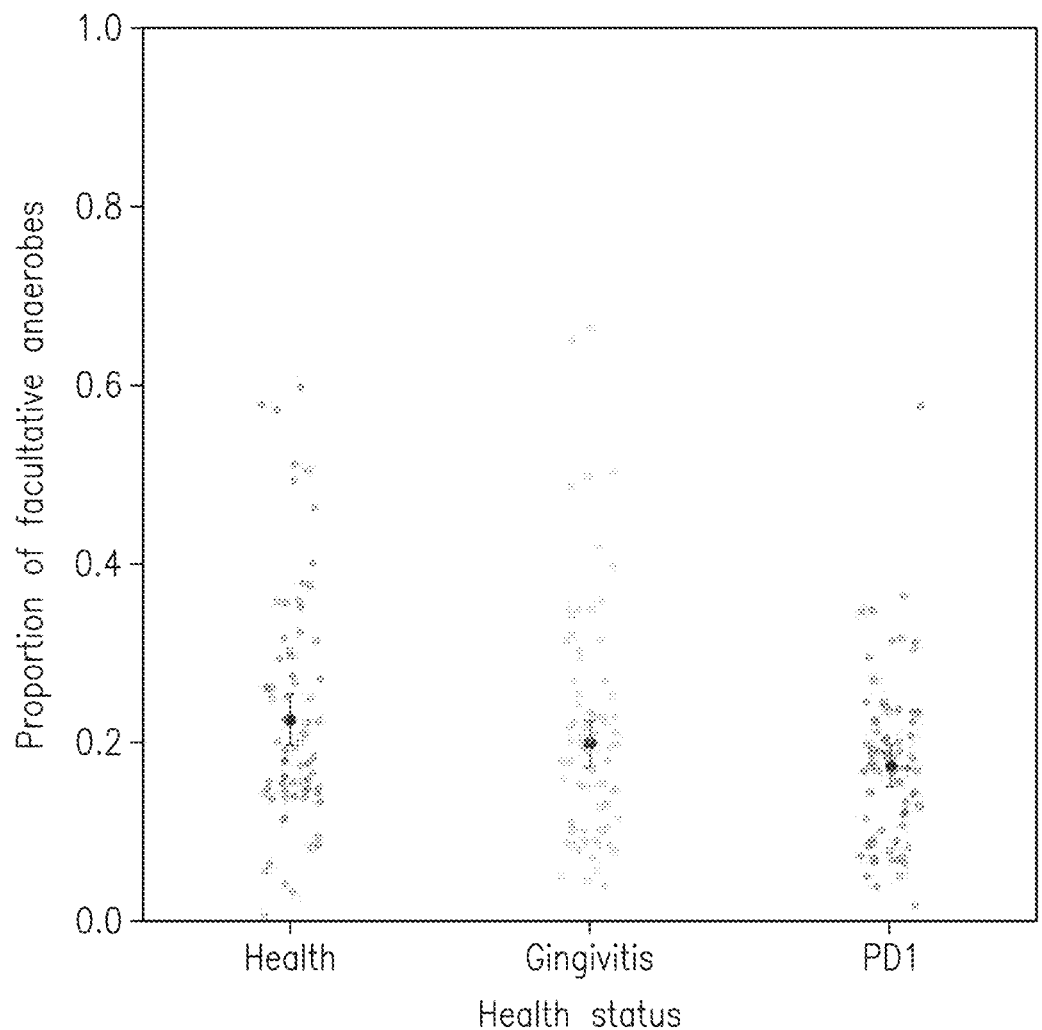
FIG. 4c shows proportions of facultative anaerobes for each sample by health status; health, gingivitis and mild periodontitis; black bars indicate mean proportion of species that are facultatively anaerobic with 95% confidence intervals.

The probable oxygen requirements were also determined by literature searches and analysed by logistic regression for proportions of aerobes, facultative anaerobes and anaerobes. Clear differences in oxygen requirements were observed between the bacterial population in healthy, gingivitis and mild periodontitis samples. Samples from dogs with healthy gingiva had significantly higher proportions of aerobes than gingivitis and periodontitis samples (P=0.006 & P<0.001 respectively) and gingivitis samples had a significantly higher proportion of aerobes than samples from dogs with mild periodontitis (P<0.001; see FIG. 4). Mild periodontitis samples had a significantly higher proportion of anaerobes than healthy and gingivitis samples (P<0.001 & P=0.005 respectively) and gingivitis samples had a significantly higher proportion than healthy samples (P=0.009). In terms of facultative anaerobes, healthy and gingivitis samples did not significantly differ (p=0.166) and the same was true for gingivitis and periodontitis samples (P=0.165). However, there were significantly more facultative anaerobes in health than mild periodontitis (P=0.006).

Species Richness and Diversity

A linear model was used to compare the number of operational taxonomic units (OTUs) including rare OTUs in health, gingivitis and mild periodontitis. This showed that all health status were significantly different (see FIG. 5). There were significantly more OTUs in plaque samples from dogs with mild periodontitis than gingivitis (P=0.022). In addition, samples from healthy gingiva contained significantly fewer OTUs than PD1 (P<0.001) and gingivitis samples (P=0.014).

Figure 5A:
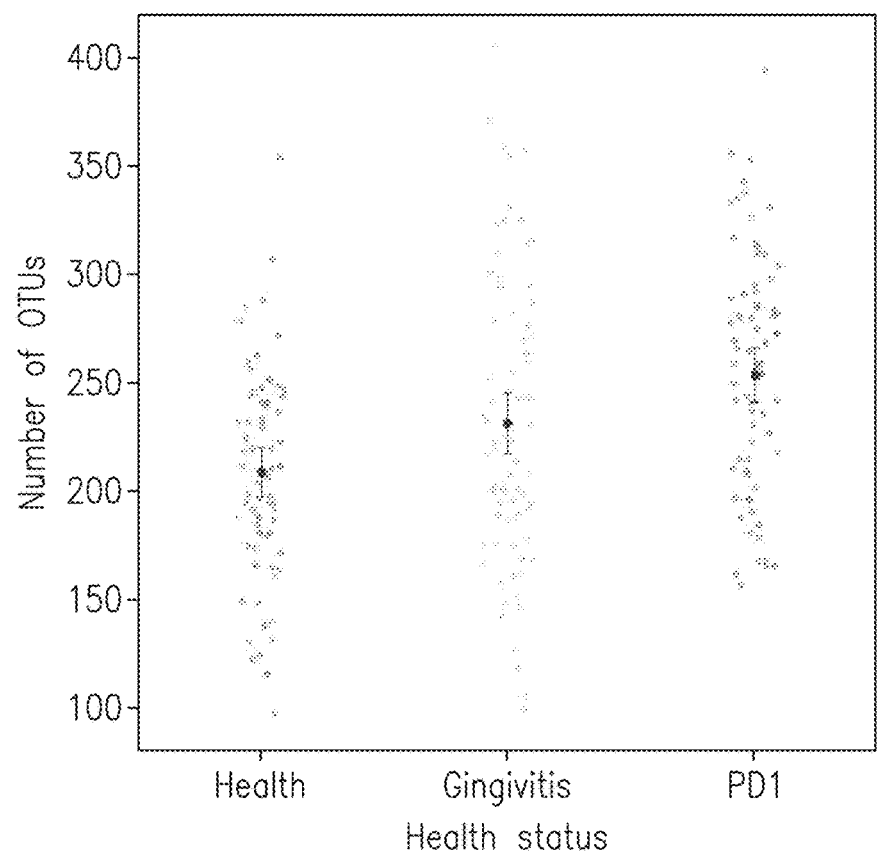
FIG. 5a shows the number of OTUs for plaque samples from healthy dogs, dogs with gingivitis and those with mild periodontitis.
Figure 5B:
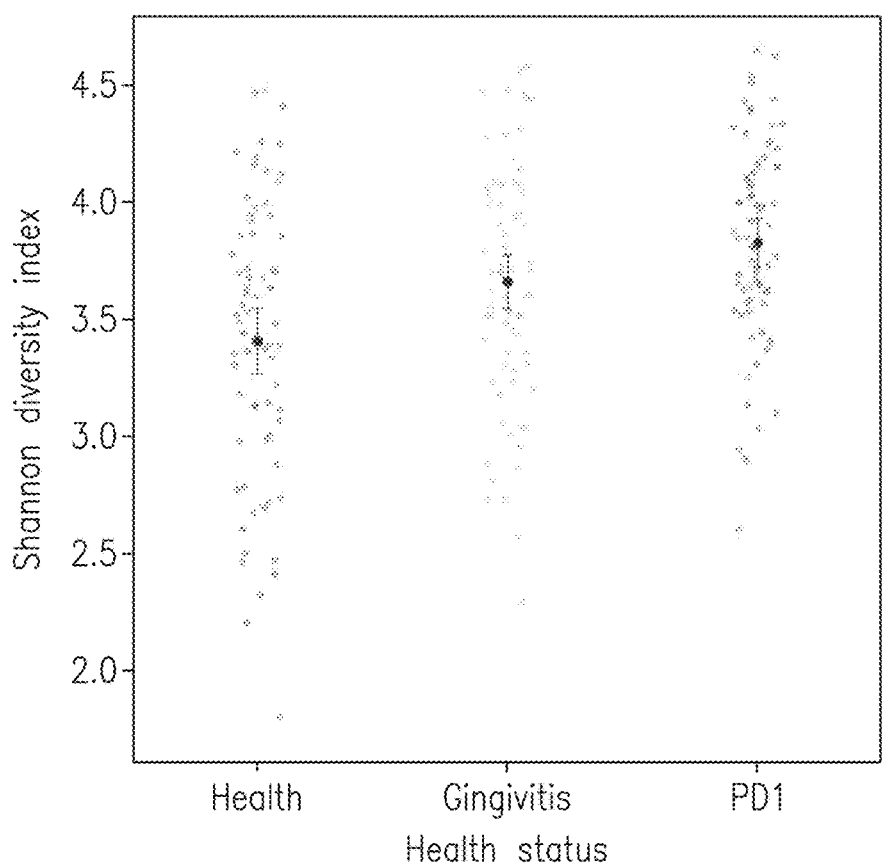
FIG. 5b shows the shannon diversity Index for plaque samples from healthy dogs, dogs with gingivitis and those with mild periodontitis.
Figure 6:
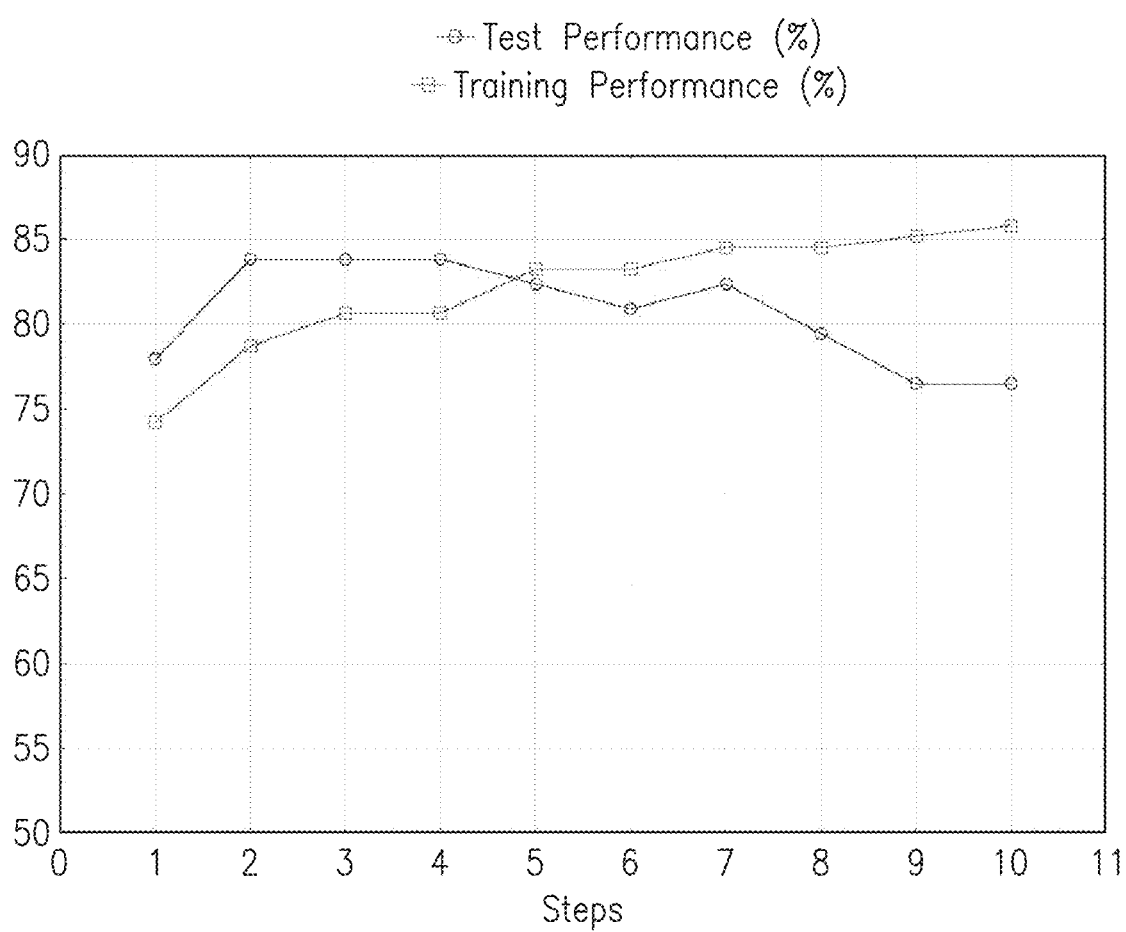
FIG. 6 shows the test performance and training performance for Model 1.
Figure 7:
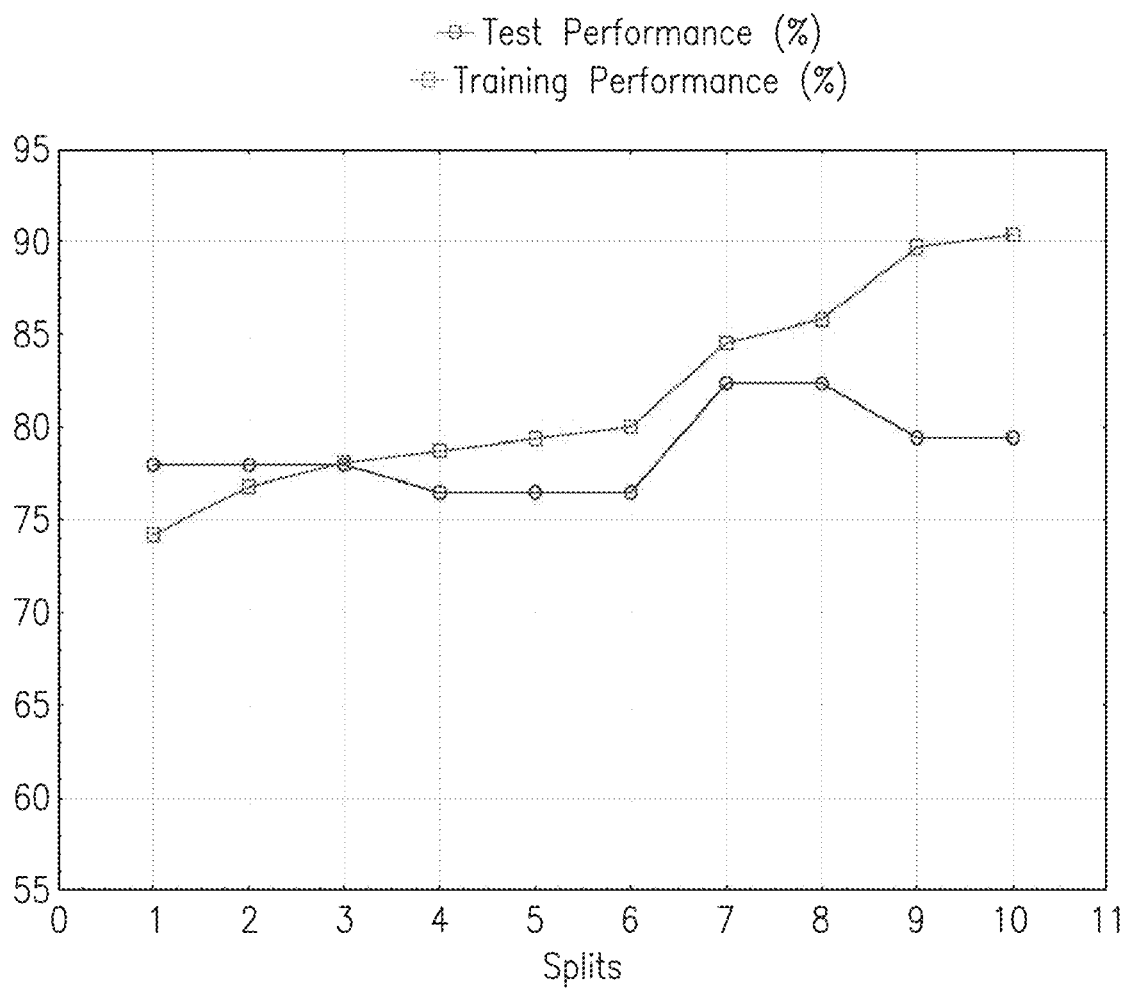
FIG. 7 shows the test performance and training performance for Model 2.
Figure 8:
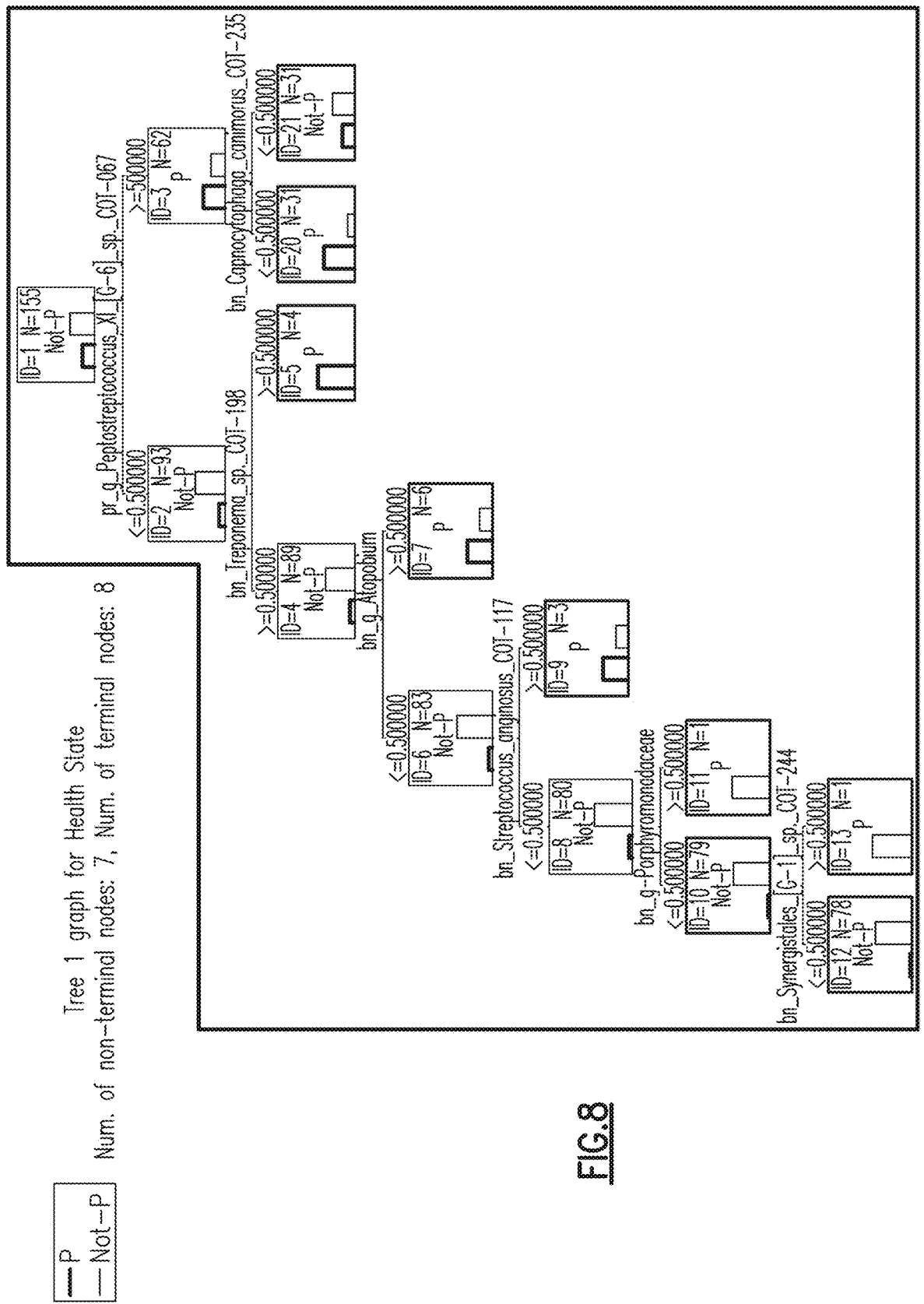
FIG. 8 shows a tree graph for P and Not-P.
Figure 9:
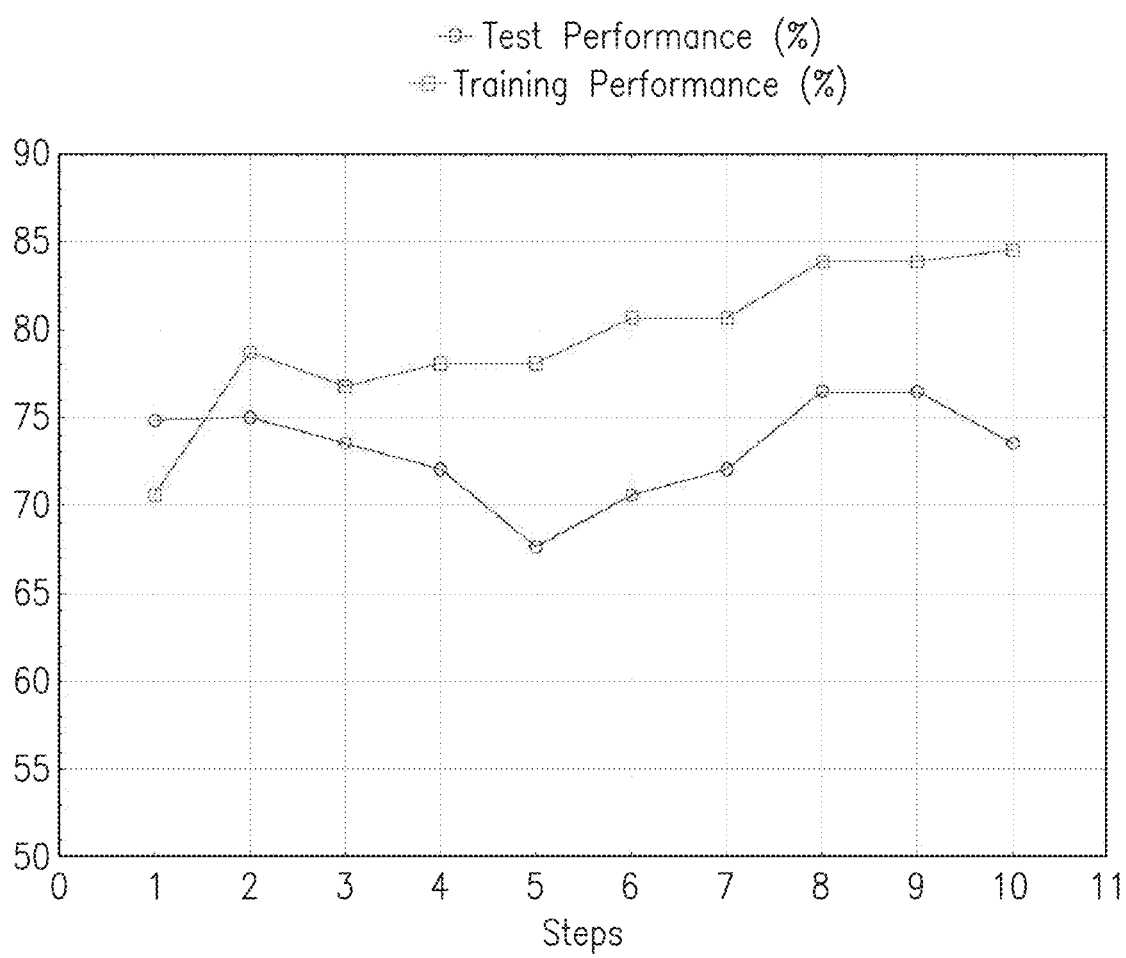
FIG. 9 shows the test performance and training performance for Model 3.
Figure 10:
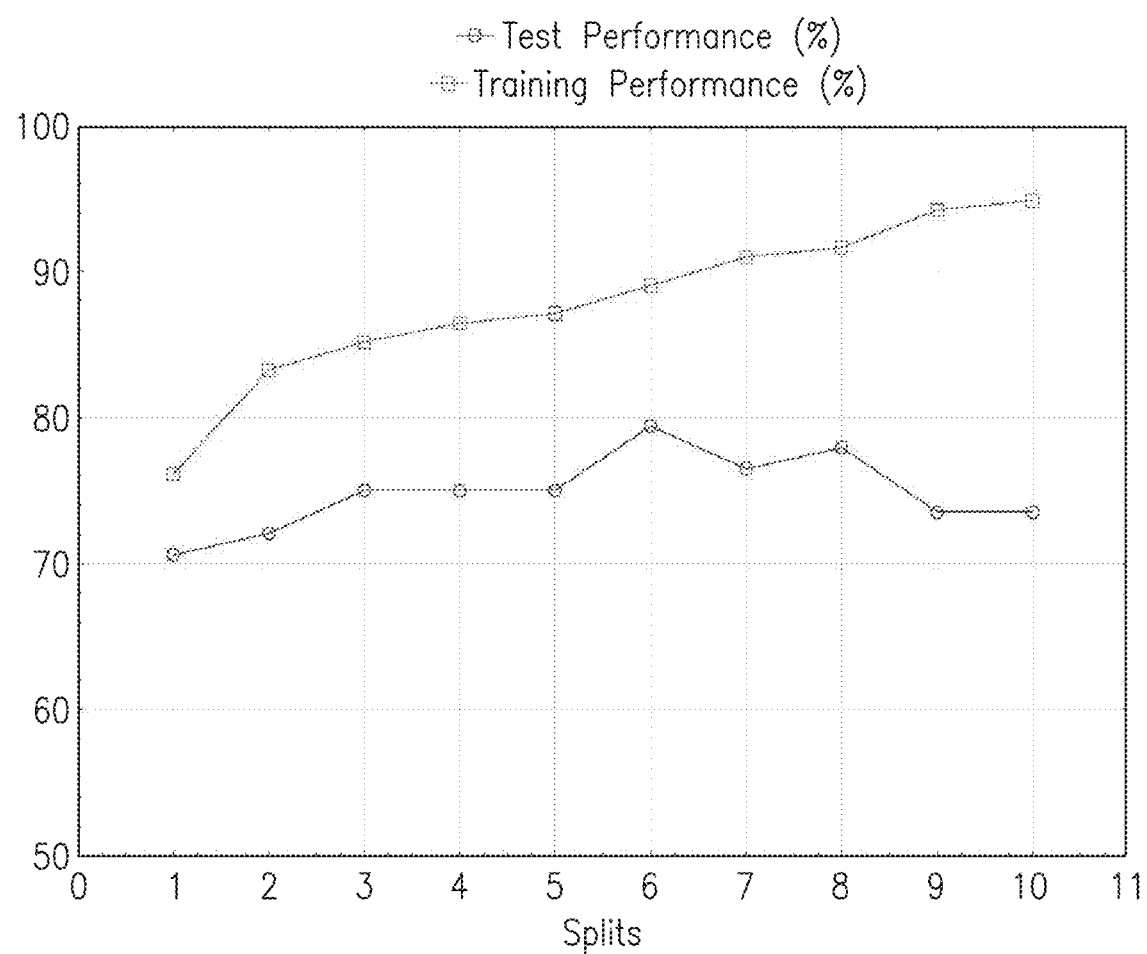
FIG. 10 shows the test performance and training performance for Model 4.
Figure 11:
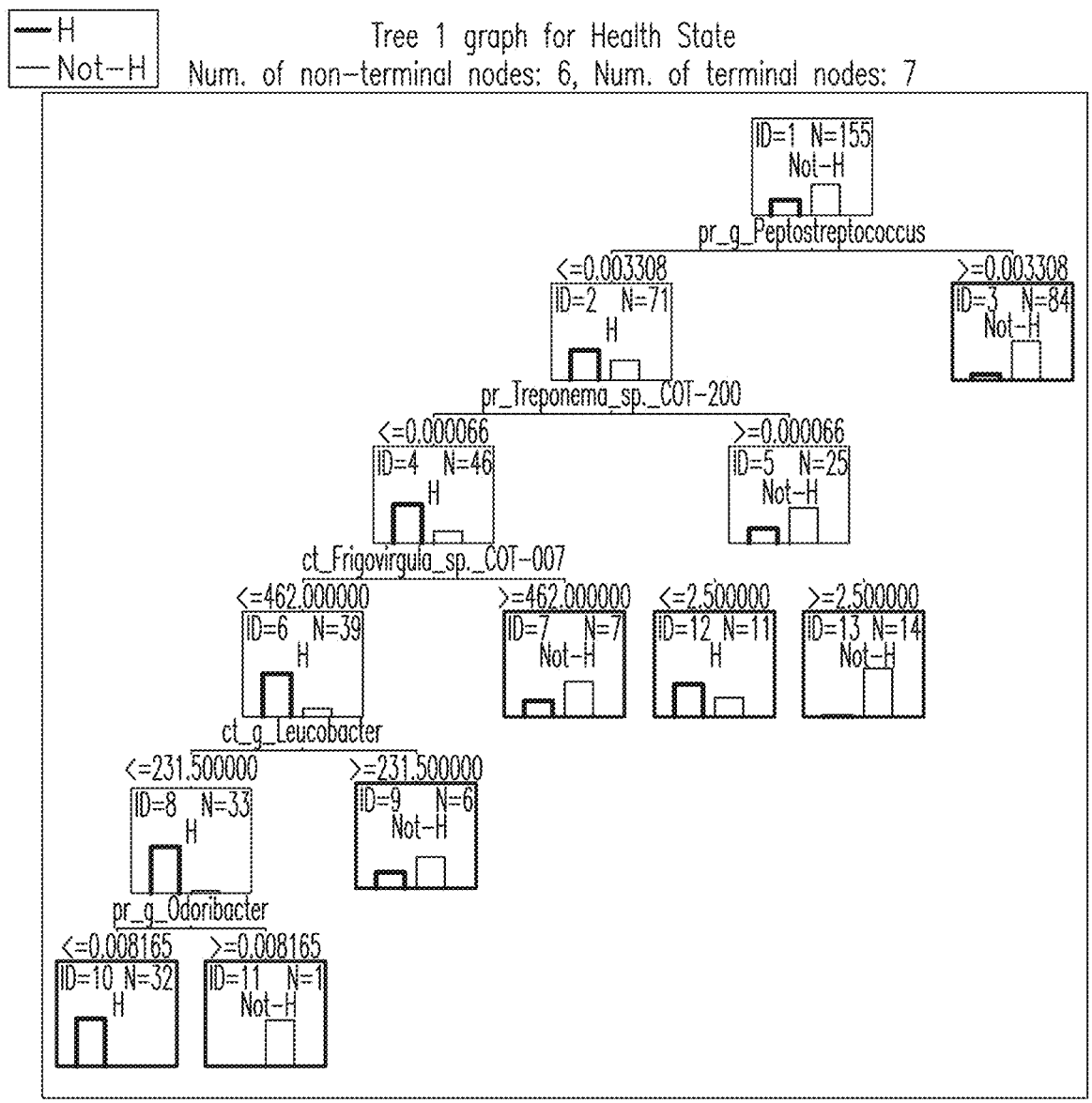
FIG. 11 shows a tree graph for H and Not-H.

A linear model was used to analyse the Shannon diversity index data and showed that all health status were significantly different (see FIG. 5). The Shannon diversity index was significantly greater in PD1 samples than health samples (P<0.001) and also in mild periodontitis versus gingivitis samples (P=0.036). The diversity index was also significantly smaller in samples from healthy dogs compared with gingivitis samples (P=0.0065). This demonstrates that plaque samples from dogs with mild periodontitis are more species rich and diverse than those obtained from dogs with healthy gingiva.

As a whole the most predominant phyla observed were the Bacteroidetes, Proteobacteria, Firmicutes and Actinobacteria from which 26 of the most abundant species made up 49.8% of all sequences. The proportions of these phyla shifted between disease stages with the Proteobacteria and Bacteroidetes being most abundant in plaque from the healthy cohort and the Firmicutes being more abundant in the mild periodontitis cohort. Comparisons with the human oral microbiota become most striking at the genus & species level. Whilst *Streptococcus* spp. are abundant in healthy humans they are rare in dogs; the lack of cariogenic *Streptococcus* spp. is presumably the reason dental caries is a rarely observed disease in dogs. Of note in this respect is the pH of canine saliva (pH 8.5), which is considerably more alkaline than that of human saliva (pH 6.5 to 7.5). It is possible that this difference in pH contributes to the lack of *Streptococci* in the dog oral cavity along with the lower level of sugars in the diet. The latter would be consistent with the recent observation that the human oral microflora evolved to a more cariogenic nature following the introduction of processed sugars to the diet during the industrial revolution (Adler et al. 2013). In healthy dogs *Porphyromonas cangingivalis* Canine Oral Taxon (COT)-109, *Moraxella* sp. COT-396 and *Bergeyella zoohelcum* COT-186 were the most abundant species. The latter two are also abundant in human health but the abundance of a Porphyromonad in healthy dogs is in contrast to the human oral microbiome where *P. gingivalis* has been synonymous with the red complex and human periodontal disease. The abundance of *Porphyromonas, Moraxella* and *Bergeyella* in healthy dogs was also observed in a recent 454 pyrosequencing study of 6 dogs.

With respect to canine periodontal disease the *Actinomyces*, Peptostreptococcaceae and *Porphyromonas* species predominated. The most abundant species being *P. cangingivalis* COT-109 (again), *Peptostreptococcus* sp. COT-033, *Actinomyces* sp. COT-374, Peptostreptococcaceae XI [G-1] sp. COT-004 and Peptostreptococcaceae XIII [G-2] sp. COT-077. *Fusobacterium* and *Treponema* spp associated with human periodontal disease where present but at lower abundance and only one *Treponema* spp. (*T. denticola*) was significantly associated with mild periodontitis (Griffen et al., 2012). This difference in the apparent importance of Treponemes in the disease state may be as a result of an earlier stage of Periodontitis being surveyed in this study than the human one. It is also accentuated by the large number of different *Treponeme* species identified in our analysis (16) leading to fragmentation of the abundance. Indeed, if grouped at the genus level the *Treponeme* species make up 2.15% of the total in disease.

Relatively few species were associated solely with gingivitis (*Leptotrichia* sp. COT-345, *Neisseria canis* AY426973 and an uncultured *Capnocytophaga* sp. HM333068). The abundance of health associated species did not always follow a linear reduction in abundance in gingivitis through to PD1, for many their abundance was also relatively high in gingivitis. This was also true for mild periodontitis associated species making it challenging to differentiate a health/gingivitis associated species from a health associated species or a gingivitis/periodontitis associated species from a periodontitis associated species. Presumably certain health associated species can compete in the gingivitis environment but not in periodontitis and vice versa for periodontitis associated species.

In human plaque Gram-positive bacteria have traditionally been regarded as health associated and anaerobic Gram-negative bacteria as disease associated. Griffen's recent survey noted that this may be an over simplification with at least one Gram-positive bacteria (*Filifactor alocis*) being abundant in human disease (Griffen et al., 2012). Our observations in dog are in contrast to those from the human oral microbiome with Gram negative species being significantly more abundant in healthy plaque samples and Gram positives significantly more abundant in periodontitis plaque samples. The lack of *Streptococci* in dog results in the health associated species being dominated by Gram-negative aerobes. In contrast to health, the abundance of periodontitis associated Firmicutes, particularly Peptostreptococcaceae spp., means that Gram-positive anaerobes predominate in the periodontitis associated species. The environmental pressures that drive selection of species presumably include nutrient sources, oxygen stress, pH and immunological factors. We hypothesise that the major health associates may be aerobic early colonisers that are able to metabolise salivary carbohydrates such as mucins and proline rich proteins. With chronic gingivitis and periodontitis, uncontrolled inflammation and bacterial activity result in the destruction of gingival tissue leading to anaerobic periodontal pockets containing protein rich gingival crevicular fluid and immunological agents. This may then drive the rise in abundance of proteolytic anaerobic *Clostridiales* and Peptostreptococcaceae and *Porphyromonads* known for their ability to resist host defenses and utilise host oxidative immune responses (Mydel et al., 2006). The ability of the Gram negative anaerobe *Porphyromonas cangingivalis* to predominate in all three health states suggests that it is both metabolically flexible enough to colonise in health and able to compete against other *Porphyromonas* spp. in the disease environment. Its ability to prosper in health which is traditionally considered to be a more aerobic environment is interesting given that *Porphyromonads* are strict anaerobes.

EXAMPLE 2

Data and Models Used for Predicting Oral Health Status

The data set used consisted of 454 sequencing data from 223 dog (H=72, G=77 & PD1=74) sub-gingival plaque samples pooled from multiple teeth of the same health state from the same individual.

Health State

The primary output of interest was the classification of cases into one of three health categories. These were:
H: Animals diagnosed as Healthy
G: Animals diagnosed with Gingivitis, and
P: Animals diagnosed with Periodontitis In the predictive modelling process, in addition to this 3-way classification, several alternative outputs were also investigated for the purpose of simplifying the models, for understanding which bacterial markers were indicative of each classification and for possible use in 'two-stage' predictive models. The primary set of outputs used was:
H/G/P
H/Not-H (aggregating G and P into a single class)
P/Not-P (aggregating G and H into a single class)
H/G (excluding P)
G/P (Excluding H)

Gingivitis Score

An output of secondary interest was the average Gingivitis score obtained from sampled teeth. Although the individual teeth receive a discrete score taking the values 0, 1, 2 or 3, the average score is a continuous variable ranging from 0 to 3, which has an impact on the types of predictive models used and the approach to assessing the performance of the models. The Test Set Performance was assessed in terms of the regression R-squared value (the percentage of the variability in the output variable explained by the model). Since the R-squared can be difficult to interpret, the Residual Standard Deviation, which provides an indication of the mean distance between the observed and predicted values, was also calculated.

In addition to the actual (continuous) mean Gingivitis score, the score rounded to the nearest integer value was also used as an output in some models. This was treated as purely categorical, which allows the performance to be assessed in the same way as for the Health State models. Since the initial results of this exercise were not very promising, no further optimisation of these models was performed.

Inputs/Predictors

Several sets of predictors were used in the predictive modelling. The following predictor variants were used:

Counts: These are the original count variables, comprising prevalence counts for individual bacterial species and genera.

Proportions: These are the counts transformed to proportions by dividing by the total count for each animal ('row-wise' transformation).

Binary (count>1): These are binary presence/absence scores obtained using counts less than or equal to one to define "absent" and counts greater than one as "present".

Binary (count>7): These are binary presence/absence scores obtained using counts less than or equal to seven to define "absent" and counts greater than seven as "present".

Relative Counts & Proportions: These are obtained by dividing the counts and proportions by the mean value for the whole predictor ('column-wise' transformation).

Relative Counts & Proportions Truncated: These are obtained by taking the Relative values and "truncating" any values greater than 1 by setting them equal to 1. This transformation results in values ranging from 0 to 1 (with, typically, a large number of truncated values).

Relative Counts & Proportions 3-level Categorical: These are categorical variables obtained by taking the Relative values and setting them into three categories using threshold values of 0.0005 (0.05% of the mean) and 0.1 (10% of the mean). These were then used as categorical predictors in the models.

Based on the results from the above separate modelling exercises, a further set of models was fitted using a subset of predictors identified as those selected by the earlier models. These are listed in table 4. These predictors were drawn from the Count, Proportion and Binary predictor sets, but omitted the Relative predictors. This allowed the models to select any combination of these predictors. For a subset of output variables, a further set of 3-level categorical predictors (those selected by the earlier models) were added to this set to allow the creation of models that included a combination of continuous/binary and categorical predictors.

Table 4—Subset of 'Best' Predictors

This list shows the subset of 'best' predictor variables identified from the early-stage modelling and used in later stages to allow the creation of models including more than one predictor type. The variable prefixes identify the variable type and should be interpreted as follows:

1. pr_g_Moraxella
2. pr_Peptostreptococcaceae_XIII_[G-2]_sp._COT-077
3. pr_Filifactor_sp._COT-064
4. pr_g_Capnocytophaga
5. ct_Escherichia_coli
6. pr_Porphyromonas_sp._COT-290
7. ct_Neisseria_sp._COT-049
8. ct_Filifactor_sp._COT-163
9. pr_Selenomonas_sputigena_COT-342
10. pr_Corynebacterium_sp._cluster 88112
11. ct_g_Leucobacter
12. ct_Xenophilus_sp._COT-174
13. pr_Peptostreptococcaceae_XI_[G-1]_sp._COT-004
14. ct_Peptostreptococcaceae_XIII_[G-1]_sp._COT-030
15. ct_Fusobacterium_sp._COT-189
16. ct_Peptostreptococcaceae_XI_[G-6]_sp._COT-068
17. ct_g_Odoribacter
18. ct_g_Schwartzia
19. pr_g_Globicatella
20. ct_Peptostreptococcaceae_XI_[G-2]_sp._COT-047
21. ct_g_Granulicatella
22. pr_g_Catonella
23. pr_g_Prevotella
24. pr_Clostridiales_III_[G-3]_sp._COT-388
25. ct_Clostridiales_[F-2.G-1]_sp._COT-100_PO005
26. pr_g_Curtobacterium
27. pr_Parvimonas_sp._COT-101
28. ct_g_Filifactor
29. pr_g_Atopobium
30. pr_g_Corynebacterium
31. ct_Capnocytophaga_canimorus_COT-235
32. pr_g_Treponema
33. pr_Peptostreptococcaceae_XI_[G-6]_sp._COT-067
34. ct_Catonella_sp._COT-257
35. ct_g_Parvimonas
36. pr_g_bacterium_cp04.17
37. pr_Peptostreptococcaceae_XI_[G-4]_sp._COT-019
38. pr_Treponema_denticola_COT-197
39. pr_g_Peptostreptococcus
40. pr_Moraxella_sp._COT-017
41. ct_Peptostreptococcaceae_XIII_[G-2]_sp._COT-077
42. pr_Spirochaeta_sp._COT-379
43. pr_Wolinella_succinogenes
44. pr_Proprionibacterium_sp._COT-300
45. pr_g_Xanthomonadaceae_bacterium
46. pr_g_Tannerella
47. ct_Actinomyces_sp.
48. ct_g_Streptococcus
49. ct_Filifactor_villosus_COT-031
50. ct_Actinomyces_sp. Cluster 7595
51. ct_Peptostreptococcaceae_XI_[G-1]_sp._COT-006
52. pr_Lachnospiraceae_XIVa_[G-3]_sp.
53. pr_Peptostreptococcaceae_XIII_[G-1]_sp._COT-030
54. pr_Cardiobacterium_sp._COT-176
55. pr_Peptostreptococcaceae_XI_[G-4]_sp._COT-021
56. ct_Capnocytophaga_canimorsus
57. pr_Pasteurella_canis_COT-273
58. pr_Moraxella_sp._COT-018
59. ct_Anaerovorax_sp._COT-125
60. pr_Fusobacterium_sp._COT-189
61. ct_g_Prevotella
62. pr_g_Fusobacterium
63. ct_Peptostreptococcaceae_XI_[G-7]_sp._COT-155
64. ct_Spirochaeta_sp._COT-314
65. pr_Peptostreptococcaceae_XI_[G-6]_sp._COT-068
66. pr_Pasteurellaceae_sp._COT-271
67. pr_g_Arcobacter
68. pr_Treponema_sp._COT-233
69. ct_Prevotella_sp._COT-195
70. pr_g_Propionivibrio
71. ct_g_Escherichia
72. ct_Parvimonas_sp._COT-101
73. ct_Proprionibacterium_sp._COT-296
74. pr_Treponema_sp._COT-200
75. ct_Frigovirgula_sp._COT-007
76. pr_g_Odoribacter
77. pr_g_Schwartzia
78. pr_Lachnospiraceae_XIVa_[G-6]_sp._COT-106
79. ct_g_Arcobacter
80. pr_g_Lautropia
81. ct_Lachnospiraceae_XIVa_[G-2]_sp._COT-062
82. ct_Porphyromonas_sp._COT-361
83. pr_Prevotella_sp._COT-298
84. ct_Catonella_sp._COT-025
85. pr_Parvimonas_sp._COT-035
86. pr_g_Xenophilus
87. pr_Chryseobacterium_sp._COT-320
88. pr_g_Actinomyces
89. pr_Actinomyces_sp._COT-252
90. ct_Actinomyces_sp. Cluster 7596
91. ct_g_Actinomyces
92. ct_Filifactor_sp._COT-064
93. pbn_Erysipelotrichaceae_[G-3]_sp._COT-302
94. bn_Capnocytophaga_canimorus_COT-235
95. bn_Porphyromonas_macacae_COT-192
96. bn_Neisseria_weaveri_COT-269
97. bn_Neisseria_sp._COT-049
98. bn_Actinobaceria_sp._COT-376
99. bn_Treponema_denticola_COT-197
100. bn_Lachnospiraceae_XIVa_[G-6]_sp._COT-161
101. bn_Porphyromonas_gulae_II_COT-052
102. bn_Proprionibacterium_sp._COT-365
103. bn_Schwartzia_sp._COT-063
104. bn_Capnocytophaga_sp._COT-362
105. bn_Filifactor_sp._COT-064
106. bn_Filifactor_sp._COT-163
107. bn_Peptostreptococcaceae_XI_[G-6]_sp._COT-067
108. bn_g_Solobacterium
109. bn_Porphyromonas_sp._COT-361
110. bn_Prevotella_sp._COT-195
111. bn_Proprionibacterium_sp._COT-296
112. bn_Treponema_sp._COT-198
113. bn_g_Atopobium
114. bn_g_Leucobacter
115. bn_g_Lautropia
116. bn_g_Parvimonas
117. bn_Capnocytophaga_canimorsus
118. bn_Lachnospiraceae_XIVa_[G-6]_sp._COT-106
119. bn_Treponema_sp._COT-351
120. bn_Actinomyces_catuli
121. bn_Bacteroides_denticanoris_COT-183 (Prevotella_sp?)
122. bn_Parvimonas_sp._COT-102
123. bn_g_Arcobacter
124. bn_Peptostreptococcaceae_XIII_[G-1]_sp._COT-030
125. bn_g_Staphylococcus
126. bn_Peptostreptococcaceae_XI_[G-1]_sp._COT-006
127. bn_Porphyromonas_gulae_I_COT-052
128. bn_g_Xanthomonadaceae_bacterium
129. bn_g_Schwartzia
130. bn_Cardiobacterium_sp._COT-176
131. bn_Actinomyces_bowdenii
132. bn_g_Leptotrichia
133. bn_Treponema_sp._COT-359

-continued 134. bn__g__Xenophilus
135. bn__Lachnospiraceae__XIVa__[G-2]__sp.__COT-062
136. bn__Frigovirgula__sp.__COT-007
137. bn__Wolinella__succinogenes
138. bn__g__Curtobacterium
139. bn__Chryseobacterium__sp.__COT-320
140. bn__Bacteroidia__[G-5]__sp.__COT-187
141. bn__Synergistales__[G-1]__sp.__COT-178
142. bn__g__Propionibacteriaceae__bacterium
143. bn__Selenomonas__sputigena__COT-342
144. bn__Streptococcus__minor__COT-116
145. bn__Porphyromonas__sp.__COT-182
146. b7__Clostridiales__III__[G-3]__sp.__COT-388
147. b7__Escherichia__coli
148. b7__g__Parvimonas
149. b7__Capnocytophaga__canimorsus
150. b7__Peptostreptococcaceae__XIII__[G-1]__sp.__COT-030
151. b7__Desulfovibrionales__sp.__COT-009
152. b7__Peptostreptococcaceae__XI__[G-7]__sp.__COT-155
153. b7__Fusobacterium__sp.__COT-169
154. b7__Anerovorax__sp.__COT-066
155. b7__Lachnospiraceae__XIVa__[G-3]__sp.
156. b7__g__bacterium__cp04.17
157. b7__Filifactor__alocis__COT-001
158. b7__Peptostreptococcaceae__XI__[G-1]__sp.__COT-258
159. b7__Peptostreptococcaceae__XI__[G-3]__sp.__COT-104
160. b7__Clostridiales__[F-2.G-1]__sp.__COT-100__PO005
161. b7__Selenomonas__sputigena__COT-342
162. b7__g__Moraxella
163. b7__g__Phascolarctobacterium
164. b7__Peptostreptococcaceae__XIII__[G-2]__sp.__COT-077
165. b7__Leucobacter__sp.__COT-288
166. b7__g__Atopobium
167. b7__g__Propionivibrio
168. b7__Spirochaeta__sp.__COT-314
169. b7__g__CDC__Group__NO-1
170. b7__Catonella__sp.__COT-257
171. b7__Corynebacterium__sp.__cluster 88112
172. b7__g__Catonella
173. b7__Fusobacterium__sp.__COT-189
174. b7__Peptostreptococcaceae__XI__[G-3]__sp.__COT-034
175. b7__Treponema__sp.__COT-233
176. b7__g__Chryseobacterium
177. b7__Actinomyces__catuli
178. b7__Peptostreptococcaceae__XI__[G-6]__sp.__COT-067
179. b7__Proprionibacterium__sp.__COT-365
180. b7__g__Xenophilus
181. b7__Capnocytophaga__sp.__COT-339
182. b7__g__Treponema
183. b7__Prevotella__sp.__COT-282
184. b7__g__Clostridiales__III__[G-3]__sp.__COT-388__1P046
185. b7__Porphyromonas__gulae__I__COT-052
186. b7__g__Escherichia
187. b7__g__Solobacterium
188. b7__Streptococcus__minor__COT-116
189. b7__g__Leptotrichia
190. b7__Pasteurellaceae__sp.__COT-271
191. b7__g__Staphylococcus
192. b7__Filifactor__sp.__COT-163
193. b7__Peptostreptococcaceae__XI__[G-1]__sp.__COT-006
194. b7__bacterium__cp04.17
195. b7__Porphyromonas__macacae__COT-192
196. b7__Spirochaeta__sp.__COT-379
197. b7__Stenotrophomonas__sp.__COT-224
198. b7__Parvinnonas__sp.__COT-035
199. b7__Capnocytophaga__sp.__COT-362 ct__ Counts
pr__ Proportions
bn__ Binary predictors using a cut-off of 1
b7__ Binary predictors using a cut-off of 7
g__ Indicates that the variable relates to a genus, rather than an individual species Predictive Modelling Standard Model Types A standard set of models (as known to the person skilled in the art) was applied to each combination of predictors and output variables. The classification model types used were:

General Stepwise Discriminant Analysis with maximum of 10 predictors

General Stepwise Discriminant Analysis with maximum of 5 predictors

Classification Trees

Classification Trees with v-fold cross-validation

Multivariate Adaptive Regression Splines

Boosted Classification Trees

Random Forests

The model types used for the prediction of Gingivitis score (a continuous output variable) were:

General Stepwise Regression Analysis with maximum of 10 predictors

General Stepwise Regression Analysis with maximum of 5 predictors

Regression Trees

Regression Trees with v-fold cross-validation

Multivariate Adaptive Regression Splines

Boosted Regression Trees

Random Forests

Two-stage Models

Because of the limited success of the attempts a two-stage approach to produce models capable of performing a (H/G/P) classification was investigated. This involved developing a set of models trained for simpler two-way classification and combining some of the best-performing two-way models to produce a final three-way (H/G/P) classification, in the following combinations:

H/Not-H with G/P

P/Not-P with H/G

H/Not-H with P/Not-P

These results provide evidence that it is possible to use the bacterial species found in canine sub-gingival plaque to diagnose oral health state.

EXAMPLE 3

Model 1

| | |
|---|---|
| Output Classes | P/Not-P |
| Model Type | Stepwise Discriminant Function |
| Predictor Set | Binary (>1) |
| Selected Model | 4 Predictors (Test Performance 83.8%) |

Misclassification Matrix

| Observed | Test Set Predicted Class | | | Training Set Predicted Class | | |
|---|---|---|---|---|---|---|
| Class | P | Not-P | Total | P | Not-P | Total |
| P | 11 | 11 | 22 | 29 | 23 | 52 |
| Not-P | 0 | 46 | 46 | 7 | 96 | 103 |

Classification Functions

| | P | Not-P |
|---|---|---|
| A priori probabilities | 0.3355 | 0.6645 |
| Intercept | −3.70073 | −2.27400 |
| bn_Capnocytophaga_canimorus_COT-235 | 1.86706 | 3.96701 |
| bn_Peptostreptococcaceae_XI_[G-6]_sp._COT-067 | 2.94594 | 1.14205 |
| bn_Porphyromonas_macacae_COT-192 | 2.37558 | 1.01832 |
| bn_g_Solobacterium | 2.26286 | 0.16566 |

EXAMPLE 4

Model 2

| Output Classes | P/Not-P |
|---|---|
| Model Type | Classification Tree |
| Predictor Set | Binary (>1) |
| Selected Model | 7 Splits (Test Performance 82.4%) |

Misclassification Matrix

| Observed | Test Set Predicted Class | | | Training Set Predicted Class | | |
|---|---|---|---|---|---|---|
| Class | P | Not-P | Total | P | Not-P | Total |
| P | 12 | 10 | 22 | 37 | 15 | 52 |
| Not-P | 2 | 44 | 46 | 9 | 94 | 103 |

Tree Structure

Tree structure 1 (Training Data)
Dependent variable: Health State
Options: Categorical response, Tree number 1

| Node # | Left branch | Right branch | Size of node | N in class P | N in class Not-P | Selected category | Split Variable | Split constant |
|---|---|---|---|---|---|---|---|---|
| 1 | 2 | 3 | 155 | 52 | 103 | Not-P | bn_Peptostreptococcaceae_XI_[G-6]_sp._COT-067 | 0.5 |
| 2 | 4 | 5 | 93 | 15 | 78 | Not-P | bn_Treponema_sp._COT-198 | 0.5 |
| 4 | 6 | 7 | 89 | 11 | 78 | Not-P | bn_g_Atopobium | 0.5 |
| 6 | 8 | 9 | 83 | 7 | 76 | Not-P | bn_Streptococcus_anginosus_COT-117 | 0.5 |
| 8 | 10 | 11 | 80 | 5 | 75 | Not-P | bn_g_Porphyromonadaceae | 0.5 |
| 10 | 12 | 13 | 79 | 4 | 75 | Not-P | bn_Synergistales_[G-1]_sp._COT-244 | 0.5 |
| 12 | | | 78 | 3 | 75 | Not-P | | |
| 13 | | | 1 | 1 | 0 | P | | |
| 11 | | | 1 | 1 | 0 | P | | |
| 9 | | | 3 | 2 | 1 | P | | |
| 7 | | | 6 | 4 | 2 | P | | |
| 5 | | | 4 | 4 | 0 | P | | |
| 3 | 20 | 21 | 62 | 37 | 25 | P | bn_Capnocytophaga_canimorus_COT-235 | 0.5 |
| 20 | | | 31 | 25 | 6 | P | | |
| 21 | | | 31 | 12 | 19 | Not-P | | |

EXAMPLE 5

Model 3

| | |
|---|---|
| Output Classes | H/Not-H |
| Model Type | Stepwise Discriminant Function |
| Predictor Set | Binary (>1) |
| Selected Model | 8 Predictors (Test Performance 76.5%) |

Misclassification Matrix

| | Test Set | | | Training Set | | |
|---|---|---|---|---|---|---|
| Observed | Predicted Class | | | Predicted Class | | |
| Class | H | Not-H | Total | H | Not-H | Total |
| H | 13 | 6 | 19 | 42 | 10 | 52 |
| Not-H | 10 | 39 | 49 | 15 | 88 | 103 |

Classification Functions

| | H | Not-H |
|---|---|---|
| A priori probabilities | 0.3355 | 0.6645 |
| Intercept | −9.75622 | −11.9690 |
| bn__Actinobaceria_sp._COT-376 | 3.20990 | 5.5783 |
| bn__Bacteroides_denticanoris__COT-183 (Prevotella_sp?) | 1.43898 | 3.0533 |
| bn__Capnocytophaga__canimorsus | 3.76502 | 2.4305 |
| bn__Lachnospiraceae__XIVa__[G-2]_sp._COT-062 | 1.37525 | 0.0051 |
| bn__Neisseria__weaveri__COT-269 | 0.71473 | −1.3992 |
| bn__Treponema__denticola__COT-197 | 12.86457 | 15.3769 |
| bn__Treponema__sp._COT-351 | −0.83313 | 0.7140 |
| bn__g__Schwartzia | −0.60100 | 1.5399 |

EXAMPLE 6

Model 4

| | |
|---|---|
| Output Classes | H/Not-H |
| Model Type | Classification Tree |
| Predictor Set | Best predictors (Counts, Proportions and Binary) |
| Selected Model | 6 Splits (Test Performance 79.4%) |

Misclassification Matrix

| | Test Set | | | Training Set | | |
|---|---|---|---|---|---|---|
| Observed | Predicted Class | | | Predicted Class | | |
| Class | H | Not-H | Total | H | Not-H | Total |
| H | 17 | 2 | 19 | 39 | 13 | 52 |
| Not-H | 12 | 37 | 49 | 4 | 99 | 103 |

Tree Structure

Tree structure 1 (Training Data)
Dependent variable: Health State
Options: Categorical response, Tree number 1

| Node # | Left branch | Right branch | Size of node | N in class H | N in class Not-H | Selected category | Split variable |
|---|---|---|---|---|---|---|---|
| 1 | 2 | 3 | 155 | 52 | 103 | Not-H | pr_g_Peptostreptococcus |
| 2 | 4 | 5 | 71 | 43 | 28 | H | pr_Treponema_sp._COT-200 |
| 4 | 6 | 7 | 46 | 36 | 10 | H | ct_Frigovirgula_sp._COT-007 |
| 6 | 8 | 9 | 39 | 34 | 5 | H | ct_g_Leucobacter |
| 8 | 10 | 11 | 33 | 32 | 1 | H | pr_g_Odoribacter |
| 10 | | | 32 | 32 | 0 | H | |
| 11 | | | 1 | 0 | 1 | Not-H | |
| 9 | | | 6 | 2 | 4 | Not-H | |
| 7 | | | 7 | 2 | 5 | Not-H | |
| 5 | 12 | 13 | 25 | 7 | 18 | Not-H | ct_Peptostreptococcaceae_XIII_[G-2]_sp._COT-077 |
| 12 | | | 11 | 7 | 4 | H | |
| 13 | | | 14 | 0 | 14 | Not-H | |
| 3 | | | 84 | 9 | 75 | Not-H | |

Misclassification Matrix for 2-stage Model A

|  | Test Set | | | | Training Set | | | |
| --- | --- | --- | --- | --- | --- | --- | --- | --- |
| Observed | Predicted Class | | | | Predicted Class | | | |
| Class | H | G | P | Total | H | G | P | Total |
| H | 17 | 2 | 0 | 19 | 39 | 12 | 1 | 52 |
| G | 8 | 19 | 0 | 27 | 4 | 43 | 4 | 51 |
| P | 4 | 7 | 11 | 22 | 0 | 23 | 29 | 52 |

EXAMPLE 7

This example shows the identification of two or more bacteria as claimed using a binary test, combined with the information give n in tables 1 to 5 and the use of statistical models gives a reliable prediction of the health status of an animal.

| Output Variable | Model Type | Novel Predictors only | Training Performance | Test Performance |
| --- | --- | --- | --- | --- |
| Classes P/Not-P | Discriminant - Forward Stepwise - 10 predictors | bn__Peptostreptococcaceae__XI__[G-6]__sp.__COT-067<br>bn__Capnocytophaga__canimorus__COT-235<br>bn__g__Solobacterium<br>bn__Fusobacterium__sp.__COT-236<br>bn__Capnocytophaga__sp.__COT-362<br>bn__Ottowia__sp.__COT-014<br>bn__Neisseria__animaloris__COT-016<br>bn__Moraxella__sp.__COT-328<br>bn__Peptostreptococcaceae__XIII__[G-2]__sp.__COT-077<br>bn__Peptostreptococcaceae__XI__[G-2]__sp.__COT-003 | 85.8 | 80.9 |
| Classes P/Not-P | Classification Trees | bn__Peptostreptococcaceae__XI__[G-6]__sp.__COT-067<br>bn__Treponema__sp.__COT-198<br>bn__g__Atopobium<br>bn__Streptococcus__anginosus__COT-117<br>bn__g__Porphyromonadaceae<br>bn__Fusobacterium__sp.__COT-189<br>bn__Streptococcus__anginosus<br>bn__Treponema__sp.__COT-351<br>bn__Capnocytophaga__sp.__COT-362<br>bn__g__Anaerovorax<br>bn__Capnocytophaga__canimorus__COT-235<br>bn__Erysipelotrichaceae__[G-3]__sp.__COT-302<br>bn__g__Leucobacter<br>bn__g__Lautropia | 89.7 | 75.0 |
| Classes H/Not-H | Discriminant - Forward Stepwise - 10 predictors | bn__g__Schwartzia<br>bn__Capnocytophaga__canimorsus<br>bn__Treponema__sp.__COT-351<br>bn__Erysipelotrichaceae__[G-3]__sp.__COT-302<br>bn__Actinobaceria__sp.__COT-376<br>bn__Pasteurella__canis__COT-273<br>bn__Anaerovorax__sp.__COT-124<br>bn__Streptococcus__sp.__cluster 2789<br>bn__Moraxella__sp.__COT-018<br>bn__Chloroflexi__[G-1]__sp.__COT-306 | 84.5 | 70.6 |
| Classes H/Not-H | Classification Trees with v-fold | pr__g__Peptostreptococcus<br>pr__Treponema__sp.__COT-200 | 83.2 | 72.1 |
| Classes H/Not-H | Discriminant - Forward Stepwise—3 predictors | bn__Peptostreptococcaceae__XIII__[G-2]__sp.__COT-077<br>bn__Capnocytophaga__canimorsus<br>bn__g__Schwartzia | 78.7 | 75.0 |
| Classes P/Not-P | Classification Trees | bn__Peptostreptococcaceae__XIII__[G-2]__sp.__COT-077<br>bn__Capnocytophaga__canimorus__COT-235<br>bn__Peptostreptococcaceae__XI__[G-6]__sp.__COT-067<br>bn__Neisseria__sp.__COT-049 | 81.3 | 77.9 |

| Output Variable | Model Type | Novel Predictors only | Training Performance | Test Performance |
|---|---|---|---|---|
| Classes P/Not-P | Discriminant - Forward Stepwise—5 predictors | bn__Peptostreptococcaceae__XIII__[G-2]__sp.__COT-077<br>bn__Capnocytophaga__canimorus__COT-235<br>bn__Peptostreptococcaceae__XI__[G-6]__sp.__COT-067<br>bn__g__Solobacterium<br>bn__Neisseria__sp.__COT-049 | 86.5 | 80.9 |
| Classes P/Not-P | Discriminant - Forward Stepwise—5 predictors | b7__Peptostreptococcaceae__XIII__[G-1]__sp.__COT-030<br>b7__g__Parvimonas<br>b7__Filifactor__alocis__COT-001<br>b7__Peptostreptococcaceae__XI__[G-1]__sp.__COT-258<br>b7__Peptostreptococcaceae__XI__[G-3]__sp.__COT-104 | 80.6 | 76.5 |
| Classes P/Not-P | MAR Splines | bn__Lachnospiraceae__XIVa__[G-6]__sp.__COT-106<br>bn__Neisseria__sp.__COT-049<br>bn__Peptostreptococcaceae__XI__[G-6]__sp.__COT-067<br>bn__Selenomonas__sputigena__COT-342 | 91.7 | 73.5 |

EXAMPLE 8

This example shows the identification of two or more bacteria as claimed using a proportional test, combined with the information give n in tables 1 to 5 and the use of statistical models gives a reliable prediction of the health status of an animal.

| Output Variable | Model Type | Novel Predictors only | Training Performance | Test Performance |
|---|---|---|---|---|
| Classes P/Not-P | Discriminant - Forward Stepwise - 5 predictors | rel_pr__Peptostreptococcaceae__XIII__[G-2]__sp.__COT-077<br>rel_pr__Filifactor__sp.__COT-064<br>rel_pr__Peptostreptococcaceae__XI__[G-4]__sp.__COT-019<br>rel_pr__Selenomonas__sputigena__COT-342<br>rel_ct__Neisseria__sp.__COT-049 | 83.9 | 75.0 |
| Classes P/Not-P | Discriminant - Forward Stepwise - 10 predictors | rel_pr__Peptostreptococcaceae__XIII__[G-2]__sp.__COT-077<br>rel_pr__Filifactor__sp.__COT-064<br>rel_pr__Peptostreptococcaceae__XI__[G-4]__sp.__COT-019<br>rel_pr__Selenomonas__sputigena__COT-342<br>rel_ct__Neisseria__sp.__COT-049<br>rel_ct__Filifactor__sp.__COT-163<br>rel_ct__Frigovirgula__sp.__COT-058<br>rel_pr__Treponema__denticola__COT-197<br>rel_pr__Erysipelotrichaceae__[G-3]__sp.__COT-302<br>rel_pr__g__Peptostreptococcus | 86.5 | 79.4 |

EXAMPLE 9

This example shows that predictive models based on known bacteria are improved once at least one novel bacteria identified as part of the present invention is included in the analysis.

| Output Variable | Model Type | Non-Novel Predictors | Training Performance | Test Performance |
|---|---|---|---|---|
| Classes P/Not-P | Discriminant - Forward Stepwise - 10 predictors | bn_Porphyromonas_macacae_COT-192<br>bn_Neisseria_weaveri_COT-269<br>bn_Helcococcus_sp._COT-140<br>bn_Bacteroides_denticanoris_COT-183<br>bn_Pasteurellaceae_sp._COT-271<br>bn_Treponema_denticola_COT-197<br>bn_Synergistales_[G-1]_sp._COT-244<br>bn_Porphyromonas_gulae_II_COT-052<br>bn_Helcococcus_sp._COT-069<br>bn_Moraxella_sp._COT-017 | 81.3 | 61.8 |
| Classes P/Not-P | Classification Trees | bn_Porphyromonas_macacae_COT-192<br>bn_Neisseria_zoodegmatis_COT-349<br>bn_Porphyromonas_gulae_I_COT-052<br>bn_Bacteroides_denticanoris_COT-183<br>bn_Synergistales_[G-1]_sp._COT-180<br>bn_Frigovirgula_sp._COT-058<br>bn_Porphyromonas_gulae_II_COT-052 | 70.3 | |
| Classes P/Not-P | Discriminant - Forward Stepwise - 11 predictors | bn_Synergistales_[G-1]_sp._COT-180<br>bn_Neisseria_weaveri_COT-269<br>bn_Treponema_denticola_COT-197<br>bn_Bacteroides_denticanoris_COT-183<br>bn_Porphyromonas_macacae_COT-192<br>bn_Porphyromonas_gulae_II_COT-052<br>bn_Helcococcus_sp._COT-140<br>bn_Porphyromonas_gulae_I_COT-052<br>bn_Bacteroides_tectus_COT-039<br>bn_Filifactor_villosus_COT-031<br>bn_Helcococcus_sp._COT-069 | 81.9 | 75.0 |

| Output Variable | Model Type | With addition of Novel Predictor(s) | Training Performance | Test Performance |
|---|---|---|---|---|
| Classes P/Not-P | Discriminant - Forward Stepwise - 10 predictors | bn_Porphyromonas_macacae_COT-192<br>bn_Neisseria_weaveri_COT-269<br>bn_Helcococcus_sp._COT-140<br>bn_Bacteroides_denticanoris_COT-183<br>bn_Pasteurellaceae_sp._COT-271<br>bn_Treponema_denticola_COT-197<br>bn_Synergistales_[G-1]_sp._COT-244<br>bn_Porphyromonas_gulae_II_COT-052<br>bn_Helcococcus_sp._COT-069<br>bn_Moraxella_sp._COT-017<br>bn_Filifactor_sp._COT-163 | 80.0 | 66.2 |
| Classes P/Not-P | Classification Trees | bn_Porphyromonas_macacae_COT-192<br>bn_Neisseria_zoodegmatis_COT-349<br>bn_Porphyromonas_gulae_I_COT-052<br>bn_Bacteroides_denticanoris_COT-183<br>bn_Synergistales_[G-1]_sp._COT-180<br>bn_Frigovirgula_sp._COT-058<br>bn_Porphyromonas_gulae_II_COT-052<br>bn_Parvimonas_sp._COT-035<br>bn_Proprionibacterium_sp._COT-296<br>bn_Proprionibacterium_sp._COT-365<br>bn_Pasteurella_dogmatis_COT-092 | 84.5 | 70.6 |
| Classes P/Not-P | Discriminant - Forward Stepwise - 11 predictors | bn_Synergistales_[G-1]_sp._COT-180<br>bn_Neisseria_weaveri_COT-269<br>bn_Treponema_denticola_COT-197<br>bn_Bacteroides_denticanoris_COT-183<br>bn_Porphyromonas_macacae_COT-192<br>bn_Porphyromonas_gulae_II_COT-052<br>bn_Actinobaceria_sp._COT-376 | 81.9 | 76.5 |

EXAMPLE 10

Novel Proportional Model

| | |
|---|---|
| Output Classes | P/Not-P |
| Model Type | Stepwise Discriminant Function |
| Predictor Set | Relative counts and proportions |
| Selected Model | 5 Predictors (Test Performance 75%) |

Misclassification Matrix

| | Training Set | | | Test Set | | |
|---|---|---|---|---|---|---|
| Observed | Predicted Class | | | Predicted Class | | |
| Class | P | Not-P | Total | P | Not-P | Total |
| P | 30 | 22 | 52 | 9 | 13 | 22 |
| Not-P | 3 | 100 | 103 | 4 | 42 | 46 |

Classification Functions

| | P | Not-P |
|---|---|---|
| A priori probabilities | 0.3355 | 0.6645 |
| Intercept | −3.34369 | −0.551900 |
| rel_ct_Neisseria_sp._COT-049 | 0.35971 | 0.092469 |
| rel_pr_Filifactor_sp._COT-064 | 0.31352 | 0.027470 |
| rel_pr_Peptostreptococcaceae_XI_[G-4]_sp._COT-019 | 0.85807 | 0.330981 |
| rel_pr_Peptostreptococcaceae_XIII_[G-2]_sp._COT-077 | 0.40666 | 0.041811 |
| rel_pr_Selenomonas_sputigena_COT-342 | 0.33040 | 0.024742 |

EXAMPLE 11

Novel Binary Discriminant Model

| | |
|---|---|
| Output Classes | H/Not-H |
| Model Type | Stepwise Discriminant Function |
| Predictor Set | Binary (>1) |
| Selected Model | 10 Predictors (Test Performance 71%) |

Misclassification Matrix

| | Training Set | | | Test Set | | |
|---|---|---|---|---|---|---|
| Observed | Predicted Class | | | Predicted Class | | |
| Class | H | Not-H | Total | H | Not-H | Total |
| H | 39 | 13 | 52 | 11 | 8 | 19 |
| Not-H | 11 | 92 | 103 | 12 | 37 | 49 |

Classification Functions

| | H | Not-H |
|---|---|---|
| A priori probabilities | 0.3355 | 0.6645 |
| Intercept | −9.72349 | −10.0961 |
| bn_Actinobaceria_sp._COT-376 | 1.68931 | 3.6721 |
| bn_Anaerovorax_sp._COT-124 | 0.86471 | −0.6651 |
| bn_Capnocytophaga_canimorsus | 2.92731 | 1.8613 |
| bn_Chloroflexi_[G-1]_sp._COT-306 | 5.03974 | 6.7966 |
| bn_Erysipelotrichaceae_[G-3]_sp._COT-302 | −0.08136 | 1.7031 |
| bn_Moraxella_sp._COT-018 | 3.56547 | 1.9579 |
| bn_Pasteurella_canis_COT-273 | 6.97270 | 5.0997 |
| bn_Streptococcus_sp._cluster 2789 | 5.21252 | 10.0025 |
| bn_Treponema_sp._COT-351 | −1.56851 | 0.5099 |
| bn_g_Schwartzia | 0.76941 | 2.6864 |

EXAMPLE 12

Novel Binary Classification Tree Model

| | |
|---|---|
| Output Classes | P/Not-P |
| Model Type | Classification Tree |
| Predictor Set | Binary (>1) - COT-077 forced |
| Selected Model | 5 Predictors (Test Performance 78%) |

Misclassification Matrix

| | Training Set | | | Test Set | | |
|---|---|---|---|---|---|---|
| Observed | Predicted Class | | | Predicted Class | | |
| Class | P | Not-P | Total | P | Not-P | Total |
| P | 35 | 17 | 52 | 14 | 8 | 22 |
| Not-P | 12 | 91 | 103 | 7 | 39 | 46 |

Tree Structure

Tree Structure (Spreadsheet in Porto Diagnostic Data - Merged Data (COT-077 first))
Response: Health State
Model: C&RT;

| | Size of node | N in class P | N in class Not-P | Selected category | Split variable | Criterion for child 1 | Criterion for child 2 | Child node 1 | Child node 2 |
|---|---|---|---|---|---|---|---|---|---|
| 1 | 155 | 52 | 103 | Not-P | bn_Peptostreptococcaceae_XIII_[G-2]_sp._COT-077 | x <= 0.5000 | x > 0.5000 | 2 | 3 |
| 2 | 51 | 5 | 46 | Not-P | | | | | |
| 3 | 104 | 47 | 57 | Not-P | bn_Capnocytophaga_canimorus_COT-235 | x <= 0.5000 | x > 0.5000 | 4 | 5 |
| 4 | 43 | 30 | 13 | P | bn_Peptostreptococcaceae_XI_[G-6]_sp._COT-067 | x <= 0.5000 | x > 0.5000 | 6 | 7 |
| 6 | 17 | 7 | 10 | Not-P | | | | | |
| 7 | 26 | 23 | 3 | P | | | | | |
| 5 | 61 | 17 | 44 | Not-P | Bn_Neisseria_sp._COT-049 | x <= 0.5000 | x > 0.5000 | 10 | 11 |
| 10 | 40 | 5 | 35 | Not-P | | | | | |
| 11 | 21 | 12 | 9 | P | | | | | |

Supplementary Information
PMML Files for Selected Models
The following PMML files show the deployment code for each of models 1 to 4.

| Model 1 |
|---|

```
<?xml version="1.0" encoding="Windows-1252" ?>
<PMML version="2.0">
<Header copyright="STATISTICA Data Miner, Copyright (c) StatSoft, Inc., www.statsoft.com."/>
<DataDictionary numberOfFields="5">
    <DataField name="Health State" optype="categorical">
        <Value value="P" NumericValue="103"/>
        <Value value="Not-P" NumericValue="104"/>
    </DataField>
    <DataField name="bn_Capnocytophaga_canimorus_COT-235" optype="continuous"/>
    <DataField name="bn_Peptostreptococcaceae_XI_[G-6]_sp._COT-067" optype="continuous"/>
    <DataField name="bn_Porphyromonas_macacae_COT-192" optype="continuous"/>
    <DataField name="bn_g_Solobacterium" optype="continuous"/>
</DataDictionary>
<GeneralDiscriminantAnalysis
    functionName="classification"
    modelName="General discriminant analysis"
    modelType="generalLinear"
    targetVariableName="Health State">
<ParameterList>
    <Parameter name="p1" label="Intercept"/>
    <Parameter name="p2" label="bn_Capnocytophaga_canimorus_COT-235"/>
    <Parameter name="p3" label="bn_Peptostreptococcaceae_XI_[G-6]_sp._COT-067"/>
    <Parameter name="p4" label="bn_Porphyromonas_macacae_COT-192"/>
    <Parameter name="p5" label="bn_g_Solobacterium"/>
</ParameterList>
<FactorList>
</FactorList>
<CovariateList>
    <Predictor name="bn_Capnocytophaga_canimorus_COT-235"/>
    <Predictor name="bn_Peptostreptococcaceae_XI_[G-6]_sp.COT-067"/>
    <Predictor name="bn_Porphyromonas_macacae_COT-192"/>
    <Predictor name="bn_g_Solobacterium"/>
</CovariateList>
<PPMatrix>
    <PPCell value="1" predictorName="bn_Capnocytophaga_canimorus_COT-235" parameterName="p2"/>
    <PPCell value="1" predictorName="bn_Peptostreptococcaceae_XI_[G-6]_sp._COT-067" parameterName="p3"/>
    <PPCell value="1" predictorName="bn_Porphyromonas_macacae_COT-192" parameterName="p4"/>
    <PPCell value="1" predictorName="bn_g_Solobacterium" parameterName="p5"/>
</PPMatrix>
<Extension name="CorrectDummyCode" value="1"/>
<Extension name="IncorrectDummyCode" value="-1"/>
<ParamMatrix>
    <PCell targetCategory="P" parameterName="p1" beta="-3.70073449195254e+000"/>
    <PCell targetCategory="P" parameterName="p2" beta="1.86705716305613e+000"/>
    <PCell targetCategory="P" parameterName="p3" beta="2.94593793157859e+000"/>
    <PCell targetCategory="P" parameterName="p4" beta="2.37557530180906e+000"/>
    <PCell targetCategory="P" parameterName="p5" beta="2.26285729194501e+000"/>
    <PCell targetCategory="Not-P" parameterName="p1" beta="-2.27399820671763e+000"/>
    <PCell targetCategory="Not-P" parameterName="p2" beta="3.96700693000221e+000"/>
    <PCell targetCategory="Not-P" parameterName="p3" beta="1.14204503369275e+000"/>
    <PCell targetCategory="Not-P" parameterName="p4" beta="1.01832179904648e+000"/>
    <PCell targetCategory="Not-P" parameterName="p5" beta="1.65660316639435e-001"/>
</ParamMatrix>
</GeneralDiscriminantAnalysis>
</PMML>
```

| Model 2 |
|---|

```xml
<?xml version="1.0" encoding="Windows-1252" ?>
<PMML version="2.0">
<Header copyright="STATISTICA Data Miner, Copyright (c) StatSoft, Inc.,
www.statsoft.com."/>
<DataDictionary numberOfFields="8">
    <DataField name="Health State" optype="categorical">
        <Value value="P" NumericValue="103"/>
        <Value value="Not-P" NumericValue="104"/>
    </DataField>
    <DataField name="bn__Capnocytophaga__canimorus__COT-235" optype="continuous"/>
    <DataField name="bn__Peptostreptococcaceae__XI__[G-6]__sp.__COT-067" optype="continuous"/>
    <DataField name="bn__Streptococcus__anginosus__COT-117" optype="continuous"/>
    <DataField name="bn__Synergistales__[G-1]__sp.__COT-244" optype="continuous"/>
    <DataField name="bn__Treponema__sp.__COT-198" optype="continuous"/>
    <DataField name="bn__g__Atopobium" optype="continuous"/>
    <DataField name="bn__g__Porphyromonadaceae" optype="continuous"/>
</DataDictionary>
<TreeModel
    functionName="classification"
    modelName="Classification and regression trees"
    splitCharacteristic="binarySplit">
<MiningSchema>
    <MiningField name="Health State" usageType="predicted"/>
    <MiningField name="bn__Capnocytophaga__canimorus__COT-235"/>
    <MiningField name="bn__Peptostreptococcaceae__XI__[G-6]__sp.__COT-067"/>
    <MiningField name="bn__Streptococcus__anginosus__COT-117"/>
    <MiningField name="bn__Synergistales__[G-1]__sp.__COT-244"/>
    <MiningField name="bn__Treponema__sp.__COT-198"/>
    <MiningField name="bn__g__Atopobium"/>
    <MiningField name="bn__g__Porphyromonadaceae"/>
</MiningSchema>
<Node score="Not-P">
<targetPrediction name="P" value="3.35483870967742e-001"/>
<targetPrediction name="Not-P" value="6.64516129032258e-001"/>
    <TRUE/>
    <Node score="Not-P">
<targetPrediction name="P" value="1.61290322580645e-001"/>
<targetPrediction name="Not-P" value="8.38709677419355e-001"/>
        <SimplePredicate field="bn__Peptostreptococcaceae__XI__[G-6]__sp.__COT-067" operator="lessOrEqual" value="5.00000000000000e-001"/>
        <Node score="Not-P">
<targetPrediction name="P" value="1.23595505617978e-001"/>
<targetPrediction name="Not-P" value="8.76404494382023e-001"/>
            <SimplePredicate field="bn__Treponema__sp.__COT-198" operator="lessOrEqual" value="5.00000000000000e-001"/>
            <Node score="Not-P">
<targetPrediction name="P" value="8.43373493975904e-002"/>
<targetPrediction name="Not-P" value="9.15662650602410e-001"/>
                <SimplePredicate field="bn__g__Atopobium" operator="lessOrEqual" value="5.00000000000000e-001"/>
                <Node score="Not-P">
<targetPrediction name="P" value="6.25000000000000e-002"/>
<targetPrediction name="Not-P" value="9.37500000000000e-001"/>
                    <SimplePredicate field="bn__Streptococcus__anginosus__COT-117" operator="lessOrEqual" value="5.00000000000000e-001"/>
                    <Node score="Not-P">
<targetPrediction name="P" value="5.06329113924051e-002"/>
<targetPrediction name="Not-P" value="9.49367088607595e-001"/>
                        <SimplePredicate field="bn__g__Porphyromonadaceae" operator="lessOrEqual" value="5.00000000000000e-001"/>
                        <Node score="Not-P">
<targetPrediction name="P" value="3.84615384615385e-002"/>
<targetPrediction name="Not-P" value="9.61538461538462e-001"/>
                            <SimplePredicate field="bn__Synergistales__[G-1]__sp.__COT-244" operator="lessOrEqual" value="5.00000000000000e-001"/>
                        </Node>
                        <Node score="P">
<targetPrediction name="P" value="1.00000000000000e+000"/>
<targetPrediction name="Not-P" value="0.00000000000000e+000"/>
                            <SimplePredicate field="bn__Synergistales__[G-1]__sp.__COT-244" operator="greaterThan" value="5.00000000000000e-001"/>
                        </Node>
                    </Node>
                    <Node score="P">
```

Model 2

```
<targetPrediction name="P" value="1.00000000000000e+000"/>
<targetPrediction name="Not-P" value="0.00000000000000e+000"/>
        <SimplePredicate
field="bn__g__Porphyromonadaceae" operator="greaterThan" value="5.00000000000000e−
001"/>
            </Node>
        </Node>
        <Node score="P">
<targetPrediction name="P" value="6.66666666666667e−001"/>
<targetPrediction name="Not-P" value="3.33333333333333e−001"/>
        <SimplePredicate
field="bn__Streptococcus__anginosus__COT-117" operator="greaterThan"
value="5.00000000000000e−001"/>
            </Node>
        </Node>
        <Node score="P">
<targetPrediction name="P" value="6.66666666666667e−001"/>
<targetPrediction name="Not-P" value="3.33333333333333e−001"/>
            <SimplePredicate field="bn__g__Atopobium"
operator="greaterThan" value="5.00000000000000e−001"/>
            </Node>
        </Node>
        <Node score="P">
<targetPrediction name="P" value="1.00000000000000e+000"/>
<targetPrediction name="Not-P" value="0.00000000000000e+000"/>
        <SimplePredicate field="bn__Treponema__sp.__COT-198"
operator="greaterThan" value="5.00000000000000e−001"/>
            </Node>
    </Node>
    <Node score="P">
<targetPrediction name="P" value="5.96774193548387e−001"/>
<targetPrediction name="Not-P" value="4.03225806451613e−001"/>
        <SimplePredicate field="bn__Peptostreptococcaceae__XI__[G-6]__sp.__COT-
067" operator="greaterThan" value="5.00000000000000e−001"/>
            <Node score="P">
<targetPrediction name="P" value="8.06451612903226e−001"/>
<targetPrediction name="Not-P" value="1.93548387096774e−001"/>
            <SimplePredicate field="bn__Capnocytophaga__canimorus__COT-235"
operator="lessOrEqual" value="5.00000000000000e−001"/>
        </Node>
        <Node score="Not-P">
<targetPrediction name="P" value="3.87096774193548e−001"/>
<targetPrediction name="Not-P" value="6.12903225806452e−001"/>
            <SimplePredicate field="bn__Capnocytophaga__canimorus__COT-235"
operator="greaterThan" value="5.00000000000000e−001"/>
            </Node>
    </Node>
</Node>
</TreeModel>
</PMML>
```

Model 3

```
<?xml version="1.0" encoding="Windows-1252" ?>
<PMML version="2.0">
<Header copyright="STATISTICA Data Miner, Copyright (c) StatSoft, Inc.,
www.statsoft.com."/>
<DataDictionary numberOfFields="9">
    <DataField name="Health State" optype="categorical">
        <Value value="H" NumericValue="102"/>
        <Value value="Not-H" NumericValue="104"/>
    </DataField>
    <DataField name="bn__Actinobaceria__sp.__COT-376" optype="continuous"/>
    <DataField name="bn__Bacteroides__denticanoris__COT-183 (Prevotella__sp?)"
optype="continuous"/>
    <DataField name="bn__Capnocytophaga__canimorsus" optype="continuous"/>
    <DataField name="bn__Lachnospiraceae__XIVa__[G-2]__sp.__COT-062"
optype="continuous"/>
    <DataField name="bn__Neisseria__weaveri__COT-269" optype="continuous"/>
    <DataField name="bn__Treponema__denticola__COT-197" optype="continuous"/>
    <DataField name="bn__Treponema__sp.__COT-351" optype="continuous"/>
    <DataField name="bn__g__Schwartzia" optype="continuous"/>
</DataDictionary>
<GeneralDiscriminantAnalysis
```

-continued

| Model 3 |
|---|

```
    functionName="classification"
    modelName="General discriminant analysis"
    modelType="generalLinear"
    targetVariableName="Health State">
<ParameterList>
    <Parameter name="p1" label="Intercept"/>
    <Parameter name="p2" label="bn_Actinobaceria_sp._COT-376"/>
    <Parameter name="p3" label="bn_Bacteroides_denticanoris_COT-183
(Prevotella_sp?)"/>
    <Parameter name="p4" label="bn_Capnocytophaga_canimorsus"/>
    <Parameter name="p5" label="bn_Lachnospiraceae_XIVa_[G-2]_sp._COT-062"/>
    <Parameter name="p6" label="bn_Neisseria_weaveri_COT-269"/>
    <Parameter name="p7" label="bn_Treponema_denticola_COT-197"/>
    <Parameter name="p8" label="bn_Treponema_sp._COT-351"/>
    <Parameter name="p9" label="bn_g_Schwartzia"/>
</ParameterList>
<FactorList>
</FactorList>
<CovariateList>
    <Predictor name="bn_Actinobaceria_sp._COT-376"/>
    <Predictor name="bn_Bacteroides_denticanoris_COT-183 (Prevotella_sp?)"/>
    <Predictor name="bn_Capnocytophaga_canimorsus"/>
    <Predictor name="bn_Lachnospiraceae_XIVa_[G-2]_sp._COT-062"/>
    <Predictor name="bn_Neisseria_weaveri_COT-269"/>
    <Predictor name="bn_Treponema_denticola_COT-197"/>
    <Predictor name="bn_Treponema_sp._COT-351"/>
    <Predictor name="bn_g_Schwartzia"/>
</CovariateList>
<PPMatrix>
    <PPCell value="1" predictorName="bn_Actinobaceria_sp._COT-376"
parameterName="p2"/>
    <PPCell value="1" predictorName="bn_Bacteroides_denticanoris_COT-183
(Prevotella_sp?)" parameterName="p3"/>
    <PPCell value="1" predictorName="bn_Capnocytophaga_canimorsus"
parameterName="p4"/>
    <PPCell value="1" predictorName="bn_Lachnospiraceae_XIVa_[G-2]_sp._COT-062"
parameterName="p5"/>
    <PPCell value="1" predictorName="bn_Neisseria_weaveri_COT-269"
parameterName="p6"/>
    <PPCell value="1" predictorName="bn_Treponema_denticola_COT-197"
parameterName="p7"/>
    <PPCell value="1" predictorName="bn_Treponema_sp._COT-351"
parameterName="p8"/>
    <PPCell value="1" predictorName="bn_g_Schwartzia" parameterName="p9"/>
</PPMatrix>
<Extension name="CorrectDummyCode" value="1"/>
<Extension name="IncorrectDummyCode" value="-1"/>
<ParamMatrix>
    <PCell targetCategory="H" parameterName="p1" beta="-
9.75622064437969e+000"/>
    <PCell targetCategory="H" parameterName="p2" beta="3.20989889837442e+000"/>
    <PCell targetCategory="H" parameterName="p3" beta="1.43898462811349e+000"/>
    <PCell targetCategory="H" parameterName="p4" beta="3.76502266494249e+000"/>
    <PCell targetCategory="H" parameterName="p5" beta="1.37524971518131e+000"/>
    <PCell targetCategory="H" parameterName="p6" beta="7.14727034546135e-001"/>
    <PCell targetCategory="H" parameterName="p7" beta="1.28645669925727e+001"/>
    <PCell targetCategory="H" parameterName="p8" beta="-8.33126809707693e-
001"/>
    <PCell targetCategory="H" parameterName="p9" beta="-6.01000099372420e-
001"/>
    <PCell targetCategory="Not-H" parameterName="p1" beta="-
1.19689712113546e+001"/>
    <PCell targetCategory="Not-H" parameterName="p2"
beta="5. 57825947432191e+000"/>
    <PCell targetCategory="Not-H" parameterName="p3"
beta="3.05332567144992e+000"/>
    <PCell targetCategory="Not-H" parameterName="p4"
beta="2.43051095188849e+000"/>
    <PCell targetCategory="Not-H" parameterName="p5" beta="5.08135558741085e-
003"/>
    <PCell targetCategory="Not-H" parameterName="p6" beta="-
1.39921917120777e+000"/>
    <PCell targetCategory="Not-H" parameterName="p7"
beta="1.53768975757821e+001"/>
    <PCell targetCategory="Not-H" parameterName="p8" beta="7.14047368351369e-
001"/>
    <PCell targetCategory="Not-H" parameterName="p9"
```

-continued

Model 3 beta="1.53986820729639e+000"/>
</ParamMatrix>
</GeneralDiscriminantAnalysis>
</PMML>

Model 4

<?xml version="1.0" encoding="Windows-1252" ?>
<PMML version="2.0">
<Header copyright="STATISTICA Data Miner, Copyright (c) StatSoft, Inc., www.statsoft.com."/>
<DataDictionary numberOfFields="7">
    <DataField name="Health State" optype="categorical">
        <Value value="H" NumericValue="102"/>
        <Value value="Not-H" NumericValue="104"/>
    </DataField>
    <DataField name="pr_g_Peptostreptococcus" optype="continuous"/>
    <DataField name="pr_Treponema_sp._COT-200" optype="continuous"/>
    <DataField name="ct_Frigovirgula_sp._COT-007" optype="continuous"/>
    <DataField name="ct_g_Leucobacter" optype="continuous"/>
    <DataField name="pr_g_Odoribacter" optype="continuous"/>
    <DataField name="ct_Peptostreptococcaceae_XIII_[G-2]_sp._COT-077" optype="continuous"/>
</DataDictionary>
<TreeModel
    functionName="classification"
    modelName="Classification and regression trees"
    splitCharacteristic="binarySplit">
<MiningSchema>
    <MiningField name="Health State" usageType="predicted"/>
    <MiningField name="pr_g_Peptostreptococcus"/>
    <MiningField name="pr_Treponema_sp._COT-200"/>
    <MiningField name="ct_Frigovirgula_sp._COT-007"/>
    <MiningField name="ct_g_Leucobacter"/>
    <MiningField name="pr_g_Odoribacter"/>
    <MiningField name="ct_Peptostreptococcaceae_XIII_[G-2]_sp._COT-077"/>
</MiningSchema>
<Node score="Not-H">
<targetPrediction name="H" value="3.35483870967742e-001"/>
<targetPrediction name="Not-H" value="6.64516129032258e-001"/>
    <TRUE/>
    <Node score="H">
<targetPrediction name="H" value="6.05633802816901e-001"/>
<targetPrediction name="Not-H" value="3.94366197183099e-001"/>
        <SimplePredicate field="pr_g_Peptostreptococcus" operator="lessOrEqual" value="3.30806684009437e-003"/>
        <Node score="H">
<targetPrediction name="H" value="7.82608695652174e-001"/>
<targetPrediction name="Not-H" value="2.17391304347826e-001"/>
            <SimplePredicate field="pr_Treponema_sp._COT-200" operator="lessOrEqual" value="6.58711443509121e-005"/>
            <Node score="H">
<targetPrediction name="H" value="8.71794871794872e-001"/>
<targetPrediction name="Not-H" value="1.28205128205128e-001"/>
                <SimplePredicate field="ct_Frigovirgula_sp._COT-007" operator="lessOrEqual" value="4.62000000000000e+002"/>
                <Node score="H">
<targetPrediction name="H" value="9.69696969696970e-001"/>
<targetPrediction name="Not-H" value="3.03030303030303e-002"/>
                    <SimplePredicate field="ct_g_Leucobacter" operator="lessOrEqual" value="2.31500000000000e+002"/>
                    <Node score="H">
<targetPrediction name="H" value="1.00000000000000e+000"/>
<targetPrediction name="Not-H" value="0.00000000000000e+000"/>
                        <SimplePredicate field="pr_g_Odoribacter" operator="lessOrEqual" value="8.16526942392993e-003"/>
                    </Node>
                    <Node score="Not-H">
<targetPrediction name="H" value="0.00000000000000e+000"/>
<targetPrediction name="Not-H" value="1.00000000000000e+000"/>
                        <SimplePredicate field="pr_g_Odoribacter" operator="greaterThan" value="8.16526942392993e-003"/>
                    </Node>
                  </Node>

-continued

Model 4

```
            <Node score="Not-H">
<targetPrediction name="H" value="3.33333333333333e-001"/>
<targetPrediction name="Not-H" value="6.66666666666667e-001"/>
                <SimplePredicate field="ct_g_Leucobacter"
operator="greaterThan" value="2.31500000000000e+002"/>
            </Node>
        </Node>
        <Node score="Not-H">
<targetPrediction name="H" value="2.85714285714286e-001"/>
<targetPrediction name="Not-H" value="7.14285714285714e-001"/>
                <SimplePredicate field="ct_Frigovirgula_sp._COT-007"
operator="greaterThan" value="4.62000000000000e+002"/>
            </Node>
        </Node>
        <Node score="Not-H">
<targetPrediction name="H" value="2.80000000000000e-001"/>
<targetPrediction name="Not-H" value="7.20000000000000e-001"/>
                <SimplePredicate field="pr_Treponema_sp._COT-200"
operator="greaterThan" value="6.58711443509121e-005"/>
            <Node score="H">
<targetPrediction name="H" value="6.36363636363636e-001"/>
<targetPrediction name="Not-H" value="3.63636363636364e-001"/>
                <SimplePredicate field="ct_Peptostreptococcaceae_XIII_[G-
2]_sp._COT-077" operator="lessOrEqual" value="2.50000000000000e+000"/>
            </Node>
            <Node score="Not-H">
<targetPrediction name="H" value="0.00000000000000e+000"/>
<targetPrediction name="Not-H" value="1.00000000000000e+000"/>
                <SimplePredicate field="ct_Peptostreptococcaceae_XIII_[G-
2]_sp._COT-077" operator="greaterThan" value="2.50000000000000e+000"/>
            </Node>
        </Node>
    </Node>
    <Node score="Not-H">
<targetPrediction name="H" value="1.07142857142857e-001"/>
<targetPrediction name="Not-H" value="8.92857142857143e-001"/>
        <SimplePredicate field="pr_g_Peptostreptococcus"
operator="greaterThan" value="3.30806684009437e-003"/>
    </Node>
</Node>
</TreeModel>
</PMML>
```

The invention claimed is:

1. A method for diagnosing and treating gingivitis and/or periodontitis in a canine animal, comprising:
   Obtaining a first sample from a conscious canine animal;
   Determining the proportion of gram negative and gram positive bacteria in the first sample;
   When the first sample comprises a proportion of gram positive bacteria of greater than 0.3 and less than 0.5, diagnosing the canine animal with gingivitis and/or periodontitis; and
   Treating the canine animal for gingivitis and/or periodontitis by
   i) brushing the teeth of the animal
   ii) providing the animal with a professional dental cleaning and/or
   iii) providing the animal a foodstuff, supplement or chew, wherein the tooth brushing, dental cleaning, foodstuff, supplement or chew are capable of treating the gingivitis and/or periodontitis.

2. The method of claim 1, wherein the sample comprises dental plaque, gingival crevicular fluid or saliva.

3. The method of claim 1, wherein determining the proportion of gram positive and gram negative bacteria in the sample comprises identifying the bacteria using Quantitative PCR, sequencing, antibody binding, fluorescent in situ hybridization or a combination of these.

4. The method of claim 3, wherein from 2 to 20 bacterial species are identified.

5. The method of claim 3, wherein from 3 to 10 bacterial species are identified.

6. The method of claim 1, wherein determining the proportion of gram negative and gram positive bacteria comprises determining the total plaque bacteria of gram negative bacteria and the total plaque bacteria of the gram positive bacteria.

7. The method of claim 1, wherein determining the proportion of gram negative and gram positive bacteria comprises determining the number of counts of each of the gram positive and gram negative bacteria.

8. The method of claim 7, wherein the number of counts is determined by sequencing or colony counts.

9. The method of claim 1, further comprising:
   Obtaining at least a second further sample from the canine animal;
   Determining the proportion of gram negative to gram positive bacteria in the further sample; and
   Repeating the treatment, sampling and determining steps until the proportion of the gram positive bacteria is not greater than 0.3 thereby treating the gingivitis and/or periodontitis.

* * * * *